US008361473B2

(12) United States Patent
Makler et al.

(10) Patent No.: US 8,361,473 B2
(45) Date of Patent: Jan. 29, 2013

(54) ANTIBODIES AND THEIR USES FOR DIAGNOSIS AND TREATMENT OF CYTOMEGALOVIRUS INFECTION AND ASSOCIATED DISEASES

(75) Inventors: Oryan Makler, Haifa (IL); Yoram Reiter, Haifa (IL)

(73) Assignee: Technion Research & Development Foundation Ltd., Haifa (IL)

( * ) Notice: Subject to any disclaimer, the term of this patent is extended or adjusted under 35 U.S.C. 154(b) by 370 days.

(21) Appl. No.: 12/450,476

(22) PCT Filed: Mar. 27, 2008

(86) PCT No.: PCT/IL2008/000437
§ 371 (c)(1),
(2), (4) Date: Jan. 6, 2010

(87) PCT Pub. No.: WO2008/120203
PCT Pub. Date: Oct. 9, 2008

(65) Prior Publication Data
US 2010/0111957 A1    May 6, 2010

Related U.S. Application Data

(60) Provisional application No. 60/929,207, filed on Jun. 18, 2007, provisional application No. 60/907,343, filed on Mar. 29, 2007.

(51) Int. Cl.
*A61K 39/42* (2006.01)
*A61K 39/395* (2006.01)
*G01N 33/53* (2006.01)

(52) U.S. Cl. .................. 424/159.1; 424/172.1; 435/7.1; 435/7.2

(58) Field of Classification Search ........................ None
See application file for complete search history.

(56) References Cited

U.S. PATENT DOCUMENTS

| 5,690,632 | A | 11/1997 | Schwartz et al. |
| 2004/0106925 | A1 | 6/2004 | Culbert |

FOREIGN PATENT DOCUMENTS

| WO | WO 98/21233 | * | 5/1998 |
| WO | WO 03/068201 | * | 8/2003 |
| WO | WO 03/070752 | | 8/2003 |
| WO | WO 2006/055704 | | 5/2006 |
| WO | WO 2006/104978 | | 10/2006 |
| WO | WO 2008/120202 | | 10/2008 |
| WO | WO 2008/120203 | | 10/2008 |

OTHER PUBLICATIONS

Andersen et al., PNAS, 1996, 93:1820-1824.*
Cohen et al., Journal of Molecular Recognition, 2003, 16:324-332.*
Diamond et al., Blood, 1997, 90(5):1751-1767.*
Pepperl et al., Journal of Virology, 2000, 74(13):6132-6146.*
Solache et al., The Journal of Immunology, 1999, 163: 5512-5518.*
Miller et al., The Journal of Immunology, 2003, 170:4854-4861.*
Restriction Office Action Dated Dec. 12, 2011 From the US Patent and Trademark Office Re. U.S. Appl. No. 12/450,479.
Response Dated Oct. 14, 2010 to Communication Pursuant to Article 94(3) EPC of Apr. 16, 2010 From the European Patent Office Re.: Application No. 08738150.5.
Communication Pursuant to Rule 2(1) EPC and Article 7 of the Decision of the President of the EPO Dated Jul. 12, 2007 on the Use of Facsimile for Filing Patent Applications and Other Documents Dated Feb. 14, 2012 From the European Patent Office Re.: Application No. 08738150.5.
Invitation Pursuant to Article 94(3) and Rule 71(1) EPC Dated Feb. 1, 2012 From the European Patent Office Re.: Application No. 08738150.5.
Office Action Dated Feb. 27, 2012 From the US Patent and Trademark Office Re. U.S. Appl. No. 12/450,479.
Communication Relating to the Results of the Partial International Search Dated Aug. 20, 2008 From the International Searching Authority Re.: Application No. PCT/IL2008/000436.
International Preliminary Report on Patentability Dated Oct. 8, 2009 From the International Bureau of WIPO Re.: Application No. PCT/IL2008/000437.
International Preliminary Report on Patentability Dated Oct. 8, 2009 From the International Bureau of WIPO Re.: Application No. PCT/IL2008/000436.
International Search Report Dated Nov. 28, 2008 From the International Searching Authority Re.: Application No. PCT/IL2008/000436.
Written Opinion Dated Nov. 28, 2008 From the International Searching Authority Re.: Application No. PCT/IL2008/000436.
Cohen et al. "Recombinant Antibodies With MHC-Restricted, Peptide-Specific, T-Cell Receptor-Like Specificity: New Tools to Study Antigen PPresentation and TCR-Peptide-MHC Interactions", Journal of Molecular Recognition, XP008050078, 16(5): 324-332, Sep. 1, 2003.
Davies et al. "Affinity Improvement of Single Antibody VH Domains: Residues in All Three Hypervariable Regions Affect Antigen Binding", Immunotechnology, XP004070292, 2(3): 169-179, Sep. 1, 1996.
Denkberg et al. "Direct Visualization of Distinct T Cell Epitopes Derived From a Melanoma Tumor-Associated Antigen by Using Human Recombinant Antibodies With MHC-Restricted T Cell Receptor-Like Specificity", Proc. Natl. Acad. Sci. USA, XP002461574, 99(14): 9421- 9426, Jul. 9, 2002.
Denkberg et al. "Selective Targeting of Melanoma and APCs Using a Recombinant Antibody With TCR-Like Specificity Directed Toward a Melanoma Differentiation Antigen", The Journal of Immunology, XP002383418, 171(5): 2197-2207, Sep. 1, 2003.
Holt et al. "Domain Antibodies: Proteins for Therapy", Trends in Biotechnology, XP004467495, 21(11): 484-490, Nov. 1, 2003.

(Continued)

*Primary Examiner* — Zachariah Lucas
*Assistant Examiner* — Nicole Kinsey White

(57) ABSTRACT

Anti CMV antibodies are provided. Thus an antibody of the present invention comprises an antigen recognition domain capable of binding an MHC molecule being complexed with a cytomegalovirus (CMV) pp65 or pp64 peptide, wherein the antibody does not bind said MHC molecule in an absence of said complexed peptide, and wherein the antibody does not bind said peptide in an absence of said MHC molecule. Also provided are methods of using the antibodies.

21 Claims, 22 Drawing Sheets
(21 of 22 Drawing Sheet(s) Filed in Color)

OTHER PUBLICATIONS

Renkvist et al. "A Listing of Human Tumor Antigens Recognized by T Cells", Cancer Immunology and Immunotherapy, XP002274524, 50(1): 3-15, Mar. 1, 2001. Table 2.
Communication Pursuant to Article 94(3) EPC Dated Apr. 16, 2010 From the European Patent Office Re.: Application No. 08738150.5.
Communication Pursuant to Article 94(3) EPC of May 6, 2011 From the European Patent Office Re.: Application No. 08738150.5.
Response Dated Apr. 17, 2011 to Communication Pursuant to Article 94(3) EPC of Oct. 28, 2010 From the European Patent Office Re.: Application No. 08738150.5.
Response Dated Sep. 6, 2011 to Communication Pursuant to Article 94(3) EPC of May 6, 2011 From the European Patent Office Re.: Application No. 08738150.5.
Response Dated Sep. 7, 2011 to Communication Pursuant to Article 94(3) EPC of May 6, 2011 From the European Patent Office Re.: Application No. 08738150.5.
Communication Pursuant to Article 94(3) EPC of Sep. 20, 2011 From the European Patent Office Re.: Application No. 08738150.5.
Office Action Dated Nov. 9, 2011 From the Israel Patent Office Re. Application No. 201243 and Its Translation Into English.
Office Action Dated Nov. 10, 2011 From the Israel Patent Office Re. Application No. 201243 and Its Translation Into English.
Liao et al. "Vaccination With Human Tyrosinase DNA Induces Antibody Responses in Dogs With Advanced Melanoma", Cancer Immunity, 6(8): 1-10, Apr. 21, 2006.
Communication Pursuant to Article 94(3) EPC Dated Oct. 28, 2010 From the European Patent Office Re.: Application No. 08738150.5.
Communication Pursuant to Rule 56(1) EPC, Missing Parts of Description or Missing Drawings Dated May 21, 2012 From the European Patent Office Re. Application No. 12165562.5.
Invitation Pursuant to Article 94(3) and Rule 71(1) EPC Dated Apr. 10, 2012 From the European Patent Office Re.: Application No. 08738150.5.
Office Action Dated Aug. 22, 2012 From the US Patent and Trademark Office Re. U.S. Appl. No. 12/450,479.
Patent Examination Report Dated Aug. 28, 2012 From the Australian Government, IP Australia Re. Application No. 2008234530.

* cited by examiner

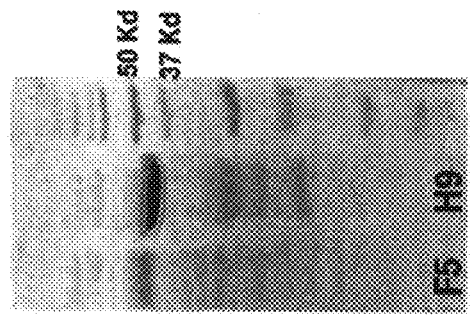
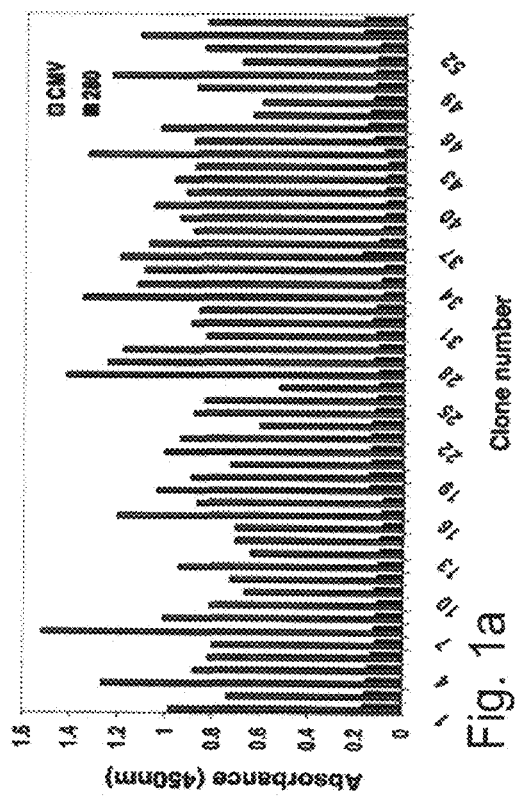

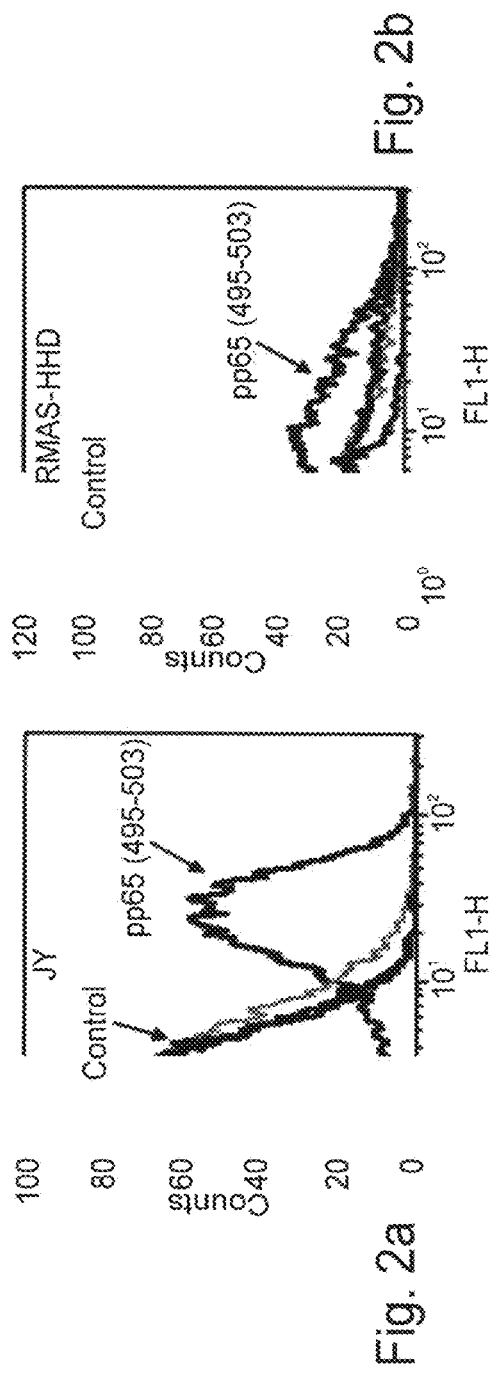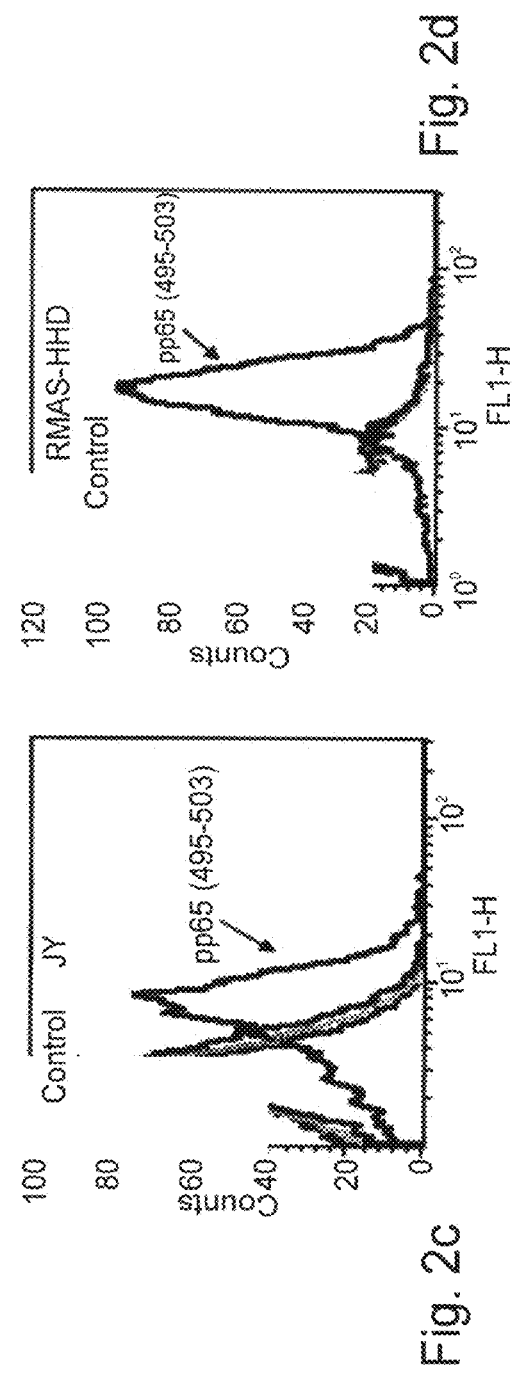

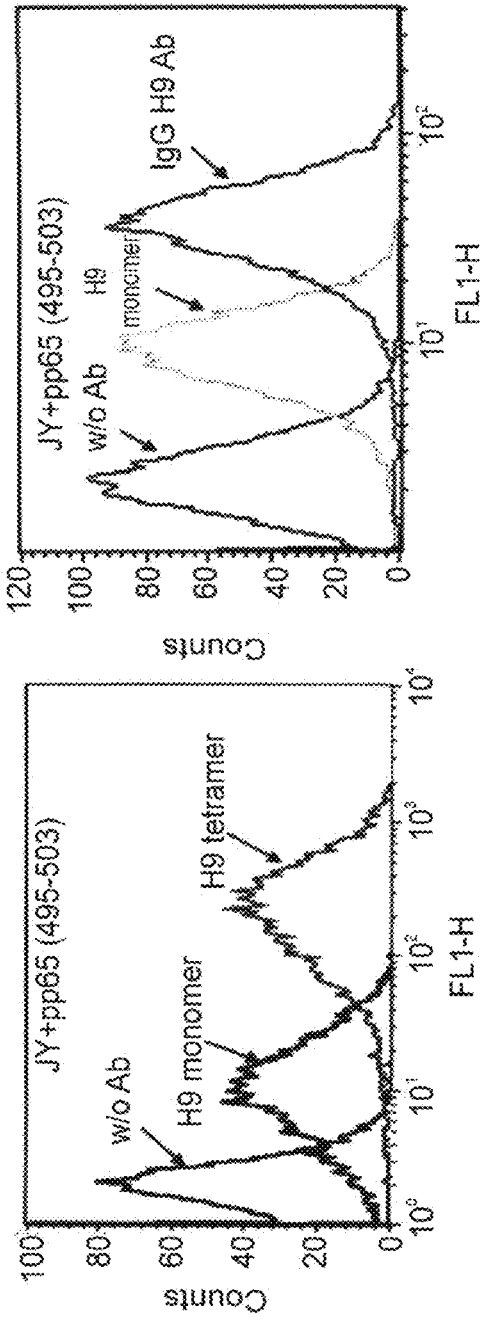
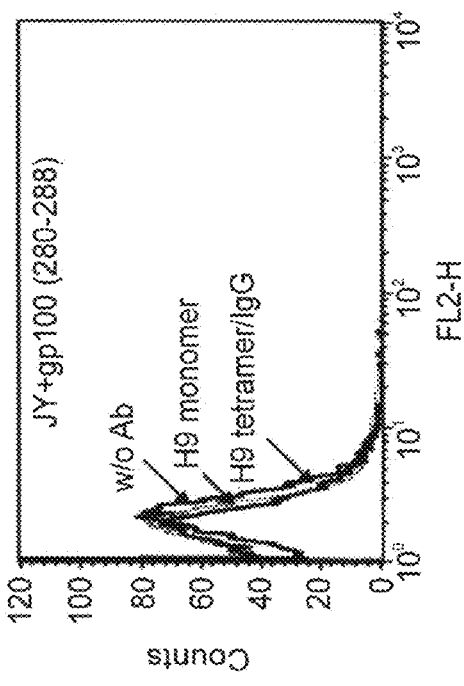
Fig. 3a
Fig. 3b
Fig. 3c

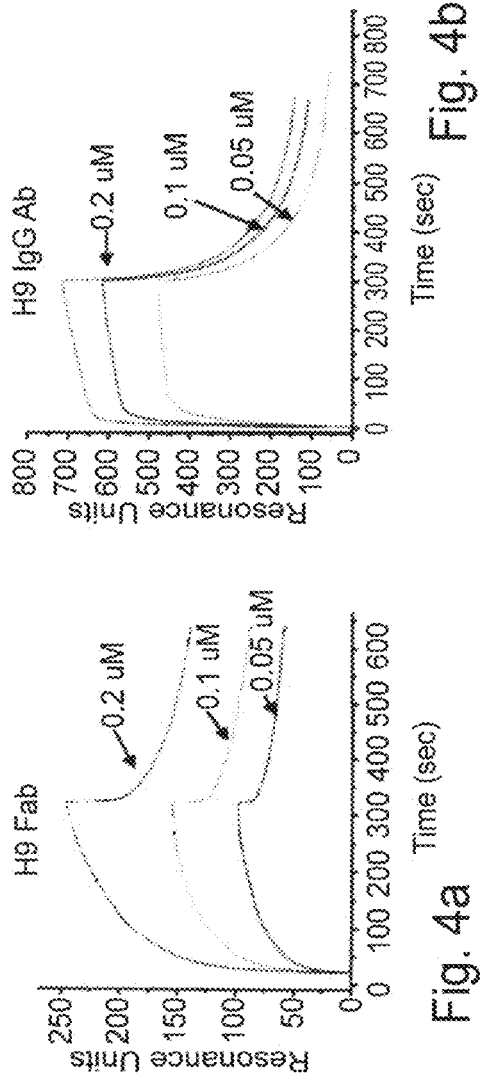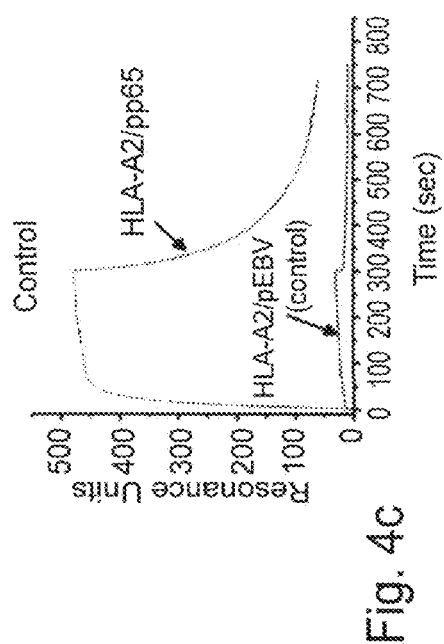

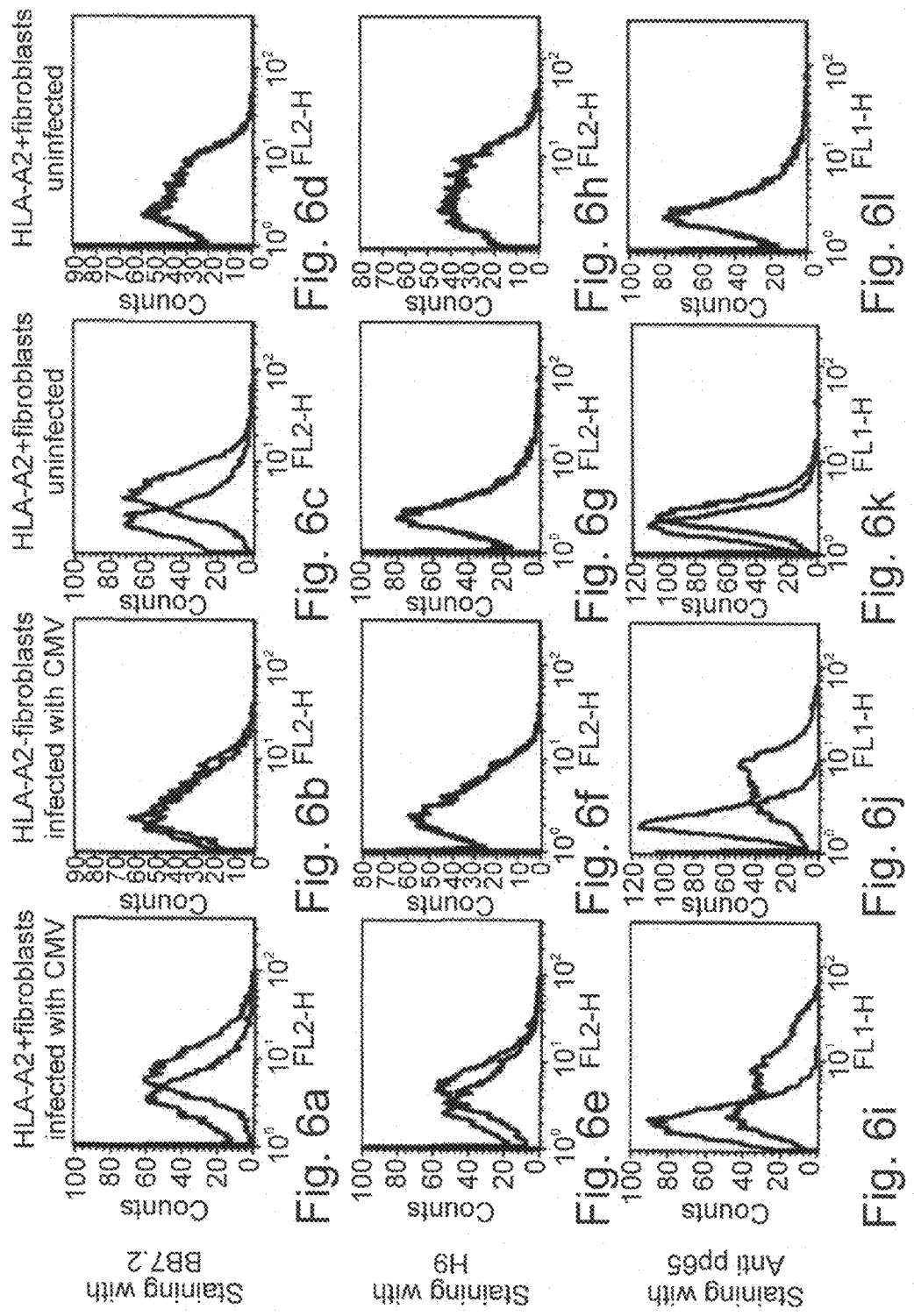

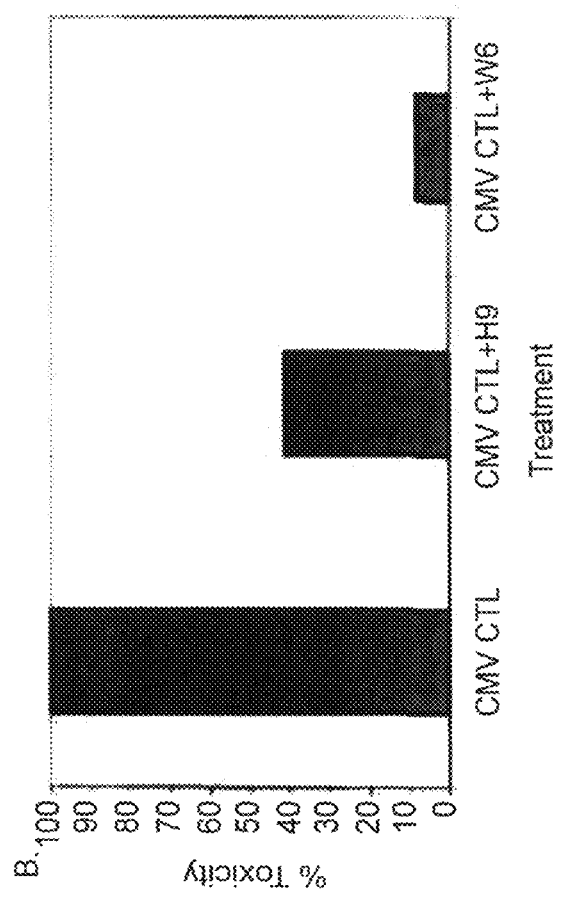

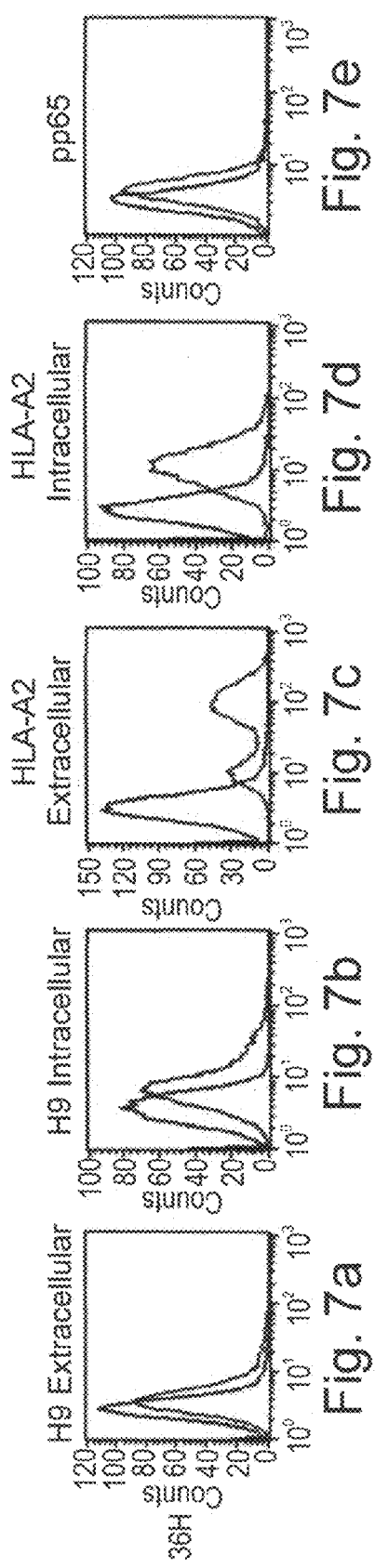
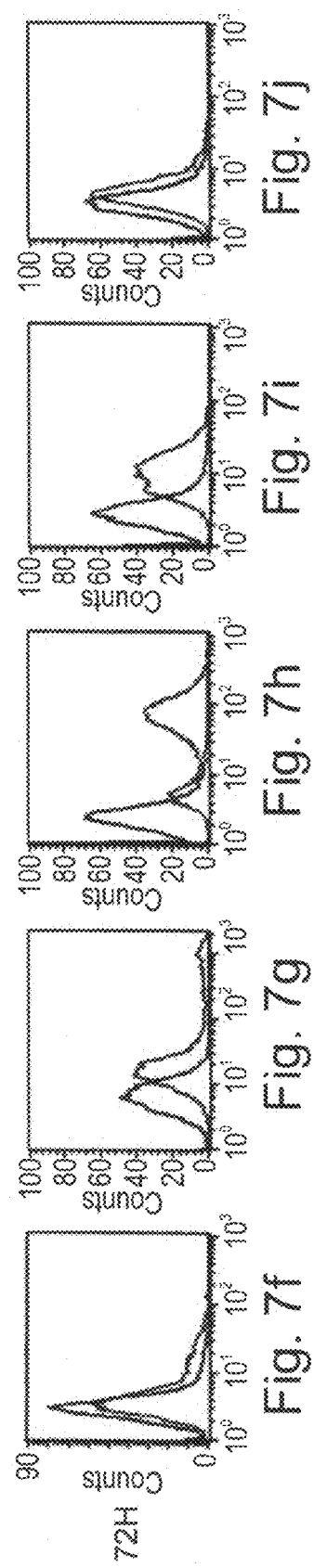
A. Infection with AD169 (WT) strain
Fig. 7a Fig. 7b Fig. 7c Fig. 7d Fig. 7e
Fig. 7f Fig. 7g Fig. 7h Fig. 7i Fig. 7j

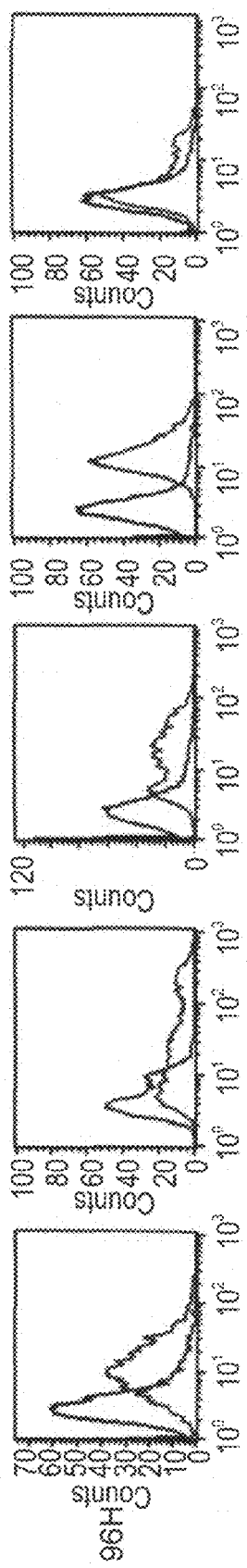
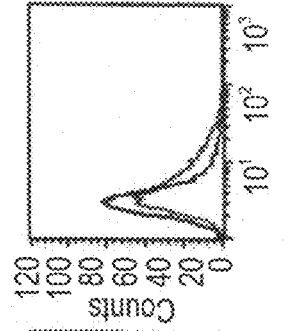
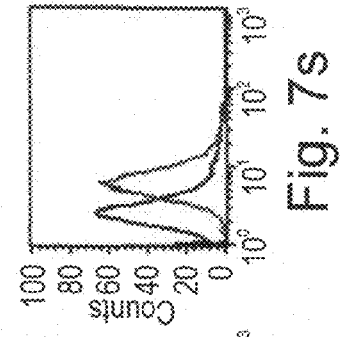
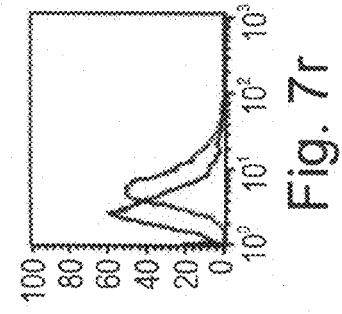
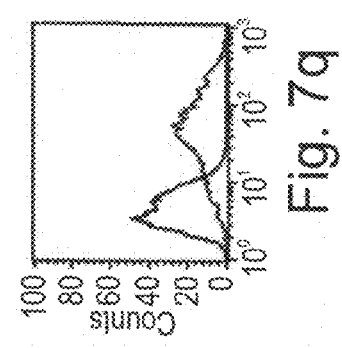
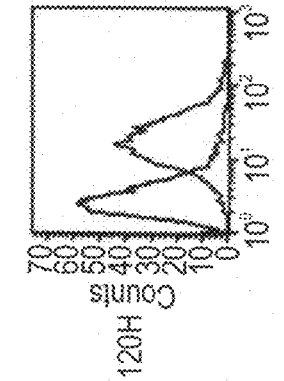

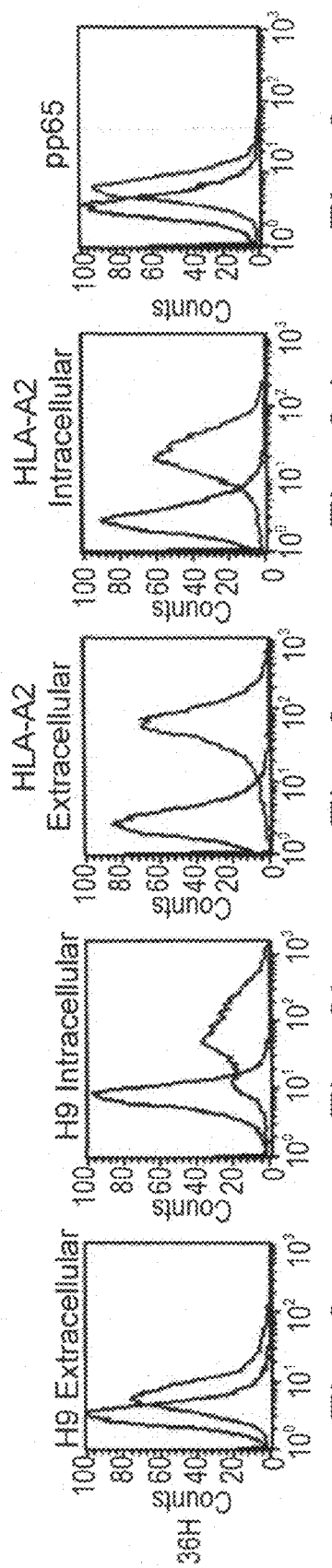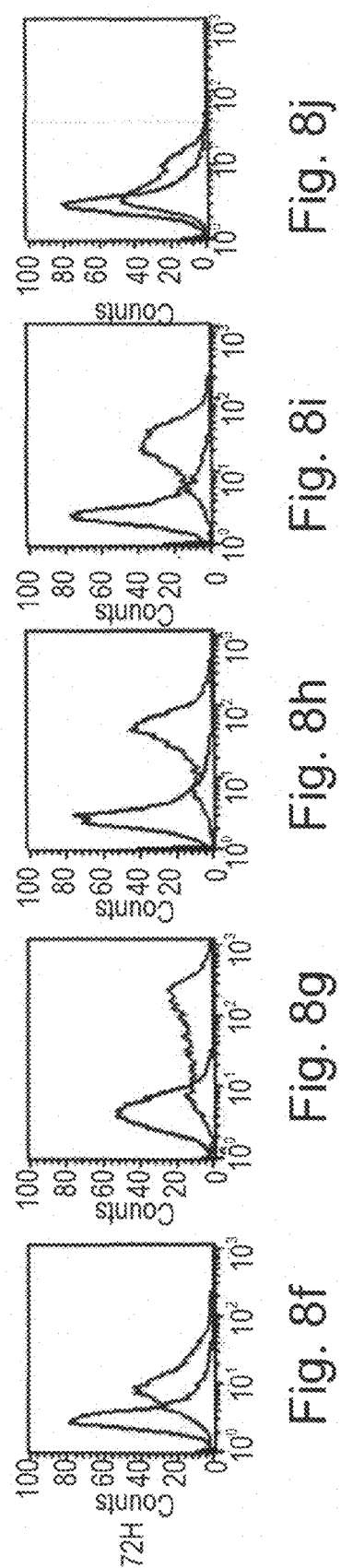

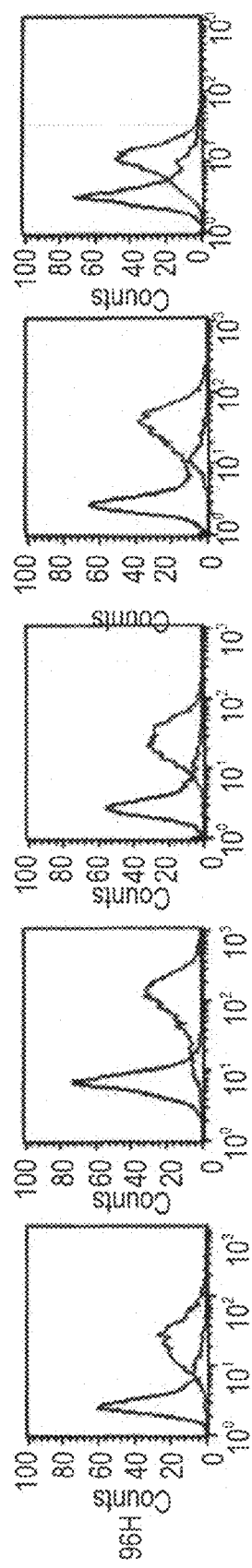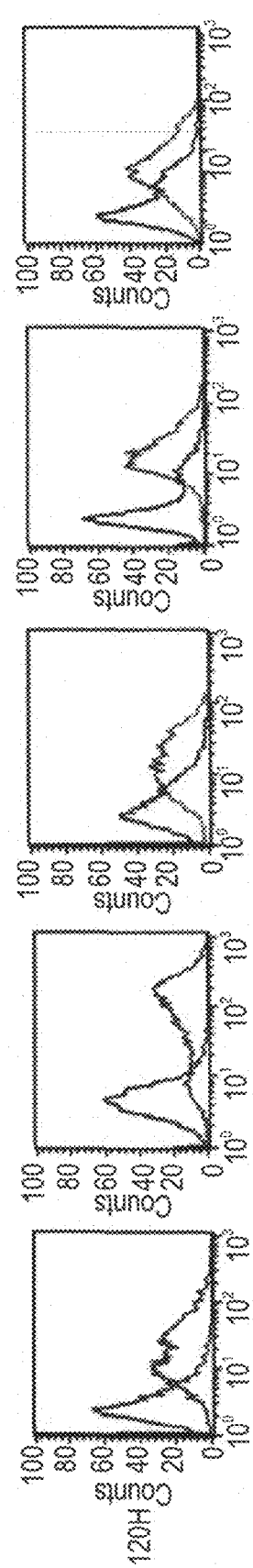
Fig. 8k, Fig. 8l, Fig. 8m, Fig. 8n, Fig. 8o, Fig. 8p, Fig. 8q, Fig. 8r, Fig. 8s, Fig. 8t

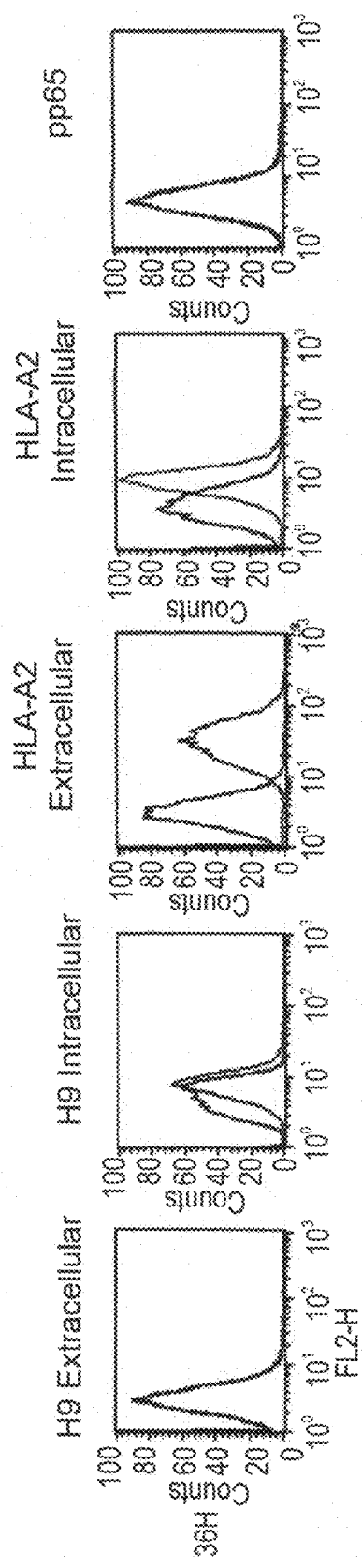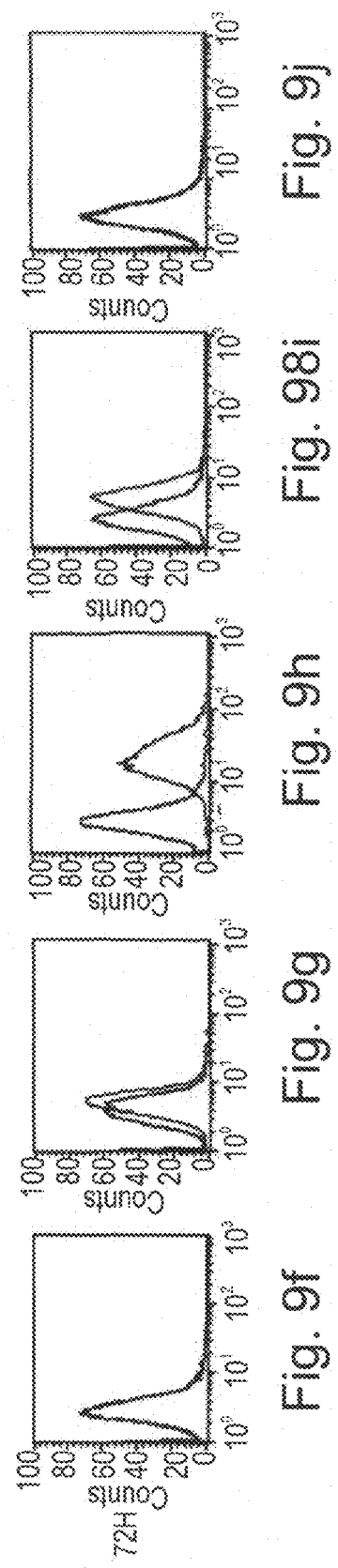
Fig. 9a–9j. C. Uninfected cells/HLA-A2-cells infected with AD169 (WT) strain

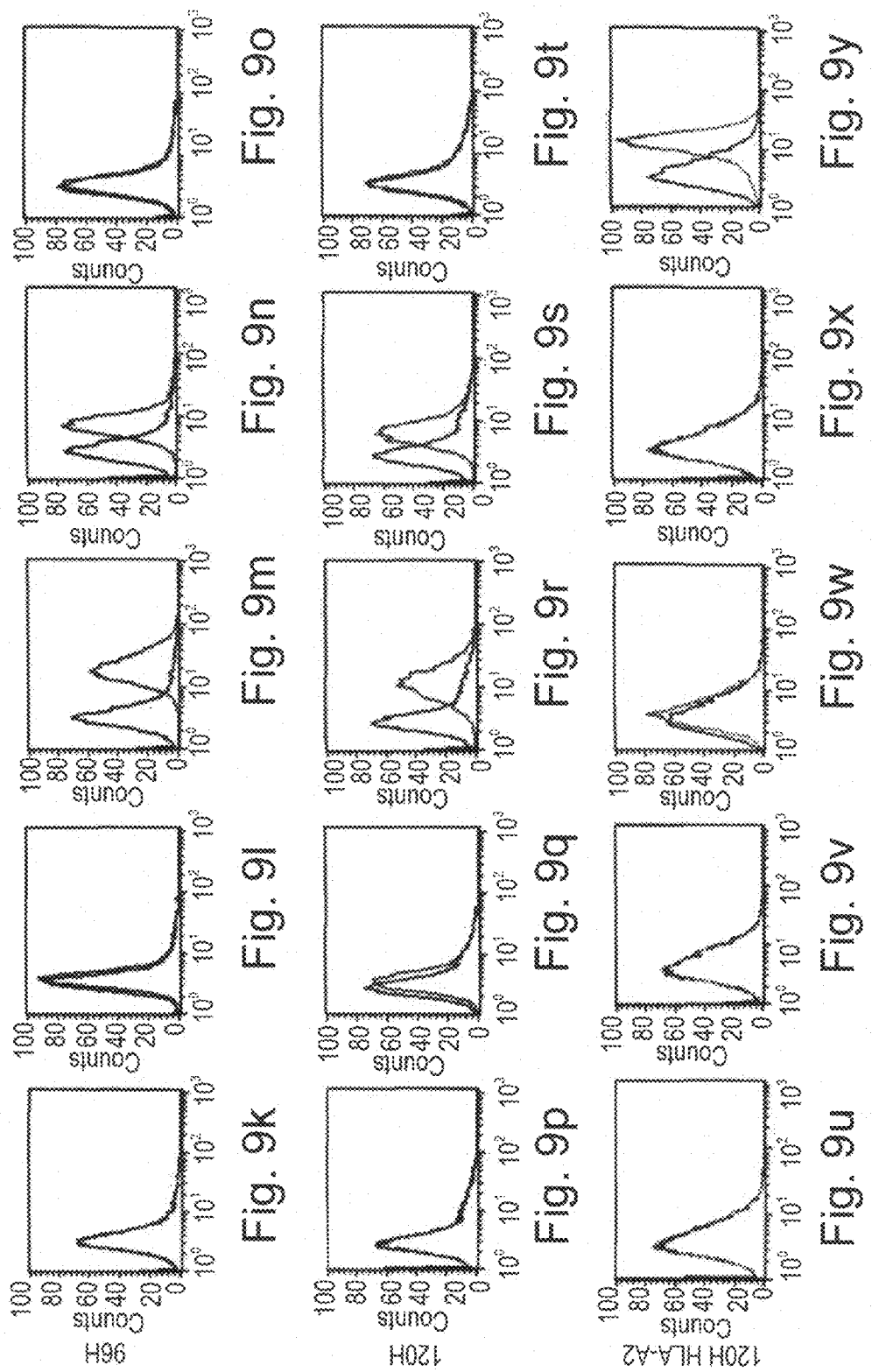

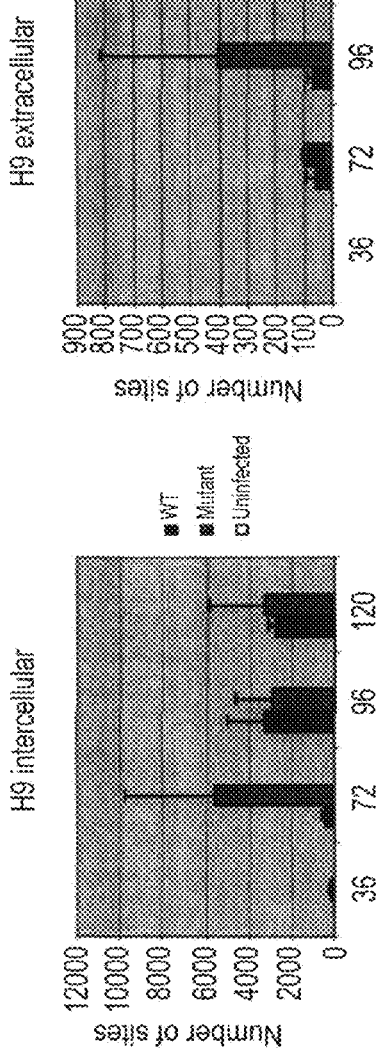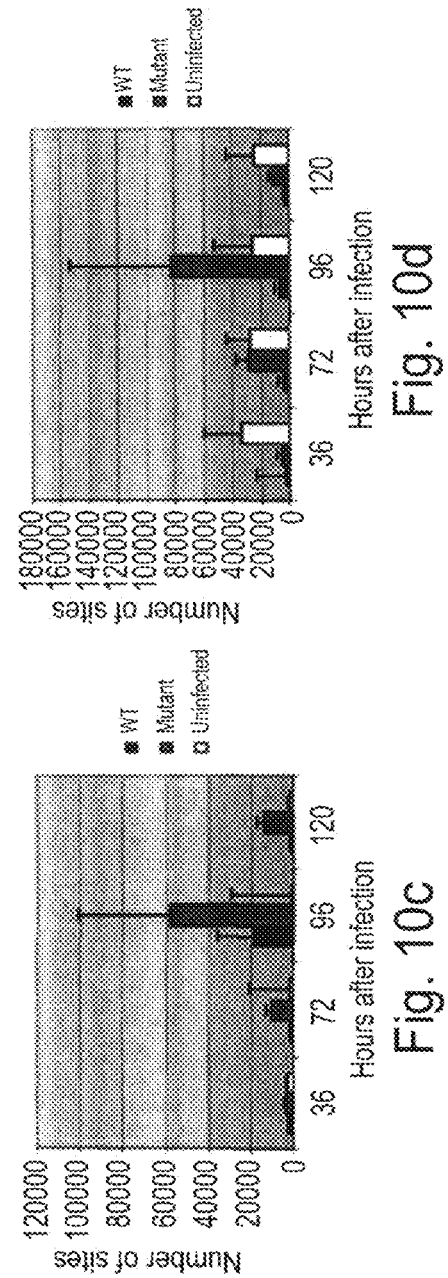

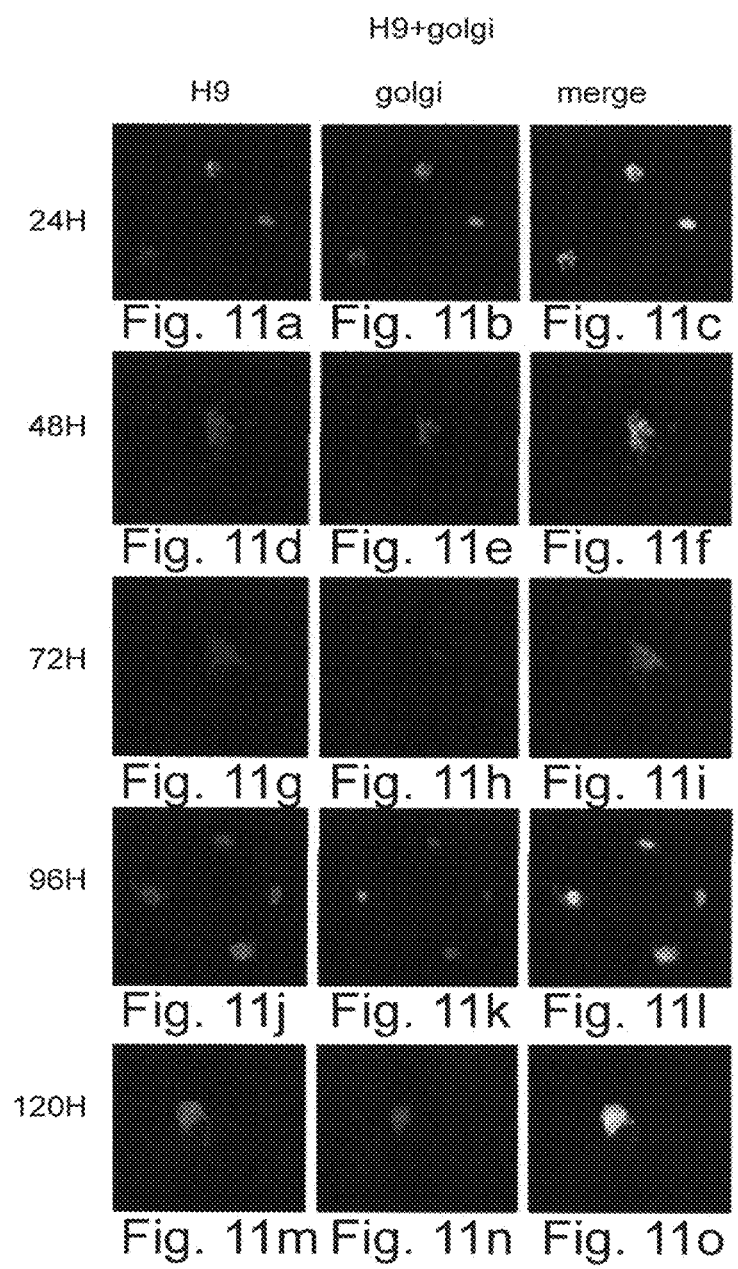

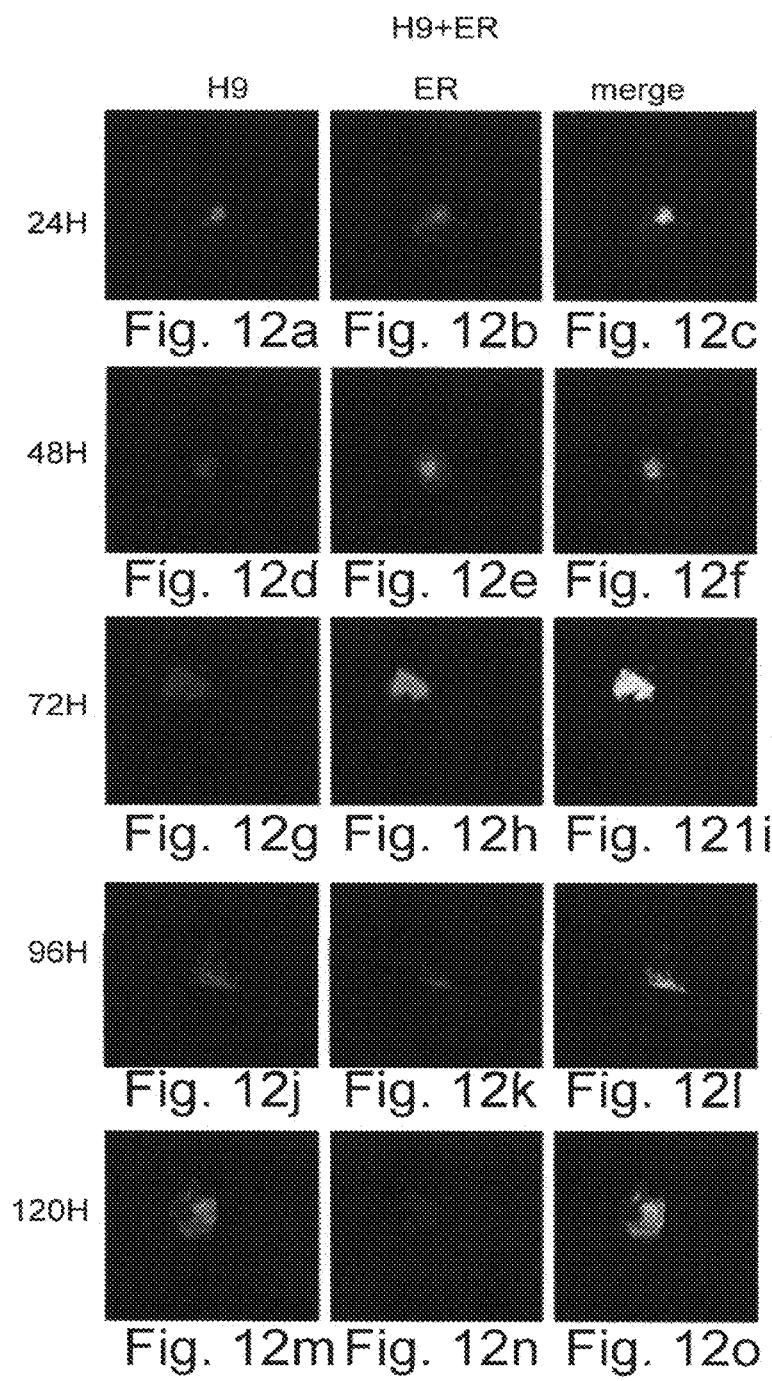

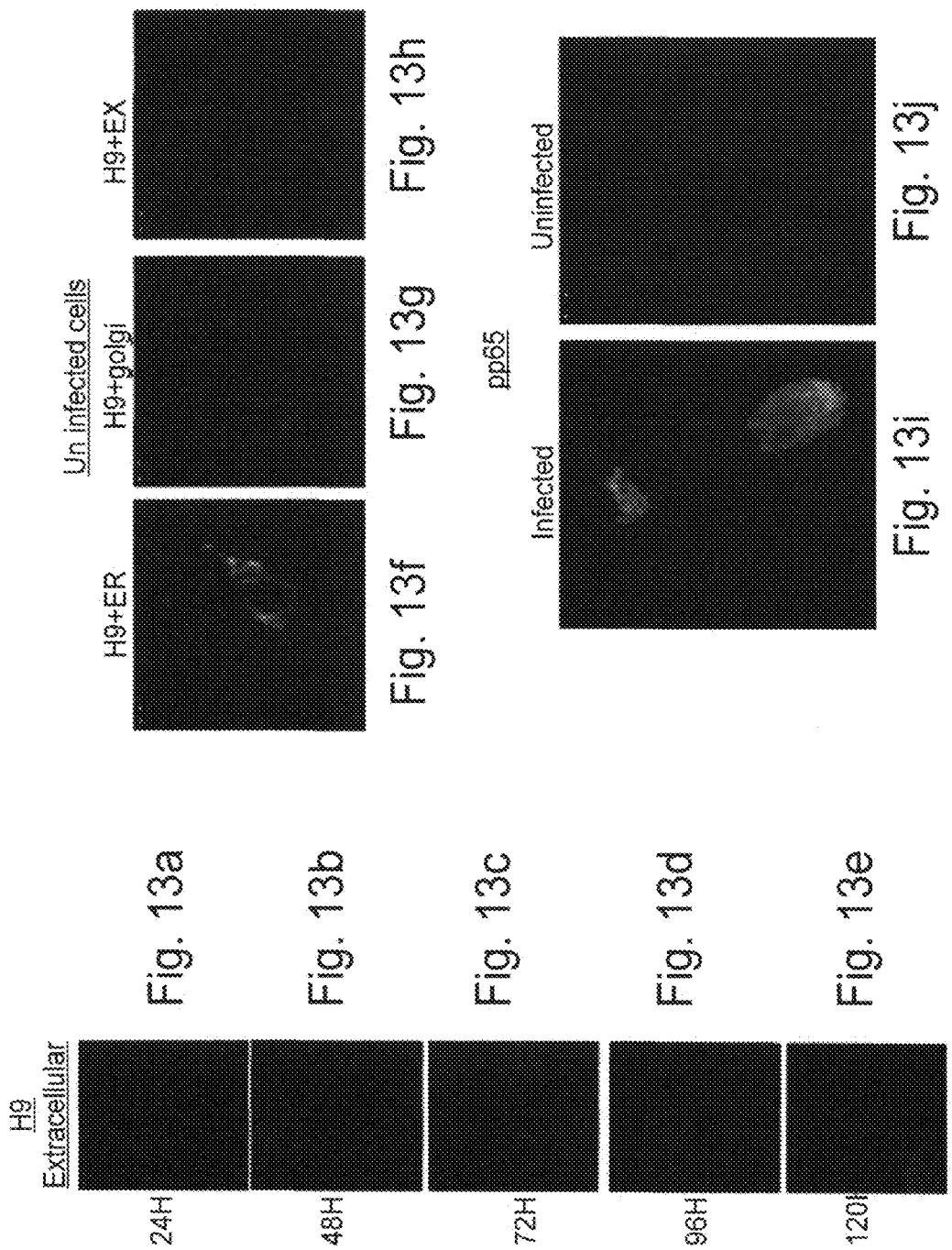

Fig. 14a
Amino acid sequence of the heavy chain of Fab H9 (SEQ ID NO:16)

EVQLVQSGAEVKKPGSSVKVSCKASGGTFSSYAISWVRQAPGQGLEWMGGI
PIFGTANYAQKFQGRVTITADESTSTAYMELSSLRSEDTAVYYCAR GDLYYY
DSSGYPRYYFDYWGQGTLVTVSSASTKGPSVFPLAPSSKSTSGGTAALGCLV
KDYFPEPVTVSWNSGALTSGVHTFPAVLQSSGLYSLSSVVTVPSSSLGTQTYI
CNVNHKPSNTKVDKKVEPKSC

Fig. 14b
Nucleic acid sequence of the heavy chain of Fab H9 (SEQ ID NO:17)

GAAGTGCAGCTGGTGCAGTCTGGGGCTGAGGTGAAGAAGCCTGGGTCCTC
GGTGAAGGTCTCCTGCAAGGCTTCTGGAGGCACCTTCAGCAGCTATGCTA
TCAGCTGGGTGCGACAGGCCCCTGGACAAGGGCTTGAGTGGATGGGAGG
GATCATCCCTATCTTTGGTACAGCAAACTACGCACAGAAGTTCCAGGG CA
GAGTCACGATTACCGCGGACGAATCCACGAGCACAGCCTACATGGAGCTG
AGCAGCCTGAGATCTGAGGACACGGCCGTGTATTACTGTGCGAG AGGGGA
TCTGTATTACTATGATAGTAGTGGTTATCCGCGATACTACTTTGACTA CTG
GGGCCAGGGCACCCTGGTCACCGTCTCAAGCGCCTCCACCAAGGGCCCAT
CGGTCTTCCCCCTGGCACCCTCCTCCAAGAGCACCTCTGGGGGCACAGCG
GCCCTGGGCTGCCTGGTCAAGGACTACTTCCCCGAACCGGTGACGGTGTC
GTGGAACTCAGGCGCCCTGACCAGCGGCGTCCACACCTTCCCGGCTGTCC
TACAGTCCTCAGGACTCTACTCCCTCAGCAGCGTAGTGACCGTGCCCTCCA
GCAGCTTGGGCACCCAGACCTACATCTGCAACGTGAATCACAAGCCCAGC
AACACCAAGGTGGACAAGAAAGTTGAGCCCAAATCTTGT

Fig. 14c
Amino acid sequence of the light chain of Fab H9 (SEQ ID NO:18)

LETTLTQSPGTLSLSPGERATLSCRASQSVSSSYLAWYQQKPGQAPRLVIY GA
SSRATGIPDRFSGSGSGTDFTLTISRLEPEDFAVYYC QHYSTSPQFTFGQGTKL
EIRRTVAAPSVFIFPPSDEQLKSGTASVVCLLNNFYPREAKVQWKVDNALQSG
NSQESVTEQDSKDSTYSLSSHQGLSSPVTKSFNRGEC stop

Fig. 14d

Nucleic acid sequence of the light chain of Fab H9 (SEQ ID NO:19)

CTTGAAACGACACTCACGCAGTCTCCAGGCACCCTGTCTTTGTCTCCAGGG
GAAAGAGCCACCCTCTCCTGCAGGGCCAGTCAGAGTGTTAGCAGCAGCTA
CTTAGCCTGGTACCAGCAGAAACCTGGCCAGGCTCCCAGGCTCGTCATCT
ATGGTGCATCCAGCAGGGCCACTGGCATCCCAGACAGGTTCAGTGGCAGT
GGGTCTGGGACAGACTTCACTCTCACCATCAGCAGACTGGAGCCTGAAGA
TTTTGCAGTTTATTACTGTC AGCACTATAGCACCTCACCTGGGTTCACT TTT
GGCCAGGGGACCAAGCTGGAGATCAGA CGAACTGTGGCTGCACCATCTGT
CTTCATCTTCCCGCCATCTGATGAGCAGTTGAAATCTGGAACTGCCTCTGT
TGTGTGCCTGCTGAATAACTTCTATCCCAGAGAGGCCAAAGTACAGTGGA
AGGTGGATAACGCCCTCCAATCGGGTAACTCCCAGGAGAGTGTCACAGAG
CAGGACAGCAAGGACAGCACCTACAGCCTCAGCAGCCATCAGGGCCTGA
GCTCGCCCGTCACAAAGAGCTTCAACAGGGGAGAGTGTTAATAA

Fig. 15a

Amino acid sequence of the heavy chain of Fab F5 (SEQ ID NO:20)

QVQLQESGPGLVKPSETLSLTCTVSGGSIS SSNYY WGWIRQPPGKGLEWIGAI
YYSGSTYYNPSLKSRVAISVDTSKNQFSLKLSSVTAADTAVYYCAR RIGVAG
QWYFDLWGRGTLVTVSS ASTKGPSVFPLAPSSKSTSGGTAALGCLVKDYFPE
PVTVSWNSGALTSGVHTFPAVLQSSGLYSLS SVVTVPSSSLGTQTYICNVNHK
PSNTKVDKKVEPKSC

Fig. 15b

Nucleic acid sequence of the heavy chain of Fab F5 (SEQ ID NO:21)

CAGGTGCAGCTGCAGGAGTCCGGCCCAGGACTGGTGAAGCCTTCGGAGAC
CCTGTCCCTCACCTGCACTGTCTCTGGTGGCTCCATCAGCAGCAGTAATTA
CTACTGGGGCTGGATCCGCCAGCCCCCAGGGAAGGGGCTGGAGTGGATTG
GTGCTATCTATTATAGTGGGAGCACCTACTACAACCCGTCCCTCAAGAGT C
GAGTCGCCATATCCGTAGACACGTCCAAGAACCAGTTCTCGCTGAAGTTG
AGTTCTGTGACCGCCGCAGACACGGCTGTCTATTACTGTGCGAGA CGTAT
AGGAGTGGCTGGCCAATGGTATTTCGATCTCTGGGGCCGTGGCACCCTGG
TCACCGTCTCAAGCGCCTCCACCAAGGGCCCATCGGTCTTCCCCCTGGCAC
CCTCCTCCAAGAGCACCTCTGGGGGCACAGCGGCCCTGGGCTGCCTGGTC
AAGGACTACTTCCCCGAACCGGTGACGGTGTCGTGGAACTCAGGCGCCCT
GACCAGCGGCGTCCACACCTTCCCGGCTGTCCTACAGTCCTCAGGACTCTA
CTCCCTCAGCAGCGTAGTGACCGTGCCCTCCAGCAGCTTGGGCACCCAGA
CCTACATCTGCAACGTGAATCACAAGCCCAGCAACACCAAGGTGGA CAAG
AAAGTTGAGCCCAAATCTTGT

Fig. 15c

Amino acid sequence of the light chain of Fab F5 (SEQ ID NO:22)

LNFMLTQPHSVSGSPGKTVTISCTRSTGSITSNYVHWYQQRPGSSPTTVICEDN
ERPSGVPDRFSGSIDISSNSASLTISGLKTEDEADYYCQSYDDSNEHSVFGTGTK
VTVLGQPKANPCLISDFYPGAVTVAWKADGSPVKAGVETTKPSKQSNNKYA
ASSYLSLTPEQWKSHRSYSCQVTHEGSTVEKTVAPAECSstop

Fig. 15d

Nucleic acid sequence of the light chain of Fab F5 (SEQ ID NO:23)

CTTAATTTTATGCTGACTCAGCCCCACTCTGTGTCGGGGTCTCCGGGGAAG
ACGGTTACCATCTCCTGCACCCGCAGCACTGGCAGCATTACCAGCAACTA
TGTGCACTGGTACCAGCAGCGCCCGGGCAGTTCCCCCACCACTGTGATCT
GTGAGGATAACGAAAGACCCTCTGGGGTCCCTGATCGATTCTCTGGCTCC
ATCGACATCTCCTCCAACTCTGCCTCCCTCACCATCTCTGGACTGAAGACT
GAGGACGAGGCTGACTACTACTGTCAGTCTTATGATGACAGCAATCATAT
TTCTGTCTTCGGTACTGGGACCAAGGTCACCGTCCTAGGTCAGCCCAAGG
CCAACCCCTGTCTGATCAGTGACTTCTACCCGGGAGCTGTGACAGTGGCCT
GGAAGGCAGATGGCAGCCCCGTCAAGGCGGGAGTGGAGACCACCAAACC
CTCCAAACAGAGCAACAACAAGTACGCGGCCAGCAGTTACCTGAGCCTG
ACGCCCGAGCAGTGGAAGTCCCACAGAAGCTACAGCTGCCAGGTCACGC
ATGAGGGGAGCACCGTGGAGAAGACAGTGGCCCCTGCAGAATGTTCATA
AACTGTCACTCTGTTCCCGCCCTCCTCTGAGGAGCTCCAAGCCAACAAGG
CCACACTAGTG

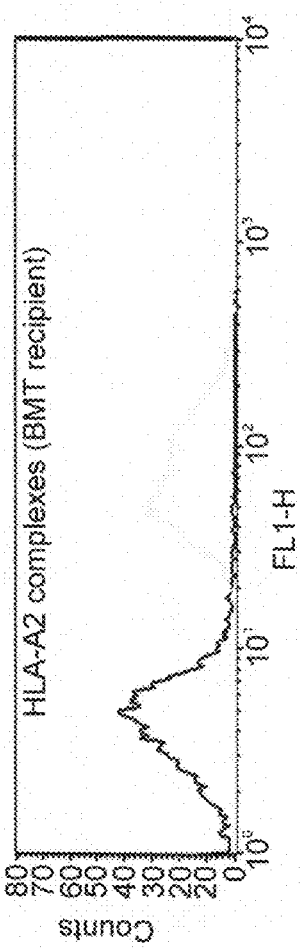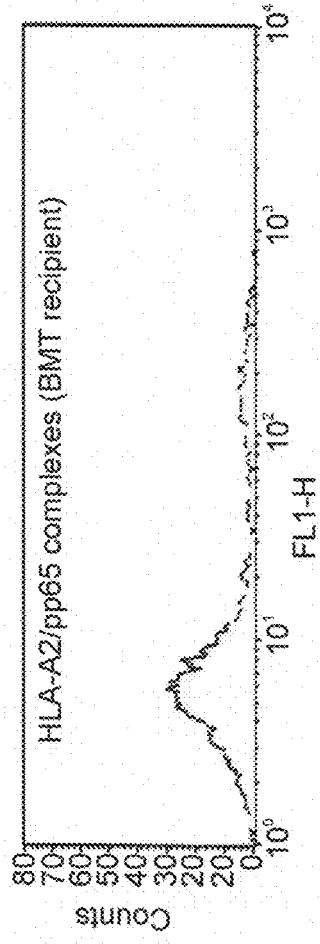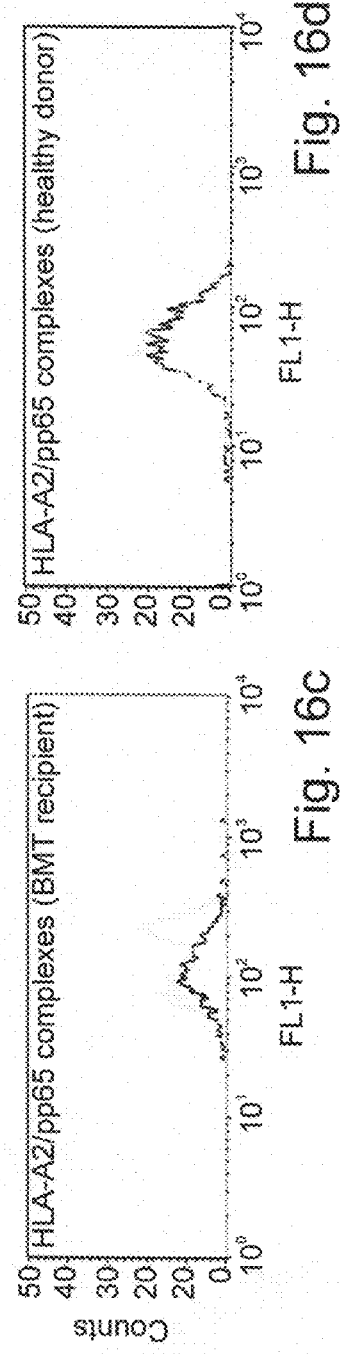

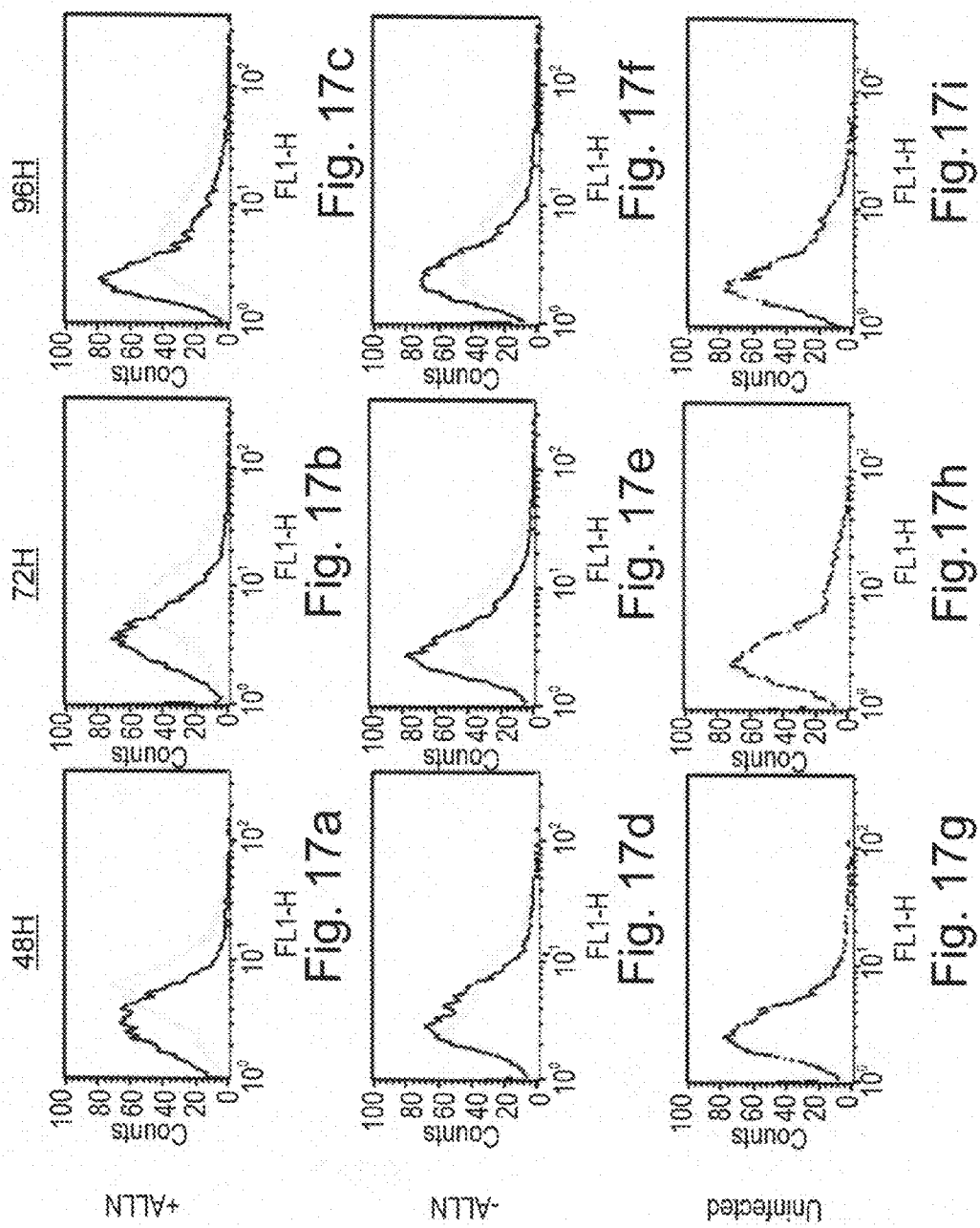

```
                              SEQUENCE LISTING

<160> NUMBER OF SEQ ID NOS: 904

<210> SEQ ID NO 1
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 1
agcggataac aatttcacac agg                                               23

<210> SEQ ID NO 2
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 2
tttgtcgtct ttccagacgt tagt                                              24

<210> SEQ ID NO 3
<211> LENGTH: 9
<212> TYPE: PRT
<213> ORGANISM: Artificial sequence
<220> FEATURE:
<223> OTHER INFORMATION: CMV pp65 (495-503) HLA-A2  restricted peptide

<400> SEQUENCE: 3

Asn Leu Val Pro Met Val Ala Thr Val
1               5

<210> SEQ ID NO 4
<211> LENGTH: 9
<212> TYPE: PRT
<213> ORGANISM: Artificial sequence
<220> FEATURE:
<223> OTHER INFORMATION: gp100 (280-288) derived HLA control peptide

<400> SEQUENCE: 4

Tyr Leu Glu Pro Gly Pro Val Thr Ala
1               5

<210> SEQ ID NO 5
```

```
<211> LENGTH: 9
<212> TYPE: PRT
<213> ORGANISM: Artificial sequence
<220> FEATURE:
<223> OTHER INFORMATION: EBV (280-288) derived HLA control peptide

<400> SEQUENCE: 5

Gly Leu Cys Thr Leu Val Ala Met Leu
1               5

<210> SEQ ID NO 6
<211> LENGTH: 9
<212> TYPE: PRT
<213> ORGANISM: Artificial sequence
<220> FEATURE:
<223> OTHER INFORMATION: hTERT (540-548) derived HLA control peptide

<400> SEQUENCE: 6

Ile Leu Ala Lys Phe Leu His Trp Leu
1               5

<210> SEQ ID NO 7
<211> LENGTH: 9
<212> TYPE: PRT
<213> ORGANISM: Artificial sequence
<220> FEATURE:
<223> OTHER INFORMATION: melanoma gp100 (209-217) derived HLA control
      peptide

<400> SEQUENCE: 7

Ile Met Asp Gln Val Pro Phe Ser Val
1               5

<210> SEQ ID NO 8
<211> LENGTH: 9
<212> TYPE: PRT
<213> ORGANISM: Artificial sequence
<220> FEATURE:
<223> OTHER INFORMATION: hTERT (865-873) derived HLA control peptide

<400> SEQUENCE: 8

Arg Leu Val Asp Asp Phe Leu Leu Val
1               5

<210> SEQ ID NO 9
<211> LENGTH: 9
<212> TYPE: PRT
<213> ORGANISM: Artificial sequence
<220> FEATURE:
<223> OTHER INFORMATION: Gag (77-85) derived HLA control peptide

<400> SEQUENCE: 9

Ser Leu Tyr Asn Thr Val Ala Thr Leu
1               5

<210> SEQ ID NO 10
<211> LENGTH: 8
<212> TYPE: PRT
<213> ORGANISM: Artificial sequence
<220> FEATURE:
<223> OTHER INFORMATION: Pol (476-484) derived HLA control peptide

<400> SEQUENCE: 10

Ile Leu Glu Pro Val His Gly Val
1               5

<210> SEQ ID NO 11
<211> LENGTH: 10
```

```
<212> TYPE: PRT
<213> ORGANISM: Artificial sequence
<220> FEATURE:
<223> OTHER INFORMATION: MART-1 (26-35) derived HLA control peptide

<400> SEQUENCE: 11

Glu Leu Ala Gly Ile Gly Ile Leu Thr Val
1               5                   10

<210> SEQ ID NO 12
<211> LENGTH: 10
<212> TYPE: PRT
<213> ORGANISM: Artificial sequence
<220> FEATURE:
<223> OTHER INFORMATION: XAGE derived HLA control peptide

<400> SEQUENCE: 12

Gly Val Phe Pro Ser Ala Pro Ser Pro Val
1               5                   10

<210> SEQ ID NO 13
<211> LENGTH: 9
<212> TYPE: PRT
<213> ORGANISM: Artificial sequence
<220> FEATURE:
<223> OTHER INFORMATION: TARP (29-37) derived HLA control peptide

<400> SEQUENCE: 13

Phe Leu Arg Asn Phe Ser Leu Met Leu
1               5

<210> SEQ ID NO 14
<211> LENGTH: 9
<212> TYPE: PRT
<213> ORGANISM: Artificial sequence
<220> FEATURE:
<223> OTHER INFORMATION: TAX (11-19) derived HLA control peptide

<400> SEQUENCE: 14

Leu Leu Phe Gly Tyr Pro Val Tyr Val
1               5

<210> SEQ ID NO 15
<211> LENGTH: 9
<212> TYPE: PRT
<213> ORGANISM: Artificial sequence
<220> FEATURE:
<223> OTHER INFORMATION: Melanoma gp100 (154-162) derived HLA control
      peptide

<400> SEQUENCE: 15

Lys Thr Trp Gly Gln Tyr Trp Gln Val
1               5

<210> SEQ ID NO 16
<211> LENGTH: 230
<212> TYPE: PRT
<213> ORGANISM: Artificial sequence
<220> FEATURE:
<223> OTHER INFORMATION: H9 Fab heavy chain polypeptide sequence

<400> SEQUENCE: 16

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
```

```
                35                  40                  45
Gly Gly Ile Ile Pro Ile Phe Gly Thr Ala Asn Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Asp Leu Tyr Tyr Tyr Asp Ser Ser Gly Tyr Pro Arg Tyr
                100                 105                 110

Tyr Phe Asp Tyr Trp Gly Gln Gly Thr Leu Val Thr Val Ser Ser Ala
            115                 120                 125

Ser Thr Lys Gly Pro Ser Val Phe Pro Leu Ala Pro Ser Ser Lys Ser
        130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
                180                 185                 190

Ser Ser Val Val Thr Val Pro Ser Ser Ser Leu Gly Thr Gln Thr Tyr
            195                 200                 205

Ile Cys Asn Val Asn His Lys Pro Ser Asn Thr Lys Val Asp Lys Lys
210                 215                 220

Val Glu Pro Lys Ser Cys
225                 230

<210> SEQ ID NO 17
<211> LENGTH: 690
<212> TYPE: DNA
<213> ORGANISM: Artificial sequence
<220> FEATURE:
<223> OTHER INFORMATION: H9 Fab heavy chain coding sequence

<400> SEQUENCE: 17
gaagtgcagc tggtgcagtc tggggctgag gtgaagaagc ctgggtcctc ggtgaaggtc     60
tcctgcaagg cttctggagg caccttcagc agctatgcta tcagctgggt gcgacaggcc    120
cctggacaag gcttgagtg gatgggaggg atcatcccta tctttggtac agcaaactac    180
gcacagaagt tccagggcag agtcacgatt accgcggacg aatccacgag cacagcctac    240
atggagctga gcagcctgag atctgaggac acggccgtgt attactgtgc gagagggat    300 ctgtattact atgatagtag tggttatccg cgatactact ttgactactg gggccaggc    360 accctggtca ccgtctcaag cgcctccacc aagggcccat cggtcttccc cctggcaccc    420
tcctccaaga gcacctctgg gggcacagcg gccctgggct gcctggtcaa ggactacttc    480
cccgaaccgg tgacggtgtc gtggaactca ggcgccctga ccagcggcgt ccacaccttc    540
ccggctgtcc tacagtcctc aggactctac tccctcagca gcgtagtgac cgtgccctcc    600
agcagcttgg gcacccagac ctacatctgc aacgtgaatc acaagcccag caacaccaag    660
gtggacaaga aagttgagcc caaatcttgt                                     690

<210> SEQ ID NO 18
<211> LENGTH: 197
<212> TYPE: PRT
<213> ORGANISM: Artificial sequence
<220> FEATURE:
<223> OTHER INFORMATION: H9 Fab light chain polypeptide sequence
```

<400> SEQUENCE: 18

```
Leu Glu Thr Thr Leu Thr Gln Ser Pro Gly Thr Leu Ser Leu Ser Pro
1               5                   10                  15

Gly Glu Arg Ala Thr Leu Ser Cys Arg Ala Ser Gln Ser Val Ser Ser
            20                  25                  30

Ser Tyr Leu Ala Trp Tyr Gln Gln Lys Pro Gly Gln Ala Pro Arg Leu
        35                  40                  45

Val Ile Tyr Gly Ala Ser Ser Arg Ala Thr Gly Ile Pro Asp Arg Phe
    50                  55                  60

Ser Gly Ser Gly Ser Gly Thr Asp Phe Thr Leu Thr Ile Ser Arg Leu
65              70                  75                  80

Glu Pro Glu Asp Phe Ala Val Tyr Tyr Cys Gln His Tyr Ser Thr Ser
                85                  90                  95

Pro Gly Phe Thr Phe Gly Gln Gly Thr Lys Leu Glu Ile Arg Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser His Gln Gly Leu Ser Ser Pro Val Thr Lys Ser Phe
            180                 185                 190

Asn Arg Gly Glu Cys
            195
```

<210> SEQ ID NO 19
<211> LENGTH: 597
<212> TYPE: DNA
<213> ORGANISM: Artificial sequence
<220> FEATURE:
<223> OTHER INFORMATION: H9 Fab light chain coding sequence

<400> SEQUENCE: 19

```
cttgaaacga cactcacgca gtctccaggc accctgtctt tgtctccagg ggaaagagcc    60
accctctcct gcagggccag tcagagtgtt agcagcagct acttagcctg gtaccagcag   120
aaacctggcc aggctcccag gctcgtcatc tatggtgcat ccagcagggc cactggcatc   180
ccagacaggt tcagtggcag tgggtctggg acagacttca ctctcaccat cagcagactg   240
gagcctgaag attttgcagt ttattactgt cagcactata gcacctcacc tgggttcact   300
tttggccagg ggaccaagct ggagatcaga cgaactgtgg ctgcaccatc tgtcttcatc   360
ttcccgccat ctgatgagca gttgaaatct ggaactgcct ctgttgtgtg cctgctgaat   420
aacttctatc ccagagaggc caaagtacag tggaaggtgg ataacgccct ccaatcgggt   480
aactcccagg agagtgtcac agagcaggac agcaaggaca gcacctacag cctcagcagc   540
catcagggcc tgagctcgcc cgtcacaaag agcttcaaca ggggagagtg ttaataa     597
```

<210> SEQ ID NO 20
<211> LENGTH: 225
<212> TYPE: PRT
<213> ORGANISM: Artificial sequence
<220> FEATURE:
<223> OTHER INFORMATION: F5 Fab heavy chain polypeptide sequence

<400> SEQUENCE: 20

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Asn Tyr Tyr Trp Gly Trp Ile Arg Gln Pro Pro Gly Lys Gly Leu Glu
        35                  40                  45

Trp Ile Gly Ala Ile Tyr Tyr Ser Gly Ser Thr Tyr Tyr Asn Pro Ser
    50                  55                  60

Leu Lys Ser Arg Val Ala Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Arg Ile Gly Val Ala Gly Gln Trp Tyr Phe Asp Leu Trp
            100                 105                 110

Gly Arg Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
        180                 185                 190

Val Pro Ser Ser Ser Leu Gly Thr Gln Thr Tyr Ile Cys Asn Val Asn
    195                 200                 205

His Lys Pro Ser Asn Thr Lys Val Asp Lys Lys Val Glu Pro Lys Ser
    210                 215                 220

Cys
225

<210> SEQ ID NO 21
<211> LENGTH: 675
<212> TYPE: DNA
<213> ORGANISM: Artificial sequence
<220> FEATURE:
<223> OTHER INFORMATION: F5 Fab heavy chain coding sequence

<400> SEQUENCE: 21
caggtgcagc tgcaggagtc cggcccagga ctggtgaagc cttcggagac cctgtccctc      60
acctgcactg tctctggtgg ctccatcagc agcagtaatt actactgggg ctggatccgc     120
cagcccccag ggaaggggct ggagtggatt ggtgctatct attatagtgg gagcacctac     180
tacaacccgt ccctcaagag tcgagtcgcc atatccgtag acacgtccaa gaaccagttc     240
tcgctgaagt tgagttctgt gaccgccgca gacacggctg tctattactg tgcgagacgt     300
ataggagtgg ctggccaatg gtatttcgat ctctggggcc gtggcaccct ggtcaccgtc     360
tcaagcgcct ccaccaaggg cccatcggtc ttccccctgg caccctcctc caagagcacc     420
tctgggggca gcgcggccct gggctgcctg gtcaaggact acttccccga accggtgacg     480
gtgtcgtgga actcaggcgc cctgaccagc ggcgtccaca ccttcccggc tgtcctacag     540
tcctcaggac tctactccct cagcagcgta gtgaccgtgc cctccagcag cttgggcacc     600
cagacctaca tctgcaacgt gaatcacaag cccagcaaca ccaaggtgga caagaaagtt     660
gagcccaaat cttgt                                                     675
```

```
<210> SEQ ID NO 22
<211> LENGTH: 199
<212> TYPE: PRT
<213> ORGANISM: Artificial sequence
<220> FEATURE:
<223> OTHER INFORMATION: F5 Fab light chain polypeptide sequence

<400> SEQUENCE: 22

Leu Asn Phe Met Leu Thr Gln Pro His Ser Val Ser Gly Ser Pro Gly
1               5                   10                  15

Lys Thr Val Thr Ile Ser Cys Thr Arg Ser Thr Gly Ser Ile Thr Ser
            20                  25                  30

Asn Tyr Val His Trp Tyr Gln Gln Arg Pro Gly Ser Ser Pro Thr Thr
        35                  40                  45

Val Ile Cys Glu Asp Asn Glu Arg Pro Ser Gly Val Pro Asp Arg Phe
    50                  55                  60

Ser Gly Ser Ile Asp Ile Ser Ser Asn Ser Ala Ser Leu Thr Ile Ser
65                  70                  75                  80

Gly Leu Lys Thr Glu Asp Glu Ala Asp Tyr Tyr Cys Gln Ser Tyr Asp
                85                  90                  95

Asp Ser Asn His Ile Ser Val Phe Gly Thr Gly Thr Lys Val Thr Val
            100                 105                 110

Leu Gly Gln Pro Lys Ala Asn Pro Cys Leu Ile Ser Asp Phe Tyr Pro
        115                 120                 125

Gly Ala Val Thr Val Ala Trp Lys Ala Asp Gly Ser Pro Val Lys Ala
    130                 135                 140

Gly Val Glu Thr Thr Lys Pro Ser Lys Gln Ser Asn Asn Lys Tyr Ala
145                 150                 155                 160

Ala Ser Ser Tyr Leu Ser Leu Thr Pro Glu Gln Trp Lys Ser His Arg
                165                 170                 175

Ser Tyr Ser Cys Gln Val Thr His Glu Gly Ser Thr Val Glu Lys Thr
            180                 185                 190

Val Ala Pro Ala Glu Cys Ser
        195

<210> SEQ ID NO 23
<211> LENGTH: 660
<212> TYPE: DNA
<213> ORGANISM: Artificial sequence
<220> FEATURE:
<223> OTHER INFORMATION: F5 Fab light chain coding sequence

<400> SEQUENCE: 23 cttaattta tgctgactca gccccactct gtgtcggggt ctccggggaa gacggttacc      60
atctcctgca cccgcagcac tggcagcatt accagcaact atgtgcactg gtaccagcag    120 cgccccgggca gttcccccac cactgtgatc tgtgaggata cgaaagacc ctctggggtc    180 cctgatcgat tctctggctc catcgacatc tcctccaact ctgcctccct caccatctct    240
ggactgaaga ctgaggacga ggctgactac tactgtcagt cttatgatga cagcaatcat    300
atttctgtct tcggtactgg gaccaaggtc accgtcctag gtcagcccaa ggccaacccc    360
tgtctgatca gtgacttcta cccgggagct gtgacagtgg cctggaaggc agatggcagc    420
cccgtcaagg cgggagtgga gaccaccaaa ccctccaaac agagcaacaa caagtacgcg    480
gccagcagct acctgagcct gacgcccgag cagtggaagt cccacagaag ctacagctgc    540
caggtcacgc atgaggggag caccgtggag aagacagtgg cccctgcaga atgttcataa    600
actgtcactc tgttcccgcc ctcctctgag gagctccaag ccaacaaggc cacactagtg    660
```

<210> SEQ ID NO 24
<211> LENGTH: 6
<212> TYPE: PRT
<213> ORGANISM: Artificial sequence
<220> FEATURE:
<223> OTHER INFORMATION: H9 Fab VH CDR1

<400> SEQUENCE: 24

Ser Tyr Ala Ile Ser Trp
1               5

<210> SEQ ID NO 25
<211> LENGTH: 17
<212> TYPE: PRT
<213> ORGANISM: Artificial sequence
<220> FEATURE:
<223> OTHER INFORMATION: H9 Fab VH CDR2

<400> SEQUENCE: 25

Gly Ile Ile Pro Ile Phe Gly Thr Ala Asn Tyr Ala Gln Lys Phe Gln
1               5                   10                  15

Gly

<210> SEQ ID NO 26
<211> LENGTH: 18
<212> TYPE: PRT
<213> ORGANISM: Artificial sequence
<220> FEATURE:
<223> OTHER INFORMATION: H9 Fab VH CDR3

<400> SEQUENCE: 26

Gly Asp Leu Tyr Tyr Tyr Asp Ser Ser Gly Tyr Pro Arg Tyr Tyr Phe
1               5                   10                  15

Asp Tyr

<210> SEQ ID NO 27
<211> LENGTH: 16
<212> TYPE: DNA
<213> ORGANISM: Artificial sequence
<220> FEATURE:
<223> OTHER INFORMATION: H9 Fab VH CDR1 coding sequence

<400> SEQUENCE: 27
gctatgctat cagctg                                                      16

<210> SEQ ID NO 28
<211> LENGTH: 50
<212> TYPE: DNA
<213> ORGANISM: Artificial sequence
<220> FEATURE:
<223> OTHER INFORMATION: H9 Fab VH CDR2 coding sequence

<400> SEQUENCE: 28
gggatcatcc ctatctttgg tacagcaaac tacgcacaga agttccaggg                 50

<210> SEQ ID NO 29
<211> LENGTH: 53
<212> TYPE: DNA
<213> ORGANISM: Artificial sequence
<220> FEATURE:
<223> OTHER INFORMATION: H9 Fab VH CDR3 coding sequence

<400> SEQUENCE: 29
ggggatctgt attactatga tagtagtggt tatccgcgat actactttga cta            53

<210> SEQ ID NO 30
<211> LENGTH: 12
<212> TYPE: PRT
<213> ORGANISM: Artificial sequence
<220> FEATURE:
<223> OTHER INFORMATION: H9 Fab VL CDR1

<400> SEQUENCE: 30

Arg Ala Ser Gln Ser Val Ser Ser Ser Tyr Leu Ala
1               5                   10

<210> SEQ ID NO 31
<211> LENGTH: 7
<212> TYPE: PRT
<213> ORGANISM: Artificial sequence
<220> FEATURE:
<223> OTHER INFORMATION: H9 Fab VL CDR2

<400> SEQUENCE: 31

Gly Ala Ser Ser Arg Ala Thr
1               5

<210> SEQ ID NO 32
<211> LENGTH: 10
<212> TYPE: PRT
<213> ORGANISM: Artificial sequence
<220> FEATURE:
<223> OTHER INFORMATION: H9 Fab VL CDR3

<400> SEQUENCE: 32

Gln His Tyr Ser Thr Ser Pro Gly Phe Thr
1               5                   10

<210> SEQ ID NO 33
<211> LENGTH: 35
<212> TYPE: DNA
<213> ORGANISM: Artificial sequence
<220> FEATURE:
<223> OTHER INFORMATION: H9 Fab VL CDR1 coding sequence

<400> SEQUENCE: 33
agggccagtc agagtgttag cagcagctac ttagc                              35

<210> SEQ ID NO 34
<211> LENGTH: 21
<212> TYPE: DNA
<213> ORGANISM: Artificial sequence
<220> FEATURE:
<223> OTHER INFORMATION: H9 Fab VL CDR2 coding sequence

<400> SEQUENCE: 34
ggtgcatcca gcagggccac t                                             21

<210> SEQ ID NO 35
<211> LENGTH: 29
<212> TYPE: DNA
<213> ORGANISM: Artificial sequence
<220> FEATURE:
<223> OTHER INFORMATION: H9 Fab VL CDR3 coding sequence

<400> SEQUENCE: 35
agcactatag cacctcacct gggttcact                                     29

<210> SEQ ID NO 36
<211> LENGTH: 7
<212> TYPE: PRT
<213> ORGANISM: Artificial sequence

```
<220> FEATURE:
<223> OTHER INFORMATION: F5 Fab VH CDR1

<400> SEQUENCE: 36

Ser Ser Asn Tyr Tyr Trp Gly
1               5

<210> SEQ ID NO 37
<211> LENGTH: 16
<212> TYPE: PRT
<213> ORGANISM: Artificial sequence
<220> FEATURE:
<223> OTHER INFORMATION: F5 Fab VH CDR2

<400> SEQUENCE: 37

Ala Ile Tyr Tyr Ser Gly Ser Thr Tyr Tyr Asn Pro Ser Leu Lys Ser
1               5                   10                  15

<210> SEQ ID NO 38
<211> LENGTH: 23
<212> TYPE: PRT
<213> ORGANISM: Artificial sequence
<220> FEATURE:
<223> OTHER INFORMATION: F5 Fab VH CDR3

<400> SEQUENCE: 38

Arg Ile Gly Val Ala Gly Gln Trp Tyr Phe Asp Leu Trp Gly Arg Gly
1               5                   10                  15

Thr Leu Val Thr Val Ser Ser
            20

<210> SEQ ID NO 39
<211> LENGTH: 21
<212> TYPE: DNA
<213> ORGANISM: Artificial sequence
<220> FEATURE:
<223> OTHER INFORMATION: F5 Fab VH CDR1 coding sequence

<400> SEQUENCE: 39
agcagtaatt actactgggg c                                             21

<210> SEQ ID NO 40
<211> LENGTH: 48
<212> TYPE: DNA
<213> ORGANISM: Artificial sequence
<220> FEATURE:
<223> OTHER INFORMATION: F5 Fab VH CDR2 coding sequence

<400> SEQUENCE: 40
gctatctatt atagtgggag cacctactac aacccgtccc tcaagagt                48

<210> SEQ ID NO 41
<211> LENGTH: 69
<212> TYPE: DNA
<213> ORGANISM: Artificial sequence
<220> FEATURE:
<223> OTHER INFORMATION: F5 Fab VH CDR3 coding sequence

<400> SEQUENCE: 41
cgtataggag tggctggcca atggtatttc gatctctggg gccgtggcac cctggtcacc   60
gtctcaagc                                                           69

<210> SEQ ID NO 42
<211> LENGTH: 13
<212> TYPE: PRT
<213> ORGANISM: Artificial sequence
```

```
<220> FEATURE:
<223> OTHER INFORMATION: F5 Fab VL CDR1

<400> SEQUENCE: 42

Thr Arg Ser Thr Gly Ser Ile Thr Ser Asn Tyr Val His
1               5                   10

<210> SEQ ID NO 43
<211> LENGTH: 7
<212> TYPE: PRT
<213> ORGANISM: Artificial sequence
<220> FEATURE:
<223> OTHER INFORMATION: F5 Fab VL CDR2

<400> SEQUENCE: 43

Glu Asp Asn Glu Arg Pro Ser
1               5

<210> SEQ ID NO 44
<211> LENGTH: 11
<212> TYPE: PRT
<213> ORGANISM: Artificial sequence
<220> FEATURE:
<223> OTHER INFORMATION: F5 Fab VL CDR3

<400> SEQUENCE: 44

Gln Ser Tyr Asp Asp Ser Asn His Ile Ser Val
1               5                   10

<210> SEQ ID NO 45
<211> LENGTH: 39
<212> TYPE: DNA
<213> ORGANISM: Artificial sequence
<220> FEATURE:
<223> OTHER INFORMATION: F5 Fab VL CDR1 coding sequence

<400> SEQUENCE: 45
acccgcagca ctggcagcat taccagcaac tatgtgcac                              39

<210> SEQ ID NO 46
<211> LENGTH: 21
<212> TYPE: DNA
<213> ORGANISM: Artificial sequence
<220> FEATURE:
<223> OTHER INFORMATION: F5 Fab VL CDR2 coding sequence

<400> SEQUENCE: 46
gaggataacg aaagaccctc t                                                 21

<210> SEQ ID NO 47
<211> LENGTH: 33
<212> TYPE: DNA
<213> ORGANISM: Artificial sequence
<220> FEATURE:
<223> OTHER INFORMATION: F5 Fab VL CDR3 coding sequence

<400> SEQUENCE: 47
cagtcttatg atgacagcaa tcatatttct gtc                                    33

<210> SEQ ID NO 48
<211> LENGTH: 4102
<212> TYPE: DNA
<213> ORGANISM: Human cytomegalovirus

<400> SEQUENCE: 48
aagcttacgg aaaatacgac agagaagacg agtcctgtca ctttagccat ggtctgcggc       60
```

```
gatctctaaa cagaggaccc tgataatggg aaacggacac taggcgtccg cgccatacgg    120
gattaaaaca aaaaaaaatc ggtggtggtg tgtgatgggg tgtggtgacg gtggggcttc    180
gcctcttttt tttgtaataa aaaaagacac tgaataatcc gcggttgtct ctgtgtagaa    240 cgttttatt tcgggttccg cgtttggtcg cctgcctatg taaggcggcg gccgcagagg    300
gcgcgccgct cagtcgccta cacccgtacg cgcaggcagc atggagtcgc gcggtcgccg    360
ttgtcccgaa atgatatccg tactgggtcc catttcgggg cacgtgctga aagccgtgtt    420
tagtcgcggc gatacgccgg tgctgccgca cgagacgcga ctcctgcaga cgggtatcca    480
cgtacgcgtg agccagccct cgctgatctt ggtatcgcag tacacgcccg actcgacgcc    540
atgccaccgc ggcgacaatc agctgcaggt gcagcacacg tactttacgg gcagcgaggt    600
ggagaacgtg tcggtcaacg tgcacaaccc cacgggccga agcatctgcc ccagccagga    660
gcccatgtcg atctatgtgt acgcgctgcc gctcaagatg ctgaacatcc ccagcatcaa    720
cgtgcaccac tacccgtcgg cggccgagcg caaacaccga cacctgcccg tagctgacgc    780
tgtgattcac gcgtcgggca agcagatgtg gcaggcgcgt ctcacggtct cgggactggc    840
ctggacgcgt cagcagaacc agtggaaaga gcccgacgtc tactacacgt cagcgttcgt    900
gtttcccacc aaggacgtgg cactgcggca cgtggtgtgc gcgcacgagc tggtttgctc    960
catggagaac acgcgcgcaa ccaagatgca ggtgataggt gaccagtacg tcaaggtgta    1020
cctggagtcc ttctgcgagg acgtgccctc cggcaagctc tttatgcacg tcacgctggg    1080
ctctgacgtg gaagaggacc tgacgatgac ccgcaacccg caaccttca tgcgccccca    1140 cgagcgcaac ggctttacgg tgttgtgtcc caaaaatatg ataatcaaac cgggcaagat    1200
ctcgcacatc atgctggatg tggcttttac ctcacacgag cattttgggc tgctgtgtcc    1260
caagagcatc ccgggcctga gcatctcagg taacctgttg atgaacgggc agcagatctt    1320
cctggaggta caagccatac gcgagaccgt ggaactgcgt cagtacgatc ccgtggctgc    1380
gctcttcttt ttcgatatcg acttgctgct gcagcgcggg cctcagtaca gcgagcaccc    1440
caccttcacc agccagtatc gcatccaggg caagcttgag taccgacaca cctgggaccg    1500
gcacgacgag ggtgccgccc agggcgacga cgacgtctgg accagcggat cggactccga    1560
cgaagaactc gtaaccaccg agcgcaagac gccccgcgtc accggcggcg gcgccatggc    1620
gggcgcctcc acttccgcgg gccgcaaacg caaatcagca tcctcggcga cggcgtgcac    1680
gtcgggcgtt atgacacgcg gccgccttaa ggccgagtcc accgtcgcgc ccgaagagga    1740
caccgacgag gattccgaca acgaaatcca caatccggcc gtgttcacct ggccgccctg    1800
gcaggccggc atcctggccc gcaacctggt gccatggtg gctacggttc agggtcagaa    1860
tctgaagtac caggaattct ctgggacgc caacgacatc taccgcatct tcgccgaatt    1920
ggaaggcgta tggcagcccg ctgcgcaacc caaacgtcgc cgccaccggc aagacgcctt    1980
gcccgggcca tgcatcgcct cgacgcccaa aaagcaccga ggttgagcca cccgccgcac    2040
gcgcttagga cgactctata aaacccacg tccactcaga cacgcaactt ttggccgcca    2100
cacctgtcac cgctgctata tttgcgacag ttgccggaac ccttcccgac ctcccacgaa    2160
gacccgttca cctttgcgca tccctgacc ctcccccat cccgccttcg caatgtctca    2220
ggcatcgtcc tcgccggtg agggaccctc gtcggaagcg gccgcgatca gcgaggcga    2280 agccgccagc ggaagctttg gtcgcctgca ctgccaggtg cttcggctca tcaccaacgt    2340
ggaaggcggc tcgctggaag ccggtcgtct gcgactcctg gacctgcgta ccaacataga    2400
ggtgagccgg ccctcggttc tctgctgttt tcaggagaac aaatctccgc acgacaccgt    2460
```

| | |
|---|---:|
| agacctgacc gacttaaaca tcaagggccg ctgcgtggtg ggcgaacagg accgactgct | 2520 |
| ggtggacctc aacaactttg gcccacgacg cctgacgcca ggctcagaaa acaacacggt | 2580 |
| ctcggtactg gcctttgcgc tgccgctgga ccgcgtgccc gttagcggac tgcacctctt | 2640 |
| tcagagccag cggcgcggcg gcgaagaaaa tcggccgcga atggaagcgc gcgccatcat | 2700 |
| ccgccgcacg gctcaccact gggccgtgcg actgaccgta acgccgaact ggcgccgcag | 2760 |
| aaccgacagc agtttggagg cagggcagat ctttgtcagc cagttcgcct ttcgcgccgg | 2820 |
| cgccatcccg ctgacgctgg tagacgccct ggagcagctg gcctgttcgg accctaacac | 2880 |
| gtacatccac aaaacggaga cggacgaacg aggccaatgg atcatgctgt ttctgcatca | 2940 |
| cgactcaccg caccgccga ccagcgtgtt tctgcacttt tcggtttaca cgcatcgcgc | 3000 |
| cgaggtggtg gcgcgacaca atccgtaccc gcacctacga cgcttgccgg acaacggctt | 3060 |
| ccagctgttg attcccaaaa gttttacgct gacgcgcata catcccgagt acatcgtgca | 3120 |
| gatccagaat gctttcgaga ccaatcagac tcacgacacc atctttttcc cggaaaacat | 3180 |
| cccgggcgtc tccatagaag ccggcccgct acccgatcgt gtgcgaatca ccctccgcgt | 3240 |
| cacgctgacc ggcgatcagg ccgttcattt ggaacaccga cagccgctag ccgcatcca | 3300 |
| cttttttccgc cgtgggtttt ggactctcac acccggtaaa ccggacaaaa tcaagcgtcc | 3360 |
| ccaggtgcag ctgcgcgccg gtctctttcc acggagcaac gtcatgcgcg gcgccgtctc | 3420 |
| cgagtttctc ccgcagtccc ccggattacc acccaccgag gaagaggagg aagaagagga | 3480 |
| agaggacgac gaagatgacc tctcctccac accgacgccg accccctgt ccgaagccat | 3540 |
| gtttgccggc ttcgaggaag ccagcggcga cgaggactcg gacacccaag ccggactgtc | 3600 |
| cccggcactg atcctgaccg gacaaagacg tcgaagcggt aacaacgggg ctctcacgct | 3660 |
| cgtcatcccc tcgtggcacg tctttgcgag ccttgacgac ttggtaccat taacggtgag | 3720 |
| cgtgcagcac gccgcactac gacctacctc ttatctgcgc agcgacatgg acggcgacgt | 3780 |
| gcgtaccgcg gcagacatca gcagcacgtt gcggtccgtg cccgcgccac gaccctcacc | 3840 |
| catcagcacc gcttccactt ccagcacccc acgcagtcga ccccgcatct agagagagac | 3900 |
| ttctttgttt ttccccccgcg tgttttttccc attccctgta tttatttcta aataataaaa | 3960 |
| acacagagac gttgataata accgcggtgt gctttattag ggtatcacgg tgtagaaaaa | 4020 |
| aaagagaggg aagccctaaa tatagcgtct ctcttactcg agcttattga gcgcagccac | 4080 |
| aaaaatccgc cgattcagat ct | 4102 |

<210> SEQ ID NO 49
<211> LENGTH: 1932
<212> TYPE: DNA
<213> ORGANISM: Human cytomegalovirus

<400> SEQUENCE: 49

| | |
|---|---:|
| gccatggcat ccgtactggg tcccatttcg gggcacgtgc tgaaagccgt gtttagtcgc | 60 |
| ggcgacacgc cggtgctgcc gcacgagacg cgactcctgc agacgggtat ccacgtgcgc | 120 |
| gtgagccagc cctcgctgat cctggtgtcg cagtacacgc ccgactcgac gccatgccac | 180 |
| cgcggcgaca atcagctgca ggtgcagcac acgtacttta cgggcagcga ggtggagaac | 240 |
| gtgtcggtca acgtgcacaa ccccacgggc cggagcatct gccccagcca agagcccatg | 300 |
| tcgatctatg tgtacgcgct gccgctcaag atgctgaaca tccccagcat caacgtgcac | 360 |
| cactacccgt cggcggccga gcgcaaaaca cgacacctgc ccgtagctga cgctgtgatt | 420 |
| cacgcgtcgg gcaagcagat gtggcaggcg cgtctcacgg tctcgggact ggcctggacg | 480 |

```
cgtcagcaga accagtggaa agagcccgac gtctactaca cgtcagcgtt cgtgtttccc     540
accaaggacg tggcactgcg gcacgtggtg tgcgcgcacg agctggtttg ctccatggag     600
aacacgcgcg caaccaagat gcaggtgata ggtgaccagt acgtcaaggt gtacctggag     660
tccttctgcg aggacgtgcc ctccggcaag ctctttatgc acgtcacgct gggctctgac     720
gtggaagagg acctgacgat gacccgcaac ccgcaaccct tcatgcgccc ccacgagcgc     780
aacggcttta cggtgttgtg tcccaaaaat atgataatca aaccgggcaa gatctcgcac     840
atcatgctgg atgtggcttt tacctcacac gagcattttg ggctgctgtg tcccaagagc     900
atcccgggcc tgagcatctc aggtaaccta ttgatgaacg ggcagcagat cttcctggag     960
gtgcaagcga tacgcgagac cgtggaactg cgtcagtacg atcccgtggc tgcgctcttc    1020
tttttcgata tcgacttgct gctgcagcgc gggcctcagt acagcgaaca ccccaccttc    1080
accagccagt atcgcatcca gggcaagctt gagtaccgac acacctggga ccggcacgac    1140
gagggtgccg cccagggcga cgacgacgtc tggaccagcg gatcggactc cgacgaggaa    1200
ctcgtaacca ccgagcgcaa gacgccccgc gttaccggcg gcggcgccat ggcgggcgcc    1260
tccacttccg cgggccgcaa acgcaaatca gcatcctcgg cgacggcgtg cacggcgggc    1320
gttatgacac gcggccgcct taaggccgag tccaccgtcg cgcccgaaga ggacaccgac    1380
gaggattccg acaacgaaat ccacaatccg gccgtgttca cctggccgcc ctggcaggcc    1440
ggcatcctgg cccgcaacct ggtgcccatg gttgctacgg ttcagggtca gaatctgaag    1500
taccaggagt tcttctggga cgccaacgac atctaccgca tcttcgccga attgaaggc     1560
gtatggcagc ccgctgcgca acccaaacgt cgccgccacc ggcaagacgc cttgcccggg    1620
ccatgcatcg cctcgacgcc caaaaagcac cgaggttgag ccacccgccg cgcacgctta    1680
ggacgactct ataaaaaccc acgtccactc agacacgcga cttttggccg ccacacctgt    1740
cgccgctgct atatttgcga cagttgccgg aacccttccc gacctccac gaagacccgt     1800
tcacctttgc gcatcccctg acccccccc tcatcccgcc ttcgcgatgt ctcaggcatc    1860
gtcctcgccc ggtgagggac cctcgtcgga agcggccgcg atcagcgagg ccgaagccgc    1920
cagcggaagc tt                                                        1932
```

```
<210> SEQ ID NO 50
<211> LENGTH: 548
<212> TYPE: PRT
<213> ORGANISM: Human cytomegalovirus

<400> SEQUENCE: 50

Met Glu Ser Arg Gly Arg Arg Cys Pro Glu Met Ile Ser Val Leu Gly
1               5                   10                  15

Pro Ile Ser Gly His Val Leu Lys Ala Val Phe Ser Arg Gly Asp Thr
            20                  25                  30

Pro Val Leu Pro His Glu Thr Arg Leu Leu Gln Thr Gly Ile His Val
        35                  40                  45

Arg Val Ser Gln Pro Ser Leu Ile Leu Val Ser Gln Tyr Thr Pro Asp
    50                  55                  60

Ser Thr Pro Cys His Arg Gly Asp Asn Gln Leu Gln Val Gln His Thr
65                  70                  75                  80

Tyr Phe Thr Gly Ser Glu Val Glu Asn Val Ser Val Asn Glu Pro Met
                85                  90                  95

Ser Ile Tyr Val Tyr Ala Leu Pro Leu Lys Met Leu Asn Ile Pro Ser
            100                 105                 110

Ile Asn Val His His Tyr Pro Ser Ala Ala Glu Arg Lys His Arg His
```

```
                    115                 120                 125
Leu Pro Val Ala Asp Ala Val Ile His Ala Ser Gly Lys Gln Met Trp
    130                 135                 140
Gln Ala Arg Leu Thr Val Ser Gly Leu Ala Trp Thr Arg Gln Gln Asn
145                 150                 155                 160
Gln Trp Lys Glu Pro Asp Val Tyr Tyr Thr Ser Ala Phe Val Phe Pro
                    165                 170                 175
Thr Lys Asp Val Ala Leu Arg His Val Cys Ala His Glu Leu Val
                180                 185                 190
Cys Ser Met Glu Asn Thr Arg Ala Thr Lys Met Gln Val Ile Gly Asp
                195                 200                 205
Gln Tyr Val Lys Val Tyr Leu Glu Ser Phe Cys Glu Asp Val Pro Ser
                210                 215                 220
Gly Lys Leu Phe Met His Val Thr Leu Gly Ser Asp Val Glu Glu Asp
225                 230                 235                 240
Leu Thr Met Thr Arg Asn Pro Gln Pro Phe Met Arg Pro His Glu Arg
                    245                 250                 255
Asn Gly Phe Thr Val Leu Cys Pro Lys Asn Met Ile Ile Lys Pro Gly
                260                 265                 270
Lys Ile Ser His Ile Met Leu Asp Val Ala Phe Thr Ser His Glu His
                275                 280                 285
Phe Gly Leu Leu Cys Pro Lys Ser Ile Pro Gly Leu Ser Ile Ser Gly
                290                 295                 300
Asn Leu Leu Met Asn Gly Gln Gln Ile Phe Leu Glu Val Gln Ala Ile
305                 310                 315                 320
Arg Glu Thr Val Glu Leu Arg Gln Tyr Asp Pro Val Ala Ala Leu Phe
                    325                 330                 335
Phe Phe Asp Ile Asp Leu Leu Leu Gln Arg Gly Pro Gln Tyr Ser Glu
                340                 345                 350
His Pro Thr Phe Thr Ser Gln Tyr Arg Ile Gln Gly Lys Leu Glu Tyr
                355                 360                 365
Arg His Thr Trp Asp Arg His Asp Glu Gly Ala Ala Gln Gly Asp Asp
                370                 375                 380
Asp Val Trp Thr Ser Gly Ser Asp Ser Asp Glu Glu Leu Val Thr Thr
385                 390                 395                 400
Glu Arg Lys Thr Pro Arg Val Thr Gly Gly Ala Met Ala Gly Ala
                    405                 410                 415
Ser Thr Ser Ala Gly Arg Lys Arg Lys Ser Ala Ser Ser Ala Thr Ala
                420                 425                 430
Cys Thr Ser Gly Val Met Thr Arg Gly Arg Leu Lys Ala Glu Ser Thr
                435                 440                 445
Val Ala Pro Glu Glu Asp Thr Asp Glu Asp Ser Asp Asn Glu Ile His
                450                 455                 460
Asn Pro Ala Val Phe Thr Trp Pro Pro Trp Gln Ala Gly Ile Leu Ala
465                 470                 475                 480
Arg Asn Leu Val Pro Met Val Ala Thr Val Gln Gly Gln Asn Leu Lys
                    485                 490                 495
Tyr Gln Glu Phe Phe Trp Asp Ala Asn Asp Ile Tyr Arg Ile Phe Ala
                500                 505                 510
Glu Leu Glu Gly Val Trp Gln Pro Ala Ala Gln Pro Lys Arg Arg Arg
                515                 520                 525
His Arg Gln Asp Ala Leu Pro Gly Pro Cys Ile Ala Ser Thr Pro Lys
                530                 535                 540
```

Lys His Arg Gly
545

<210> SEQ ID NO 51
<211> LENGTH: 551
<212> TYPE: PRT
<213> ORGANISM: Human cytomegalovirus

<400> SEQUENCE: 51

Met Ala Ser Val Leu Gly Pro Ile Ser Gly His Val Leu Lys Ala Val
1               5                   10                  15

Phe Ser Arg Gly Asp Thr Pro Val Leu Pro His Glu Thr Arg Leu Leu
            20                  25                  30

Gln Thr Gly Ile His Val Arg Val Ser Gln Pro Ser Leu Ile Leu Val
        35                  40                  45

Ser Gln Tyr Thr Pro Asp Ser Thr Pro Cys His Arg Gly Asp Asn Gln
    50                  55                  60

Leu Gln Val Gln His Thr Tyr Phe Thr Gly Ser Glu Val Glu Asn Val
65                  70                  75                  80

Ser Val Asn Val His Asn Pro Thr Gly Arg Ser Ile Cys Pro Ser Gln
                85                  90                  95

Glu Pro Met Ser Ile Tyr Val Tyr Ala Leu Pro Leu Lys Met Leu Asn
            100                 105                 110

Ile Pro Ser Ile Asn Val His His Tyr Pro Ser Ala Ala Glu Arg Lys
        115                 120                 125

His Arg His Leu Pro Val Ala Asp Ala Val Ile His Ala Ser Gly Lys
    130                 135                 140

Gln Met Trp Gln Ala Arg Leu Thr Val Ser Gly Leu Ala Trp Thr Arg
145                 150                 155                 160

Gln Gln Asn Gln Trp Lys Glu Pro Asp Val Tyr Tyr Thr Ser Ala Phe
                165                 170                 175

Val Phe Pro Thr Lys Asp Val Ala Leu Arg His Val Val Cys Ala His
            180                 185                 190

Glu Leu Val Cys Ser Met Glu Asn Thr Arg Ala Thr Lys Met Gln Val
        195                 200                 205

Ile Gly Asp Gln Tyr Val Lys Val Tyr Leu Glu Ser Phe Cys Glu Asp
    210                 215                 220

Val Pro Ser Gly Lys Leu Phe Met His Val Thr Leu Gly Ser Asp Val
225                 230                 235                 240

Glu Glu Asp Leu Thr Met Thr Arg Asn Pro Gln Pro Phe Met Arg Pro
                245                 250                 255

His Glu Arg Asn Gly Phe Thr Val Leu Cys Pro Lys Asn Met Ile Ile
            260                 265                 270

Lys Pro Gly Lys Ile Ser His Ile Met Leu Asp Val Ala Phe Thr Ser
        275                 280                 285

His Glu His Phe Gly Leu Leu Cys Pro Lys Ser Ile Pro Gly Leu Ser
    290                 295                 300

Ile Ser Gly Asn Leu Leu Met Asn Gly Gln Gln Ile Phe Leu Glu Val
305                 310                 315                 320

Gln Ala Ile Arg Glu Thr Val Glu Leu Arg Gln Tyr Asp Pro Val Ala
                325                 330                 335

Ala Leu Phe Phe Phe Asp Ile Asp Leu Leu Leu Gln Arg Gly Pro Gln
            340                 345                 350

Tyr Ser Glu His Pro Thr Phe Thr Ser Gln Tyr Arg Ile Gln Gly Lys
        355                 360                 365

```
Leu Glu Tyr Arg His Thr Trp Asp Arg His Asp Glu Gly Ala Ala Gln
        370                 375                 380

Gly Asp Asp Asp Val Trp Thr Ser Gly Ser Asp Ser Asp Glu Glu Leu
385                 390                 395                 400

Val Thr Thr Glu Arg Lys Thr Pro Arg Val Thr Gly Gly Gly Ala Met
                405                 410                 415

Ala Gly Ala Ser Thr Ser Ala Gly Arg Lys Arg Lys Ser Ala Ser Ser
            420                 425                 430

Ala Thr Ala Cys Thr Ala Gly Val Met Thr Arg Gly Arg Leu Lys Ala
        435                 440                 445

Glu Ser Thr Val Ala Pro Glu Glu Asp Thr Asp Glu Asp Ser Asp Asn
    450                 455                 460

Glu Ile His Asn Pro Ala Val Phe Thr Trp Pro Pro Trp Gln Ala Gly
465                 470                 475                 480

Ile Leu Ala Arg Asn Leu Val Pro Met Val Ala Thr Val Gln Gly Gln
                485                 490                 495

Asn Leu Lys Tyr Gln Glu Phe Phe Trp Asp Ala Asn Asp Ile Tyr Arg
            500                 505                 510

Ile Phe Ala Glu Leu Glu Gly Val Trp Gln Pro Ala Ala Gln Pro Lys
        515                 520                 525

Arg Arg Arg His Arg Gln Asp Ala Leu Pro Gly Pro Cys Ile Ala Ser
    530                 535                 540

Thr Pro Lys Lys His Arg Gly
545                 550

<210> SEQ ID NO 52
<211> LENGTH: 551
<212> TYPE: PRT
<213> ORGANISM: Human cytomegalovirus

<400> SEQUENCE: 52

Met Ala Ser Val Leu Gly Pro Ile Ser Gly His Val Leu Lys Ala Val
1               5                   10                  15

Phe Ser Arg Gly Asp Thr Pro Val Leu Pro His Glu Thr Arg Leu Leu
                20                  25                  30

Gln Thr Gly Ile His Val Arg Val Ser Gln Pro Ser Leu Ile Leu Val
            35                  40                  45

Ser Gln Tyr Thr Pro Asp Ser Thr Pro Cys His Arg Gly Asp Asn Gln
    50                  55                  60

Leu Gln Val Gln His Thr Tyr Phe Thr Gly Ser Glu Val Glu Asn Val
65                  70                  75                  80

Ser Val Asn Val His Asn Pro Thr Gly Arg Ser Ile Cys Pro Ser Gln
                85                  90                  95

Glu Pro Met Ser Ile Tyr Val Tyr Ala Leu Pro Leu Lys Met Leu Asn
                100                 105                 110

Ile Pro Ser Ile Asn Val His His Tyr Pro Ser Ala Ala Glu Arg Lys
            115                 120                 125

His Arg His Leu Pro Val Ala Asp Ala Val Ile His Ala Ser Gly Lys
    130                 135                 140

Gln Met Trp Gln Ala Arg Leu Thr Val Ser Gly Leu Ala Trp Thr Arg
145                 150                 155                 160

Gln Gln Asn Gln Trp Lys Glu Pro Asp Val Tyr Tyr Thr Ser Ala Phe
                165                 170                 175

Val Phe Pro Thr Lys Asp Val Ala Leu Arg His Val Val Cys Ala His
            180                 185                 190
```

```
Glu Leu Val Cys Ser Met Glu Asn Thr Arg Ala Thr Lys Met Gln Val
        195                 200                 205

Ile Gly Asp Gln Tyr Val Lys Val Tyr Leu Glu Ser Phe Cys Glu Asp
210                 215                 220

Val Pro Ser Gly Lys Leu Phe Met His Val Thr Leu Gly Ser Asp Val
225                 230                 235                 240

Glu Glu Asp Leu Thr Met Thr Arg Asn Pro Gln Pro Phe Met Arg Pro
            245                 250                 255

His Glu Arg Asn Gly Phe Thr Val Leu Cys Pro Lys Asn Met Ile Ile
        260                 265                 270

Lys Pro Gly Lys Ile Ser His Ile Met Leu Asp Val Ala Phe Thr Ser
    275                 280                 285

His Glu His Phe Gly Leu Leu Cys Pro Lys Ser Ile Pro Gly Leu Ser
    290                 295                 300

Ile Ser Gly Asn Leu Leu Met Asn Gly Gln Gln Ile Phe Leu Glu Val
305                 310                 315                 320

Gln Ala Ile Arg Glu Thr Val Glu Leu Arg Gln Tyr Asp Pro Val Ala
                325                 330                 335

Ala Leu Phe Phe Phe Asp Ile Asp Leu Leu Leu Gln Arg Gly Pro Gln
            340                 345                 350

Tyr Ser Glu His Pro Thr Phe Thr Ser Gln Tyr Arg Ile Gln Gly Lys
        355                 360                 365

Leu Glu Tyr Arg His Thr Trp Asp Arg His Asp Glu Gly Ala Ala Gln
    370                 375                 380

Gly Asp Asp Asp Val Trp Thr Ser Gly Ser Asp Ser Asp Glu Glu Leu
385                 390                 395                 400

Val Thr Thr Glu Arg Lys Thr Pro Arg Val Thr Gly Gly Gly Ala Met
                405                 410                 415

Ala Gly Ala Ser Thr Ser Ala Gly Arg Lys Arg Lys Ser Ala Ser Ser
            420                 425                 430

Ala Thr Ala Cys Thr Ala Gly Val Met Thr Arg Gly Arg Leu Lys Ala
        435                 440                 445

Glu Ser Thr Val Ala Pro Glu Glu Asp Thr Asp Glu Asp Ser Asp Asn
    450                 455                 460

Glu Ile His Asn Pro Ala Val Phe Thr Trp Pro Pro Trp Gln Ala Gly
465                 470                 475                 480

Ile Leu Ala Arg Asn Leu Val Pro Met Val Ala Thr Val Gln Gly Gln
                485                 490                 495

Asn Leu Lys Tyr Gln Glu Phe Phe Trp Asp Ala Asn Asp Ile Tyr Arg
            500                 505                 510

Ile Phe Ala Glu Leu Glu Gly Val Trp Gln Pro Ala Ala Gln Pro Lys
        515                 520                 525

Arg Arg Arg His Arg Gln Asp Ala Leu Pro Gly Pro Cys Ile Ala Ser
    530                 535                 540

Thr Pro Lys Lys His Arg Gly
545                 550

<210> SEQ ID NO 53
<211> LENGTH: 561
<212> TYPE: PRT
<213> ORGANISM: Human cytomegalovirus

<400> SEQUENCE: 53

Met Glu Ser Arg Gly Arg Arg Cys Pro Glu Met Ile Ser Val Leu Gly
1               5                   10                  15
```

-continued

```
Pro Ile Ser Gly His Val Leu Lys Ala Val Phe Ser Arg Gly Asp Thr
             20                  25                  30

Pro Val Leu Pro His Glu Thr Arg Leu Leu Gln Thr Gly Ile His Val
         35                  40                  45

Arg Val Ser Gln Pro Ser Leu Ile Leu Val Ser Gln Tyr Thr Pro Asp
     50                  55                  60

Ser Thr Pro Cys His Arg Gly Asp Asn Gln Leu Gln Val Gln His Thr
 65                  70                  75                  80

Tyr Phe Thr Gly Ser Glu Val Glu Asn Val Ser Val Asn Val His Asn
                 85                  90                  95

Pro Thr Gly Arg Ser Ile Cys Pro Ser Gln Pro Met Ser Ile Tyr
             100                 105                 110

Val Tyr Ala Leu Pro Leu Lys Met Leu Asn Ile Pro Ser Ile Asn Val
         115                 120                 125

His His Tyr Pro Ser Ala Ala Glu Arg Lys His Arg His Leu Pro Val
     130                 135                 140

Ala Asp Ala Val Ile His Ala Ser Gly Lys Gln Met Trp Gln Ala Arg
145                 150                 155                 160

Leu Thr Val Ser Gly Leu Ala Trp Thr Arg Gln Gln Asn Gln Trp Lys
                165                 170                 175

Glu Pro Asp Val Tyr Tyr Thr Ser Ala Phe Val Phe Pro Thr Lys Asp
            180                 185                 190

Val Ala Leu Arg His Val Val Cys Ala His Glu Leu Val Cys Ser Met
        195                 200                 205

Glu Asn Thr Arg Ala Thr Lys Met Gln Val Ile Gly Asp Gln Tyr Val
    210                 215                 220

Lys Val Tyr Leu Glu Ser Phe Cys Glu Asp Val Pro Ser Gly Lys Leu
225                 230                 235                 240

Phe Met His Val Thr Leu Gly Ser Asp Val Glu Glu Asp Leu Thr Met
                245                 250                 255

Thr Arg Asn Pro Gln Pro Phe Met Arg Pro His Glu Arg Asn Gly Phe
            260                 265                 270

Thr Val Leu Cys Pro Lys Asn Met Ile Ile Lys Pro Gly Lys Ile Ser
        275                 280                 285

His Ile Met Leu Asp Val Ala Phe Thr Ser His Glu His Phe Gly Leu
    290                 295                 300

Leu Cys Pro Lys Ser Ile Pro Gly Leu Ser Ile Ser Gly Asn Leu Leu
305                 310                 315                 320

Met Asn Gly Gln Gln Ile Phe Leu Glu Val Gln Ala Ile Arg Glu Thr
                325                 330                 335

Val Glu Leu Arg Gln Tyr Asp Pro Val Ala Ala Leu Phe Phe Phe Asp
            340                 345                 350

Ile Asp Leu Leu Leu Gln Arg Gly Pro Gln Tyr Ser Glu His Pro Thr
        355                 360                 365

Phe Thr Ser Gln Tyr Arg Ile Gln Gly Lys Leu Glu Tyr Arg His Thr
    370                 375                 380

Trp Asp Arg His Asp Glu Gly Ala Ala Gln Gly Asp Asp Val Trp
385                 390                 395                 400

Thr Ser Gly Ser Asp Ser Asp Glu Glu Leu Val Thr Thr Glu Arg Lys
                405                 410                 415

Thr Pro Arg Val Thr Gly Gly Gly Ala Met Ala Gly Ala Ser Thr Ser
            420                 425                 430

Ala Gly Arg Lys Arg Lys Ser Ala Ser Ser Ala Thr Ala Cys Thr Ser
        435                 440                 445
```

Gly Val Met Thr Arg Gly Arg Leu Lys Ala Glu Ser Thr Val Ala Pro
    450                 455                 460

Glu Glu Asp Thr Asp Glu Asp Ser Asp Asn Glu Ile His Asn Pro Ala
465                 470                 475                 480

Val Phe Thr Trp Pro Pro Trp Gln Ala Gly Ile Leu Ala Arg Asn Leu
                485                 490                 495

Val Pro Met Val Ala Thr Val Gln Gly Gln Asn Leu Lys Tyr Gln Glu
            500                 505                 510

Phe Phe Trp Asp Ala Asn Asp Ile Tyr Arg Ile Phe Ala Glu Leu Glu
                515                 520                 525

Gly Val Trp Gln Pro Ala Ala Gln Pro Lys Arg Arg Arg His Arg Gln
    530                 535                 540

Asp Ala Leu Pro Gly Pro Cys Ile Ala Ser Thr Pro Lys Lys His Arg
545                 550                 555                 560

Gly

<210> SEQ ID NO 54
<211> LENGTH: 9
<212> TYPE: PRT
<213> ORGANISM: Artificial sequence
<220> FEATURE:
<223> OTHER INFORMATION: HLA restricted peptide

<400> SEQUENCE: 54

Ala Ala Glu Arg Lys His Arg His Leu
1               5

<210> SEQ ID NO 55
<211> LENGTH: 9
<212> TYPE: PRT
<213> ORGANISM: Artificial sequence
<220> FEATURE:
<223> OTHER INFORMATION: HLA restricted peptide

<400> SEQUENCE: 55

Ala Ala Leu Phe Phe Phe Asp Ile Asp
1               5

<210> SEQ ID NO 56
<211> LENGTH: 10
<212> TYPE: PRT
<213> ORGANISM: Artificial sequence
<220> FEATURE:
<223> OTHER INFORMATION: HLA restricted peptide

<400> SEQUENCE: 56

Ala Ala Leu Phe Phe Phe Asp Ile Asp Leu
1               5                   10

<210> SEQ ID NO 57
<211> LENGTH: 9
<212> TYPE: PRT
<213> ORGANISM: Artificial sequence
<220> FEATURE:
<223> OTHER INFORMATION: HLA restricted peptide

<400> SEQUENCE: 57

Ala Ala Gln Gly Asp Asp Asp Val Trp
1               5

<210> SEQ ID NO 58
<211> LENGTH: 10
<212> TYPE: PRT

<213> ORGANISM: Artificial sequence
<220> FEATURE:
<223> OTHER INFORMATION: HLA restricted peptide

<400> SEQUENCE: 58

Ala Ala Gln Gly Asp Asp Asp Val Trp Thr
1               5                   10

<210> SEQ ID NO 59
<211> LENGTH: 9
<212> TYPE: PRT
<213> ORGANISM: Artificial sequence
<220> FEATURE:
<223> OTHER INFORMATION: HLA restricted peptide

<400> SEQUENCE: 59

Ala Ala Gln Pro Lys Arg Arg Arg His
1               5

<210> SEQ ID NO 60
<211> LENGTH: 10
<212> TYPE: PRT
<213> ORGANISM: Artificial sequence
<220> FEATURE:
<223> OTHER INFORMATION: HLA restricted peptide

<400> SEQUENCE: 60

Ala Ala Gln Pro Lys Arg Arg Arg His Arg
1               5                   10

<210> SEQ ID NO 61
<211> LENGTH: 9
<212> TYPE: PRT
<213> ORGANISM: Artificial sequence
<220> FEATURE:
<223> OTHER INFORMATION: HLA restricted peptide

<400> SEQUENCE: 61

Ala Cys Thr Ala Gly Val Met Thr Arg
1               5

<210> SEQ ID NO 62
<211> LENGTH: 9
<212> TYPE: PRT
<213> ORGANISM: Artificial sequence
<220> FEATURE:
<223> OTHER INFORMATION: HLA restricted peptide

<400> SEQUENCE: 62

Ala Cys Thr Ser Gly Val Met Thr Arg
1               5

<210> SEQ ID NO 63
<211> LENGTH: 10
<212> TYPE: PRT
<213> ORGANISM: Artificial sequence
<220> FEATURE:
<223> OTHER INFORMATION: HLA restricted peptide

<400> SEQUENCE: 63

Ala Asp Ala Val Ile His Ala Ser Gly Lys
1               5                   10

<210> SEQ ID NO 64
<211> LENGTH: 9
<212> TYPE: PRT
<213> ORGANISM: Artificial sequence
<220> FEATURE:

<223> OTHER INFORMATION: HLA restricted peptide

<400> SEQUENCE: 64

Ala Glu Leu Glu Gly Val Trp Gln Pro
1               5

<210> SEQ ID NO 65
<211> LENGTH: 10
<212> TYPE: PRT
<213> ORGANISM: Artificial sequence
<220> FEATURE:
<223> OTHER INFORMATION: HLA restricted peptide

<400> SEQUENCE: 65

Ala Glu Leu Glu Gly Val Trp Gln Pro Ala
1               5                   10

<210> SEQ ID NO 66
<211> LENGTH: 10
<212> TYPE: PRT
<213> ORGANISM: Artificial sequence
<220> FEATURE:
<223> OTHER INFORMATION: HLA restricted peptide

<400> SEQUENCE: 66

Ala Glu Arg Lys His Arg His Leu Pro Val
1               5                   10

<210> SEQ ID NO 67
<211> LENGTH: 9
<212> TYPE: PRT
<213> ORGANISM: Artificial sequence
<220> FEATURE:
<223> OTHER INFORMATION: HLA restricted peptide

<400> SEQUENCE: 67

Ala Glu Ser Thr Val Ala Pro Glu Glu
1               5

<210> SEQ ID NO 68
<211> LENGTH: 10
<212> TYPE: PRT
<213> ORGANISM: Artificial sequence
<220> FEATURE:
<223> OTHER INFORMATION: HLA restricted peptide

<400> SEQUENCE: 68

Ala Glu Ser Thr Val Ala Pro Glu Glu Asp
1               5                   10

<210> SEQ ID NO 69
<211> LENGTH: 10
<212> TYPE: PRT
<213> ORGANISM: Artificial sequence
<220> FEATURE:
<223> OTHER INFORMATION: HLA restricted peptide

<400> SEQUENCE: 69

Ala Phe Thr Ser His Glu His Phe Gly Leu
1               5                   10

<210> SEQ ID NO 70
<211> LENGTH: 9
<212> TYPE: PRT
<213> ORGANISM: Artificial sequence
<220> FEATURE:
<223> OTHER INFORMATION: HLA restricted peptide -continued

```
<400> SEQUENCE: 70

Ala Phe Val Phe Pro Thr Lys Asp Val
1               5

<210> SEQ ID NO 71
<211> LENGTH: 10
<212> TYPE: PRT
<213> ORGANISM: Artificial sequence
<220> FEATURE:
<223> OTHER INFORMATION: HLA restricted peptide

<400> SEQUENCE: 71

Ala Phe Val Phe Pro Thr Lys Asp Val Ala
1               5                   10

<210> SEQ ID NO 72
<211> LENGTH: 9
<212> TYPE: PRT
<213> ORGANISM: Artificial sequence
<220> FEATURE:
<223> OTHER INFORMATION: HLA restricted peptide

<400> SEQUENCE: 72

Ala Gly Ala Ser Thr Ser Ala Gly Arg
1               5

<210> SEQ ID NO 73
<211> LENGTH: 10
<212> TYPE: PRT
<213> ORGANISM: Artificial sequence
<220> FEATURE:
<223> OTHER INFORMATION: HLA restricted peptide

<400> SEQUENCE: 73

Ala Gly Ala Ser Thr Ser Ala Gly Arg Lys
1               5                   10

<210> SEQ ID NO 74
<211> LENGTH: 9
<212> TYPE: PRT
<213> ORGANISM: Artificial sequence
<220> FEATURE:
<223> OTHER INFORMATION: HLA restricted peptide

<400> SEQUENCE: 74

Ala Gly Ile Leu Ala Arg Asn Leu Val
1               5

<210> SEQ ID NO 75
<211> LENGTH: 10
<212> TYPE: PRT
<213> ORGANISM: Artificial sequence
<220> FEATURE:
<223> OTHER INFORMATION: HLA restricted peptide

<400> SEQUENCE: 75

Ala Gly Ile Leu Ala Arg Asn Leu Val Pro
1               5                   10

<210> SEQ ID NO 76
<211> LENGTH: 9
<212> TYPE: PRT
<213> ORGANISM: Artificial sequence
<220> FEATURE:
<223> OTHER INFORMATION: HLA restricted peptide

<400> SEQUENCE: 76
```

```
Ala Gly Arg Lys Arg Lys Ser Ala Ser
1               5

<210> SEQ ID NO 77
<211> LENGTH: 10
<212> TYPE: PRT
<213> ORGANISM: Artificial sequence
<220> FEATURE:
<223> OTHER INFORMATION: HLA restricted peptide

<400> SEQUENCE: 77

Ala Gly Arg Lys Arg Lys Ser Ala Ser Ser
1               5                   10

<210> SEQ ID NO 78
<211> LENGTH: 9
<212> TYPE: PRT
<213> ORGANISM: Artificial sequence
<220> FEATURE:
<223> OTHER INFORMATION: HLA restricted peptide

<400> SEQUENCE: 78

Ala Gly Val Met Thr Arg Gly Arg Leu
1               5

<210> SEQ ID NO 79
<211> LENGTH: 10
<212> TYPE: PRT
<213> ORGANISM: Artificial sequence
<220> FEATURE:
<223> OTHER INFORMATION: HLA restricted peptide

<400> SEQUENCE: 79

Ala Gly Val Met Thr Arg Gly Arg Leu Lys
1               5                   10

<210> SEQ ID NO 80
<211> LENGTH: 9
<212> TYPE: PRT
<213> ORGANISM: Artificial sequence
<220> FEATURE:
<223> OTHER INFORMATION: HLA restricted peptide

<400> SEQUENCE: 80

Ala His Glu Leu Val Cys Ser Met Glu
1               5

<210> SEQ ID NO 81
<211> LENGTH: 10
<212> TYPE: PRT
<213> ORGANISM: Artificial sequence
<220> FEATURE:
<223> OTHER INFORMATION: HLA restricted peptide

<400> SEQUENCE: 81

Ala His Glu Leu Val Cys Ser Met Glu Asn
1               5                   10

<210> SEQ ID NO 82
<211> LENGTH: 9
<212> TYPE: PRT
<213> ORGANISM: Artificial sequence
<220> FEATURE:
<223> OTHER INFORMATION: HLA restricted peptide

<400> SEQUENCE: 82

Ala Ile Arg Glu Thr Val Glu Leu Arg
1               5
```

```
<210> SEQ ID NO 83
<211> LENGTH: 9
<212> TYPE: PRT
<213> ORGANISM: Artificial sequence
<220> FEATURE:
<223> OTHER INFORMATION: HLA restricted peptide

<400> SEQUENCE: 83

Ala Leu Phe Phe Phe Asp Ile Asp Leu
1               5

<210> SEQ ID NO 84
<211> LENGTH: 10
<212> TYPE: PRT
<213> ORGANISM: Artificial sequence
<220> FEATURE:
<223> OTHER INFORMATION: HLA restricted peptide

<400> SEQUENCE: 84

Ala Leu Phe Phe Phe Asp Ile Asp Leu Leu
1               5                   10

<210> SEQ ID NO 85
<211> LENGTH: 9
<212> TYPE: PRT
<213> ORGANISM: Artificial sequence
<220> FEATURE:
<223> OTHER INFORMATION: HLA restricted peptide

<400> SEQUENCE: 85

Ala Leu Pro Gly Pro Cys Ile Ala Ser
1               5

<210> SEQ ID NO 86
<211> LENGTH: 10
<212> TYPE: PRT
<213> ORGANISM: Artificial sequence
<220> FEATURE:
<223> OTHER INFORMATION: HLA restricted peptide

<400> SEQUENCE: 86

Ala Leu Pro Gly Pro Cys Ile Ala Ser Thr
1               5                   10

<210> SEQ ID NO 87
<211> LENGTH: 9
<212> TYPE: PRT
<213> ORGANISM: Artificial sequence
<220> FEATURE:
<223> OTHER INFORMATION: HLA restricted peptide

<400> SEQUENCE: 87

Ala Leu Pro Leu Lys Met Leu Asn Ile
1               5

<210> SEQ ID NO 88
<211> LENGTH: 9
<212> TYPE: PRT
<213> ORGANISM: Artificial sequence
<220> FEATURE:
<223> OTHER INFORMATION: HLA restricted peptide

<400> SEQUENCE: 88

Ala Leu Arg His Val Val Cys Ala His
1               5
```

```
<210> SEQ ID NO 89
<211> LENGTH: 10
<212> TYPE: PRT
<213> ORGANISM: Artificial sequence
<220> FEATURE:
<223> OTHER INFORMATION: HLA restricted peptide

<400> SEQUENCE: 89

Ala Leu Arg His Val Val Cys Ala His Glu
1               5                   10

<210> SEQ ID NO 90
<211> LENGTH: 9
<212> TYPE: PRT
<213> ORGANISM: Artificial sequence
<220> FEATURE:
<223> OTHER INFORMATION: HLA restricted peptide

<400> SEQUENCE: 90

Ala Met Ala Gly Ala Ser Thr Ser Ala
1               5

<210> SEQ ID NO 91
<211> LENGTH: 9
<212> TYPE: PRT
<213> ORGANISM: Artificial sequence
<220> FEATURE:
<223> OTHER INFORMATION: HLA restricted peptide

<400> SEQUENCE: 91

Ala Asn Asp Ile Tyr Arg Ile Phe Ala
1               5

<210> SEQ ID NO 92
<211> LENGTH: 9
<212> TYPE: PRT
<213> ORGANISM: Artificial sequence
<220> FEATURE:
<223> OTHER INFORMATION: HLA restricted peptide

<400> SEQUENCE: 92

Ala Pro Glu Glu Asp Thr Asp Glu Asp
1               5

<210> SEQ ID NO 93
<211> LENGTH: 10
<212> TYPE: PRT
<213> ORGANISM: Artificial sequence
<220> FEATURE:
<223> OTHER INFORMATION: HLA restricted peptide

<400> SEQUENCE: 93

Ala Pro Glu Glu Asp Thr Asp Glu Asp Ser
1               5                   10

<210> SEQ ID NO 94
<211> LENGTH: 9
<212> TYPE: PRT
<213> ORGANISM: Artificial sequence
<220> FEATURE:
<223> OTHER INFORMATION: HLA restricted peptide

<400> SEQUENCE: 94

Ala Gln Gly Asp Asp Asp Val Trp Thr
1               5

<210> SEQ ID NO 95
<211> LENGTH: 10
```

```
<212> TYPE: PRT
<213> ORGANISM: Artificial sequence
<220> FEATURE:
<223> OTHER INFORMATION: HLA restricted peptide

<400> SEQUENCE: 95

Ala Gln Gly Asp Asp Val Trp Thr Ser
1               5               10

<210> SEQ ID NO 96
<211> LENGTH: 9
<212> TYPE: PRT
<213> ORGANISM: Artificial sequence
<220> FEATURE:
<223> OTHER INFORMATION: HLA restricted peptide

<400> SEQUENCE: 96

Ala Gln Pro Lys Arg Arg Arg His Arg
1               5

<210> SEQ ID NO 97
<211> LENGTH: 10
<212> TYPE: PRT
<213> ORGANISM: Artificial sequence
<220> FEATURE:
<223> OTHER INFORMATION: HLA restricted peptide

<400> SEQUENCE: 97

Ala Gln Pro Lys Arg Arg Arg His Arg Gln
1               5               10

<210> SEQ ID NO 98
<211> LENGTH: 9
<212> TYPE: PRT
<213> ORGANISM: Artificial sequence
<220> FEATURE:
<223> OTHER INFORMATION: HLA restricted peptide

<400> SEQUENCE: 98

Ala Arg Leu Thr Val Ser Gly Leu Ala
1               5

<210> SEQ ID NO 99
<211> LENGTH: 10
<212> TYPE: PRT
<213> ORGANISM: Artificial sequence
<220> FEATURE:
<223> OTHER INFORMATION: HLA restricted peptide

<400> SEQUENCE: 99

Ala Arg Leu Thr Val Ser Gly Leu Ala Trp
1               5               10

<210> SEQ ID NO 100
<211> LENGTH: 9
<212> TYPE: PRT
<213> ORGANISM: Artificial sequence
<220> FEATURE:
<223> OTHER INFORMATION: HLA restricted peptide

<400> SEQUENCE: 100

Ala Arg Asn Leu Val Pro Met Val Ala
1               5

<210> SEQ ID NO 101
<211> LENGTH: 10
<212> TYPE: PRT
<213> ORGANISM: Artificial sequence
```

```
<220> FEATURE:
<223> OTHER INFORMATION: HLA restricted peptide

<400> SEQUENCE: 101

Ala Arg Asn Leu Val Pro Met Val Ala Thr
1               5                   10

<210> SEQ ID NO 102
<211> LENGTH: 9
<212> TYPE: PRT
<213> ORGANISM: Artificial sequence
<220> FEATURE:
<223> OTHER INFORMATION: HLA restricted peptide

<400> SEQUENCE: 102

Ala Ser Gly Lys Gln Met Trp Gln Ala
1               5

<210> SEQ ID NO 103
<211> LENGTH: 10
<212> TYPE: PRT
<213> ORGANISM: Artificial sequence
<220> FEATURE:
<223> OTHER INFORMATION: HLA restricted peptide

<400> SEQUENCE: 103

Ala Ser Gly Lys Gln Met Trp Gln Ala Arg
1               5                   10

<210> SEQ ID NO 104
<211> LENGTH: 9
<212> TYPE: PRT
<213> ORGANISM: Artificial sequence
<220> FEATURE:
<223> OTHER INFORMATION: HLA restricted peptide

<400> SEQUENCE: 104

Ala Ser Ser Ala Thr Ala Cys Thr Ala
1               5

<210> SEQ ID NO 105
<211> LENGTH: 9
<212> TYPE: PRT
<213> ORGANISM: Artificial sequence
<220> FEATURE:
<223> OTHER INFORMATION: HLA restricted peptide

<400> SEQUENCE: 105

Ala Ser Ser Ala Thr Ala Cys Thr Ser
1               5

<210> SEQ ID NO 106
<211> LENGTH: 9
<212> TYPE: PRT
<213> ORGANISM: Artificial sequence
<220> FEATURE:
<223> OTHER INFORMATION: HLA restricted peptide

<400> SEQUENCE: 106

Ala Ser Thr Ser Ala Gly Arg Lys Arg
1               5

<210> SEQ ID NO 107
<211> LENGTH: 10
<212> TYPE: PRT
<213> ORGANISM: Artificial sequence
<220> FEATURE:
<223> OTHER INFORMATION: HLA restricted peptide
```

```
<400> SEQUENCE: 107

Ala Ser Thr Ser Ala Gly Arg Lys Arg Lys
1               5                   10

<210> SEQ ID NO 108
<211> LENGTH: 10
<212> TYPE: PRT
<213> ORGANISM: Artificial sequence
<220> FEATURE:
<223> OTHER INFORMATION: HLA restricted peptide

<400> SEQUENCE: 108

Ala Ser Val Leu Gly Pro Ile Ser Gly His
1               5                   10

<210> SEQ ID NO 109
<211> LENGTH: 9
<212> TYPE: PRT
<213> ORGANISM: Artificial sequence
<220> FEATURE:
<223> OTHER INFORMATION: HLA restricted peptide

<400> SEQUENCE: 109

Ala Thr Ala Cys Thr Ala Gly Val Met
1               5

<210> SEQ ID NO 110
<211> LENGTH: 10
<212> TYPE: PRT
<213> ORGANISM: Artificial sequence
<220> FEATURE:
<223> OTHER INFORMATION: HLA restricted peptide

<400> SEQUENCE: 110

Ala Thr Ala Cys Thr Ala Gly Val Met Thr
1               5                   10

<210> SEQ ID NO 111
<211> LENGTH: 9
<212> TYPE: PRT
<213> ORGANISM: Artificial sequence
<220> FEATURE:
<223> OTHER INFORMATION: HLA restricted peptide

<400> SEQUENCE: 111

Ala Thr Ala Cys Thr Ser Gly Val Met
1               5

<210> SEQ ID NO 112
<211> LENGTH: 10
<212> TYPE: PRT
<213> ORGANISM: Artificial sequence
<220> FEATURE:
<223> OTHER INFORMATION: HLA restricted peptide

<400> SEQUENCE: 112

Ala Thr Ala Cys Thr Ser Gly Val Met Thr
1               5                   10

<210> SEQ ID NO 113
<211> LENGTH: 9
<212> TYPE: PRT
<213> ORGANISM: Artificial sequence
<220> FEATURE:
<223> OTHER INFORMATION: HLA restricted peptide

<400> SEQUENCE: 113
```

```
Ala Thr Val Gln Gly Gln Asn Leu Lys
1               5
```

<210> SEQ ID NO 114
<211> LENGTH: 10
<212> TYPE: PRT
<213> ORGANISM: Artificial sequence
<220> FEATURE:
<223> OTHER INFORMATION: HLA restricted peptide

<400> SEQUENCE: 114

```
Ala Thr Val Gln Gly Gln Asn Leu Lys Tyr
1               5                   10
```

<210> SEQ ID NO 115
<211> LENGTH: 10
<212> TYPE: PRT
<213> ORGANISM: Artificial sequence
<220> FEATURE:
<223> OTHER INFORMATION: HLA restricted peptide

<400> SEQUENCE: 115

```
Ala Val Phe Ser Arg Gly Asp Thr Pro Val
1               5                   10
```

<210> SEQ ID NO 116
<211> LENGTH: 10
<212> TYPE: PRT
<213> ORGANISM: Artificial sequence
<220> FEATURE:
<223> OTHER INFORMATION: HLA restricted peptide

<400> SEQUENCE: 116

```
Ala Val Phe Thr Trp Pro Pro Trp Gln Ala
1               5                   10
```

<210> SEQ ID NO 117
<211> LENGTH: 10
<212> TYPE: PRT
<213> ORGANISM: Artificial sequence
<220> FEATURE:
<223> OTHER INFORMATION: HLA restricted peptide

<400> SEQUENCE: 117

```
Ala Val Ile His Ala Ser Gly Lys Gln Met
1               5                   10
```

<210> SEQ ID NO 118
<211> LENGTH: 9
<212> TYPE: PRT
<213> ORGANISM: Artificial sequence
<220> FEATURE:
<223> OTHER INFORMATION: HLA restricted peptide

<400> SEQUENCE: 118

```
Ala Trp Thr Arg Gln Gln Asn Gln Trp
1               5
```

<210> SEQ ID NO 119
<211> LENGTH: 10
<212> TYPE: PRT
<213> ORGANISM: Artificial sequence
<220> FEATURE:
<223> OTHER INFORMATION: HLA restricted peptide

<400> SEQUENCE: 119

```
Ala Trp Thr Arg Gln Gln Asn Gln Trp Lys
```

-continued

```
1               5                   10

<210> SEQ ID NO 120
<211> LENGTH: 9
<212> TYPE: PRT
<213> ORGANISM: Artificial sequence
<220> FEATURE:
<223> OTHER INFORMATION: HLA restricted peptide

<400> SEQUENCE: 120

Cys Ala His Glu Leu Val Cys Ser Met
1               5

<210> SEQ ID NO 121
<211> LENGTH: 9
<212> TYPE: PRT
<213> ORGANISM: Artificial sequence
<220> FEATURE:
<223> OTHER INFORMATION: HLA restricted peptide

<400> SEQUENCE: 121

Cys Glu Asp Val Pro Ser Gly Lys Leu
1               5

<210> SEQ ID NO 122
<211> LENGTH: 10
<212> TYPE: PRT
<213> ORGANISM: Artificial sequence
<220> FEATURE:
<223> OTHER INFORMATION: HLA restricted peptide

<400> SEQUENCE: 122

Cys Glu Asp Val Pro Ser Gly Lys Leu Phe
1               5                   10

<210> SEQ ID NO 123
<211> LENGTH: 10
<212> TYPE: PRT
<213> ORGANISM: Artificial sequence
<220> FEATURE:
<223> OTHER INFORMATION: HLA restricted peptide

<400> SEQUENCE: 123

Cys His Arg Gly Asp Asn Gln Leu Gln Val
1               5                   10

<210> SEQ ID NO 124
<211> LENGTH: 10
<212> TYPE: PRT
<213> ORGANISM: Artificial sequence
<220> FEATURE:
<223> OTHER INFORMATION: HLA restricted peptide

<400> SEQUENCE: 124

Cys Ile Ala Ser Thr Pro Lys Lys His Arg
1               5                   10

<210> SEQ ID NO 125
<211> LENGTH: 9
<212> TYPE: PRT
<213> ORGANISM: Artificial sequence
<220> FEATURE:
<223> OTHER INFORMATION: HLA restricted peptide

<400> SEQUENCE: 125

Cys Pro Glu Met Ile Ser Val Leu Gly
1               5
```

```
<210> SEQ ID NO 126
<211> LENGTH: 10
<212> TYPE: PRT
<213> ORGANISM: Artificial sequence
<220> FEATURE:
<223> OTHER INFORMATION: HLA restricted peptide

<400> SEQUENCE: 126

Cys Pro Glu Met Ile Ser Val Leu Gly Pro
1               5                   10

<210> SEQ ID NO 127
<211> LENGTH: 9
<212> TYPE: PRT
<213> ORGANISM: Artificial sequence
<220> FEATURE:
<223> OTHER INFORMATION: HLA restricted peptide

<400> SEQUENCE: 127

Cys Pro Lys Asn Met Ile Ile Lys Pro
1               5

<210> SEQ ID NO 128
<211> LENGTH: 10
<212> TYPE: PRT
<213> ORGANISM: Artificial sequence
<220> FEATURE:
<223> OTHER INFORMATION: HLA restricted peptide

<400> SEQUENCE: 128

Cys Pro Lys Asn Met Ile Ile Lys Pro Gly
1               5                   10

<210> SEQ ID NO 129
<211> LENGTH: 9
<212> TYPE: PRT
<213> ORGANISM: Artificial sequence
<220> FEATURE:
<223> OTHER INFORMATION: HLA restricted peptide

<400> SEQUENCE: 129

Cys Pro Lys Ser Ile Pro Gly Leu Ser
1               5

<210> SEQ ID NO 130
<211> LENGTH: 10
<212> TYPE: PRT
<213> ORGANISM: Artificial sequence
<220> FEATURE:
<223> OTHER INFORMATION: HLA restricted peptide

<400> SEQUENCE: 130

Cys Pro Lys Ser Ile Pro Gly Leu Ser Ile
1               5                   10

<210> SEQ ID NO 131
<211> LENGTH: 9
<212> TYPE: PRT
<213> ORGANISM: Artificial sequence
<220> FEATURE:
<223> OTHER INFORMATION: HLA restricted peptide

<400> SEQUENCE: 131

Cys Pro Ser Gln Glu Pro Met Ser Ile
1               5

<210> SEQ ID NO 132
```

```
<211> LENGTH: 10
<212> TYPE: PRT
<213> ORGANISM: Artificial sequence
<220> FEATURE:
<223> OTHER INFORMATION: HLA restricted peptide

<400> SEQUENCE: 132

Cys Pro Ser Gln Glu Pro Met Ser Ile Tyr
1               5                   10

<210> SEQ ID NO 133
<211> LENGTH: 9
<212> TYPE: PRT
<213> ORGANISM: Artificial sequence
<220> FEATURE:
<223> OTHER INFORMATION: HLA restricted peptide

<400> SEQUENCE: 133

Cys Ser Met Glu Asn Thr Arg Ala Thr
1               5

<210> SEQ ID NO 134
<211> LENGTH: 10
<212> TYPE: PRT
<213> ORGANISM: Artificial sequence
<220> FEATURE:
<223> OTHER INFORMATION: HLA restricted peptide

<400> SEQUENCE: 134

Cys Ser Met Glu Asn Thr Arg Ala Thr Lys
1               5                   10

<210> SEQ ID NO 135
<211> LENGTH: 10
<212> TYPE: PRT
<213> ORGANISM: Artificial sequence
<220> FEATURE:
<223> OTHER INFORMATION: HLA restricted peptide

<400> SEQUENCE: 135

Cys Thr Ala Gly Val Met Thr Arg Gly Arg
1               5                   10

<210> SEQ ID NO 136
<211> LENGTH: 10
<212> TYPE: PRT
<213> ORGANISM: Artificial sequence
<220> FEATURE:
<223> OTHER INFORMATION: HLA restricted peptide

<400> SEQUENCE: 136

Cys Thr Ser Gly Val Met Thr Arg Gly Arg
1               5                   10

<210> SEQ ID NO 137
<211> LENGTH: 9
<212> TYPE: PRT
<213> ORGANISM: Artificial sequence
<220> FEATURE:
<223> OTHER INFORMATION: HLA restricted peptide

<400> SEQUENCE: 137

Asp Ala Leu Pro Gly Pro Cys Ile Ala
1               5

<210> SEQ ID NO 138
<211> LENGTH: 10
<212> TYPE: PRT
```

<213> ORGANISM: Artificial sequence
<220> FEATURE:
<223> OTHER INFORMATION: HLA restricted peptide

<400> SEQUENCE: 138

Asp Ala Leu Pro Gly Pro Cys Ile Ala Ser
1               5                   10

<210> SEQ ID NO 139
<211> LENGTH: 9
<212> TYPE: PRT
<213> ORGANISM: Artificial sequence
<220> FEATURE:
<223> OTHER INFORMATION: HLA restricted peptide

<400> SEQUENCE: 139

Asp Ala Asn Asp Ile Tyr Arg Ile Phe
1               5

<210> SEQ ID NO 140
<211> LENGTH: 10
<212> TYPE: PRT
<213> ORGANISM: Artificial sequence
<220> FEATURE:
<223> OTHER INFORMATION: HLA restricted peptide

<400> SEQUENCE: 140

Asp Ala Asn Asp Ile Tyr Arg Ile Phe Ala
1               5                   10

<210> SEQ ID NO 141
<211> LENGTH: 9
<212> TYPE: PRT
<213> ORGANISM: Artificial sequence
<220> FEATURE:
<223> OTHER INFORMATION: HLA restricted peptide

<400> SEQUENCE: 141

Asp Ala Val Ile His Ala Ser Gly Lys
1               5

<210> SEQ ID NO 142
<211> LENGTH: 10
<212> TYPE: PRT
<213> ORGANISM: Artificial sequence
<220> FEATURE:
<223> OTHER INFORMATION: HLA restricted peptide

<400> SEQUENCE: 142

Asp Ala Val Ile His Ala Ser Gly Lys Gln
1               5                   10

<210> SEQ ID NO 143
<211> LENGTH: 9
<212> TYPE: PRT
<213> ORGANISM: Artificial sequence
<220> FEATURE:
<223> OTHER INFORMATION: HLA restricted peptide

<400> SEQUENCE: 143

Asp Asp Asp Val Trp Thr Ser Gly Ser
1               5

<210> SEQ ID NO 144
<211> LENGTH: 10
<212> TYPE: PRT
<213> ORGANISM: Artificial sequence
<220> FEATURE:

<223> OTHER INFORMATION: HLA restricted peptide

<400> SEQUENCE: 144

Asp Asp Val Trp Thr Ser Gly Ser Asp Ser
1               5                   10

<210> SEQ ID NO 145
<211> LENGTH: 9
<212> TYPE: PRT
<213> ORGANISM: Artificial sequence
<220> FEATURE:
<223> OTHER INFORMATION: HLA restricted peptide

<400> SEQUENCE: 145

Asp Glu Asp Ser Asp Asn Glu Ile His
1               5

<210> SEQ ID NO 146
<211> LENGTH: 10
<212> TYPE: PRT
<213> ORGANISM: Artificial sequence
<220> FEATURE:
<223> OTHER INFORMATION: HLA restricted peptide

<400> SEQUENCE: 146

Asp Glu Asp Ser Asp Asn Glu Ile His Asn
1               5                   10

<210> SEQ ID NO 147
<211> LENGTH: 9
<212> TYPE: PRT
<213> ORGANISM: Artificial sequence
<220> FEATURE:
<223> OTHER INFORMATION: HLA restricted peptide

<400> SEQUENCE: 147

Asp Glu Glu Leu Val Thr Thr Glu Arg
1               5

<210> SEQ ID NO 148
<211> LENGTH: 10
<212> TYPE: PRT
<213> ORGANISM: Artificial sequence
<220> FEATURE:
<223> OTHER INFORMATION: HLA restricted peptide

<400> SEQUENCE: 148

Asp Glu Glu Leu Val Thr Thr Glu Arg Lys
1               5                   10

<210> SEQ ID NO 149
<211> LENGTH: 9
<212> TYPE: PRT
<213> ORGANISM: Artificial sequence
<220> FEATURE:
<223> OTHER INFORMATION: HLA restricted peptide

<400> SEQUENCE: 149

Asp Glu Gly Ala Ala Gln Gly Asp Asp
1               5

<210> SEQ ID NO 150
<211> LENGTH: 10
<212> TYPE: PRT
<213> ORGANISM: Artificial sequence
<220> FEATURE:
<223> OTHER INFORMATION: HLA restricted peptide -continued

```
<400> SEQUENCE: 150

Asp Glu Gly Ala Ala Gln Gly Asp Asp Asp
1               5                   10

<210> SEQ ID NO 151
<211> LENGTH: 9
<212> TYPE: PRT
<213> ORGANISM: Artificial sequence
<220> FEATURE:
<223> OTHER INFORMATION: HLA restricted peptide

<400> SEQUENCE: 151

Asp Ile Tyr Arg Ile Phe Ala Glu Leu
1               5

<210> SEQ ID NO 152
<211> LENGTH: 10
<212> TYPE: PRT
<213> ORGANISM: Artificial sequence
<220> FEATURE:
<223> OTHER INFORMATION: HLA restricted peptide

<400> SEQUENCE: 152

Asp Leu Leu Leu Gln Arg Gly Pro Gln Tyr
1               5                   10

<210> SEQ ID NO 153
<211> LENGTH: 9
<212> TYPE: PRT
<213> ORGANISM: Artificial sequence
<220> FEATURE:
<223> OTHER INFORMATION: HLA restricted peptide

<400> SEQUENCE: 153

Asp Asn Glu Ile His Asn Pro Ala Val
1               5

<210> SEQ ID NO 154
<211> LENGTH: 10
<212> TYPE: PRT
<213> ORGANISM: Artificial sequence
<220> FEATURE:
<223> OTHER INFORMATION: HLA restricted peptide

<400> SEQUENCE: 154

Asp Asn Glu Ile His Asn Pro Ala Val Phe
1               5                   10

<210> SEQ ID NO 155
<211> LENGTH: 10
<212> TYPE: PRT
<213> ORGANISM: Artificial sequence
<220> FEATURE:
<223> OTHER INFORMATION: HLA restricted peptide

<400> SEQUENCE: 155

Asp Asn Gln Leu Gln Val Gln His Thr Tyr
1               5                   10

<210> SEQ ID NO 156
<211> LENGTH: 9
<212> TYPE: PRT
<213> ORGANISM: Artificial sequence
<220> FEATURE:
<223> OTHER INFORMATION: HLA restricted peptide

<400> SEQUENCE: 156
```

```
Asp Pro Val Ala Ala Leu Phe Phe Phe
1               5

<210> SEQ ID NO 157
<211> LENGTH: 10
<212> TYPE: PRT
<213> ORGANISM: Artificial sequence
<220> FEATURE:
<223> OTHER INFORMATION: HLA restricted peptide

<400> SEQUENCE: 157

Asp Pro Val Ala Ala Leu Phe Phe Phe Asp
1               5                   10

<210> SEQ ID NO 158
<211> LENGTH: 9
<212> TYPE: PRT
<213> ORGANISM: Artificial sequence
<220> FEATURE:
<223> OTHER INFORMATION: HLA restricted peptide

<400> SEQUENCE: 158

Asp Gln Tyr Val Lys Val Tyr Leu Glu
1               5

<210> SEQ ID NO 159
<211> LENGTH: 10
<212> TYPE: PRT
<213> ORGANISM: Artificial sequence
<220> FEATURE:
<223> OTHER INFORMATION: HLA restricted peptide

<400> SEQUENCE: 159

Asp Gln Tyr Val Lys Val Tyr Leu Glu Ser
1               5                   10

<210> SEQ ID NO 160
<211> LENGTH: 9
<212> TYPE: PRT
<213> ORGANISM: Artificial sequence
<220> FEATURE:
<223> OTHER INFORMATION: HLA restricted peptide

<400> SEQUENCE: 160

Asp Arg His Asp Glu Gly Ala Ala Gln
1               5

<210> SEQ ID NO 161
<211> LENGTH: 10
<212> TYPE: PRT
<213> ORGANISM: Artificial sequence
<220> FEATURE:
<223> OTHER INFORMATION: HLA restricted peptide

<400> SEQUENCE: 161

Asp Arg His Asp Glu Gly Ala Ala Gln Gly
1               5                   10

<210> SEQ ID NO 162
<211> LENGTH: 9
<212> TYPE: PRT
<213> ORGANISM: Artificial sequence
<220> FEATURE:
<223> OTHER INFORMATION: HLA restricted peptide

<400> SEQUENCE: 162

Asp Ser Asp Glu Glu Leu Val Thr Thr
1               5
```

<210> SEQ ID NO 163
<211> LENGTH: 10
<212> TYPE: PRT
<213> ORGANISM: Artificial sequence
<220> FEATURE:
<223> OTHER INFORMATION: HLA restricted peptide

<400> SEQUENCE: 163

Asp Ser Asp Asn Glu Ile His Asn Pro Ala
1               5                   10

<210> SEQ ID NO 164
<211> LENGTH: 10
<212> TYPE: PRT
<213> ORGANISM: Artificial sequence
<220> FEATURE:
<223> OTHER INFORMATION: HLA restricted peptide

<400> SEQUENCE: 164

Asp Thr Asp Glu Asp Ser Asp Asn Glu Ile
1               5                   10

<210> SEQ ID NO 165
<211> LENGTH: 9
<212> TYPE: PRT
<213> ORGANISM: Artificial sequence
<220> FEATURE:
<223> OTHER INFORMATION: HLA restricted peptide

<400> SEQUENCE: 165

Asp Thr Pro Val Leu Pro His Glu Thr
1               5

<210> SEQ ID NO 166
<211> LENGTH: 10
<212> TYPE: PRT
<213> ORGANISM: Artificial sequence
<220> FEATURE:
<223> OTHER INFORMATION: HLA restricted peptide

<400> SEQUENCE: 166

Asp Thr Pro Val Leu Pro His Glu Thr Arg
1               5                   10

<210> SEQ ID NO 167
<211> LENGTH: 9
<212> TYPE: PRT
<213> ORGANISM: Artificial sequence
<220> FEATURE:
<223> OTHER INFORMATION: HLA restricted peptide

<400> SEQUENCE: 167

Asp Val Ala Phe Thr Ser His Glu His
1               5

<210> SEQ ID NO 168
<211> LENGTH: 10
<212> TYPE: PRT
<213> ORGANISM: Artificial sequence
<220> FEATURE:
<223> OTHER INFORMATION: HLA restricted peptide

<400> SEQUENCE: 168

Asp Val Ala Phe Thr Ser His Glu His Phe
1               5                   10

```
<210> SEQ ID NO 169
<211> LENGTH: 9
<212> TYPE: PRT
<213> ORGANISM: Artificial sequence
<220> FEATURE:
<223> OTHER INFORMATION: HLA restricted peptide

<400> SEQUENCE: 169

Asp Val Ala Leu Arg His Val Val Cys
1               5

<210> SEQ ID NO 170
<211> LENGTH: 10
<212> TYPE: PRT
<213> ORGANISM: Artificial sequence
<220> FEATURE:
<223> OTHER INFORMATION: HLA restricted peptide

<400> SEQUENCE: 170

Asp Val Ala Leu Arg His Val Val Cys Ala
1               5                   10

<210> SEQ ID NO 171
<211> LENGTH: 9
<212> TYPE: PRT
<213> ORGANISM: Artificial sequence
<220> FEATURE:
<223> OTHER INFORMATION: HLA restricted peptide

<400> SEQUENCE: 171

Asp Val Glu Glu Asp Leu Thr Met Thr
1               5

<210> SEQ ID NO 172
<211> LENGTH: 10
<212> TYPE: PRT
<213> ORGANISM: Artificial sequence
<220> FEATURE:
<223> OTHER INFORMATION: HLA restricted peptide

<400> SEQUENCE: 172

Asp Val Glu Glu Asp Leu Thr Met Thr Arg
1               5                   10

<210> SEQ ID NO 173
<211> LENGTH: 9
<212> TYPE: PRT
<213> ORGANISM: Artificial sequence
<220> FEATURE:
<223> OTHER INFORMATION: HLA restricted peptide

<400> SEQUENCE: 173

Asp Val Pro Ser Gly Lys Leu Phe Met
1               5

<210> SEQ ID NO 174
<211> LENGTH: 10
<212> TYPE: PRT
<213> ORGANISM: Artificial sequence
<220> FEATURE:
<223> OTHER INFORMATION: HLA restricted peptide

<400> SEQUENCE: 174

Asp Val Pro Ser Gly Lys Leu Phe Met His
1               5                   10

<210> SEQ ID NO 175
<211> LENGTH: 9
```

```
<212> TYPE: PRT
<213> ORGANISM: Artificial sequence
<220> FEATURE:
<223> OTHER INFORMATION: HLA restricted peptide

<400> SEQUENCE: 175

Asp Val Trp Thr Ser Gly Ser Asp Ser
1               5

<210> SEQ ID NO 176
<211> LENGTH: 10
<212> TYPE: PRT
<213> ORGANISM: Artificial sequence
<220> FEATURE:
<223> OTHER INFORMATION: HLA restricted peptide

<400> SEQUENCE: 176

Asp Val Trp Thr Ser Gly Ser Asp Ser Asp
1               5                   10

<210> SEQ ID NO 177
<211> LENGTH: 9
<212> TYPE: PRT
<213> ORGANISM: Artificial sequence
<220> FEATURE:
<223> OTHER INFORMATION: HLA restricted peptide

<400> SEQUENCE: 177

Asp Val Tyr Tyr Thr Ser Ala Phe Val
1               5

<210> SEQ ID NO 178
<211> LENGTH: 10
<212> TYPE: PRT
<213> ORGANISM: Artificial sequence
<220> FEATURE:
<223> OTHER INFORMATION: HLA restricted peptide

<400> SEQUENCE: 178

Asp Val Tyr Tyr Thr Ser Ala Phe Val Phe
1               5                   10

<210> SEQ ID NO 179
<211> LENGTH: 9
<212> TYPE: PRT
<213> ORGANISM: Artificial sequence
<220> FEATURE:
<223> OTHER INFORMATION: HLA restricted peptide

<400> SEQUENCE: 179

Glu Asp Ser Asp Asn Glu Ile His Asn
1               5

<210> SEQ ID NO 180
<211> LENGTH: 9
<212> TYPE: PRT
<213> ORGANISM: Artificial sequence
<220> FEATURE:
<223> OTHER INFORMATION: HLA restricted peptide

<400> SEQUENCE: 180

Glu Asp Thr Asp Glu Asp Ser Asp Asn
1               5

<210> SEQ ID NO 181
<211> LENGTH: 9
<212> TYPE: PRT
<213> ORGANISM: Artificial sequence
```

```
<220> FEATURE:
<223> OTHER INFORMATION: HLA restricted peptide

<400> SEQUENCE: 181

Glu Asp Val Pro Ser Gly Lys Leu Phe
1               5

<210> SEQ ID NO 182
<211> LENGTH: 10
<212> TYPE: PRT
<213> ORGANISM: Artificial sequence
<220> FEATURE:
<223> OTHER INFORMATION: HLA restricted peptide

<400> SEQUENCE: 182

Glu Asp Val Pro Ser Gly Lys Leu Phe Met
1               5                   10

<210> SEQ ID NO 183
<211> LENGTH: 9
<212> TYPE: PRT
<213> ORGANISM: Artificial sequence
<220> FEATURE:
<223> OTHER INFORMATION: HLA restricted peptide

<400> SEQUENCE: 183

Glu Glu Asp Leu Thr Met Thr Arg Asn
1               5

<210> SEQ ID NO 184
<211> LENGTH: 10
<212> TYPE: PRT
<213> ORGANISM: Artificial sequence
<220> FEATURE:
<223> OTHER INFORMATION: HLA restricted peptide

<400> SEQUENCE: 184

Glu Glu Asp Thr Asp Glu Asp Ser Asp Asn
1               5                   10

<210> SEQ ID NO 185
<211> LENGTH: 9
<212> TYPE: PRT
<213> ORGANISM: Artificial sequence
<220> FEATURE:
<223> OTHER INFORMATION: HLA restricted peptide

<400> SEQUENCE: 185

Glu Glu Leu Val Thr Thr Glu Arg Lys
1               5

<210> SEQ ID NO 186
<211> LENGTH: 10
<212> TYPE: PRT
<213> ORGANISM: Artificial sequence
<220> FEATURE:
<223> OTHER INFORMATION: HLA restricted peptide

<400> SEQUENCE: 186

Glu Glu Leu Val Thr Thr Glu Arg Lys Thr
1               5                   10

<210> SEQ ID NO 187
<211> LENGTH: 9
<212> TYPE: PRT
<213> ORGANISM: Artificial sequence
<220> FEATURE:
<223> OTHER INFORMATION: HLA restricted peptide
```

```
<400> SEQUENCE: 187

Glu Phe Phe Trp Asp Ala Asn Asp Ile
1               5

<210> SEQ ID NO 188
<211> LENGTH: 10
<212> TYPE: PRT
<213> ORGANISM: Artificial sequence
<220> FEATURE:
<223> OTHER INFORMATION: HLA restricted peptide

<400> SEQUENCE: 188

Glu Phe Phe Trp Asp Ala Asn Asp Ile Tyr
1               5                   10

<210> SEQ ID NO 189
<211> LENGTH: 10
<212> TYPE: PRT
<213> ORGANISM: Artificial sequence
<220> FEATURE:
<223> OTHER INFORMATION: HLA restricted peptide

<400> SEQUENCE: 189

Glu Gly Ala Ala Gln Gly Asp Asp Asp Val
1               5                   10

<210> SEQ ID NO 190
<211> LENGTH: 9
<212> TYPE: PRT
<213> ORGANISM: Artificial sequence
<220> FEATURE:
<223> OTHER INFORMATION: HLA restricted peptide

<400> SEQUENCE: 190

Glu His Phe Gly Leu Leu Cys Pro Lys
1               5

<210> SEQ ID NO 191
<211> LENGTH: 10
<212> TYPE: PRT
<213> ORGANISM: Artificial sequence
<220> FEATURE:
<223> OTHER INFORMATION: HLA restricted peptide

<400> SEQUENCE: 191

Glu His Phe Gly Leu Leu Cys Pro Lys Ser
1               5                   10

<210> SEQ ID NO 192
<211> LENGTH: 9
<212> TYPE: PRT
<213> ORGANISM: Artificial sequence
<220> FEATURE:
<223> OTHER INFORMATION: HLA restricted peptide

<400> SEQUENCE: 192

Glu His Pro Thr Phe Thr Ser Gln Tyr
1               5

<210> SEQ ID NO 193
<211> LENGTH: 10
<212> TYPE: PRT
<213> ORGANISM: Artificial sequence
<220> FEATURE:
<223> OTHER INFORMATION: HLA restricted peptide

<400> SEQUENCE: 193
```

```
Glu His Pro Thr Phe Thr Ser Gln Tyr Arg
1               5                   10

<210> SEQ ID NO 194
<211> LENGTH: 9
<212> TYPE: PRT
<213> ORGANISM: Artificial sequence
<220> FEATURE:
<223> OTHER INFORMATION: HLA restricted peptide

<400> SEQUENCE: 194

Glu Ile His Asn Pro Ala Val Phe Thr
1               5

<210> SEQ ID NO 195
<211> LENGTH: 10
<212> TYPE: PRT
<213> ORGANISM: Artificial sequence
<220> FEATURE:
<223> OTHER INFORMATION: HLA restricted peptide

<400> SEQUENCE: 195

Glu Ile His Asn Pro Ala Val Phe Thr Trp
1               5                   10

<210> SEQ ID NO 196
<211> LENGTH: 9
<212> TYPE: PRT
<213> ORGANISM: Artificial sequence
<220> FEATURE:
<223> OTHER INFORMATION: HLA restricted peptide

<400> SEQUENCE: 196

Glu Leu Glu Gly Val Trp Gln Pro Ala
1               5

<210> SEQ ID NO 197
<211> LENGTH: 10
<212> TYPE: PRT
<213> ORGANISM: Artificial sequence
<220> FEATURE:
<223> OTHER INFORMATION: HLA restricted peptide

<400> SEQUENCE: 197

Glu Leu Glu Gly Val Trp Gln Pro Ala Ala
1               5                   10

<210> SEQ ID NO 198
<211> LENGTH: 9
<212> TYPE: PRT
<213> ORGANISM: Artificial sequence
<220> FEATURE:
<223> OTHER INFORMATION: HLA restricted peptide

<400> SEQUENCE: 198

Glu Leu Arg Gln Tyr Asp Pro Val Ala
1               5

<210> SEQ ID NO 199
<211> LENGTH: 10
<212> TYPE: PRT
<213> ORGANISM: Artificial sequence
<220> FEATURE:
<223> OTHER INFORMATION: HLA restricted peptide

<400> SEQUENCE: 199

Glu Leu Arg Gln Tyr Asp Pro Val Ala Ala
```

-continued

```
1               5                   10

<210> SEQ ID NO 200
<211> LENGTH: 9
<212> TYPE: PRT
<213> ORGANISM: Artificial sequence
<220> FEATURE:
<223> OTHER INFORMATION: HLA restricted peptide

<400> SEQUENCE: 200

Glu Leu Val Cys Ser Met Glu Asn Thr
1               5

<210> SEQ ID NO 201
<211> LENGTH: 10
<212> TYPE: PRT
<213> ORGANISM: Artificial sequence
<220> FEATURE:
<223> OTHER INFORMATION: HLA restricted peptide

<400> SEQUENCE: 201

Glu Leu Val Cys Ser Met Glu Asn Thr Arg
1               5                   10

<210> SEQ ID NO 202
<211> LENGTH: 9
<212> TYPE: PRT
<213> ORGANISM: Artificial sequence
<220> FEATURE:
<223> OTHER INFORMATION: HLA restricted peptide

<400> SEQUENCE: 202

Glu Leu Val Thr Thr Glu Arg Lys Thr
1               5

<210> SEQ ID NO 203
<211> LENGTH: 9
<212> TYPE: PRT
<213> ORGANISM: Artificial sequence
<220> FEATURE:
<223> OTHER INFORMATION: HLA restricted peptide

<400> SEQUENCE: 203

Glu Met Ile Ser Val Leu Gly Pro Ile
1               5

<210> SEQ ID NO 204
<211> LENGTH: 10
<212> TYPE: PRT
<213> ORGANISM: Artificial sequence
<220> FEATURE:
<223> OTHER INFORMATION: HLA restricted peptide

<400> SEQUENCE: 204

Glu Met Ile Ser Val Leu Gly Pro Ile Ser
1               5                   10

<210> SEQ ID NO 205
<211> LENGTH: 10
<212> TYPE: PRT
<213> ORGANISM: Artificial sequence
<220> FEATURE:
<223> OTHER INFORMATION: HLA restricted peptide

<400> SEQUENCE: 205

Glu Asn Thr Arg Ala Thr Lys Met Gln Val
1               5                   10
```

```
<210> SEQ ID NO 206
<211> LENGTH: 9
<212> TYPE: PRT
<213> ORGANISM: Artificial sequence
<220> FEATURE:
<223> OTHER INFORMATION: HLA restricted peptide

<400> SEQUENCE: 206

Glu Pro Asp Val Tyr Tyr Thr Ser Ala
1               5

<210> SEQ ID NO 207
<211> LENGTH: 10
<212> TYPE: PRT
<213> ORGANISM: Artificial sequence
<220> FEATURE:
<223> OTHER INFORMATION: HLA restricted peptide

<400> SEQUENCE: 207

Glu Pro Asp Val Tyr Tyr Thr Ser Ala Phe
1               5                   10

<210> SEQ ID NO 208
<211> LENGTH: 9
<212> TYPE: PRT
<213> ORGANISM: Artificial sequence
<220> FEATURE:
<223> OTHER INFORMATION: HLA restricted peptide

<400> SEQUENCE: 208

Glu Pro Met Ser Ile Tyr Val Tyr Ala
1               5

<210> SEQ ID NO 209
<211> LENGTH: 10
<212> TYPE: PRT
<213> ORGANISM: Artificial sequence
<220> FEATURE:
<223> OTHER INFORMATION: HLA restricted peptide

<400> SEQUENCE: 209

Glu Pro Met Ser Ile Tyr Val Tyr Ala Leu
1               5                   10

<210> SEQ ID NO 210
<211> LENGTH: 9
<212> TYPE: PRT
<213> ORGANISM: Artificial sequence
<220> FEATURE:
<223> OTHER INFORMATION: HLA restricted peptide

<400> SEQUENCE: 210

Glu Arg Lys His Arg His Leu Pro Val
1               5

<210> SEQ ID NO 211
<211> LENGTH: 10
<212> TYPE: PRT
<213> ORGANISM: Artificial sequence
<220> FEATURE:
<223> OTHER INFORMATION: HLA restricted peptide

<400> SEQUENCE: 211

Glu Arg Lys His Arg His Leu Pro Val Ala
1               5                   10

<210> SEQ ID NO 212
```

```
<211> LENGTH: 9
<212> TYPE: PRT
<213> ORGANISM: Artificial sequence
<220> FEATURE:
<223> OTHER INFORMATION: HLA restricted peptide

<400> SEQUENCE: 212

Glu Arg Lys Thr Pro Arg Val Thr Gly
1               5

<210> SEQ ID NO 213
<211> LENGTH: 10
<212> TYPE: PRT
<213> ORGANISM: Artificial sequence
<220> FEATURE:
<223> OTHER INFORMATION: HLA restricted peptide

<400> SEQUENCE: 213

Glu Arg Lys Thr Pro Arg Val Thr Gly Gly
1               5                   10

<210> SEQ ID NO 214
<211> LENGTH: 9
<212> TYPE: PRT
<213> ORGANISM: Artificial sequence
<220> FEATURE:
<223> OTHER INFORMATION: HLA restricted peptide

<400> SEQUENCE: 214

Glu Arg Asn Gly Phe Thr Val Leu Cys
1               5

<210> SEQ ID NO 215
<211> LENGTH: 10
<212> TYPE: PRT
<213> ORGANISM: Artificial sequence
<220> FEATURE:
<223> OTHER INFORMATION: HLA restricted peptide

<400> SEQUENCE: 215

Glu Arg Asn Gly Phe Thr Val Leu Cys Pro
1               5                   10

<210> SEQ ID NO 216
<211> LENGTH: 9
<212> TYPE: PRT
<213> ORGANISM: Artificial sequence
<220> FEATURE:
<223> OTHER INFORMATION: HLA restricted peptide

<400> SEQUENCE: 216

Glu Ser Phe Cys Glu Asp Val Pro Ser
1               5

<210> SEQ ID NO 217
<211> LENGTH: 10
<212> TYPE: PRT
<213> ORGANISM: Artificial sequence
<220> FEATURE:
<223> OTHER INFORMATION: HLA restricted peptide

<400> SEQUENCE: 217

Glu Ser Arg Gly Arg Arg Cys Pro Glu Met
1               5                   10

<210> SEQ ID NO 218
<211> LENGTH: 10
<212> TYPE: PRT
```

-continued

<213> ORGANISM: Artificial sequence
<220> FEATURE:
<223> OTHER INFORMATION: HLA restricted peptide

<400> SEQUENCE: 218

Glu Ser Thr Val Ala Pro Glu Glu Asp Thr
1               5                   10

<210> SEQ ID NO 219
<211> LENGTH: 9
<212> TYPE: PRT
<213> ORGANISM: Artificial sequence
<220> FEATURE:
<223> OTHER INFORMATION: HLA restricted peptide

<400> SEQUENCE: 219

Glu Thr Arg Leu Leu Gln Thr Gly Ile
1               5

<210> SEQ ID NO 220
<211> LENGTH: 10
<212> TYPE: PRT
<213> ORGANISM: Artificial sequence
<220> FEATURE:
<223> OTHER INFORMATION: HLA restricted peptide

<400> SEQUENCE: 220

Glu Thr Arg Leu Leu Gln Thr Gly Ile His
1               5                   10

<210> SEQ ID NO 221
<211> LENGTH: 9
<212> TYPE: PRT
<213> ORGANISM: Artificial sequence
<220> FEATURE:
<223> OTHER INFORMATION: HLA restricted peptide

<400> SEQUENCE: 221

Glu Val Glu Asn Val Ser Val Asn Val
1               5

<210> SEQ ID NO 222
<211> LENGTH: 10
<212> TYPE: PRT
<213> ORGANISM: Artificial sequence
<220> FEATURE:
<223> OTHER INFORMATION: HLA restricted peptide

<400> SEQUENCE: 222

Glu Val Glu Asn Val Ser Val Asn Val His
1               5                   10

<210> SEQ ID NO 223
<211> LENGTH: 9
<212> TYPE: PRT
<213> ORGANISM: Artificial sequence
<220> FEATURE:
<223> OTHER INFORMATION: HLA restricted peptide

<400> SEQUENCE: 223

Glu Val Gln Ala Ile Arg Glu Thr Val
1               5

<210> SEQ ID NO 224
<211> LENGTH: 10
<212> TYPE: PRT
<213> ORGANISM: Artificial sequence
<220> FEATURE:

<223> OTHER INFORMATION: HLA restricted peptide

<400> SEQUENCE: 224

Glu Val Gln Ala Ile Arg Glu Thr Val Glu
1               5                   10

<210> SEQ ID NO 225
<211> LENGTH: 9
<212> TYPE: PRT
<213> ORGANISM: Artificial sequence
<220> FEATURE:
<223> OTHER INFORMATION: HLA restricted peptide

<400> SEQUENCE: 225

Glu Tyr Arg His Thr Trp Asp Arg His
1               5

<210> SEQ ID NO 226
<211> LENGTH: 9
<212> TYPE: PRT
<213> ORGANISM: Artificial sequence
<220> FEATURE:
<223> OTHER INFORMATION: HLA restricted peptide

<400> SEQUENCE: 226

Phe Ala Glu Leu Glu Gly Val Trp Gln
1               5

<210> SEQ ID NO 227
<211> LENGTH: 9
<212> TYPE: PRT
<213> ORGANISM: Artificial sequence
<220> FEATURE:
<223> OTHER INFORMATION: HLA restricted peptide

<400> SEQUENCE: 227

Phe Cys Glu Asp Val Pro Ser Gly Lys
1               5

<210> SEQ ID NO 228
<211> LENGTH: 10
<212> TYPE: PRT
<213> ORGANISM: Artificial sequence
<220> FEATURE:
<223> OTHER INFORMATION: HLA restricted peptide

<400> SEQUENCE: 228

Phe Cys Glu Asp Val Pro Ser Gly Lys Leu
1               5                   10

<210> SEQ ID NO 229
<211> LENGTH: 9
<212> TYPE: PRT
<213> ORGANISM: Artificial sequence
<220> FEATURE:
<223> OTHER INFORMATION: HLA restricted peptide

<400> SEQUENCE: 229

Phe Asp Ile Asp Leu Leu Leu Gln Arg
1               5

<210> SEQ ID NO 230
<211> LENGTH: 9
<212> TYPE: PRT
<213> ORGANISM: Artificial sequence
<220> FEATURE:
<223> OTHER INFORMATION: HLA restricted peptide

```
<400> SEQUENCE: 230

Phe Phe Asp Ile Asp Leu Leu Leu Gln
1               5

<210> SEQ ID NO 231
<211> LENGTH: 10
<212> TYPE: PRT
<213> ORGANISM: Artificial sequence
<220> FEATURE:
<223> OTHER INFORMATION: HLA restricted peptide

<400> SEQUENCE: 231

Phe Phe Asp Ile Asp Leu Leu Leu Gln Arg
1               5                   10

<210> SEQ ID NO 232
<211> LENGTH: 9
<212> TYPE: PRT
<213> ORGANISM: Artificial sequence
<220> FEATURE:
<223> OTHER INFORMATION: HLA restricted peptide

<400> SEQUENCE: 232

Phe Phe Phe Asp Ile Asp Leu Leu Leu
1               5

<210> SEQ ID NO 233
<211> LENGTH: 10
<212> TYPE: PRT
<213> ORGANISM: Artificial sequence
<220> FEATURE:
<223> OTHER INFORMATION: HLA restricted peptide

<400> SEQUENCE: 233

Phe Phe Phe Asp Ile Asp Leu Leu Leu Gln
1               5                   10

<210> SEQ ID NO 234
<211> LENGTH: 9
<212> TYPE: PRT
<213> ORGANISM: Artificial sequence
<220> FEATURE:
<223> OTHER INFORMATION: HLA restricted peptide

<400> SEQUENCE: 234

Phe Phe Trp Asp Ala Asn Asp Ile Tyr
1               5

<210> SEQ ID NO 235
<211> LENGTH: 10
<212> TYPE: PRT
<213> ORGANISM: Artificial sequence
<220> FEATURE:
<223> OTHER INFORMATION: HLA restricted peptide

<400> SEQUENCE: 235

Phe Phe Trp Asp Ala Asn Asp Ile Tyr Arg
1               5                   10

<210> SEQ ID NO 236
<211> LENGTH: 9
<212> TYPE: PRT
<213> ORGANISM: Artificial sequence
<220> FEATURE:
<223> OTHER INFORMATION: HLA restricted peptide

<400> SEQUENCE: 236
```

```
Phe Gly Leu Leu Cys Pro Lys Ser Ile
1               5

<210> SEQ ID NO 237
<211> LENGTH: 10
<212> TYPE: PRT
<213> ORGANISM: Artificial sequence
<220> FEATURE:
<223> OTHER INFORMATION: HLA restricted peptide

<400> SEQUENCE: 237

Phe Gly Leu Leu Cys Pro Lys Ser Ile Pro
1               5                   10

<210> SEQ ID NO 238
<211> LENGTH: 10
<212> TYPE: PRT
<213> ORGANISM: Artificial sequence
<220> FEATURE:
<223> OTHER INFORMATION: HLA restricted peptide

<400> SEQUENCE: 238

Phe Leu Glu Val Gln Ala Ile Arg Glu Thr
1               5                   10

<210> SEQ ID NO 239
<211> LENGTH: 10
<212> TYPE: PRT
<213> ORGANISM: Artificial sequence
<220> FEATURE:
<223> OTHER INFORMATION: HLA restricted peptide

<400> SEQUENCE: 239

Phe Met His Val Thr Leu Gly Ser Asp Val
1               5                   10

<210> SEQ ID NO 240
<211> LENGTH: 10
<212> TYPE: PRT
<213> ORGANISM: Artificial sequence
<220> FEATURE:
<223> OTHER INFORMATION: HLA restricted peptide

<400> SEQUENCE: 240

Phe Met Arg Pro His Glu Arg Asn Gly Phe
1               5                   10

<210> SEQ ID NO 241
<211> LENGTH: 9
<212> TYPE: PRT
<213> ORGANISM: Artificial sequence
<220> FEATURE:
<223> OTHER INFORMATION: HLA restricted peptide

<400> SEQUENCE: 241

Phe Pro Thr Lys Asp Val Ala Leu Arg
1               5

<210> SEQ ID NO 242
<211> LENGTH: 10
<212> TYPE: PRT
<213> ORGANISM: Artificial sequence
<220> FEATURE:
<223> OTHER INFORMATION: HLA restricted peptide

<400> SEQUENCE: 242

Phe Pro Thr Lys Asp Val Ala Leu Arg His
1               5                   10
```

<210> SEQ ID NO 243
<211> LENGTH: 9
<212> TYPE: PRT
<213> ORGANISM: Artificial sequence
<220> FEATURE:
<223> OTHER INFORMATION: HLA restricted peptide

<400> SEQUENCE: 243

Phe Ser Arg Gly Asp Thr Pro Val Leu
1               5

<210> SEQ ID NO 244
<211> LENGTH: 9
<212> TYPE: PRT
<213> ORGANISM: Artificial sequence
<220> FEATURE:
<223> OTHER INFORMATION: HLA restricted peptide

<400> SEQUENCE: 244

Phe Thr Gly Ser Glu Val Glu Asn Val
1               5

<210> SEQ ID NO 245
<211> LENGTH: 10
<212> TYPE: PRT
<213> ORGANISM: Artificial sequence
<220> FEATURE:
<223> OTHER INFORMATION: HLA restricted peptide

<400> SEQUENCE: 245

Phe Thr Gly Ser Glu Val Glu Asn Val Ser
1               5                   10

<210> SEQ ID NO 246
<211> LENGTH: 9
<212> TYPE: PRT
<213> ORGANISM: Artificial sequence
<220> FEATURE:
<223> OTHER INFORMATION: HLA restricted peptide

<400> SEQUENCE: 246

Phe Thr Ser His Glu His Phe Gly Leu
1               5

<210> SEQ ID NO 247
<211> LENGTH: 10
<212> TYPE: PRT
<213> ORGANISM: Artificial sequence
<220> FEATURE:
<223> OTHER INFORMATION: HLA restricted peptide

<400> SEQUENCE: 247

Phe Thr Ser His Glu His Phe Gly Leu Leu
1               5                   10

<210> SEQ ID NO 248
<211> LENGTH: 10
<212> TYPE: PRT
<213> ORGANISM: Artificial sequence
<220> FEATURE:
<223> OTHER INFORMATION: HLA restricted peptide

<400> SEQUENCE: 248

Phe Thr Ser Gln Tyr Arg Ile Gln Gly Lys
1               5                   10

```
<210> SEQ ID NO 249
<211> LENGTH: 9
<212> TYPE: PRT
<213> ORGANISM: Artificial sequence
<220> FEATURE:
<223> OTHER INFORMATION: HLA restricted peptide

<400> SEQUENCE: 249

Phe Thr Val Leu Cys Pro Lys Asn Met
1               5

<210> SEQ ID NO 250
<211> LENGTH: 10
<212> TYPE: PRT
<213> ORGANISM: Artificial sequence
<220> FEATURE:
<223> OTHER INFORMATION: HLA restricted peptide

<400> SEQUENCE: 250

Phe Thr Val Leu Cys Pro Lys Asn Met Ile
1               5                   10

<210> SEQ ID NO 251
<211> LENGTH: 10
<212> TYPE: PRT
<213> ORGANISM: Artificial sequence
<220> FEATURE:
<223> OTHER INFORMATION: HLA restricted peptide

<400> SEQUENCE: 251

Phe Thr Trp Pro Pro Trp Gln Ala Gly Ile
1               5                   10

<210> SEQ ID NO 252
<211> LENGTH: 9
<212> TYPE: PRT
<213> ORGANISM: Artificial sequence
<220> FEATURE:
<223> OTHER INFORMATION: HLA restricted peptide

<400> SEQUENCE: 252

Phe Val Phe Pro Thr Lys Asp Val Ala
1               5

<210> SEQ ID NO 253
<211> LENGTH: 10
<212> TYPE: PRT
<213> ORGANISM: Artificial sequence
<220> FEATURE:
<223> OTHER INFORMATION: HLA restricted peptide

<400> SEQUENCE: 253

Phe Val Phe Pro Thr Lys Asp Val Ala Leu
1               5                   10

<210> SEQ ID NO 254
<211> LENGTH: 9
<212> TYPE: PRT
<213> ORGANISM: Artificial sequence
<220> FEATURE:
<223> OTHER INFORMATION: HLA restricted peptide

<400> SEQUENCE: 254

Phe Trp Asp Ala Asn Asp Ile Tyr Arg
1               5

<210> SEQ ID NO 255
<211> LENGTH: 10
```

```
<212> TYPE: PRT
<213> ORGANISM: Artificial sequence
<220> FEATURE:
<223> OTHER INFORMATION: HLA restricted peptide

<400> SEQUENCE: 255

Phe Trp Asp Ala Asn Asp Ile Tyr Arg Ile
1               5                   10

<210> SEQ ID NO 256
<211> LENGTH: 9
<212> TYPE: PRT
<213> ORGANISM: Artificial sequence
<220> FEATURE:
<223> OTHER INFORMATION: HLA restricted peptide

<400> SEQUENCE: 256

Gly Ala Ala Gln Gly Asp Asp Asp Val
1               5

<210> SEQ ID NO 257
<211> LENGTH: 10
<212> TYPE: PRT
<213> ORGANISM: Artificial sequence
<220> FEATURE:
<223> OTHER INFORMATION: HLA restricted peptide

<400> SEQUENCE: 257

Gly Ala Ala Gln Gly Asp Asp Asp Val Trp
1               5                   10

<210> SEQ ID NO 258
<211> LENGTH: 9
<212> TYPE: PRT
<213> ORGANISM: Artificial sequence
<220> FEATURE:
<223> OTHER INFORMATION: HLA restricted peptide

<400> SEQUENCE: 258

Gly Ala Met Ala Gly Ala Ser Thr Ser
1               5

<210> SEQ ID NO 259
<211> LENGTH: 10
<212> TYPE: PRT
<213> ORGANISM: Artificial sequence
<220> FEATURE:
<223> OTHER INFORMATION: HLA restricted peptide

<400> SEQUENCE: 259

Gly Ala Met Ala Gly Ala Ser Thr Ser Ala
1               5                   10

<210> SEQ ID NO 260
<211> LENGTH: 9
<212> TYPE: PRT
<213> ORGANISM: Artificial sequence
<220> FEATURE:
<223> OTHER INFORMATION: HLA restricted peptide

<400> SEQUENCE: 260

Gly Ala Ser Thr Ser Ala Gly Arg Lys
1               5

<210> SEQ ID NO 261
<211> LENGTH: 10
<212> TYPE: PRT
<213> ORGANISM: Artificial sequence
```

```
<220> FEATURE:
<223> OTHER INFORMATION: HLA restricted peptide

<400> SEQUENCE: 261

Gly Ala Ser Thr Ser Ala Gly Arg Lys Arg
1               5                   10

<210> SEQ ID NO 262
<211> LENGTH: 10
<212> TYPE: PRT
<213> ORGANISM: Artificial sequence
<220> FEATURE:
<223> OTHER INFORMATION: HLA restricted peptide

<400> SEQUENCE: 262

Gly Asp Asp Asp Val Trp Thr Ser Gly Ser
1               5                   10

<210> SEQ ID NO 263
<211> LENGTH: 10
<212> TYPE: PRT
<213> ORGANISM: Artificial sequence
<220> FEATURE:
<223> OTHER INFORMATION: HLA restricted peptide

<400> SEQUENCE: 263

Gly Asp Asn Gln Leu Gln Val Gln His Thr
1               5                   10

<210> SEQ ID NO 264
<211> LENGTH: 9
<212> TYPE: PRT
<213> ORGANISM: Artificial sequence
<220> FEATURE:
<223> OTHER INFORMATION: HLA restricted peptide

<400> SEQUENCE: 264

Gly Asp Gln Tyr Val Lys Val Tyr Leu
1               5

<210> SEQ ID NO 265
<211> LENGTH: 10
<212> TYPE: PRT
<213> ORGANISM: Artificial sequence
<220> FEATURE:
<223> OTHER INFORMATION: HLA restricted peptide

<400> SEQUENCE: 265

Gly Asp Gln Tyr Val Lys Val Tyr Leu Glu
1               5                   10

<210> SEQ ID NO 266
<211> LENGTH: 10
<212> TYPE: PRT
<213> ORGANISM: Artificial sequence
<220> FEATURE:
<223> OTHER INFORMATION: HLA restricted peptide

<400> SEQUENCE: 266

Gly Asp Thr Pro Val Leu Pro His Glu Thr
1               5                   10

<210> SEQ ID NO 267
<211> LENGTH: 9
<212> TYPE: PRT
<213> ORGANISM: Artificial sequence
<220> FEATURE:
<223> OTHER INFORMATION: HLA restricted peptide
```

```
<400> SEQUENCE: 267

Gly Phe Thr Val Leu Cys Pro Lys Asn
1               5

<210> SEQ ID NO 268
<211> LENGTH: 10
<212> TYPE: PRT
<213> ORGANISM: Artificial sequence
<220> FEATURE:
<223> OTHER INFORMATION: HLA restricted peptide

<400> SEQUENCE: 268

Gly Phe Thr Val Leu Cys Pro Lys Asn Met
1               5                   10

<210> SEQ ID NO 269
<211> LENGTH: 9
<212> TYPE: PRT
<213> ORGANISM: Artificial sequence
<220> FEATURE:
<223> OTHER INFORMATION: HLA restricted peptide

<400> SEQUENCE: 269

Gly Gly Ala Met Ala Gly Ala Ser Thr
1               5

<210> SEQ ID NO 270
<211> LENGTH: 10
<212> TYPE: PRT
<213> ORGANISM: Artificial sequence
<220> FEATURE:
<223> OTHER INFORMATION: HLA restricted peptide

<400> SEQUENCE: 270

Gly Gly Ala Met Ala Gly Ala Ser Thr Ser
1               5                   10

<210> SEQ ID NO 271
<211> LENGTH: 9
<212> TYPE: PRT
<213> ORGANISM: Artificial sequence
<220> FEATURE:
<223> OTHER INFORMATION: HLA restricted peptide

<400> SEQUENCE: 271

Gly Gly Gly Ala Met Ala Gly Ala Ser
1               5

<210> SEQ ID NO 272
<211> LENGTH: 10
<212> TYPE: PRT
<213> ORGANISM: Artificial sequence
<220> FEATURE:
<223> OTHER INFORMATION: HLA restricted peptide

<400> SEQUENCE: 272

Gly Gly Gly Ala Met Ala Gly Ala Ser Thr
1               5                   10

<210> SEQ ID NO 273
<211> LENGTH: 9
<212> TYPE: PRT
<213> ORGANISM: Artificial sequence
<220> FEATURE:
<223> OTHER INFORMATION: HLA restricted peptide

<400> SEQUENCE: 273
```

-continued

```
Gly His Val Leu Lys Ala Val Phe Ser
1               5

<210> SEQ ID NO 274
<211> LENGTH: 10
<212> TYPE: PRT
<213> ORGANISM: Artificial sequence
<220> FEATURE:
<223> OTHER INFORMATION: HLA restricted peptide

<400> SEQUENCE: 274

Gly His Val Leu Lys Ala Val Phe Ser Arg
1               5                   10

<210> SEQ ID NO 275
<211> LENGTH: 10
<212> TYPE: PRT
<213> ORGANISM: Artificial sequence
<220> FEATURE:
<223> OTHER INFORMATION: HLA restricted peptide

<400> SEQUENCE: 275

Gly Ile His Val Arg Val Ser Gln Pro Ser
1               5                   10

<210> SEQ ID NO 276
<211> LENGTH: 10
<212> TYPE: PRT
<213> ORGANISM: Artificial sequence
<220> FEATURE:
<223> OTHER INFORMATION: HLA restricted peptide

<400> SEQUENCE: 276

Gly Ile Leu Ala Arg Asn Leu Val Pro Met
1               5                   10

<210> SEQ ID NO 277
<211> LENGTH: 10
<212> TYPE: PRT
<213> ORGANISM: Artificial sequence
<220> FEATURE:
<223> OTHER INFORMATION: HLA restricted peptide

<400> SEQUENCE: 277

Gly Lys Ile Ser His Ile Met Leu Asp Val
1               5                   10

<210> SEQ ID NO 278
<211> LENGTH: 9
<212> TYPE: PRT
<213> ORGANISM: Artificial sequence
<220> FEATURE:
<223> OTHER INFORMATION: HLA restricted peptide

<400> SEQUENCE: 278

Gly Lys Leu Glu Tyr Arg His Thr Trp
1               5

<210> SEQ ID NO 279
<211> LENGTH: 10
<212> TYPE: PRT
<213> ORGANISM: Artificial sequence
<220> FEATURE:
<223> OTHER INFORMATION: HLA restricted peptide

<400> SEQUENCE: 279

Gly Lys Leu Glu Tyr Arg His Thr Trp Asp
```

```
1               5                   10
```

<210> SEQ ID NO 280
<211> LENGTH: 9
<212> TYPE: PRT
<213> ORGANISM: Artificial sequence
<220> FEATURE:
<223> OTHER INFORMATION: HLA restricted peptide

<400> SEQUENCE: 280

```
Gly Lys Leu Phe Met His Val Thr Leu
1               5
```

<210> SEQ ID NO 281
<211> LENGTH: 9
<212> TYPE: PRT
<213> ORGANISM: Artificial sequence
<220> FEATURE:
<223> OTHER INFORMATION: HLA restricted peptide

<400> SEQUENCE: 281

```
Gly Lys Gln Met Trp Gln Ala Arg Leu
1               5
```

<210> SEQ ID NO 282
<211> LENGTH: 10
<212> TYPE: PRT
<213> ORGANISM: Artificial sequence
<220> FEATURE:
<223> OTHER INFORMATION: HLA restricted peptide

<400> SEQUENCE: 282

```
Gly Lys Gln Met Trp Gln Ala Arg Leu Thr
1               5                   10
```

<210> SEQ ID NO 283
<211> LENGTH: 9
<212> TYPE: PRT
<213> ORGANISM: Artificial sequence
<220> FEATURE:
<223> OTHER INFORMATION: HLA restricted peptide

<400> SEQUENCE: 283

```
Gly Leu Ala Trp Thr Arg Gln Gln Asn
1               5
```

<210> SEQ ID NO 284
<211> LENGTH: 9
<212> TYPE: PRT
<213> ORGANISM: Artificial sequence
<220> FEATURE:
<223> OTHER INFORMATION: HLA restricted peptide

<400> SEQUENCE: 284

```
Gly Leu Ser Ile Ser Gly Asn Leu Leu
1               5
```

<210> SEQ ID NO 285
<211> LENGTH: 10
<212> TYPE: PRT
<213> ORGANISM: Artificial sequence
<220> FEATURE:
<223> OTHER INFORMATION: HLA restricted peptide

<400> SEQUENCE: 285

```
Gly Leu Ser Ile Ser Gly Asn Leu Leu Met
1               5                   10
```

<210> SEQ ID NO 286
<211> LENGTH: 10
<212> TYPE: PRT
<213> ORGANISM: Artificial sequence
<220> FEATURE:
<223> OTHER INFORMATION: HLA restricted peptide

<400> SEQUENCE: 286

Gly Asn Leu Leu Met Asn Gly Gln Gln Ile
1               5                   10

<210> SEQ ID NO 287
<211> LENGTH: 9
<212> TYPE: PRT
<213> ORGANISM: Artificial sequence
<220> FEATURE:
<223> OTHER INFORMATION: HLA restricted peptide

<400> SEQUENCE: 287

Gly Pro Cys Ile Ala Ser Thr Pro Lys
1               5

<210> SEQ ID NO 288
<211> LENGTH: 10
<212> TYPE: PRT
<213> ORGANISM: Artificial sequence
<220> FEATURE:
<223> OTHER INFORMATION: HLA restricted peptide

<400> SEQUENCE: 288

Gly Pro Cys Ile Ala Ser Thr Pro Lys Lys
1               5                   10

<210> SEQ ID NO 289
<211> LENGTH: 9
<212> TYPE: PRT
<213> ORGANISM: Artificial sequence
<220> FEATURE:
<223> OTHER INFORMATION: HLA restricted peptide

<400> SEQUENCE: 289

Gly Pro Ile Ser Gly His Val Leu Lys
1               5

<210> SEQ ID NO 290
<211> LENGTH: 10
<212> TYPE: PRT
<213> ORGANISM: Artificial sequence
<220> FEATURE:
<223> OTHER INFORMATION: HLA restricted peptide

<400> SEQUENCE: 290

Gly Pro Ile Ser Gly His Val Leu Lys Ala
1               5                   10

<210> SEQ ID NO 291
<211> LENGTH: 9
<212> TYPE: PRT
<213> ORGANISM: Artificial sequence
<220> FEATURE:
<223> OTHER INFORMATION: HLA restricted peptide

<400> SEQUENCE: 291

Gly Pro Gln Tyr Ser Glu His Pro Thr
1               5

<210> SEQ ID NO 292

```
<211> LENGTH: 10
<212> TYPE: PRT
<213> ORGANISM: Artificial sequence
<220> FEATURE:
<223> OTHER INFORMATION: HLA restricted peptide

<400> SEQUENCE: 292

Gly Pro Gln Tyr Ser Glu His Pro Thr Phe
1               5                   10

<210> SEQ ID NO 293
<211> LENGTH: 9
<212> TYPE: PRT
<213> ORGANISM: Artificial sequence
<220> FEATURE:
<223> OTHER INFORMATION: HLA restricted peptide

<400> SEQUENCE: 293

Gly Gln Asn Leu Lys Tyr Gln Glu Phe
1               5

<210> SEQ ID NO 294
<211> LENGTH: 10
<212> TYPE: PRT
<213> ORGANISM: Artificial sequence
<220> FEATURE:
<223> OTHER INFORMATION: HLA restricted peptide

<400> SEQUENCE: 294

Gly Gln Asn Leu Lys Tyr Gln Glu Phe Phe
1               5                   10

<210> SEQ ID NO 295
<211> LENGTH: 9
<212> TYPE: PRT
<213> ORGANISM: Artificial sequence
<220> FEATURE:
<223> OTHER INFORMATION: HLA restricted peptide

<400> SEQUENCE: 295

Gly Gln Gln Ile Phe Leu Glu Val Gln
1               5

<210> SEQ ID NO 296
<211> LENGTH: 10
<212> TYPE: PRT
<213> ORGANISM: Artificial sequence
<220> FEATURE:
<223> OTHER INFORMATION: HLA restricted peptide

<400> SEQUENCE: 296

Gly Gln Gln Ile Phe Leu Glu Val Gln Ala
1               5                   10

<210> SEQ ID NO 297
<211> LENGTH: 9
<212> TYPE: PRT
<213> ORGANISM: Artificial sequence
<220> FEATURE:
<223> OTHER INFORMATION: HLA restricted peptide

<400> SEQUENCE: 297

Gly Arg Lys Arg Lys Ser Ala Ser Ser
1               5

<210> SEQ ID NO 298
<211> LENGTH: 10
<212> TYPE: PRT
```

-continued

<213> ORGANISM: Artificial sequence
<220> FEATURE:
<223> OTHER INFORMATION: HLA restricted peptide

<400> SEQUENCE: 298

Gly Arg Lys Arg Lys Ser Ala Ser Ser Ala
1               5                   10

<210> SEQ ID NO 299
<211> LENGTH: 9
<212> TYPE: PRT
<213> ORGANISM: Artificial sequence
<220> FEATURE:
<223> OTHER INFORMATION: HLA restricted peptide

<400> SEQUENCE: 299

Gly Arg Leu Lys Ala Glu Ser Thr Val
1               5

<210> SEQ ID NO 300
<211> LENGTH: 10
<212> TYPE: PRT
<213> ORGANISM: Artificial sequence
<220> FEATURE:
<223> OTHER INFORMATION: HLA restricted peptide

<400> SEQUENCE: 300

Gly Arg Leu Lys Ala Glu Ser Thr Val Ala
1               5                   10

<210> SEQ ID NO 301
<211> LENGTH: 9
<212> TYPE: PRT
<213> ORGANISM: Artificial sequence
<220> FEATURE:
<223> OTHER INFORMATION: HLA restricted peptide

<400> SEQUENCE: 301

Gly Arg Arg Cys Pro Glu Met Ile Ser
1               5

<210> SEQ ID NO 302
<211> LENGTH: 10
<212> TYPE: PRT
<213> ORGANISM: Artificial sequence
<220> FEATURE:
<223> OTHER INFORMATION: HLA restricted peptide

<400> SEQUENCE: 302

Gly Arg Arg Cys Pro Glu Met Ile Ser Val
1               5                   10

<210> SEQ ID NO 303
<211> LENGTH: 9
<212> TYPE: PRT
<213> ORGANISM: Artificial sequence
<220> FEATURE:
<223> OTHER INFORMATION: HLA restricted peptide

<400> SEQUENCE: 303

Gly Arg Ser Ile Cys Pro Ser Gln Glu
1               5

<210> SEQ ID NO 304
<211> LENGTH: 10
<212> TYPE: PRT
<213> ORGANISM: Artificial sequence
<220> FEATURE:

```
<223> OTHER INFORMATION: HLA restricted peptide

<400> SEQUENCE: 304

Gly Arg Ser Ile Cys Pro Ser Gln Glu Pro
1               5                   10

<210> SEQ ID NO 305
<211> LENGTH: 9
<212> TYPE: PRT
<213> ORGANISM: Artificial sequence
<220> FEATURE:
<223> OTHER INFORMATION: HLA restricted peptide

<400> SEQUENCE: 305

Gly Ser Asp Ser Asp Glu Glu Leu Val
1               5

<210> SEQ ID NO 306
<211> LENGTH: 10
<212> TYPE: PRT
<213> ORGANISM: Artificial sequence
<220> FEATURE:
<223> OTHER INFORMATION: HLA restricted peptide

<400> SEQUENCE: 306

Gly Ser Asp Ser Asp Glu Glu Leu Val Thr
1               5                   10

<210> SEQ ID NO 307
<211> LENGTH: 9
<212> TYPE: PRT
<213> ORGANISM: Artificial sequence
<220> FEATURE:
<223> OTHER INFORMATION: HLA restricted peptide

<400> SEQUENCE: 307

Gly Ser Asp Val Glu Glu Asp Leu Thr
1               5

<210> SEQ ID NO 308
<211> LENGTH: 10
<212> TYPE: PRT
<213> ORGANISM: Artificial sequence
<220> FEATURE:
<223> OTHER INFORMATION: HLA restricted peptide

<400> SEQUENCE: 308

Gly Ser Asp Val Glu Glu Asp Leu Thr Met
1               5                   10

<210> SEQ ID NO 309
<211> LENGTH: 9
<212> TYPE: PRT
<213> ORGANISM: Artificial sequence
<220> FEATURE:
<223> OTHER INFORMATION: HLA restricted peptide

<400> SEQUENCE: 309

Gly Ser Glu Val Glu Asn Val Ser Val
1               5

<210> SEQ ID NO 310
<211> LENGTH: 10
<212> TYPE: PRT
<213> ORGANISM: Artificial sequence
<220> FEATURE:
<223> OTHER INFORMATION: HLA restricted peptide
```

```
<400> SEQUENCE: 310

Gly Ser Glu Val Glu Asn Val Ser Val Asn
1               5                   10

<210> SEQ ID NO 311
<211> LENGTH: 9
<212> TYPE: PRT
<213> ORGANISM: Artificial sequence
<220> FEATURE:
<223> OTHER INFORMATION: HLA restricted peptide

<400> SEQUENCE: 311

Gly Val Met Thr Arg Gly Arg Leu Lys
1               5

<210> SEQ ID NO 312
<211> LENGTH: 10
<212> TYPE: PRT
<213> ORGANISM: Artificial sequence
<220> FEATURE:
<223> OTHER INFORMATION: HLA restricted peptide

<400> SEQUENCE: 312

Gly Val Met Thr Arg Gly Arg Leu Lys Ala
1               5                   10

<210> SEQ ID NO 313
<211> LENGTH: 10
<212> TYPE: PRT
<213> ORGANISM: Artificial sequence
<220> FEATURE:
<223> OTHER INFORMATION: HLA restricted peptide

<400> SEQUENCE: 313

Gly Val Trp Gln Pro Ala Ala Gln Pro Lys
1               5                   10

<210> SEQ ID NO 314
<211> LENGTH: 10
<212> TYPE: PRT
<213> ORGANISM: Artificial sequence
<220> FEATURE:
<223> OTHER INFORMATION: HLA restricted peptide

<400> SEQUENCE: 314

His Ala Ser Gly Lys Gln Met Trp Gln Ala
1               5                   10

<210> SEQ ID NO 315
<211> LENGTH: 10
<212> TYPE: PRT
<213> ORGANISM: Artificial sequence
<220> FEATURE:
<223> OTHER INFORMATION: HLA restricted peptide

<400> SEQUENCE: 315

His Glu His Phe Gly Leu Leu Cys Pro Lys
1               5                   10

<210> SEQ ID NO 316
<211> LENGTH: 9
<212> TYPE: PRT
<213> ORGANISM: Artificial sequence
<220> FEATURE:
<223> OTHER INFORMATION: HLA restricted peptide

<400> SEQUENCE: 316
```

-continued

```
His Glu Leu Val Cys Ser Met Glu Asn
1               5

<210> SEQ ID NO 317
<211> LENGTH: 10
<212> TYPE: PRT
<213> ORGANISM: Artificial sequence
<220> FEATURE:
<223> OTHER INFORMATION: HLA restricted peptide

<400> SEQUENCE: 317

His Glu Leu Val Cys Ser Met Glu Asn Thr
1               5                   10

<210> SEQ ID NO 318
<211> LENGTH: 9
<212> TYPE: PRT
<213> ORGANISM: Artificial sequence
<220> FEATURE:
<223> OTHER INFORMATION: HLA restricted peptide

<400> SEQUENCE: 318

His Glu Arg Asn Gly Phe Thr Val Leu
1               5

<210> SEQ ID NO 319
<211> LENGTH: 10
<212> TYPE: PRT
<213> ORGANISM: Artificial sequence
<220> FEATURE:
<223> OTHER INFORMATION: HLA restricted peptide

<400> SEQUENCE: 319

His Glu Arg Asn Gly Phe Thr Val Leu Cys
1               5                   10

<210> SEQ ID NO 320
<211> LENGTH: 10
<212> TYPE: PRT
<213> ORGANISM: Artificial sequence
<220> FEATURE:
<223> OTHER INFORMATION: HLA restricted peptide

<400> SEQUENCE: 320

His Glu Thr Arg Leu Leu Gln Thr Gly Ile
1               5                   10

<210> SEQ ID NO 321
<211> LENGTH: 9
<212> TYPE: PRT
<213> ORGANISM: Artificial sequence
<220> FEATURE:
<223> OTHER INFORMATION: HLA restricted peptide

<400> SEQUENCE: 321

His Phe Gly Leu Leu Cys Pro Lys Ser
1               5

<210> SEQ ID NO 322
<211> LENGTH: 10
<212> TYPE: PRT
<213> ORGANISM: Artificial sequence
<220> FEATURE:
<223> OTHER INFORMATION: HLA restricted peptide

<400> SEQUENCE: 322

His Phe Gly Leu Leu Cys Pro Lys Ser Ile
1               5                   10
```

<210> SEQ ID NO 323
<211> LENGTH: 9
<212> TYPE: PRT
<213> ORGANISM: Artificial sequence
<220> FEATURE:
<223> OTHER INFORMATION: HLA restricted peptide

<400> SEQUENCE: 323

His His Tyr Pro Ser Ala Ala Glu Arg
1               5

<210> SEQ ID NO 324
<211> LENGTH: 10
<212> TYPE: PRT
<213> ORGANISM: Artificial sequence
<220> FEATURE:
<223> OTHER INFORMATION: HLA restricted peptide

<400> SEQUENCE: 324

His His Tyr Pro Ser Ala Ala Glu Arg Lys
1               5                   10

<210> SEQ ID NO 325
<211> LENGTH: 9
<212> TYPE: PRT
<213> ORGANISM: Artificial sequence
<220> FEATURE:
<223> OTHER INFORMATION: HLA restricted peptide

<400> SEQUENCE: 325

His Ile Met Leu Asp Val Ala Phe Thr
1               5

<210> SEQ ID NO 326
<211> LENGTH: 10
<212> TYPE: PRT
<213> ORGANISM: Artificial sequence
<220> FEATURE:
<223> OTHER INFORMATION: HLA restricted peptide

<400> SEQUENCE: 326

His Ile Met Leu Asp Val Ala Phe Thr Ser
1               5                   10

<210> SEQ ID NO 327
<211> LENGTH: 9
<212> TYPE: PRT
<213> ORGANISM: Artificial sequence
<220> FEATURE:
<223> OTHER INFORMATION: HLA restricted peptide

<400> SEQUENCE: 327

His Leu Pro Val Ala Asp Ala Val Ile
1               5

<210> SEQ ID NO 328
<211> LENGTH: 10
<212> TYPE: PRT
<213> ORGANISM: Artificial sequence
<220> FEATURE:
<223> OTHER INFORMATION: HLA restricted peptide

<400> SEQUENCE: 328

His Leu Pro Val Ala Asp Ala Val Ile His
1               5                   10

```
<210> SEQ ID NO 329
<211> LENGTH: 9
<212> TYPE: PRT
<213> ORGANISM: Artificial sequence
<220> FEATURE:
<223> OTHER INFORMATION: HLA restricted peptide

<400> SEQUENCE: 329

His Asn Pro Thr Gly Arg Ser Ile Cys
1               5

<210> SEQ ID NO 330
<211> LENGTH: 9
<212> TYPE: PRT
<213> ORGANISM: Artificial sequence
<220> FEATURE:
<223> OTHER INFORMATION: HLA restricted peptide

<400> SEQUENCE: 330

His Pro Thr Phe Thr Ser Gln Tyr Arg
1               5

<210> SEQ ID NO 331
<211> LENGTH: 10
<212> TYPE: PRT
<213> ORGANISM: Artificial sequence
<220> FEATURE:
<223> OTHER INFORMATION: HLA restricted peptide

<400> SEQUENCE: 331

His Pro Thr Phe Thr Ser Gln Tyr Arg Ile
1               5                   10

<210> SEQ ID NO 332
<211> LENGTH: 9
<212> TYPE: PRT
<213> ORGANISM: Artificial sequence
<220> FEATURE:
<223> OTHER INFORMATION: HLA restricted peptide

<400> SEQUENCE: 332

His Arg Gly Asp Asn Gln Leu Gln Val
1               5

<210> SEQ ID NO 333
<211> LENGTH: 10
<212> TYPE: PRT
<213> ORGANISM: Artificial sequence
<220> FEATURE:
<223> OTHER INFORMATION: HLA restricted peptide

<400> SEQUENCE: 333

His Arg Gly Asp Asn Gln Leu Gln Val Gln
1               5                   10

<210> SEQ ID NO 334
<211> LENGTH: 9
<212> TYPE: PRT
<213> ORGANISM: Artificial sequence
<220> FEATURE:
<223> OTHER INFORMATION: HLA restricted peptide

<400> SEQUENCE: 334

His Arg His Leu Pro Val Ala Asp Ala
1               5

<210> SEQ ID NO 335
<211> LENGTH: 10
```

```
<212> TYPE: PRT
<213> ORGANISM: Artificial sequence
<220> FEATURE:
<223> OTHER INFORMATION: HLA restricted peptide

<400> SEQUENCE: 335

His Arg His Leu Pro Val Ala Asp Ala Val
1               5                   10

<210> SEQ ID NO 336
<211> LENGTH: 9
<212> TYPE: PRT
<213> ORGANISM: Artificial sequence
<220> FEATURE:
<223> OTHER INFORMATION: HLA restricted peptide

<400> SEQUENCE: 336

His Arg Gln Asp Ala Leu Pro Gly Pro
1               5

<210> SEQ ID NO 337
<211> LENGTH: 10
<212> TYPE: PRT
<213> ORGANISM: Artificial sequence
<220> FEATURE:
<223> OTHER INFORMATION: HLA restricted peptide

<400> SEQUENCE: 337

His Arg Gln Asp Ala Leu Pro Gly Pro Cys
1               5                   10

<210> SEQ ID NO 338
<211> LENGTH: 10
<212> TYPE: PRT
<213> ORGANISM: Artificial sequence
<220> FEATURE:
<223> OTHER INFORMATION: HLA restricted peptide

<400> SEQUENCE: 338

His Thr Trp Asp Arg His Asp Glu Gly Ala
1               5                   10

<210> SEQ ID NO 339
<211> LENGTH: 9
<212> TYPE: PRT
<213> ORGANISM: Artificial sequence
<220> FEATURE:
<223> OTHER INFORMATION: HLA restricted peptide

<400> SEQUENCE: 339

His Thr Tyr Phe Thr Gly Ser Glu Val
1               5

<210> SEQ ID NO 340
<211> LENGTH: 9
<212> TYPE: PRT
<213> ORGANISM: Artificial sequence
<220> FEATURE:
<223> OTHER INFORMATION: HLA restricted peptide

<400> SEQUENCE: 340

His Val Leu Lys Ala Val Phe Ser Arg
1               5

<210> SEQ ID NO 341
<211> LENGTH: 9
<212> TYPE: PRT
<213> ORGANISM: Artificial sequence
```

```
<220> FEATURE:
<223> OTHER INFORMATION: HLA restricted peptide

<400> SEQUENCE: 341

His Val Arg Val Ser Gln Pro Ser Leu
1               5

<210> SEQ ID NO 342
<211> LENGTH: 10
<212> TYPE: PRT
<213> ORGANISM: Artificial sequence
<220> FEATURE:
<223> OTHER INFORMATION: HLA restricted peptide

<400> SEQUENCE: 342

His Val Arg Val Ser Gln Pro Ser Leu Ile
1               5                   10

<210> SEQ ID NO 343
<211> LENGTH: 9
<212> TYPE: PRT
<213> ORGANISM: Artificial sequence
<220> FEATURE:
<223> OTHER INFORMATION: HLA restricted peptide

<400> SEQUENCE: 343

His Val Val Cys Ala His Glu Leu Val
1               5

<210> SEQ ID NO 344
<211> LENGTH: 10
<212> TYPE: PRT
<213> ORGANISM: Artificial sequence
<220> FEATURE:
<223> OTHER INFORMATION: HLA restricted peptide

<400> SEQUENCE: 344

His Val Val Cys Ala His Glu Leu Val Cys
1               5                   10

<210> SEQ ID NO 345
<211> LENGTH: 9
<212> TYPE: PRT
<213> ORGANISM: Artificial sequence
<220> FEATURE:
<223> OTHER INFORMATION: HLA restricted peptide

<400> SEQUENCE: 345

His Tyr Pro Ser Ala Ala Glu Arg Lys
1               5

<210> SEQ ID NO 346
<211> LENGTH: 9
<212> TYPE: PRT
<213> ORGANISM: Artificial sequence
<220> FEATURE:
<223> OTHER INFORMATION: HLA restricted peptide

<400> SEQUENCE: 346

Ile Ala Ser Thr Pro Lys Lys His Arg
1               5

<210> SEQ ID NO 347
<211> LENGTH: 10
<212> TYPE: PRT
<213> ORGANISM: Artificial sequence
<220> FEATURE:
<223> OTHER INFORMATION: HLA restricted peptide
```

```
<400> SEQUENCE: 347

Ile Ala Ser Thr Pro Lys Lys His Arg Gly
1               5                   10

<210> SEQ ID NO 348
<211> LENGTH: 9
<212> TYPE: PRT
<213> ORGANISM: Artificial sequence
<220> FEATURE:
<223> OTHER INFORMATION: HLA restricted peptide

<400> SEQUENCE: 348

Ile Cys Pro Ser Gln Glu Pro Met Ser
1               5

<210> SEQ ID NO 349
<211> LENGTH: 10
<212> TYPE: PRT
<213> ORGANISM: Artificial sequence
<220> FEATURE:
<223> OTHER INFORMATION: HLA restricted peptide

<400> SEQUENCE: 349

Ile Cys Pro Ser Gln Glu Pro Met Ser Ile
1               5                   10

<210> SEQ ID NO 350
<211> LENGTH: 9
<212> TYPE: PRT
<213> ORGANISM: Artificial sequence
<220> FEATURE:
<223> OTHER INFORMATION: HLA restricted peptide

<400> SEQUENCE: 350

Ile Phe Ala Glu Leu Glu Gly Val Trp
1               5

<210> SEQ ID NO 351
<211> LENGTH: 9
<212> TYPE: PRT
<213> ORGANISM: Artificial sequence
<220> FEATURE:
<223> OTHER INFORMATION: HLA restricted peptide

<400> SEQUENCE: 351

Ile Phe Leu Glu Val Gln Ala Ile Arg
1               5

<210> SEQ ID NO 352
<211> LENGTH: 9
<212> TYPE: PRT
<213> ORGANISM: Artificial sequence
<220> FEATURE:
<223> OTHER INFORMATION: HLA restricted peptide

<400> SEQUENCE: 352

Ile Gly Asp Gln Tyr Val Lys Val Tyr
1               5

<210> SEQ ID NO 353
<211> LENGTH: 10
<212> TYPE: PRT
<213> ORGANISM: Artificial sequence
<220> FEATURE:
<223> OTHER INFORMATION: HLA restricted peptide

<400> SEQUENCE: 353
```

```
Ile Gly Asp Gln Tyr Val Lys Val Tyr Leu
1               5                   10

<210> SEQ ID NO 354
<211> LENGTH: 9
<212> TYPE: PRT
<213> ORGANISM: Artificial sequence
<220> FEATURE:
<223> OTHER INFORMATION: HLA restricted peptide

<400> SEQUENCE: 354

Ile His Ala Ser Gly Lys Gln Met Trp
1               5

<210> SEQ ID NO 355
<211> LENGTH: 9
<212> TYPE: PRT
<213> ORGANISM: Artificial sequence
<220> FEATURE:
<223> OTHER INFORMATION: HLA restricted peptide

<400> SEQUENCE: 355

Ile His Asn Pro Ala Val Phe Thr Trp
1               5

<210> SEQ ID NO 356
<211> LENGTH: 9
<212> TYPE: PRT
<213> ORGANISM: Artificial sequence
<220> FEATURE:
<223> OTHER INFORMATION: HLA restricted peptide

<400> SEQUENCE: 356

Ile His Val Arg Val Ser Gln Pro Ser
1               5

<210> SEQ ID NO 357
<211> LENGTH: 10
<212> TYPE: PRT
<213> ORGANISM: Artificial sequence
<220> FEATURE:
<223> OTHER INFORMATION: HLA restricted peptide

<400> SEQUENCE: 357

Ile His Val Arg Val Ser Gln Pro Ser Leu
1               5                   10

<210> SEQ ID NO 358
<211> LENGTH: 9
<212> TYPE: PRT
<213> ORGANISM: Artificial sequence
<220> FEATURE:
<223> OTHER INFORMATION: HLA restricted peptide

<400> SEQUENCE: 358

Ile Ile Lys Pro Gly Lys Ile Ser His
1               5

<210> SEQ ID NO 359
<211> LENGTH: 10
<212> TYPE: PRT
<213> ORGANISM: Artificial sequence
<220> FEATURE:
<223> OTHER INFORMATION: HLA restricted peptide

<400> SEQUENCE: 359

Ile Ile Lys Pro Gly Lys Ile Ser His Ile
```

-continued

```
1               5              10

<210> SEQ ID NO 360
<211> LENGTH: 9
<212> TYPE: PRT
<213> ORGANISM: Artificial sequence
<220> FEATURE:
<223> OTHER INFORMATION: HLA restricted peptide

<400> SEQUENCE: 360

Ile Lys Pro Gly Lys Ile Ser His Ile
1               5

<210> SEQ ID NO 361
<211> LENGTH: 10
<212> TYPE: PRT
<213> ORGANISM: Artificial sequence
<220> FEATURE:
<223> OTHER INFORMATION: HLA restricted peptide

<400> SEQUENCE: 361

Ile Lys Pro Gly Lys Ile Ser His Ile Met
1               5              10

<210> SEQ ID NO 362
<211> LENGTH: 9
<212> TYPE: PRT
<213> ORGANISM: Artificial sequence
<220> FEATURE:
<223> OTHER INFORMATION: HLA restricted peptide

<400> SEQUENCE: 362

Ile Leu Ala Arg Asn Leu Val Pro Met
1               5

<210> SEQ ID NO 363
<211> LENGTH: 10
<212> TYPE: PRT
<213> ORGANISM: Artificial sequence
<220> FEATURE:
<223> OTHER INFORMATION: HLA restricted peptide

<400> SEQUENCE: 363

Ile Leu Ala Arg Asn Leu Val Pro Met Val
1               5              10

<210> SEQ ID NO 364
<211> LENGTH: 10
<212> TYPE: PRT
<213> ORGANISM: Artificial sequence
<220> FEATURE:
<223> OTHER INFORMATION: HLA restricted peptide

<400> SEQUENCE: 364

Ile Leu Val Ser Gln Tyr Thr Pro Asp Ser
1               5              10

<210> SEQ ID NO 365
<211> LENGTH: 9
<212> TYPE: PRT
<213> ORGANISM: Artificial sequence
<220> FEATURE:
<223> OTHER INFORMATION: HLA restricted peptide

<400> SEQUENCE: 365

Ile Met Leu Asp Val Ala Phe Thr Ser
1               5
```

```
<210> SEQ ID NO 366
<211> LENGTH: 10
<212> TYPE: PRT
<213> ORGANISM: Artificial sequence
<220> FEATURE:
<223> OTHER INFORMATION: HLA restricted peptide

<400> SEQUENCE: 366

Ile Met Leu Asp Val Ala Phe Thr Ser His
1               5                   10

<210> SEQ ID NO 367
<211> LENGTH: 9
<212> TYPE: PRT
<213> ORGANISM: Artificial sequence
<220> FEATURE:
<223> OTHER INFORMATION: HLA restricted peptide

<400> SEQUENCE: 367

Ile Asn Val His His Tyr Pro Ser Ala
1               5

<210> SEQ ID NO 368
<211> LENGTH: 10
<212> TYPE: PRT
<213> ORGANISM: Artificial sequence
<220> FEATURE:
<223> OTHER INFORMATION: HLA restricted peptide

<400> SEQUENCE: 368

Ile Asn Val His His Tyr Pro Ser Ala Ala
1               5                   10

<210> SEQ ID NO 369
<211> LENGTH: 9
<212> TYPE: PRT
<213> ORGANISM: Artificial sequence
<220> FEATURE:
<223> OTHER INFORMATION: HLA restricted peptide

<400> SEQUENCE: 369

Ile Pro Gly Leu Ser Ile Ser Gly Asn
1               5

<210> SEQ ID NO 370
<211> LENGTH: 10
<212> TYPE: PRT
<213> ORGANISM: Artificial sequence
<220> FEATURE:
<223> OTHER INFORMATION: HLA restricted peptide

<400> SEQUENCE: 370

Ile Pro Gly Leu Ser Ile Ser Gly Asn Leu
1               5                   10

<210> SEQ ID NO 371
<211> LENGTH: 9
<212> TYPE: PRT
<213> ORGANISM: Artificial sequence
<220> FEATURE:
<223> OTHER INFORMATION: HLA restricted peptide

<400> SEQUENCE: 371

Ile Pro Ser Ile Asn Val His His Tyr
1               5

<210> SEQ ID NO 372
```

```
<211> LENGTH: 10
<212> TYPE: PRT
<213> ORGANISM: Artificial sequence
<220> FEATURE:
<223> OTHER INFORMATION: HLA restricted peptide

<400> SEQUENCE: 372

Ile Pro Ser Ile Asn Val His His Tyr Pro
1               5                   10

<210> SEQ ID NO 373
<211> LENGTH: 9
<212> TYPE: PRT
<213> ORGANISM: Artificial sequence
<220> FEATURE:
<223> OTHER INFORMATION: HLA restricted peptide

<400> SEQUENCE: 373

Ile Gln Gly Lys Leu Glu Tyr Arg His
1               5

<210> SEQ ID NO 374
<211> LENGTH: 10
<212> TYPE: PRT
<213> ORGANISM: Artificial sequence
<220> FEATURE:
<223> OTHER INFORMATION: HLA restricted peptide

<400> SEQUENCE: 374

Ile Gln Gly Lys Leu Glu Tyr Arg His Thr
1               5                   10

<210> SEQ ID NO 375
<211> LENGTH: 9
<212> TYPE: PRT
<213> ORGANISM: Artificial sequence
<220> FEATURE:
<223> OTHER INFORMATION: HLA restricted peptide

<400> SEQUENCE: 375

Ile Arg Glu Thr Val Glu Leu Arg Gln
1               5

<210> SEQ ID NO 376
<211> LENGTH: 10
<212> TYPE: PRT
<213> ORGANISM: Artificial sequence
<220> FEATURE:
<223> OTHER INFORMATION: HLA restricted peptide

<400> SEQUENCE: 376

Ile Arg Glu Thr Val Glu Leu Arg Gln Tyr
1               5                   10

<210> SEQ ID NO 377
<211> LENGTH: 9
<212> TYPE: PRT
<213> ORGANISM: Artificial sequence
<220> FEATURE:
<223> OTHER INFORMATION: HLA restricted peptide

<400> SEQUENCE: 377

Ile Ser Gly His Val Leu Lys Ala Val
1               5

<210> SEQ ID NO 378
<211> LENGTH: 10
<212> TYPE: PRT
```

```
<213> ORGANISM: Artificial sequence
<220> FEATURE:
<223> OTHER INFORMATION: HLA restricted peptide

<400> SEQUENCE: 378

Ile Ser Gly His Val Leu Lys Ala Val Phe
1               5                   10

<210> SEQ ID NO 379
<211> LENGTH: 9
<212> TYPE: PRT
<213> ORGANISM: Artificial sequence
<220> FEATURE:
<223> OTHER INFORMATION: HLA restricted peptide

<400> SEQUENCE: 379

Ile Ser His Ile Met Leu Asp Val Ala
1               5

<210> SEQ ID NO 380
<211> LENGTH: 10
<212> TYPE: PRT
<213> ORGANISM: Artificial sequence
<220> FEATURE:
<223> OTHER INFORMATION: HLA restricted peptide

<400> SEQUENCE: 380

Ile Ser His Ile Met Leu Asp Val Ala Phe
1               5                   10

<210> SEQ ID NO 381
<211> LENGTH: 10
<212> TYPE: PRT
<213> ORGANISM: Artificial sequence
<220> FEATURE:
<223> OTHER INFORMATION: HLA restricted peptide

<400> SEQUENCE: 381

Ile Ser Val Leu Gly Pro Ile Ser Gly His
1               5                   10

<210> SEQ ID NO 382
<211> LENGTH: 9
<212> TYPE: PRT
<213> ORGANISM: Artificial sequence
<220> FEATURE:
<223> OTHER INFORMATION: HLA restricted peptide

<400> SEQUENCE: 382

Ile Tyr Val Tyr Ala Leu Pro Leu Lys
1               5

<210> SEQ ID NO 383
<211> LENGTH: 10
<212> TYPE: PRT
<213> ORGANISM: Artificial sequence
<220> FEATURE:
<223> OTHER INFORMATION: HLA restricted peptide

<400> SEQUENCE: 383

Ile Tyr Val Tyr Ala Leu Pro Leu Lys Met
1               5                   10

<210> SEQ ID NO 384
<211> LENGTH: 9
<212> TYPE: PRT
<213> ORGANISM: Artificial sequence
<220> FEATURE:
```

<223> OTHER INFORMATION: HLA restricted peptide

<400> SEQUENCE: 384

Lys Ala Val Phe Ser Arg Gly Asp Thr
1               5

<210> SEQ ID NO 385
<211> LENGTH: 10
<212> TYPE: PRT
<213> ORGANISM: Artificial sequence
<220> FEATURE:
<223> OTHER INFORMATION: HLA restricted peptide

<400> SEQUENCE: 385

Lys Ala Val Phe Ser Arg Gly Asp Thr Pro
1               5                   10

<210> SEQ ID NO 386
<211> LENGTH: 9
<212> TYPE: PRT
<213> ORGANISM: Artificial sequence
<220> FEATURE:
<223> OTHER INFORMATION: HLA restricted peptide

<400> SEQUENCE: 386

Lys Asp Val Ala Leu Arg His Val Val
1               5

<210> SEQ ID NO 387
<211> LENGTH: 10
<212> TYPE: PRT
<213> ORGANISM: Artificial sequence
<220> FEATURE:
<223> OTHER INFORMATION: HLA restricted peptide

<400> SEQUENCE: 387

Lys Asp Val Ala Leu Arg His Val Val Cys
1               5                   10

<210> SEQ ID NO 388
<211> LENGTH: 9
<212> TYPE: PRT
<213> ORGANISM: Artificial sequence
<220> FEATURE:
<223> OTHER INFORMATION: HLA restricted peptide

<400> SEQUENCE: 388

Lys Glu Pro Asp Val Tyr Tyr Thr Ser
1               5

<210> SEQ ID NO 389
<211> LENGTH: 10
<212> TYPE: PRT
<213> ORGANISM: Artificial sequence
<220> FEATURE:
<223> OTHER INFORMATION: HLA restricted peptide

<400> SEQUENCE: 389

Lys Glu Pro Asp Val Tyr Tyr Thr Ser Ala
1               5                   10

<210> SEQ ID NO 390
<211> LENGTH: 10
<212> TYPE: PRT
<213> ORGANISM: Artificial sequence
<220> FEATURE:
<223> OTHER INFORMATION: HLA restricted peptide

```
<400> SEQUENCE: 390

Lys His Arg His Leu Pro Val Ala Asp Ala
1               5                   10

<210> SEQ ID NO 391
<211> LENGTH: 9
<212> TYPE: PRT
<213> ORGANISM: Artificial sequence
<220> FEATURE:
<223> OTHER INFORMATION: HLA restricted peptide

<400> SEQUENCE: 391

Lys Ile Ser His Ile Met Leu Asp Val
1               5

<210> SEQ ID NO 392
<211> LENGTH: 10
<212> TYPE: PRT
<213> ORGANISM: Artificial sequence
<220> FEATURE:
<223> OTHER INFORMATION: HLA restricted peptide

<400> SEQUENCE: 392

Lys Ile Ser His Ile Met Leu Asp Val Ala
1               5                   10

<210> SEQ ID NO 393
<211> LENGTH: 10
<212> TYPE: PRT
<213> ORGANISM: Artificial sequence
<220> FEATURE:
<223> OTHER INFORMATION: HLA restricted peptide

<400> SEQUENCE: 393

Lys Leu Glu Tyr Arg His Thr Trp Asp Arg
1               5                   10

<210> SEQ ID NO 394
<211> LENGTH: 9
<212> TYPE: PRT
<213> ORGANISM: Artificial sequence
<220> FEATURE:
<223> OTHER INFORMATION: HLA restricted peptide

<400> SEQUENCE: 394

Lys Leu Phe Met His Val Thr Leu Gly
1               5

<210> SEQ ID NO 395
<211> LENGTH: 10
<212> TYPE: PRT
<213> ORGANISM: Artificial sequence
<220> FEATURE:
<223> OTHER INFORMATION: HLA restricted peptide

<400> SEQUENCE: 395

Lys Leu Phe Met His Val Thr Leu Gly Ser
1               5                   10

<210> SEQ ID NO 396
<211> LENGTH: 9
<212> TYPE: PRT
<213> ORGANISM: Artificial sequence
<220> FEATURE:
<223> OTHER INFORMATION: HLA restricted peptide

<400> SEQUENCE: 396
```

```
Lys Met Leu Asn Ile Pro Ser Ile Asn
1               5
```

<210> SEQ ID NO 397
<211> LENGTH: 10
<212> TYPE: PRT
<213> ORGANISM: Artificial sequence
<220> FEATURE:
<223> OTHER INFORMATION: HLA restricted peptide

<400> SEQUENCE: 397

```
Lys Met Leu Asn Ile Pro Ser Ile Asn Val
1               5                   10
```

<210> SEQ ID NO 398
<211> LENGTH: 9
<212> TYPE: PRT
<213> ORGANISM: Artificial sequence
<220> FEATURE:
<223> OTHER INFORMATION: HLA restricted peptide

<400> SEQUENCE: 398

```
Lys Met Gln Val Ile Gly Asp Gln Tyr
1               5
```

<210> SEQ ID NO 399
<211> LENGTH: 10
<212> TYPE: PRT
<213> ORGANISM: Artificial sequence
<220> FEATURE:
<223> OTHER INFORMATION: HLA restricted peptide

<400> SEQUENCE: 399

```
Lys Met Gln Val Ile Gly Asp Gln Tyr Val
1               5                   10
```

<210> SEQ ID NO 400
<211> LENGTH: 9
<212> TYPE: PRT
<213> ORGANISM: Artificial sequence
<220> FEATURE:
<223> OTHER INFORMATION: HLA restricted peptide

<400> SEQUENCE: 400

```
Lys Asn Met Ile Ile Lys Pro Gly Lys
1               5
```

<210> SEQ ID NO 401
<211> LENGTH: 10
<212> TYPE: PRT
<213> ORGANISM: Artificial sequence
<220> FEATURE:
<223> OTHER INFORMATION: HLA restricted peptide

<400> SEQUENCE: 401

```
Lys Asn Met Ile Ile Lys Pro Gly Lys Ile
1               5                   10
```

<210> SEQ ID NO 402
<211> LENGTH: 9
<212> TYPE: PRT
<213> ORGANISM: Artificial sequence
<220> FEATURE:
<223> OTHER INFORMATION: HLA restricted peptide

<400> SEQUENCE: 402

```
Lys Pro Gly Lys Ile Ser His Ile Met
1               5
```

<210> SEQ ID NO 403
<211> LENGTH: 10
<212> TYPE: PRT
<213> ORGANISM: Artificial sequence
<220> FEATURE:
<223> OTHER INFORMATION: HLA restricted peptide

<400> SEQUENCE: 403

Lys Pro Gly Lys Ile Ser His Ile Met Leu
1               5                   10

<210> SEQ ID NO 404
<211> LENGTH: 9
<212> TYPE: PRT
<213> ORGANISM: Artificial sequence
<220> FEATURE:
<223> OTHER INFORMATION: HLA restricted peptide

<400> SEQUENCE: 404

Lys Gln Met Trp Gln Ala Arg Leu Thr
1               5

<210> SEQ ID NO 405
<211> LENGTH: 10
<212> TYPE: PRT
<213> ORGANISM: Artificial sequence
<220> FEATURE:
<223> OTHER INFORMATION: HLA restricted peptide

<400> SEQUENCE: 405

Lys Gln Met Trp Gln Ala Arg Leu Thr Val
1               5                   10

<210> SEQ ID NO 406
<211> LENGTH: 9
<212> TYPE: PRT
<213> ORGANISM: Artificial sequence
<220> FEATURE:
<223> OTHER INFORMATION: HLA restricted peptide

<400> SEQUENCE: 406

Lys Arg Lys Ser Ala Ser Ser Ala Thr
1               5

<210> SEQ ID NO 407
<211> LENGTH: 10
<212> TYPE: PRT
<213> ORGANISM: Artificial sequence
<220> FEATURE:
<223> OTHER INFORMATION: HLA restricted peptide

<400> SEQUENCE: 407

Lys Arg Lys Ser Ala Ser Ser Ala Thr Ala
1               5                   10

<210> SEQ ID NO 408
<211> LENGTH: 9
<212> TYPE: PRT
<213> ORGANISM: Artificial sequence
<220> FEATURE:
<223> OTHER INFORMATION: HLA restricted peptide

<400> SEQUENCE: 408

Lys Arg Arg Arg His Arg Gln Asp Ala
1               5

```
<210> SEQ ID NO 409
<211> LENGTH: 10
<212> TYPE: PRT
<213> ORGANISM: Artificial sequence
<220> FEATURE:
<223> OTHER INFORMATION: HLA restricted peptide

<400> SEQUENCE: 409

Lys Arg Arg Arg His Arg Gln Asp Ala Leu
1               5                   10

<210> SEQ ID NO 410
<211> LENGTH: 9
<212> TYPE: PRT
<213> ORGANISM: Artificial sequence
<220> FEATURE:
<223> OTHER INFORMATION: HLA restricted peptide

<400> SEQUENCE: 410

Lys Ser Ala Ser Ser Ala Thr Ala Cys
1               5

<210> SEQ ID NO 411
<211> LENGTH: 10
<212> TYPE: PRT
<213> ORGANISM: Artificial sequence
<220> FEATURE:
<223> OTHER INFORMATION: HLA restricted peptide

<400> SEQUENCE: 411

Lys Ser Ala Ser Ser Ala Thr Ala Cys Thr
1               5                   10

<210> SEQ ID NO 412
<211> LENGTH: 9
<212> TYPE: PRT
<213> ORGANISM: Artificial sequence
<220> FEATURE:
<223> OTHER INFORMATION: HLA restricted peptide

<400> SEQUENCE: 412

Lys Ser Ile Pro Gly Leu Ser Ile Ser
1               5

<210> SEQ ID NO 413
<211> LENGTH: 10
<212> TYPE: PRT
<213> ORGANISM: Artificial sequence
<220> FEATURE:
<223> OTHER INFORMATION: HLA restricted peptide

<400> SEQUENCE: 413

Lys Ser Ile Pro Gly Leu Ser Ile Ser Gly
1               5                   10

<210> SEQ ID NO 414
<211> LENGTH: 10
<212> TYPE: PRT
<213> ORGANISM: Artificial sequence
<220> FEATURE:
<223> OTHER INFORMATION: HLA restricted peptide

<400> SEQUENCE: 414

Lys Thr Pro Arg Val Thr Gly Gly Gly Ala
1               5                   10

<210> SEQ ID NO 415
<211> LENGTH: 9
```

```
<212> TYPE: PRT
<213> ORGANISM: Artificial sequence
<220> FEATURE:
<223> OTHER INFORMATION: HLA restricted peptide

<400> SEQUENCE: 415

Lys Val Tyr Leu Glu Ser Phe Cys Glu
1               5

<210> SEQ ID NO 416
<211> LENGTH: 10
<212> TYPE: PRT
<213> ORGANISM: Artificial sequence
<220> FEATURE:
<223> OTHER INFORMATION: HLA restricted peptide

<400> SEQUENCE: 416

Lys Val Tyr Leu Glu Ser Phe Cys Glu Asp
1               5                   10

<210> SEQ ID NO 417
<211> LENGTH: 9
<212> TYPE: PRT
<213> ORGANISM: Artificial sequence
<220> FEATURE:
<223> OTHER INFORMATION: HLA restricted peptide

<400> SEQUENCE: 417

Lys Tyr Gln Glu Phe Phe Trp Asp Ala
1               5

<210> SEQ ID NO 418
<211> LENGTH: 10
<212> TYPE: PRT
<213> ORGANISM: Artificial sequence
<220> FEATURE:
<223> OTHER INFORMATION: HLA restricted peptide

<400> SEQUENCE: 418

Lys Tyr Gln Glu Phe Phe Trp Asp Ala Asn
1               5                   10

<210> SEQ ID NO 419
<211> LENGTH: 9
<212> TYPE: PRT
<213> ORGANISM: Artificial sequence
<220> FEATURE:
<223> OTHER INFORMATION: HLA restricted peptide

<400> SEQUENCE: 419

Leu Ala Arg Asn Leu Val Pro Met Val
1               5

<210> SEQ ID NO 420
<211> LENGTH: 10
<212> TYPE: PRT
<213> ORGANISM: Artificial sequence
<220> FEATURE:
<223> OTHER INFORMATION: HLA restricted peptide

<400> SEQUENCE: 420

Leu Ala Arg Asn Leu Val Pro Met Val Ala
1               5                   10

<210> SEQ ID NO 421
<211> LENGTH: 9
<212> TYPE: PRT
<213> ORGANISM: Artificial sequence
```

<220> FEATURE:
<223> OTHER INFORMATION: HLA restricted peptide

<400> SEQUENCE: 421

Leu Ala Trp Thr Arg Gln Gln Asn Gln
1               5

<210> SEQ ID NO 422
<211> LENGTH: 10
<212> TYPE: PRT
<213> ORGANISM: Artificial sequence
<220> FEATURE:
<223> OTHER INFORMATION: HLA restricted peptide

<400> SEQUENCE: 422

Leu Ala Trp Thr Arg Gln Gln Asn Gln Trp
1               5                   10

<210> SEQ ID NO 423
<211> LENGTH: 9
<212> TYPE: PRT
<213> ORGANISM: Artificial sequence
<220> FEATURE:
<223> OTHER INFORMATION: HLA restricted peptide

<400> SEQUENCE: 423

Leu Cys Pro Lys Asn Met Ile Ile Lys
1               5

<210> SEQ ID NO 424
<211> LENGTH: 9
<212> TYPE: PRT
<213> ORGANISM: Artificial sequence
<220> FEATURE:
<223> OTHER INFORMATION: HLA restricted peptide

<400> SEQUENCE: 424

Leu Cys Pro Lys Ser Ile Pro Gly Leu
1               5

<210> SEQ ID NO 425
<211> LENGTH: 10
<212> TYPE: PRT
<213> ORGANISM: Artificial sequence
<220> FEATURE:
<223> OTHER INFORMATION: HLA restricted peptide

<400> SEQUENCE: 425

Leu Cys Pro Lys Ser Ile Pro Gly Leu Ser
1               5                   10

<210> SEQ ID NO 426
<211> LENGTH: 9
<212> TYPE: PRT
<213> ORGANISM: Artificial sequence
<220> FEATURE:
<223> OTHER INFORMATION: HLA restricted peptide

<400> SEQUENCE: 426

Leu Glu Gly Val Trp Gln Pro Ala Ala
1               5

<210> SEQ ID NO 427
<211> LENGTH: 10
<212> TYPE: PRT
<213> ORGANISM: Artificial sequence
<220> FEATURE:
<223> OTHER INFORMATION: HLA restricted peptide

```
<400> SEQUENCE: 427

Leu Glu Ser Phe Cys Glu Asp Val Pro Ser
1               5                   10

<210> SEQ ID NO 428
<211> LENGTH: 9
<212> TYPE: PRT
<213> ORGANISM: Artificial sequence
<220> FEATURE:
<223> OTHER INFORMATION: HLA restricted peptide

<400> SEQUENCE: 428

Leu Glu Val Gln Ala Ile Arg Glu Thr
1               5

<210> SEQ ID NO 429
<211> LENGTH: 10
<212> TYPE: PRT
<213> ORGANISM: Artificial sequence
<220> FEATURE:
<223> OTHER INFORMATION: HLA restricted peptide

<400> SEQUENCE: 429

Leu Glu Val Gln Ala Ile Arg Glu Thr Val
1               5                   10

<210> SEQ ID NO 430
<211> LENGTH: 9
<212> TYPE: PRT
<213> ORGANISM: Artificial sequence
<220> FEATURE:
<223> OTHER INFORMATION: HLA restricted peptide

<400> SEQUENCE: 430

Leu Glu Tyr Arg His Thr Trp Asp Arg
1               5

<210> SEQ ID NO 431
<211> LENGTH: 10
<212> TYPE: PRT
<213> ORGANISM: Artificial sequence
<220> FEATURE:
<223> OTHER INFORMATION: HLA restricted peptide

<400> SEQUENCE: 431

Leu Glu Tyr Arg His Thr Trp Asp Arg His
1               5                   10

<210> SEQ ID NO 432
<211> LENGTH: 9
<212> TYPE: PRT
<213> ORGANISM: Artificial sequence
<220> FEATURE:
<223> OTHER INFORMATION: HLA restricted peptide

<400> SEQUENCE: 432

Leu Phe Phe Phe Asp Ile Asp Leu Leu
1               5

<210> SEQ ID NO 433
<211> LENGTH: 10
<212> TYPE: PRT
<213> ORGANISM: Artificial sequence
<220> FEATURE:
<223> OTHER INFORMATION: HLA restricted peptide

<400> SEQUENCE: 433
```

Leu Phe Phe Phe Asp Ile Asp Leu Leu Leu
1               5                   10

<210> SEQ ID NO 434
<211> LENGTH: 9
<212> TYPE: PRT
<213> ORGANISM: Artificial sequence
<220> FEATURE:
<223> OTHER INFORMATION: HLA restricted peptide

<400> SEQUENCE: 434

Leu Phe Met His Val Thr Leu Gly Ser
1               5

<210> SEQ ID NO 435
<211> LENGTH: 10
<212> TYPE: PRT
<213> ORGANISM: Artificial sequence
<220> FEATURE:
<223> OTHER INFORMATION: HLA restricted peptide

<400> SEQUENCE: 435

Leu Phe Met His Val Thr Leu Gly Ser Asp
1               5                   10

<210> SEQ ID NO 436
<211> LENGTH: 9
<212> TYPE: PRT
<213> ORGANISM: Artificial sequence
<220> FEATURE:
<223> OTHER INFORMATION: HLA restricted peptide

<400> SEQUENCE: 436

Leu Gly Pro Ile Ser Gly His Val Leu
1               5

<210> SEQ ID NO 437
<211> LENGTH: 10
<212> TYPE: PRT
<213> ORGANISM: Artificial sequence
<220> FEATURE:
<223> OTHER INFORMATION: HLA restricted peptide

<400> SEQUENCE: 437

Leu Gly Pro Ile Ser Gly His Val Leu Lys
1               5                   10

<210> SEQ ID NO 438
<211> LENGTH: 9
<212> TYPE: PRT
<213> ORGANISM: Artificial sequence
<220> FEATURE:
<223> OTHER INFORMATION: HLA restricted peptide

<400> SEQUENCE: 438

Leu Gly Ser Asp Val Glu Glu Asp Leu
1               5

<210> SEQ ID NO 439
<211> LENGTH: 10
<212> TYPE: PRT
<213> ORGANISM: Artificial sequence
<220> FEATURE:
<223> OTHER INFORMATION: HLA restricted peptide

<400> SEQUENCE: 439

Leu Gly Ser Asp Val Glu Glu Asp Leu Thr

```
1               5                   10
```

<210> SEQ ID NO 440
<211> LENGTH: 10
<212> TYPE: PRT
<213> ORGANISM: Artificial sequence
<220> FEATURE:
<223> OTHER INFORMATION: HLA restricted peptide

<400> SEQUENCE: 440

```
Leu Lys Ala Val Phe Ser Arg Gly Asp Thr
1               5                   10
```

<210> SEQ ID NO 441
<211> LENGTH: 9
<212> TYPE: PRT
<213> ORGANISM: Artificial sequence
<220> FEATURE:
<223> OTHER INFORMATION: HLA restricted peptide

<400> SEQUENCE: 441

```
Leu Lys Met Leu Asn Ile Pro Ser Ile
1               5
```

<210> SEQ ID NO 442
<211> LENGTH: 10
<212> TYPE: PRT
<213> ORGANISM: Artificial sequence
<220> FEATURE:
<223> OTHER INFORMATION: HLA restricted peptide

<400> SEQUENCE: 442

```
Leu Lys Met Leu Asn Ile Pro Ser Ile Asn
1               5                   10
```

<210> SEQ ID NO 443
<211> LENGTH: 10
<212> TYPE: PRT
<213> ORGANISM: Artificial sequence
<220> FEATURE:
<223> OTHER INFORMATION: HLA restricted peptide

<400> SEQUENCE: 443

```
Leu Lys Tyr Gln Glu Phe Phe Trp Asp Ala
1               5                   10
```

<210> SEQ ID NO 444
<211> LENGTH: 10
<212> TYPE: PRT
<213> ORGANISM: Artificial sequence
<220> FEATURE:
<223> OTHER INFORMATION: HLA restricted peptide

<400> SEQUENCE: 444

```
Leu Leu Cys Pro Lys Ser Ile Pro Gly Leu
1               5                   10
```

<210> SEQ ID NO 445
<211> LENGTH: 9
<212> TYPE: PRT
<213> ORGANISM: Artificial sequence
<220> FEATURE:
<223> OTHER INFORMATION: HLA restricted peptide

<400> SEQUENCE: 445

```
Leu Leu Leu Gln Arg Gly Pro Gln Tyr
1               5
```

```
<210> SEQ ID NO 446
<211> LENGTH: 10
<212> TYPE: PRT
<213> ORGANISM: Artificial sequence
<220> FEATURE:
<223> OTHER INFORMATION: HLA restricted peptide

<400> SEQUENCE: 446

Leu Leu Leu Gln Arg Gly Pro Gln Tyr Ser
1               5                   10

<210> SEQ ID NO 447
<211> LENGTH: 9
<212> TYPE: PRT
<213> ORGANISM: Artificial sequence
<220> FEATURE:
<223> OTHER INFORMATION: HLA restricted peptide

<400> SEQUENCE: 447

Leu Leu Met Asn Gly Gln Gln Ile Phe
1               5

<210> SEQ ID NO 448
<211> LENGTH: 10
<212> TYPE: PRT
<213> ORGANISM: Artificial sequence
<220> FEATURE:
<223> OTHER INFORMATION: HLA restricted peptide

<400> SEQUENCE: 448

Leu Leu Met Asn Gly Gln Gln Ile Phe Leu
1               5                   10

<210> SEQ ID NO 449
<211> LENGTH: 9
<212> TYPE: PRT
<213> ORGANISM: Artificial sequence
<220> FEATURE:
<223> OTHER INFORMATION: HLA restricted peptide

<400> SEQUENCE: 449

Leu Leu Gln Arg Gly Pro Gln Tyr Ser
1               5

<210> SEQ ID NO 450
<211> LENGTH: 9
<212> TYPE: PRT
<213> ORGANISM: Artificial sequence
<220> FEATURE:
<223> OTHER INFORMATION: HLA restricted peptide

<400> SEQUENCE: 450

Leu Leu Gln Thr Gly Ile His Val Arg
1               5

<210> SEQ ID NO 451
<211> LENGTH: 10
<212> TYPE: PRT
<213> ORGANISM: Artificial sequence
<220> FEATURE:
<223> OTHER INFORMATION: HLA restricted peptide

<400> SEQUENCE: 451

Leu Leu Gln Thr Gly Ile His Val Arg Val
1               5                   10

<210> SEQ ID NO 452
```

```
<211> LENGTH: 9
<212> TYPE: PRT
<213> ORGANISM: Artificial sequence
<220> FEATURE:
<223> OTHER INFORMATION: HLA restricted peptide

<400> SEQUENCE: 452

Leu Met Asn Gly Gln Gln Ile Phe Leu
1               5

<210> SEQ ID NO 453
<211> LENGTH: 9
<212> TYPE: PRT
<213> ORGANISM: Artificial sequence
<220> FEATURE:
<223> OTHER INFORMATION: HLA restricted peptide

<400> SEQUENCE: 453

Leu Asn Ile Pro Ser Ile Asn Val His
1               5

<210> SEQ ID NO 454
<211> LENGTH: 10
<212> TYPE: PRT
<213> ORGANISM: Artificial sequence
<220> FEATURE:
<223> OTHER INFORMATION: HLA restricted peptide

<400> SEQUENCE: 454

Leu Asn Ile Pro Ser Ile Asn Val His His
1               5                   10

<210> SEQ ID NO 455
<211> LENGTH: 9
<212> TYPE: PRT
<213> ORGANISM: Artificial sequence
<220> FEATURE:
<223> OTHER INFORMATION: HLA restricted peptide

<400> SEQUENCE: 455

Leu Pro Gly Pro Cys Ile Ala Ser Thr
1               5

<210> SEQ ID NO 456
<211> LENGTH: 10
<212> TYPE: PRT
<213> ORGANISM: Artificial sequence
<220> FEATURE:
<223> OTHER INFORMATION: HLA restricted peptide

<400> SEQUENCE: 456

Leu Pro Gly Pro Cys Ile Ala Ser Thr Pro
1               5                   10

<210> SEQ ID NO 457
<211> LENGTH: 9
<212> TYPE: PRT
<213> ORGANISM: Artificial sequence
<220> FEATURE:
<223> OTHER INFORMATION: HLA restricted peptide

<400> SEQUENCE: 457

Leu Pro His Glu Thr Arg Leu Leu Gln
1               5

<210> SEQ ID NO 458
<211> LENGTH: 10
<212> TYPE: PRT
```

```
<213> ORGANISM: Artificial sequence
<220> FEATURE:
<223> OTHER INFORMATION: HLA restricted peptide

<400> SEQUENCE: 458

Leu Pro His Glu Thr Arg Leu Leu Gln Thr
1               5                   10

<210> SEQ ID NO 459
<211> LENGTH: 9
<212> TYPE: PRT
<213> ORGANISM: Artificial sequence
<220> FEATURE:
<223> OTHER INFORMATION: HLA restricted peptide

<400> SEQUENCE: 459

Leu Pro Leu Lys Met Leu Asn Ile Pro
1               5

<210> SEQ ID NO 460
<211> LENGTH: 10
<212> TYPE: PRT
<213> ORGANISM: Artificial sequence
<220> FEATURE:
<223> OTHER INFORMATION: HLA restricted peptide

<400> SEQUENCE: 460

Leu Pro Leu Lys Met Leu Asn Ile Pro Ser
1               5                   10

<210> SEQ ID NO 461
<211> LENGTH: 9
<212> TYPE: PRT
<213> ORGANISM: Artificial sequence
<220> FEATURE:
<223> OTHER INFORMATION: HLA restricted peptide

<400> SEQUENCE: 461

Leu Pro Val Ala Asp Ala Val Ile His
1               5

<210> SEQ ID NO 462
<211> LENGTH: 10
<212> TYPE: PRT
<213> ORGANISM: Artificial sequence
<220> FEATURE:
<223> OTHER INFORMATION: HLA restricted peptide

<400> SEQUENCE: 462

Leu Pro Val Ala Asp Ala Val Ile His Ala
1               5                   10

<210> SEQ ID NO 463
<211> LENGTH: 9
<212> TYPE: PRT
<213> ORGANISM: Artificial sequence
<220> FEATURE:
<223> OTHER INFORMATION: HLA restricted peptide

<400> SEQUENCE: 463

Leu Gln Arg Gly Pro Gln Tyr Ser Glu
1               5

<210> SEQ ID NO 464
<211> LENGTH: 10
<212> TYPE: PRT
<213> ORGANISM: Artificial sequence
<220> FEATURE:
```

<223> OTHER INFORMATION: HLA restricted peptide

<400> SEQUENCE: 464

Leu Gln Arg Gly Pro Gln Tyr Ser Glu His
1               5                   10

<210> SEQ ID NO 465
<211> LENGTH: 9
<212> TYPE: PRT
<213> ORGANISM: Artificial sequence
<220> FEATURE:
<223> OTHER INFORMATION: HLA restricted peptide

<400> SEQUENCE: 465

Leu Gln Thr Gly Ile His Val Arg Val
1               5

<210> SEQ ID NO 466
<211> LENGTH: 10
<212> TYPE: PRT
<213> ORGANISM: Artificial sequence
<220> FEATURE:
<223> OTHER INFORMATION: HLA restricted peptide

<400> SEQUENCE: 466

Leu Gln Thr Gly Ile His Val Arg Val Ser
1               5                   10

<210> SEQ ID NO 467
<211> LENGTH: 9
<212> TYPE: PRT
<213> ORGANISM: Artificial sequence
<220> FEATURE:
<223> OTHER INFORMATION: HLA restricted peptide

<400> SEQUENCE: 467

Leu Gln Val Gln His Thr Tyr Phe Thr
1               5

<210> SEQ ID NO 468
<211> LENGTH: 10
<212> TYPE: PRT
<213> ORGANISM: Artificial sequence
<220> FEATURE:
<223> OTHER INFORMATION: HLA restricted peptide

<400> SEQUENCE: 468

Leu Gln Val Gln His Thr Tyr Phe Thr Gly
1               5                   10

<210> SEQ ID NO 469
<211> LENGTH: 9
<212> TYPE: PRT
<213> ORGANISM: Artificial sequence
<220> FEATURE:
<223> OTHER INFORMATION: HLA restricted peptide

<400> SEQUENCE: 469

Leu Arg His Val Val Cys Ala His Glu
1               5

<210> SEQ ID NO 470
<211> LENGTH: 10
<212> TYPE: PRT
<213> ORGANISM: Artificial sequence
<220> FEATURE:
<223> OTHER INFORMATION: HLA restricted peptide

```
<400> SEQUENCE: 470

Leu Arg His Val Val Cys Ala His Glu Leu
1               5                   10

<210> SEQ ID NO 471
<211> LENGTH: 9
<212> TYPE: PRT
<213> ORGANISM: Artificial sequence
<220> FEATURE:
<223> OTHER INFORMATION: HLA restricted peptide

<400> SEQUENCE: 471

Leu Arg Gln Tyr Asp Pro Val Ala Ala
1               5

<210> SEQ ID NO 472
<211> LENGTH: 10
<212> TYPE: PRT
<213> ORGANISM: Artificial sequence
<220> FEATURE:
<223> OTHER INFORMATION: HLA restricted peptide

<400> SEQUENCE: 472

Leu Arg Gln Tyr Asp Pro Val Ala Ala Leu
1               5                   10

<210> SEQ ID NO 473
<211> LENGTH: 9
<212> TYPE: PRT
<213> ORGANISM: Artificial sequence
<220> FEATURE:
<223> OTHER INFORMATION: HLA restricted peptide

<400> SEQUENCE: 473

Leu Ser Ile Ser Gly Asn Leu Leu Met
1               5

<210> SEQ ID NO 474
<211> LENGTH: 10
<212> TYPE: PRT
<213> ORGANISM: Artificial sequence
<220> FEATURE:
<223> OTHER INFORMATION: HLA restricted peptide

<400> SEQUENCE: 474

Leu Ser Ile Ser Gly Asn Leu Leu Met Asn
1               5                   10

<210> SEQ ID NO 475
<211> LENGTH: 10
<212> TYPE: PRT
<213> ORGANISM: Artificial sequence
<220> FEATURE:
<223> OTHER INFORMATION: HLA restricted peptide

<400> SEQUENCE: 475

Leu Thr Met Thr Arg Asn Pro Gln Pro Phe
1               5                   10

<210> SEQ ID NO 476
<211> LENGTH: 9
<212> TYPE: PRT
<213> ORGANISM: Artificial sequence
<220> FEATURE:
<223> OTHER INFORMATION: HLA restricted peptide

<400> SEQUENCE: 476
```

```
Leu Thr Val Ser Gly Leu Ala Trp Thr
1               5
```

```
<210> SEQ ID NO 477
<211> LENGTH: 10
<212> TYPE: PRT
<213> ORGANISM: Artificial sequence
<220> FEATURE:
<223> OTHER INFORMATION: HLA restricted peptide

<400> SEQUENCE: 477

Leu Thr Val Ser Gly Leu Ala Trp Thr Arg
1               5                   10
```

```
<210> SEQ ID NO 478
<211> LENGTH: 9
<212> TYPE: PRT
<213> ORGANISM: Artificial sequence
<220> FEATURE:
<223> OTHER INFORMATION: HLA restricted peptide

<400> SEQUENCE: 478

Leu Val Cys Ser Met Glu Asn Thr Arg
1               5
```

```
<210> SEQ ID NO 479
<211> LENGTH: 10
<212> TYPE: PRT
<213> ORGANISM: Artificial sequence
<220> FEATURE:
<223> OTHER INFORMATION: HLA restricted peptide

<400> SEQUENCE: 479

Leu Val Cys Ser Met Glu Asn Thr Arg Ala
1               5                   10
```

```
<210> SEQ ID NO 480
<211> LENGTH: 9
<212> TYPE: PRT
<213> ORGANISM: Artificial sequence
<220> FEATURE:
<223> OTHER INFORMATION: HLA restricted peptide

<400> SEQUENCE: 480

Leu Val Ser Gln Tyr Thr Pro Asp Ser
1               5
```

```
<210> SEQ ID NO 481
<211> LENGTH: 10
<212> TYPE: PRT
<213> ORGANISM: Artificial sequence
<220> FEATURE:
<223> OTHER INFORMATION: HLA restricted peptide

<400> SEQUENCE: 481

Leu Val Ser Gln Tyr Thr Pro Asp Ser Thr
1               5                   10
```

```
<210> SEQ ID NO 482
<211> LENGTH: 10
<212> TYPE: PRT
<213> ORGANISM: Artificial sequence
<220> FEATURE:
<223> OTHER INFORMATION: HLA restricted peptide

<400> SEQUENCE: 482

Leu Val Thr Thr Glu Arg Lys Thr Pro Arg
1               5                   10
```

<210> SEQ ID NO 483
<211> LENGTH: 10
<212> TYPE: PRT
<213> ORGANISM: Artificial sequence
<220> FEATURE:
<223> OTHER INFORMATION: HLA restricted peptide

<400> SEQUENCE: 483

Met Ala Gly Ala Ser Thr Ser Ala Gly Arg
1               5                   10

<210> SEQ ID NO 484
<211> LENGTH: 9
<212> TYPE: PRT
<213> ORGANISM: Artificial sequence
<220> FEATURE:
<223> OTHER INFORMATION: HLA restricted peptide

<400> SEQUENCE: 484

Met Ala Ser Val Leu Gly Pro Ile Ser
1               5

<210> SEQ ID NO 485
<211> LENGTH: 9
<212> TYPE: PRT
<213> ORGANISM: Artificial sequence
<220> FEATURE:
<223> OTHER INFORMATION: HLA restricted peptide

<400> SEQUENCE: 485

Met Glu Asn Thr Arg Ala Thr Lys Met
1               5

<210> SEQ ID NO 486
<211> LENGTH: 10
<212> TYPE: PRT
<213> ORGANISM: Artificial sequence
<220> FEATURE:
<223> OTHER INFORMATION: HLA restricted peptide

<400> SEQUENCE: 486

Met Glu Asn Thr Arg Ala Thr Lys Met Gln
1               5                   10

<210> SEQ ID NO 487
<211> LENGTH: 9
<212> TYPE: PRT
<213> ORGANISM: Artificial sequence
<220> FEATURE:
<223> OTHER INFORMATION: HLA restricted peptide

<400> SEQUENCE: 487

Met His Val Thr Leu Gly Ser Asp Val
1               5

<210> SEQ ID NO 488
<211> LENGTH: 10
<212> TYPE: PRT
<213> ORGANISM: Artificial sequence
<220> FEATURE:
<223> OTHER INFORMATION: HLA restricted peptide

<400> SEQUENCE: 488

Met Ile Ile Lys Pro Gly Lys Ile Ser His
1               5                   10

```
<210> SEQ ID NO 489
<211> LENGTH: 9
<212> TYPE: PRT
<213> ORGANISM: Artificial sequence
<220> FEATURE:
<223> OTHER INFORMATION: HLA restricted peptide

<400> SEQUENCE: 489

Met Ile Ser Val Leu Gly Pro Ile Ser
1               5

<210> SEQ ID NO 490
<211> LENGTH: 9
<212> TYPE: PRT
<213> ORGANISM: Artificial sequence
<220> FEATURE:
<223> OTHER INFORMATION: HLA restricted peptide

<400> SEQUENCE: 490

Met Leu Asp Val Ala Phe Thr Ser His
1               5

<210> SEQ ID NO 491
<211> LENGTH: 9
<212> TYPE: PRT
<213> ORGANISM: Artificial sequence
<220> FEATURE:
<223> OTHER INFORMATION: HLA restricted peptide

<400> SEQUENCE: 491

Met Leu Asn Ile Pro Ser Ile Asn Val
1               5

<210> SEQ ID NO 492
<211> LENGTH: 10
<212> TYPE: PRT
<213> ORGANISM: Artificial sequence
<220> FEATURE:
<223> OTHER INFORMATION: HLA restricted peptide

<400> SEQUENCE: 492

Met Leu Asn Ile Pro Ser Ile Asn Val His
1               5                   10

<210> SEQ ID NO 493
<211> LENGTH: 10
<212> TYPE: PRT
<213> ORGANISM: Artificial sequence
<220> FEATURE:
<223> OTHER INFORMATION: HLA restricted peptide

<400> SEQUENCE: 493

Met Asn Gly Gln Gln Ile Phe Leu Glu Val
1               5                   10

<210> SEQ ID NO 494
<211> LENGTH: 9
<212> TYPE: PRT
<213> ORGANISM: Artificial sequence
<220> FEATURE:
<223> OTHER INFORMATION: HLA restricted peptide

<400> SEQUENCE: 494

Met Gln Val Ile Gly Asp Gln Tyr Val
1               5

<210> SEQ ID NO 495
<211> LENGTH: 10
```

```
<212> TYPE: PRT
<213> ORGANISM: Artificial sequence
<220> FEATURE:
<223> OTHER INFORMATION: HLA restricted peptide

<400> SEQUENCE: 495

Met Gln Val Ile Gly Asp Gln Tyr Val Lys
1               5                   10

<210> SEQ ID NO 496
<211> LENGTH: 9
<212> TYPE: PRT
<213> ORGANISM: Artificial sequence
<220> FEATURE:
<223> OTHER INFORMATION: HLA restricted peptide

<400> SEQUENCE: 496

Met Arg Pro His Glu Arg Asn Gly Phe
1               5

<210> SEQ ID NO 497
<211> LENGTH: 10
<212> TYPE: PRT
<213> ORGANISM: Artificial sequence
<220> FEATURE:
<223> OTHER INFORMATION: HLA restricted peptide

<400> SEQUENCE: 497

Met Arg Pro His Glu Arg Asn Gly Phe Thr
1               5                   10

<210> SEQ ID NO 498
<211> LENGTH: 10
<212> TYPE: PRT
<213> ORGANISM: Artificial sequence
<220> FEATURE:
<223> OTHER INFORMATION: HLA restricted peptide

<400> SEQUENCE: 498

Met Ser Ile Tyr Val Tyr Ala Leu Pro Leu
1               5                   10

<210> SEQ ID NO 499
<211> LENGTH: 10
<212> TYPE: PRT
<213> ORGANISM: Artificial sequence
<220> FEATURE:
<223> OTHER INFORMATION: HLA restricted peptide

<400> SEQUENCE: 499

Met Thr Arg Gly Arg Leu Lys Ala Glu Ser
1               5                   10

<210> SEQ ID NO 500
<211> LENGTH: 9
<212> TYPE: PRT
<213> ORGANISM: Artificial sequence
<220> FEATURE:
<223> OTHER INFORMATION: HLA restricted peptide

<400> SEQUENCE: 500

Met Thr Arg Asn Pro Gln Pro Phe Met
1               5

<210> SEQ ID NO 501
<211> LENGTH: 10
<212> TYPE: PRT
<213> ORGANISM: Artificial sequence
```

<220> FEATURE:
<223> OTHER INFORMATION: HLA restricted peptide

<400> SEQUENCE: 501

Met Thr Arg Asn Pro Gln Pro Phe Met Arg
1               5                   10

<210> SEQ ID NO 502
<211> LENGTH: 9
<212> TYPE: PRT
<213> ORGANISM: Artificial sequence
<220> FEATURE:
<223> OTHER INFORMATION: HLA restricted peptide

<400> SEQUENCE: 502

Met Val Ala Thr Val Gln Gly Gln Asn
1               5

<210> SEQ ID NO 503
<211> LENGTH: 10
<212> TYPE: PRT
<213> ORGANISM: Artificial sequence
<220> FEATURE:
<223> OTHER INFORMATION: HLA restricted peptide

<400> SEQUENCE: 503

Met Val Ala Thr Val Gln Gly Gln Asn Leu
1               5                   10

<210> SEQ ID NO 504
<211> LENGTH: 10
<212> TYPE: PRT
<213> ORGANISM: Artificial sequence
<220> FEATURE:
<223> OTHER INFORMATION: HLA restricted peptide

<400> SEQUENCE: 504

Asn Asp Ile Tyr Arg Ile Phe Ala Glu Leu
1               5                   10

<210> SEQ ID NO 505
<211> LENGTH: 9
<212> TYPE: PRT
<213> ORGANISM: Artificial sequence
<220> FEATURE:
<223> OTHER INFORMATION: HLA restricted peptide

<400> SEQUENCE: 505

Asn Glu Ile His Asn Pro Ala Val Phe
1               5

<210> SEQ ID NO 506
<211> LENGTH: 10
<212> TYPE: PRT
<213> ORGANISM: Artificial sequence
<220> FEATURE:
<223> OTHER INFORMATION: HLA restricted peptide

<400> SEQUENCE: 506

Asn Glu Ile His Asn Pro Ala Val Phe Thr
1               5                   10

<210> SEQ ID NO 507
<211> LENGTH: 9
<212> TYPE: PRT
<213> ORGANISM: Artificial sequence
<220> FEATURE:
<223> OTHER INFORMATION: HLA restricted peptide

```
<400> SEQUENCE: 507

Asn Gly Phe Thr Val Leu Cys Pro Lys
1               5

<210> SEQ ID NO 508
<211> LENGTH: 10
<212> TYPE: PRT
<213> ORGANISM: Artificial sequence
<220> FEATURE:
<223> OTHER INFORMATION: HLA restricted peptide

<400> SEQUENCE: 508

Asn Gly Phe Thr Val Leu Cys Pro Lys Asn
1               5                   10

<210> SEQ ID NO 509
<211> LENGTH: 9
<212> TYPE: PRT
<213> ORGANISM: Artificial sequence
<220> FEATURE:
<223> OTHER INFORMATION: HLA restricted peptide

<400> SEQUENCE: 509

Asn Gly Gln Gln Ile Phe Leu Glu Val
1               5

<210> SEQ ID NO 510
<211> LENGTH: 9
<212> TYPE: PRT
<213> ORGANISM: Artificial sequence
<220> FEATURE:
<223> OTHER INFORMATION: HLA restricted peptide

<400> SEQUENCE: 510

Asn Ile Pro Ser Ile Asn Val His His
1               5

<210> SEQ ID NO 511
<211> LENGTH: 10
<212> TYPE: PRT
<213> ORGANISM: Artificial sequence
<220> FEATURE:
<223> OTHER INFORMATION: HLA restricted peptide

<400> SEQUENCE: 511

Asn Ile Pro Ser Ile Asn Val His His Tyr
1               5                   10

<210> SEQ ID NO 512
<211> LENGTH: 9
<212> TYPE: PRT
<213> ORGANISM: Artificial sequence
<220> FEATURE:
<223> OTHER INFORMATION: HLA restricted peptide

<400> SEQUENCE: 512

Asn Leu Lys Tyr Gln Glu Phe Phe Trp
1               5

<210> SEQ ID NO 513
<211> LENGTH: 9
<212> TYPE: PRT
<213> ORGANISM: Artificial sequence
<220> FEATURE:
<223> OTHER INFORMATION: HLA restricted peptide

<400> SEQUENCE: 513
```

```
Asn Leu Leu Met Asn Gly Gln Gln Ile
1               5

<210> SEQ ID NO 514
<211> LENGTH: 10
<212> TYPE: PRT
<213> ORGANISM: Artificial sequence
<220> FEATURE:
<223> OTHER INFORMATION: HLA restricted peptide

<400> SEQUENCE: 514

Asn Leu Leu Met Asn Gly Gln Gln Ile Phe
1               5                   10

<210> SEQ ID NO 515
<211> LENGTH: 10
<212> TYPE: PRT
<213> ORGANISM: Artificial sequence
<220> FEATURE:
<223> OTHER INFORMATION: HLA restricted peptide

<400> SEQUENCE: 515

Tyr Tyr Thr Ser Ala Phe Val Phe Pro Thr
1               5                   10

<210> SEQ ID NO 516
<211> LENGTH: 9
<212> TYPE: PRT
<213> ORGANISM: Artificial sequence
<220> FEATURE:
<223> OTHER INFORMATION: HLA restricted peptide

<400> SEQUENCE: 516

Asn Met Ile Ile Lys Pro Gly Lys Ile
1               5

<210> SEQ ID NO 517
<211> LENGTH: 10
<212> TYPE: PRT
<213> ORGANISM: Artificial sequence
<220> FEATURE:
<223> OTHER INFORMATION: HLA restricted peptide

<400> SEQUENCE: 517

Asn Met Ile Ile Lys Pro Gly Lys Ile Ser
1               5                   10

<210> SEQ ID NO 518
<211> LENGTH: 9
<212> TYPE: PRT
<213> ORGANISM: Artificial sequence
<220> FEATURE:
<223> OTHER INFORMATION: HLA restricted peptide

<400> SEQUENCE: 518

Asn Pro Ala Val Phe Thr Trp Pro Pro
1               5

<210> SEQ ID NO 519
<211> LENGTH: 10
<212> TYPE: PRT
<213> ORGANISM: Artificial sequence
<220> FEATURE:
<223> OTHER INFORMATION: HLA restricted peptide

<400> SEQUENCE: 519

Asn Pro Ala Val Phe Thr Trp Pro Pro Trp
```

```
1               5                  10

<210> SEQ ID NO 520
<211> LENGTH: 9
<212> TYPE: PRT
<213> ORGANISM: Artificial sequence
<220> FEATURE:
<223> OTHER INFORMATION: HLA restricted peptide

<400> SEQUENCE: 520

Asn Pro Gln Pro Phe Met Arg Pro His
1               5

<210> SEQ ID NO 521
<211> LENGTH: 10
<212> TYPE: PRT
<213> ORGANISM: Artificial sequence
<220> FEATURE:
<223> OTHER INFORMATION: HLA restricted peptide

<400> SEQUENCE: 521

Asn Pro Gln Pro Phe Met Arg Pro His Glu
1               5                  10

<210> SEQ ID NO 522
<211> LENGTH: 9
<212> TYPE: PRT
<213> ORGANISM: Artificial sequence
<220> FEATURE:
<223> OTHER INFORMATION: HLA restricted peptide

<400> SEQUENCE: 522

Asn Pro Thr Gly Arg Ser Ile Cys Pro
1               5

<210> SEQ ID NO 523
<211> LENGTH: 10
<212> TYPE: PRT
<213> ORGANISM: Artificial sequence
<220> FEATURE:
<223> OTHER INFORMATION: HLA restricted peptide

<400> SEQUENCE: 523

Asn Pro Thr Gly Arg Ser Ile Cys Pro Ser
1               5                  10

<210> SEQ ID NO 524
<211> LENGTH: 9
<212> TYPE: PRT
<213> ORGANISM: Artificial sequence
<220> FEATURE:
<223> OTHER INFORMATION: HLA restricted peptide

<400> SEQUENCE: 524

Asn Gln Leu Gln Val Gln His Thr Tyr
1               5

<210> SEQ ID NO 525
<211> LENGTH: 10
<212> TYPE: PRT
<213> ORGANISM: Artificial sequence
<220> FEATURE:
<223> OTHER INFORMATION: HLA restricted peptide

<400> SEQUENCE: 525

Asn Gln Leu Gln Val Gln His Thr Tyr Phe
1               5                  10
```

```
<210> SEQ ID NO 526
<211> LENGTH: 9
<212> TYPE: PRT
<213> ORGANISM: Artificial sequence
<220> FEATURE:
<223> OTHER INFORMATION: HLA restricted peptide

<400> SEQUENCE: 526

Asn Gln Trp Lys Glu Pro Asp Val Tyr
1               5

<210> SEQ ID NO 527
<211> LENGTH: 10
<212> TYPE: PRT
<213> ORGANISM: Artificial sequence
<220> FEATURE:
<223> OTHER INFORMATION: HLA restricted peptide

<400> SEQUENCE: 527

Asn Gln Trp Lys Glu Pro Asp Val Tyr Tyr
1               5                   10

<210> SEQ ID NO 528
<211> LENGTH: 9
<212> TYPE: PRT
<213> ORGANISM: Artificial sequence
<220> FEATURE:
<223> OTHER INFORMATION: HLA restricted peptide

<400> SEQUENCE: 528

Asn Thr Arg Ala Thr Lys Met Gln Val
1               5

<210> SEQ ID NO 529
<211> LENGTH: 10
<212> TYPE: PRT
<213> ORGANISM: Artificial sequence
<220> FEATURE:
<223> OTHER INFORMATION: HLA restricted peptide

<400> SEQUENCE: 529

Asn Thr Arg Ala Thr Lys Met Gln Val Ile
1               5                   10

<210> SEQ ID NO 530
<211> LENGTH: 9
<212> TYPE: PRT
<213> ORGANISM: Artificial sequence
<220> FEATURE:
<223> OTHER INFORMATION: HLA restricted peptide

<400> SEQUENCE: 530

Asn Val His His Tyr Pro Ser Ala Ala
1               5

<210> SEQ ID NO 531
<211> LENGTH: 9
<212> TYPE: PRT
<213> ORGANISM: Artificial sequence
<220> FEATURE:
<223> OTHER INFORMATION: HLA restricted peptide

<400> SEQUENCE: 531

Asn Val His Asn Pro Thr Gly Arg Ser
1               5

<210> SEQ ID NO 532
```

```
<211> LENGTH: 10
<212> TYPE: PRT
<213> ORGANISM: Artificial sequence
<220> FEATURE:
<223> OTHER INFORMATION: HLA restricted peptide

<400> SEQUENCE: 532

Asn Val His Asn Pro Thr Gly Arg Ser Ile
1               5                   10

<210> SEQ ID NO 533
<211> LENGTH: 10
<212> TYPE: PRT
<213> ORGANISM: Artificial sequence
<220> FEATURE:
<223> OTHER INFORMATION: HLA restricted peptide

<400> SEQUENCE: 533

Asn Val Ser Val Asn Val His Asn Pro Thr
1               5                   10

<210> SEQ ID NO 534
<211> LENGTH: 9
<212> TYPE: PRT
<213> ORGANISM: Artificial sequence
<220> FEATURE:
<223> OTHER INFORMATION: HLA restricted peptide

<400> SEQUENCE: 534

Pro Ala Ala Gln Pro Lys Arg Arg Arg
1               5

<210> SEQ ID NO 535
<211> LENGTH: 9
<212> TYPE: PRT
<213> ORGANISM: Artificial sequence
<220> FEATURE:
<223> OTHER INFORMATION: HLA restricted peptide

<400> SEQUENCE: 535

Pro Ala Val Phe Thr Trp Pro Pro Trp
1               5

<210> SEQ ID NO 536
<211> LENGTH: 9
<212> TYPE: PRT
<213> ORGANISM: Artificial sequence
<220> FEATURE:
<223> OTHER INFORMATION: HLA restricted peptide

<400> SEQUENCE: 536

Pro Cys His Arg Gly Asp Asn Gln Leu
1               5

<210> SEQ ID NO 537
<211> LENGTH: 9
<212> TYPE: PRT
<213> ORGANISM: Artificial sequence
<220> FEATURE:
<223> OTHER INFORMATION: HLA restricted peptide

<400> SEQUENCE: 537

Pro Cys Ile Ala Ser Thr Pro Lys Lys
1               5

<210> SEQ ID NO 538
<211> LENGTH: 9
<212> TYPE: PRT
```

<213> ORGANISM: Artificial sequence
<220> FEATURE:
<223> OTHER INFORMATION: HLA restricted peptide

<400> SEQUENCE: 538

Pro Asp Val Tyr Tyr Thr Ser Ala Phe
1               5

<210> SEQ ID NO 539
<211> LENGTH: 10
<212> TYPE: PRT
<213> ORGANISM: Artificial sequence
<220> FEATURE:
<223> OTHER INFORMATION: HLA restricted peptide

<400> SEQUENCE: 539

Pro Asp Val Tyr Tyr Thr Ser Ala Phe Val
1               5                   10

<210> SEQ ID NO 540
<211> LENGTH: 10
<212> TYPE: PRT
<213> ORGANISM: Artificial sequence
<220> FEATURE:
<223> OTHER INFORMATION: HLA restricted peptide

<400> SEQUENCE: 540

Pro Glu Met Ile Ser Val Leu Gly Pro Ile
1               5                   10

<210> SEQ ID NO 541
<211> LENGTH: 9
<212> TYPE: PRT
<213> ORGANISM: Artificial sequence
<220> FEATURE:
<223> OTHER INFORMATION: HLA restricted peptide

<400> SEQUENCE: 541

Pro Gly Lys Ile Ser His Ile Met Leu
1               5

<210> SEQ ID NO 542
<211> LENGTH: 9
<212> TYPE: PRT
<213> ORGANISM: Artificial sequence
<220> FEATURE:
<223> OTHER INFORMATION: HLA restricted peptide

<400> SEQUENCE: 542

Pro Gly Leu Ser Ile Ser Gly Asn Leu
1               5

<210> SEQ ID NO 543
<211> LENGTH: 10
<212> TYPE: PRT
<213> ORGANISM: Artificial sequence
<220> FEATURE:
<223> OTHER INFORMATION: HLA restricted peptide

<400> SEQUENCE: 543

Pro Gly Leu Ser Ile Ser Gly Asn Leu Leu
1               5                   10

<210> SEQ ID NO 544
<211> LENGTH: 9
<212> TYPE: PRT
<213> ORGANISM: Artificial sequence
<220> FEATURE:

<223> OTHER INFORMATION: HLA restricted peptide

<400> SEQUENCE: 544

Pro His Glu Arg Asn Gly Phe Thr Val
1               5

<210> SEQ ID NO 545
<211> LENGTH: 10
<212> TYPE: PRT
<213> ORGANISM: Artificial sequence
<220> FEATURE:
<223> OTHER INFORMATION: HLA restricted peptide

<400> SEQUENCE: 545

Pro His Glu Arg Asn Gly Phe Thr Val Leu
1               5                   10

<210> SEQ ID NO 546
<211> LENGTH: 9
<212> TYPE: PRT
<213> ORGANISM: Artificial sequence
<220> FEATURE:
<223> OTHER INFORMATION: HLA restricted peptide

<400> SEQUENCE: 546

Pro His Glu Thr Arg Leu Leu Gln Thr
1               5

<210> SEQ ID NO 547
<211> LENGTH: 9
<212> TYPE: PRT
<213> ORGANISM: Artificial sequence
<220> FEATURE:
<223> OTHER INFORMATION: HLA restricted peptide

<400> SEQUENCE: 547

Pro Met Ser Ile Tyr Val Tyr Ala Leu
1               5

<210> SEQ ID NO 548
<211> LENGTH: 9
<212> TYPE: PRT
<213> ORGANISM: Artificial sequence
<220> FEATURE:
<223> OTHER INFORMATION: HLA restricted peptide

<400> SEQUENCE: 548

Pro Pro Trp Gln Ala Gly Ile Leu Ala
1               5

<210> SEQ ID NO 549
<211> LENGTH: 10
<212> TYPE: PRT
<213> ORGANISM: Artificial sequence
<220> FEATURE:
<223> OTHER INFORMATION: HLA restricted peptide

<400> SEQUENCE: 549

Pro Pro Trp Gln Ala Gly Ile Leu Ala Arg
1               5                   10

<210> SEQ ID NO 550
<211> LENGTH: 10
<212> TYPE: PRT
<213> ORGANISM: Artificial sequence
<220> FEATURE:
<223> OTHER INFORMATION: HLA restricted peptide -continued

```
<400> SEQUENCE: 550

Pro Gln Pro Phe Met Arg Pro His Glu Arg
1               5                   10

<210> SEQ ID NO 551
<211> LENGTH: 9
<212> TYPE: PRT
<213> ORGANISM: Artificial sequence
<220> FEATURE:
<223> OTHER INFORMATION: HLA restricted peptide

<400> SEQUENCE: 551

Pro Gln Tyr Ser Glu His Pro Thr Phe
1               5

<210> SEQ ID NO 552
<211> LENGTH: 10
<212> TYPE: PRT
<213> ORGANISM: Artificial sequence
<220> FEATURE:
<223> OTHER INFORMATION: HLA restricted peptide

<400> SEQUENCE: 552

Pro Gln Tyr Ser Glu His Pro Thr Phe Thr
1               5                   10

<210> SEQ ID NO 553
<211> LENGTH: 9
<212> TYPE: PRT
<213> ORGANISM: Artificial sequence
<220> FEATURE:
<223> OTHER INFORMATION: HLA restricted peptide

<400> SEQUENCE: 553

Pro Arg Val Thr Gly Gly Gly Ala Met
1               5

<210> SEQ ID NO 554
<211> LENGTH: 10
<212> TYPE: PRT
<213> ORGANISM: Artificial sequence
<220> FEATURE:
<223> OTHER INFORMATION: HLA restricted peptide

<400> SEQUENCE: 554

Pro Arg Val Thr Gly Gly Gly Ala Met Ala
1               5                   10

<210> SEQ ID NO 555
<211> LENGTH: 9
<212> TYPE: PRT
<213> ORGANISM: Artificial sequence
<220> FEATURE:
<223> OTHER INFORMATION: HLA restricted peptide

<400> SEQUENCE: 555

Pro Ser Ala Ala Glu Arg Lys His Arg
1               5

<210> SEQ ID NO 556
<211> LENGTH: 9
<212> TYPE: PRT
<213> ORGANISM: Artificial sequence
<220> FEATURE:
<223> OTHER INFORMATION: HLA restricted peptide

<400> SEQUENCE: 556
```

```
Pro Ser Leu Ile Leu Val Ser Gln Tyr
1               5
```

<210> SEQ ID NO 557
<211> LENGTH: 9
<212> TYPE: PRT
<213> ORGANISM: Artificial sequence
<220> FEATURE:
<223> OTHER INFORMATION: HLA restricted peptide

<400> SEQUENCE: 557

```
Pro Ser Gln Glu Pro Met Ser Ile Tyr
1               5
```

<210> SEQ ID NO 558
<211> LENGTH: 9
<212> TYPE: PRT
<213> ORGANISM: Artificial sequence
<220> FEATURE:
<223> OTHER INFORMATION: HLA restricted peptide

<400> SEQUENCE: 558

```
Pro Thr Phe Thr Ser Gln Tyr Arg Ile
1               5
```

<210> SEQ ID NO 559
<211> LENGTH: 9
<212> TYPE: PRT
<213> ORGANISM: Artificial sequence
<220> FEATURE:
<223> OTHER INFORMATION: HLA restricted peptide

<400> SEQUENCE: 559

```
Pro Val Ala Asp Ala Val Ile His Ala
1               5
```

<210> SEQ ID NO 560
<211> LENGTH: 9
<212> TYPE: PRT
<213> ORGANISM: Artificial sequence
<220> FEATURE:
<223> OTHER INFORMATION: HLA restricted peptide

<400> SEQUENCE: 560

```
Pro Val Leu Pro His Glu Thr Arg Leu
1               5
```

<210> SEQ ID NO 561
<211> LENGTH: 10
<212> TYPE: PRT
<213> ORGANISM: Artificial sequence
<220> FEATURE:
<223> OTHER INFORMATION: HLA restricted peptide

<400> SEQUENCE: 561

```
Pro Val Leu Pro His Glu Thr Arg Leu Leu
1               5                   10
```

<210> SEQ ID NO 562
<211> LENGTH: 9
<212> TYPE: PRT
<213> ORGANISM: Artificial sequence
<220> FEATURE:
<223> OTHER INFORMATION: HLA restricted peptide

<400> SEQUENCE: 562

```
Gln Ala Gly Ile Leu Ala Arg Asn Leu
1               5
```

<210> SEQ ID NO 563
<211> LENGTH: 10
<212> TYPE: PRT
<213> ORGANISM: Artificial sequence
<220> FEATURE:
<223> OTHER INFORMATION: HLA restricted peptide

<400> SEQUENCE: 563

Gln Ala Gly Ile Leu Ala Arg Asn Leu Val
1               5                   10

<210> SEQ ID NO 564
<211> LENGTH: 9
<212> TYPE: PRT
<213> ORGANISM: Artificial sequence
<220> FEATURE:
<223> OTHER INFORMATION: HLA restricted peptide

<400> SEQUENCE: 564

Gln Ala Ile Arg Glu Thr Val Glu Leu
1               5

<210> SEQ ID NO 565
<211> LENGTH: 10
<212> TYPE: PRT
<213> ORGANISM: Artificial sequence
<220> FEATURE:
<223> OTHER INFORMATION: HLA restricted peptide

<400> SEQUENCE: 565

Gln Ala Ile Arg Glu Thr Val Glu Leu Arg
1               5                   10

<210> SEQ ID NO 566
<211> LENGTH: 9
<212> TYPE: PRT
<213> ORGANISM: Artificial sequence
<220> FEATURE:
<223> OTHER INFORMATION: HLA restricted peptide

<400> SEQUENCE: 566

Gln Ala Arg Leu Thr Val Ser Gly Leu
1               5

<210> SEQ ID NO 567
<211> LENGTH: 10
<212> TYPE: PRT
<213> ORGANISM: Artificial sequence
<220> FEATURE:
<223> OTHER INFORMATION: HLA restricted peptide

<400> SEQUENCE: 567

Gln Ala Arg Leu Thr Val Ser Gly Leu Ala
1               5                   10

<210> SEQ ID NO 568
<211> LENGTH: 9
<212> TYPE: PRT
<213> ORGANISM: Artificial sequence
<220> FEATURE:
<223> OTHER INFORMATION: HLA restricted peptide

<400> SEQUENCE: 568

Gln Asp Ala Leu Pro Gly Pro Cys Ile
1               5

```
<210> SEQ ID NO 569
<211> LENGTH: 10
<212> TYPE: PRT
<213> ORGANISM: Artificial sequence
<220> FEATURE:
<223> OTHER INFORMATION: HLA restricted peptide

<400> SEQUENCE: 569

Gln Asp Ala Leu Pro Gly Pro Cys Ile Ala
1               5                   10

<210> SEQ ID NO 570
<211> LENGTH: 9
<212> TYPE: PRT
<213> ORGANISM: Artificial sequence
<220> FEATURE:
<223> OTHER INFORMATION: HLA restricted peptide

<400> SEQUENCE: 570

Gln Glu Phe Phe Trp Asp Ala Asn Asp
1               5

<210> SEQ ID NO 571
<211> LENGTH: 10
<212> TYPE: PRT
<213> ORGANISM: Artificial sequence
<220> FEATURE:
<223> OTHER INFORMATION: HLA restricted peptide

<400> SEQUENCE: 571

Gln Glu Phe Phe Trp Asp Ala Asn Asp Ile
1               5                   10

<210> SEQ ID NO 572
<211> LENGTH: 9
<212> TYPE: PRT
<213> ORGANISM: Artificial sequence
<220> FEATURE:
<223> OTHER INFORMATION: HLA restricted peptide

<400> SEQUENCE: 572

Gln Glu Pro Met Ser Ile Tyr Val Tyr
1               5

<210> SEQ ID NO 573
<211> LENGTH: 10
<212> TYPE: PRT
<213> ORGANISM: Artificial sequence
<220> FEATURE:
<223> OTHER INFORMATION: HLA restricted peptide

<400> SEQUENCE: 573

Gln Glu Pro Met Ser Ile Tyr Val Tyr Ala
1               5                   10

<210> SEQ ID NO 574
<211> LENGTH: 9
<212> TYPE: PRT
<213> ORGANISM: Artificial sequence
<220> FEATURE:
<223> OTHER INFORMATION: HLA restricted peptide

<400> SEQUENCE: 574

Gln Gly Asp Asp Asp Val Trp Thr Ser
1               5

<210> SEQ ID NO 575
<211> LENGTH: 9
```

```
<212> TYPE: PRT
<213> ORGANISM: Artificial sequence
<220> FEATURE:
<223> OTHER INFORMATION: HLA restricted peptide

<400> SEQUENCE: 575

Gln Gly Lys Leu Glu Tyr Arg His Thr
1               5

<210> SEQ ID NO 576
<211> LENGTH: 10
<212> TYPE: PRT
<213> ORGANISM: Artificial sequence
<220> FEATURE:
<223> OTHER INFORMATION: HLA restricted peptide

<400> SEQUENCE: 576

Gln Gly Lys Leu Glu Tyr Arg His Thr Trp
1               5                   10

<210> SEQ ID NO 577
<211> LENGTH: 10
<212> TYPE: PRT
<213> ORGANISM: Artificial sequence
<220> FEATURE:
<223> OTHER INFORMATION: HLA restricted peptide

<400> SEQUENCE: 577

Gln Gly Gln Asn Leu Lys Tyr Gln Glu Phe
1               5                   10

<210> SEQ ID NO 578
<211> LENGTH: 10
<212> TYPE: PRT
<213> ORGANISM: Artificial sequence
<220> FEATURE:
<223> OTHER INFORMATION: HLA restricted peptide

<400> SEQUENCE: 578

Gln His Thr Tyr Phe Thr Gly Ser Glu Val
1               5                   10

<210> SEQ ID NO 579
<211> LENGTH: 9
<212> TYPE: PRT
<213> ORGANISM: Artificial sequence
<220> FEATURE:
<223> OTHER INFORMATION: HLA restricted peptide

<400> SEQUENCE: 579

Gln Ile Phe Leu Glu Val Gln Ala Ile
1               5

<210> SEQ ID NO 580
<211> LENGTH: 10
<212> TYPE: PRT
<213> ORGANISM: Artificial sequence
<220> FEATURE:
<223> OTHER INFORMATION: HLA restricted peptide

<400> SEQUENCE: 580

Gln Ile Phe Leu Glu Val Gln Ala Ile Arg
1               5                   10

<210> SEQ ID NO 581
<211> LENGTH: 9
<212> TYPE: PRT
<213> ORGANISM: Artificial sequence
```

```
<220> FEATURE:
<223> OTHER INFORMATION: HLA restricted peptide

<400> SEQUENCE: 581

Gln Leu Gln Val Gln His Thr Tyr Phe
1               5

<210> SEQ ID NO 582
<211> LENGTH: 10
<212> TYPE: PRT
<213> ORGANISM: Artificial sequence
<220> FEATURE:
<223> OTHER INFORMATION: HLA restricted peptide

<400> SEQUENCE: 582

Gln Leu Gln Val Gln His Thr Tyr Phe Thr
1               5                   10

<210> SEQ ID NO 583
<211> LENGTH: 9
<212> TYPE: PRT
<213> ORGANISM: Artificial sequence
<220> FEATURE:
<223> OTHER INFORMATION: HLA restricted peptide

<400> SEQUENCE: 583

Gln Met Trp Gln Ala Arg Leu Thr Val
1               5

<210> SEQ ID NO 584
<211> LENGTH: 10
<212> TYPE: PRT
<213> ORGANISM: Artificial sequence
<220> FEATURE:
<223> OTHER INFORMATION: HLA restricted peptide

<400> SEQUENCE: 584

Gln Met Trp Gln Ala Arg Leu Thr Val Ser
1               5                   10

<210> SEQ ID NO 585
<211> LENGTH: 9
<212> TYPE: PRT
<213> ORGANISM: Artificial sequence
<220> FEATURE:
<223> OTHER INFORMATION: HLA restricted peptide

<400> SEQUENCE: 585

Gln Asn Leu Lys Tyr Gln Glu Phe Phe
1               5

<210> SEQ ID NO 586
<211> LENGTH: 10
<212> TYPE: PRT
<213> ORGANISM: Artificial sequence
<220> FEATURE:
<223> OTHER INFORMATION: HLA restricted peptide

<400> SEQUENCE: 586

Gln Asn Leu Lys Tyr Gln Glu Phe Phe Trp
1               5                   10

<210> SEQ ID NO 587
<211> LENGTH: 9
<212> TYPE: PRT
<213> ORGANISM: Artificial sequence
<220> FEATURE:
<223> OTHER INFORMATION: HLA restricted peptide
```

<400> SEQUENCE: 587

Gln Asn Gln Trp Lys Glu Pro Asp Val
1               5

<210> SEQ ID NO 588
<211> LENGTH: 10
<212> TYPE: PRT
<213> ORGANISM: Artificial sequence
<220> FEATURE:
<223> OTHER INFORMATION: HLA restricted peptide

<400> SEQUENCE: 588

Gln Asn Gln Trp Lys Glu Pro Asp Val Tyr
1               5                   10

<210> SEQ ID NO 589
<211> LENGTH: 9
<212> TYPE: PRT
<213> ORGANISM: Artificial sequence
<220> FEATURE:
<223> OTHER INFORMATION: HLA restricted peptide

<400> SEQUENCE: 589

Gln Pro Ala Ala Gln Pro Lys Arg Arg
1               5

<210> SEQ ID NO 590
<211> LENGTH: 10
<212> TYPE: PRT
<213> ORGANISM: Artificial sequence
<220> FEATURE:
<223> OTHER INFORMATION: HLA restricted peptide

<400> SEQUENCE: 590

Gln Pro Ala Ala Gln Pro Lys Arg Arg Arg
1               5                   10

<210> SEQ ID NO 591
<211> LENGTH: 9
<212> TYPE: PRT
<213> ORGANISM: Artificial sequence
<220> FEATURE:
<223> OTHER INFORMATION: HLA restricted peptide

<400> SEQUENCE: 591

Gln Pro Phe Met Arg Pro His Glu Arg
1               5

<210> SEQ ID NO 592
<211> LENGTH: 10
<212> TYPE: PRT
<213> ORGANISM: Artificial sequence
<220> FEATURE:
<223> OTHER INFORMATION: HLA restricted peptide

<400> SEQUENCE: 592

Gln Pro Phe Met Arg Pro His Glu Arg Asn
1               5                   10

<210> SEQ ID NO 593
<211> LENGTH: 9
<212> TYPE: PRT
<213> ORGANISM: Artificial sequence
<220> FEATURE:
<223> OTHER INFORMATION: HLA restricted peptide

<400> SEQUENCE: 593

```
Gln Pro Lys Arg Arg Arg His Arg Gln
1               5
```

<210> SEQ ID NO 594
<211> LENGTH: 10
<212> TYPE: PRT
<213> ORGANISM: Artificial sequence
<220> FEATURE:
<223> OTHER INFORMATION: HLA restricted peptide

<400> SEQUENCE: 594

```
Gln Pro Lys Arg Arg Arg His Arg Gln Asp
1               5                   10
```

<210> SEQ ID NO 595
<211> LENGTH: 9
<212> TYPE: PRT
<213> ORGANISM: Artificial sequence
<220> FEATURE:
<223> OTHER INFORMATION: HLA restricted peptide

<400> SEQUENCE: 595

```
Gln Pro Ser Leu Ile Leu Val Ser Gln
1               5
```

<210> SEQ ID NO 596
<211> LENGTH: 10
<212> TYPE: PRT
<213> ORGANISM: Artificial sequence
<220> FEATURE:
<223> OTHER INFORMATION: HLA restricted peptide

<400> SEQUENCE: 596

```
Gln Pro Ser Leu Ile Leu Val Ser Gln Tyr
1               5                   10
```

<210> SEQ ID NO 597
<211> LENGTH: 9
<212> TYPE: PRT
<213> ORGANISM: Artificial sequence
<220> FEATURE:
<223> OTHER INFORMATION: HLA restricted peptide

<400> SEQUENCE: 597

```
Gln Gln Ile Phe Leu Glu Val Gln Ala
1               5
```

<210> SEQ ID NO 598
<211> LENGTH: 10
<212> TYPE: PRT
<213> ORGANISM: Artificial sequence
<220> FEATURE:
<223> OTHER INFORMATION: HLA restricted peptide

<400> SEQUENCE: 598

```
Gln Gln Ile Phe Leu Glu Val Gln Ala Ile
1               5                   10
```

<210> SEQ ID NO 599
<211> LENGTH: 9
<212> TYPE: PRT
<213> ORGANISM: Artificial sequence
<220> FEATURE:
<223> OTHER INFORMATION: HLA restricted peptide

<400> SEQUENCE: 599

```
Gln Gln Asn Gln Trp Lys Glu Pro Asp
```

<210> SEQ ID NO 600
<211> LENGTH: 10
<212> TYPE: PRT
<213> ORGANISM: Artificial sequence
<220> FEATURE:
<223> OTHER INFORMATION: HLA restricted peptide

<400> SEQUENCE: 600

Gln Gln Asn Gln Trp Lys Glu Pro Asp Val
1               5                   10

<210> SEQ ID NO 601
<211> LENGTH: 9
<212> TYPE: PRT
<213> ORGANISM: Artificial sequence
<220> FEATURE:
<223> OTHER INFORMATION: HLA restricted peptide

<400> SEQUENCE: 601

Gln Arg Gly Pro Gln Tyr Ser Glu His
1               5

<210> SEQ ID NO 602
<211> LENGTH: 10
<212> TYPE: PRT
<213> ORGANISM: Artificial sequence
<220> FEATURE:
<223> OTHER INFORMATION: HLA restricted peptide

<400> SEQUENCE: 602

Gln Arg Gly Pro Gln Tyr Ser Glu His Pro
1               5                   10

<210> SEQ ID NO 603
<211> LENGTH: 9
<212> TYPE: PRT
<213> ORGANISM: Artificial sequence
<220> FEATURE:
<223> OTHER INFORMATION: HLA restricted peptide

<400> SEQUENCE: 603

Gln Val Ile Gly Asp Gln Tyr Val Lys
1               5

<210> SEQ ID NO 604
<211> LENGTH: 10
<212> TYPE: PRT
<213> ORGANISM: Artificial sequence
<220> FEATURE:
<223> OTHER INFORMATION: HLA restricted peptide

<400> SEQUENCE: 604

Gln Val Ile Gly Asp Gln Tyr Val Lys Val
1               5                   10

<210> SEQ ID NO 605
<211> LENGTH: 10
<212> TYPE: PRT
<213> ORGANISM: Artificial sequence
<220> FEATURE:
<223> OTHER INFORMATION: HLA restricted peptide

<400> SEQUENCE: 605

Gln Val Gln His Thr Tyr Phe Thr Gly Ser
1               5                   10

```
<210> SEQ ID NO 606
<211> LENGTH: 9
<212> TYPE: PRT
<213> ORGANISM: Artificial sequence
<220> FEATURE:
<223> OTHER INFORMATION: HLA restricted peptide

<400> SEQUENCE: 606

Gln Trp Lys Glu Pro Asp Val Tyr Tyr
1               5

<210> SEQ ID NO 607
<211> LENGTH: 10
<212> TYPE: PRT
<213> ORGANISM: Artificial sequence
<220> FEATURE:
<223> OTHER INFORMATION: HLA restricted peptide

<400> SEQUENCE: 607

Gln Trp Lys Glu Pro Asp Val Tyr Tyr Thr
1               5                   10

<210> SEQ ID NO 608
<211> LENGTH: 9
<212> TYPE: PRT
<213> ORGANISM: Artificial sequence
<220> FEATURE:
<223> OTHER INFORMATION: HLA restricted peptide

<400> SEQUENCE: 608

Gln Tyr Asp Pro Val Ala Ala Leu Phe
1               5

<210> SEQ ID NO 609
<211> LENGTH: 10
<212> TYPE: PRT
<213> ORGANISM: Artificial sequence
<220> FEATURE:
<223> OTHER INFORMATION: HLA restricted peptide

<400> SEQUENCE: 609

Gln Tyr Asp Pro Val Ala Ala Leu Phe Phe
1               5                   10

<210> SEQ ID NO 610
<211> LENGTH: 10
<212> TYPE: PRT
<213> ORGANISM: Artificial sequence
<220> FEATURE:
<223> OTHER INFORMATION: HLA restricted peptide

<400> SEQUENCE: 610

Gln Tyr Arg Ile Gln Gly Lys Leu Glu Tyr
1               5                   10

<210> SEQ ID NO 611
<211> LENGTH: 9
<212> TYPE: PRT
<213> ORGANISM: Artificial sequence
<220> FEATURE:
<223> OTHER INFORMATION: HLA restricted peptide

<400> SEQUENCE: 611

Gln Tyr Ser Glu His Pro Thr Phe Thr
1               5

<210> SEQ ID NO 612
```

```
<211> LENGTH: 10
<212> TYPE: PRT
<213> ORGANISM: Artificial sequence
<220> FEATURE:
<223> OTHER INFORMATION: HLA restricted peptide

<400> SEQUENCE: 612

Gln Tyr Ser Glu His Pro Thr Phe Thr Ser
1               5                   10

<210> SEQ ID NO 613
<211> LENGTH: 9
<212> TYPE: PRT
<213> ORGANISM: Artificial sequence
<220> FEATURE:
<223> OTHER INFORMATION: HLA restricted peptide

<400> SEQUENCE: 613

Gln Tyr Thr Pro Asp Ser Thr Pro Cys
1               5

<210> SEQ ID NO 614
<211> LENGTH: 9
<212> TYPE: PRT
<213> ORGANISM: Artificial sequence
<220> FEATURE:
<223> OTHER INFORMATION: HLA restricted peptide

<400> SEQUENCE: 614

Gln Tyr Val Lys Val Tyr Leu Glu Ser
1               5

<210> SEQ ID NO 615
<211> LENGTH: 10
<212> TYPE: PRT
<213> ORGANISM: Artificial sequence
<220> FEATURE:
<223> OTHER INFORMATION: HLA restricted peptide

<400> SEQUENCE: 615

Gln Tyr Val Lys Val Tyr Leu Glu Ser Phe
1               5                   10

<210> SEQ ID NO 616
<211> LENGTH: 9
<212> TYPE: PRT
<213> ORGANISM: Artificial sequence
<220> FEATURE:
<223> OTHER INFORMATION: HLA restricted peptide

<400> SEQUENCE: 616

Arg Cys Pro Glu Met Ile Ser Val Leu
1               5

<210> SEQ ID NO 617
<211> LENGTH: 9
<212> TYPE: PRT
<213> ORGANISM: Artificial sequence
<220> FEATURE:
<223> OTHER INFORMATION: HLA restricted peptide

<400> SEQUENCE: 617

Arg Glu Thr Val Glu Leu Arg Gln Tyr
1               5

<210> SEQ ID NO 618
<211> LENGTH: 9
<212> TYPE: PRT
```

<213> ORGANISM: Artificial sequence
<220> FEATURE:
<223> OTHER INFORMATION: HLA restricted peptide

<400> SEQUENCE: 618

Arg Gly Asp Asn Gln Leu Gln Val Gln
1               5

<210> SEQ ID NO 619
<211> LENGTH: 10
<212> TYPE: PRT
<213> ORGANISM: Artificial sequence
<220> FEATURE:
<223> OTHER INFORMATION: HLA restricted peptide

<400> SEQUENCE: 619

Arg Gly Asp Asn Gln Leu Gln Val Gln His
1               5                   10

<210> SEQ ID NO 620
<211> LENGTH: 9
<212> TYPE: PRT
<213> ORGANISM: Artificial sequence
<220> FEATURE:
<223> OTHER INFORMATION: HLA restricted peptide

<400> SEQUENCE: 620

Arg Gly Asp Thr Pro Val Leu Pro His
1               5

<210> SEQ ID NO 621
<211> LENGTH: 10
<212> TYPE: PRT
<213> ORGANISM: Artificial sequence
<220> FEATURE:
<223> OTHER INFORMATION: HLA restricted peptide

<400> SEQUENCE: 621

Arg Gly Pro Gln Tyr Ser Glu His Pro Thr
1               5                   10

<210> SEQ ID NO 622
<211> LENGTH: 9
<212> TYPE: PRT
<213> ORGANISM: Artificial sequence
<220> FEATURE:
<223> OTHER INFORMATION: HLA restricted peptide

<400> SEQUENCE: 622

Arg Gly Arg Leu Lys Ala Glu Ser Thr
1               5

<210> SEQ ID NO 623
<211> LENGTH: 10
<212> TYPE: PRT
<213> ORGANISM: Artificial sequence
<220> FEATURE:
<223> OTHER INFORMATION: HLA restricted peptide

<400> SEQUENCE: 623

Arg Gly Arg Leu Lys Ala Glu Ser Thr Val
1               5                   10

<210> SEQ ID NO 624
<211> LENGTH: 9
<212> TYPE: PRT
<213> ORGANISM: Artificial sequence
<220> FEATURE:

<223> OTHER INFORMATION: HLA restricted peptide

<400> SEQUENCE: 624

Arg Gly Arg Arg Cys Pro Glu Met Ile
1               5

<210> SEQ ID NO 625
<211> LENGTH: 10
<212> TYPE: PRT
<213> ORGANISM: Artificial sequence
<220> FEATURE:
<223> OTHER INFORMATION: HLA restricted peptide

<400> SEQUENCE: 625

Arg Gly Arg Arg Cys Pro Glu Met Ile Ser
1               5                   10

<210> SEQ ID NO 626
<211> LENGTH: 9
<212> TYPE: PRT
<213> ORGANISM: Artificial sequence
<220> FEATURE:
<223> OTHER INFORMATION: HLA restricted peptide

<400> SEQUENCE: 626

Arg His Asp Glu Gly Ala Ala Gln Gly
1               5

<210> SEQ ID NO 627
<211> LENGTH: 10
<212> TYPE: PRT
<213> ORGANISM: Artificial sequence
<220> FEATURE:
<223> OTHER INFORMATION: HLA restricted peptide

<400> SEQUENCE: 627

Arg His Asp Glu Gly Ala Ala Gln Gly Asp
1               5                   10

<210> SEQ ID NO 628
<211> LENGTH: 9
<212> TYPE: PRT
<213> ORGANISM: Artificial sequence
<220> FEATURE:
<223> OTHER INFORMATION: HLA restricted peptide

<400> SEQUENCE: 628

Arg His Leu Pro Val Ala Asp Ala Val
1               5

<210> SEQ ID NO 629
<211> LENGTH: 10
<212> TYPE: PRT
<213> ORGANISM: Artificial sequence
<220> FEATURE:
<223> OTHER INFORMATION: HLA restricted peptide

<400> SEQUENCE: 629

Arg His Leu Pro Val Ala Asp Ala Val Ile
1               5                   10

<210> SEQ ID NO 630
<211> LENGTH: 9
<212> TYPE: PRT
<213> ORGANISM: Artificial sequence
<220> FEATURE:
<223> OTHER INFORMATION: HLA restricted peptide

```
<400> SEQUENCE: 630

Arg His Val Val Cys Ala His Glu Leu
1               5

<210> SEQ ID NO 631
<211> LENGTH: 10
<212> TYPE: PRT
<213> ORGANISM: Artificial sequence
<220> FEATURE:
<223> OTHER INFORMATION: HLA restricted peptide

<400> SEQUENCE: 631

Arg His Val Val Cys Ala His Glu Leu Val
1               5                   10

<210> SEQ ID NO 632
<211> LENGTH: 9
<212> TYPE: PRT
<213> ORGANISM: Artificial sequence
<220> FEATURE:
<223> OTHER INFORMATION: HLA restricted peptide

<400> SEQUENCE: 632

Arg Ile Phe Ala Glu Leu Glu Gly Val
1               5

<210> SEQ ID NO 633
<211> LENGTH: 10
<212> TYPE: PRT
<213> ORGANISM: Artificial sequence
<220> FEATURE:
<223> OTHER INFORMATION: HLA restricted peptide

<400> SEQUENCE: 633

Arg Ile Phe Ala Glu Leu Glu Gly Val Trp
1               5                   10

<210> SEQ ID NO 634
<211> LENGTH: 9
<212> TYPE: PRT
<213> ORGANISM: Artificial sequence
<220> FEATURE:
<223> OTHER INFORMATION: HLA restricted peptide

<400> SEQUENCE: 634

Arg Ile Gln Gly Lys Leu Glu Tyr Arg
1               5

<210> SEQ ID NO 635
<211> LENGTH: 10
<212> TYPE: PRT
<213> ORGANISM: Artificial sequence
<220> FEATURE:
<223> OTHER INFORMATION: HLA restricted peptide

<400> SEQUENCE: 635

Arg Ile Gln Gly Lys Leu Glu Tyr Arg His
1               5                   10

<210> SEQ ID NO 636
<211> LENGTH: 9
<212> TYPE: PRT
<213> ORGANISM: Artificial sequence
<220> FEATURE:
<223> OTHER INFORMATION: HLA restricted peptide

<400> SEQUENCE: 636
```

Arg Lys His Arg His Leu Pro Val Ala
1               5

<210> SEQ ID NO 637
<211> LENGTH: 9
<212> TYPE: PRT
<213> ORGANISM: Artificial sequence
<220> FEATURE:
<223> OTHER INFORMATION: HLA restricted peptide

<400> SEQUENCE: 637

Arg Lys Ser Ala Ser Ser Ala Thr Ala
1               5

<210> SEQ ID NO 638
<211> LENGTH: 10
<212> TYPE: PRT
<213> ORGANISM: Artificial sequence
<220> FEATURE:
<223> OTHER INFORMATION: HLA restricted peptide

<400> SEQUENCE: 638

Arg Lys Ser Ala Ser Ser Ala Thr Ala Cys
1               5                   10

<210> SEQ ID NO 639
<211> LENGTH: 9
<212> TYPE: PRT
<213> ORGANISM: Artificial sequence
<220> FEATURE:
<223> OTHER INFORMATION: HLA restricted peptide

<400> SEQUENCE: 639

Arg Leu Lys Ala Glu Ser Thr Val Ala
1               5

<210> SEQ ID NO 640
<211> LENGTH: 9
<212> TYPE: PRT
<213> ORGANISM: Artificial sequence
<220> FEATURE:
<223> OTHER INFORMATION: HLA restricted peptide

<400> SEQUENCE: 640

Arg Leu Leu Gln Thr Gly Ile His Val
1               5

<210> SEQ ID NO 641
<211> LENGTH: 10
<212> TYPE: PRT
<213> ORGANISM: Artificial sequence
<220> FEATURE:
<223> OTHER INFORMATION: HLA restricted peptide

<400> SEQUENCE: 641

Arg Leu Leu Gln Thr Gly Ile His Val Arg
1               5                   10

<210> SEQ ID NO 642
<211> LENGTH: 9
<212> TYPE: PRT
<213> ORGANISM: Artificial sequence
<220> FEATURE:
<223> OTHER INFORMATION: HLA restricted peptide

<400> SEQUENCE: 642

Arg Leu Thr Val Ser Gly Leu Ala Trp
1               5

```
<210> SEQ ID NO 643
<211> LENGTH: 10
<212> TYPE: PRT
<213> ORGANISM: Artificial sequence
<220> FEATURE:
<223> OTHER INFORMATION: HLA restricted peptide

<400> SEQUENCE: 643

Arg Leu Thr Val Ser Gly Leu Ala Trp Thr
1               5                   10

<210> SEQ ID NO 644
<211> LENGTH: 10
<212> TYPE: PRT
<213> ORGANISM: Artificial sequence
<220> FEATURE:
<223> OTHER INFORMATION: HLA restricted peptide

<400> SEQUENCE: 644

Arg Asn Gly Phe Thr Val Leu Cys Pro Lys
1               5                   10

<210> SEQ ID NO 645
<211> LENGTH: 9
<212> TYPE: PRT
<213> ORGANISM: Artificial sequence
<220> FEATURE:
<223> OTHER INFORMATION: HLA restricted peptide

<400> SEQUENCE: 645

Arg Asn Leu Val Pro Met Val Ala Thr
1               5

<210> SEQ ID NO 646
<211> LENGTH: 10
<212> TYPE: PRT
<213> ORGANISM: Artificial sequence
<220> FEATURE:
<223> OTHER INFORMATION: HLA restricted peptide

<400> SEQUENCE: 646

Arg Asn Leu Val Pro Met Val Ala Thr Val
1               5                   10

<210> SEQ ID NO 647
<211> LENGTH: 10
<212> TYPE: PRT
<213> ORGANISM: Artificial sequence
<220> FEATURE:
<223> OTHER INFORMATION: HLA restricted peptide

<400> SEQUENCE: 647

Arg Asn Pro Gln Pro Phe Met Arg Pro His
1               5                   10

<210> SEQ ID NO 648
<211> LENGTH: 9
<212> TYPE: PRT
<213> ORGANISM: Artificial sequence
<220> FEATURE:
<223> OTHER INFORMATION: HLA restricted peptide

<400> SEQUENCE: 648

Arg Pro His Glu Arg Asn Gly Phe Thr
1               5
```

```
<210> SEQ ID NO 649
<211> LENGTH: 10
<212> TYPE: PRT
<213> ORGANISM: Artificial sequence
<220> FEATURE:
<223> OTHER INFORMATION: HLA restricted peptide

<400> SEQUENCE: 649

Arg Pro His Glu Arg Asn Gly Phe Thr Val
1               5                   10

<210> SEQ ID NO 650
<211> LENGTH: 9
<212> TYPE: PRT
<213> ORGANISM: Artificial sequence
<220> FEATURE:
<223> OTHER INFORMATION: HLA restricted peptide

<400> SEQUENCE: 650

Arg Gln Asp Ala Leu Pro Gly Pro Cys
1               5

<210> SEQ ID NO 651
<211> LENGTH: 10
<212> TYPE: PRT
<213> ORGANISM: Artificial sequence
<220> FEATURE:
<223> OTHER INFORMATION: HLA restricted peptide

<400> SEQUENCE: 651

Arg Gln Asp Ala Leu Pro Gly Pro Cys Ile
1               5                   10

<210> SEQ ID NO 652
<211> LENGTH: 9
<212> TYPE: PRT
<213> ORGANISM: Artificial sequence
<220> FEATURE:
<223> OTHER INFORMATION: HLA restricted peptide

<400> SEQUENCE: 652

Arg Gln Gln Asn Gln Trp Lys Glu Pro
1               5

<210> SEQ ID NO 653
<211> LENGTH: 10
<212> TYPE: PRT
<213> ORGANISM: Artificial sequence
<220> FEATURE:
<223> OTHER INFORMATION: HLA restricted peptide

<400> SEQUENCE: 653

Arg Gln Gln Asn Gln Trp Lys Glu Pro Asp
1               5                   10

<210> SEQ ID NO 654
<211> LENGTH: 9
<212> TYPE: PRT
<213> ORGANISM: Artificial sequence
<220> FEATURE:
<223> OTHER INFORMATION: HLA restricted peptide

<400> SEQUENCE: 654

Arg Gln Tyr Asp Pro Val Ala Ala Leu
1               5

<210> SEQ ID NO 655
<211> LENGTH: 10
```

```
<212> TYPE: PRT
<213> ORGANISM: Artificial sequence
<220> FEATURE:
<223> OTHER INFORMATION: HLA restricted peptide

<400> SEQUENCE: 655

Arg Gln Tyr Asp Pro Val Ala Ala Leu Phe
1               5                   10

<210> SEQ ID NO 656
<211> LENGTH: 9
<212> TYPE: PRT
<213> ORGANISM: Artificial sequence
<220> FEATURE:
<223> OTHER INFORMATION: HLA restricted peptide

<400> SEQUENCE: 656

Arg Arg Cys Pro Glu Met Ile Ser Val
1               5

<210> SEQ ID NO 657
<211> LENGTH: 10
<212> TYPE: PRT
<213> ORGANISM: Artificial sequence
<220> FEATURE:
<223> OTHER INFORMATION: HLA restricted peptide

<400> SEQUENCE: 657

Arg Arg Cys Pro Glu Met Ile Ser Val Leu
1               5                   10

<210> SEQ ID NO 658
<211> LENGTH: 9
<212> TYPE: PRT
<213> ORGANISM: Artificial sequence
<220> FEATURE:
<223> OTHER INFORMATION: HLA restricted peptide

<400> SEQUENCE: 658

Arg Arg His Arg Gln Asp Ala Leu Pro
1               5

<210> SEQ ID NO 659
<211> LENGTH: 10
<212> TYPE: PRT
<213> ORGANISM: Artificial sequence
<220> FEATURE:
<223> OTHER INFORMATION: HLA restricted peptide

<400> SEQUENCE: 659

Arg Arg His Arg Gln Asp Ala Leu Pro Gly
1               5                   10

<210> SEQ ID NO 660
<211> LENGTH: 9
<212> TYPE: PRT
<213> ORGANISM: Artificial sequence
<220> FEATURE:
<223> OTHER INFORMATION: HLA restricted peptide

<400> SEQUENCE: 660

Arg Arg Arg His Arg Gln Asp Ala Leu
1               5

<210> SEQ ID NO 661
<211> LENGTH: 10
<212> TYPE: PRT
<213> ORGANISM: Artificial sequence
```

<220> FEATURE:
<223> OTHER INFORMATION: HLA restricted peptide

<400> SEQUENCE: 661

Arg Arg Arg His Arg Gln Asp Ala Leu Pro
1               5                   10

<210> SEQ ID NO 662
<211> LENGTH: 10
<212> TYPE: PRT
<213> ORGANISM: Artificial sequence
<220> FEATURE:
<223> OTHER INFORMATION: HLA restricted peptide

<400> SEQUENCE: 662

Arg Ser Ile Cys Pro Ser Gln Glu Pro Met
1               5                   10

<210> SEQ ID NO 663
<211> LENGTH: 9
<212> TYPE: PRT
<213> ORGANISM: Artificial sequence
<220> FEATURE:
<223> OTHER INFORMATION: HLA restricted peptide

<400> SEQUENCE: 663

Arg Val Ser Gln Pro Ser Leu Ile Leu
1               5

<210> SEQ ID NO 664
<211> LENGTH: 10
<212> TYPE: PRT
<213> ORGANISM: Artificial sequence
<220> FEATURE:
<223> OTHER INFORMATION: HLA restricted peptide

<400> SEQUENCE: 664

Arg Val Ser Gln Pro Ser Leu Ile Leu Val
1               5                   10

<210> SEQ ID NO 665
<211> LENGTH: 9
<212> TYPE: PRT
<213> ORGANISM: Artificial sequence
<220> FEATURE:
<223> OTHER INFORMATION: HLA restricted peptide

<400> SEQUENCE: 665

Arg Val Thr Gly Gly Gly Ala Met Ala
1               5

<210> SEQ ID NO 666
<211> LENGTH: 9
<212> TYPE: PRT
<213> ORGANISM: Artificial sequence
<220> FEATURE:
<223> OTHER INFORMATION: HLA restricted peptide

<400> SEQUENCE: 666

Ser Ala Ala Glu Arg Lys His Arg His
1               5

<210> SEQ ID NO 667
<211> LENGTH: 10
<212> TYPE: PRT
<213> ORGANISM: Artificial sequence
<220> FEATURE:
<223> OTHER INFORMATION: HLA restricted peptide

```
<400> SEQUENCE: 667

Ser Ala Ala Glu Arg Lys His Arg His Leu
1               5                   10

<210> SEQ ID NO 668
<211> LENGTH: 9
<212> TYPE: PRT
<213> ORGANISM: Artificial sequence
<220> FEATURE:
<223> OTHER INFORMATION: HLA restricted peptide

<400> SEQUENCE: 668

Ser Ala Phe Val Phe Pro Thr Lys Asp
1               5

<210> SEQ ID NO 669
<211> LENGTH: 10
<212> TYPE: PRT
<213> ORGANISM: Artificial sequence
<220> FEATURE:
<223> OTHER INFORMATION: HLA restricted peptide

<400> SEQUENCE: 669

Ser Ala Phe Val Phe Pro Thr Lys Asp Val
1               5                   10

<210> SEQ ID NO 670
<211> LENGTH: 9
<212> TYPE: PRT
<213> ORGANISM: Artificial sequence
<220> FEATURE:
<223> OTHER INFORMATION: HLA restricted peptide

<400> SEQUENCE: 670

Ser Ala Gly Arg Lys Arg Lys Ser Ala
1               5

<210> SEQ ID NO 671
<211> LENGTH: 10
<212> TYPE: PRT
<213> ORGANISM: Artificial sequence
<220> FEATURE:
<223> OTHER INFORMATION: HLA restricted peptide

<400> SEQUENCE: 671

Ser Ala Gly Arg Lys Arg Lys Ser Ala Ser
1               5                   10

<210> SEQ ID NO 672
<211> LENGTH: 9
<212> TYPE: PRT
<213> ORGANISM: Artificial sequence
<220> FEATURE:
<223> OTHER INFORMATION: HLA restricted peptide

<400> SEQUENCE: 672

Ser Ala Ser Ser Ala Thr Ala Cys Thr
1               5

<210> SEQ ID NO 673
<211> LENGTH: 10
<212> TYPE: PRT
<213> ORGANISM: Artificial sequence
<220> FEATURE:
<223> OTHER INFORMATION: HLA restricted peptide

<400> SEQUENCE: 673
```

Ser Ala Ser Ser Ala Thr Ala Cys Thr Ala
1               5                   10

<210> SEQ ID NO 674
<211> LENGTH: 10
<212> TYPE: PRT
<213> ORGANISM: Artificial sequence
<220> FEATURE:
<223> OTHER INFORMATION: HLA restricted peptide

<400> SEQUENCE: 674

Ser Ala Ser Ser Ala Thr Ala Cys Thr Ser
1               5                   10

<210> SEQ ID NO 675
<211> LENGTH: 9
<212> TYPE: PRT
<213> ORGANISM: Artificial sequence
<220> FEATURE:
<223> OTHER INFORMATION: HLA restricted peptide

<400> SEQUENCE: 675

Ser Ala Thr Ala Cys Thr Ala Gly Val
1               5

<210> SEQ ID NO 676
<211> LENGTH: 10
<212> TYPE: PRT
<213> ORGANISM: Artificial sequence
<220> FEATURE:
<223> OTHER INFORMATION: HLA restricted peptide

<400> SEQUENCE: 676

Ser Ala Thr Ala Cys Thr Ala Gly Val Met
1               5                   10

<210> SEQ ID NO 677
<211> LENGTH: 9
<212> TYPE: PRT
<213> ORGANISM: Artificial sequence
<220> FEATURE:
<223> OTHER INFORMATION: HLA restricted peptide

<400> SEQUENCE: 677

Ser Ala Thr Ala Cys Thr Ser Gly Val
1               5

<210> SEQ ID NO 678
<211> LENGTH: 10
<212> TYPE: PRT
<213> ORGANISM: Artificial sequence
<220> FEATURE:
<223> OTHER INFORMATION: HLA restricted peptide

<400> SEQUENCE: 678

Ser Ala Thr Ala Cys Thr Ser Gly Val Met
1               5                   10

<210> SEQ ID NO 679
<211> LENGTH: 9
<212> TYPE: PRT
<213> ORGANISM: Artificial sequence
<220> FEATURE:
<223> OTHER INFORMATION: HLA restricted peptide

<400> SEQUENCE: 679

Ser Asp Asn Glu Ile His Asn Pro Ala

```
<210> SEQ ID NO 680
<211> LENGTH: 10
<212> TYPE: PRT
<213> ORGANISM: Artificial sequence
<220> FEATURE:
<223> OTHER INFORMATION: HLA restricted peptide

<400> SEQUENCE: 680

Ser Asp Asn Glu Ile His Asn Pro Ala Val
1               5                   10

<210> SEQ ID NO 681
<211> LENGTH: 9
<212> TYPE: PRT
<213> ORGANISM: Artificial sequence
<220> FEATURE:
<223> OTHER INFORMATION: HLA restricted peptide

<400> SEQUENCE: 681

Ser Asp Ser Asp Glu Glu Leu Val Thr
1               5

<210> SEQ ID NO 682
<211> LENGTH: 10
<212> TYPE: PRT
<213> ORGANISM: Artificial sequence
<220> FEATURE:
<223> OTHER INFORMATION: HLA restricted peptide

<400> SEQUENCE: 682

Ser Asp Ser Asp Glu Glu Leu Val Thr Thr
1               5                   10

<210> SEQ ID NO 683
<211> LENGTH: 9
<212> TYPE: PRT
<213> ORGANISM: Artificial sequence
<220> FEATURE:
<223> OTHER INFORMATION: HLA restricted peptide

<400> SEQUENCE: 683

Ser Asp Val Glu Glu Asp Leu Thr Met
1               5

<210> SEQ ID NO 684
<211> LENGTH: 10
<212> TYPE: PRT
<213> ORGANISM: Artificial sequence
<220> FEATURE:
<223> OTHER INFORMATION: HLA restricted peptide

<400> SEQUENCE: 684

Ser Asp Val Glu Glu Asp Leu Thr Met Thr
1               5                   10

<210> SEQ ID NO 685
<211> LENGTH: 9
<212> TYPE: PRT
<213> ORGANISM: Artificial sequence
<220> FEATURE:
<223> OTHER INFORMATION: HLA restricted peptide

<400> SEQUENCE: 685

Ser Glu His Pro Thr Phe Thr Ser Gln
1               5
```

```
<210> SEQ ID NO 686
<211> LENGTH: 10
<212> TYPE: PRT
<213> ORGANISM: Artificial sequence
<220> FEATURE:
<223> OTHER INFORMATION: HLA restricted peptide

<400> SEQUENCE: 686

Ser Glu His Pro Thr Phe Thr Ser Gln Tyr
1               5                   10

<210> SEQ ID NO 687
<211> LENGTH: 9
<212> TYPE: PRT
<213> ORGANISM: Artificial sequence
<220> FEATURE:
<223> OTHER INFORMATION: HLA restricted peptide

<400> SEQUENCE: 687

Ser Glu Val Glu Asn Val Ser Val Asn
1               5

<210> SEQ ID NO 688
<211> LENGTH: 10
<212> TYPE: PRT
<213> ORGANISM: Artificial sequence
<220> FEATURE:
<223> OTHER INFORMATION: HLA restricted peptide

<400> SEQUENCE: 688

Ser Glu Val Glu Asn Val Ser Val Asn Val
1               5                   10

<210> SEQ ID NO 689
<211> LENGTH: 9
<212> TYPE: PRT
<213> ORGANISM: Artificial sequence
<220> FEATURE:
<223> OTHER INFORMATION: HLA restricted peptide

<400> SEQUENCE: 689

Ser Phe Cys Glu Asp Val Pro Ser Gly
1               5

<210> SEQ ID NO 690
<211> LENGTH: 10
<212> TYPE: PRT
<213> ORGANISM: Artificial sequence
<220> FEATURE:
<223> OTHER INFORMATION: HLA restricted peptide

<400> SEQUENCE: 690

Ser Phe Cys Glu Asp Val Pro Ser Gly Lys
1               5                   10

<210> SEQ ID NO 691
<211> LENGTH: 9
<212> TYPE: PRT
<213> ORGANISM: Artificial sequence
<220> FEATURE:
<223> OTHER INFORMATION: HLA restricted peptide

<400> SEQUENCE: 691

Ser Gly His Val Leu Lys Ala Val Phe
1               5

<210> SEQ ID NO 692
```

```
<211> LENGTH: 10
<212> TYPE: PRT
<213> ORGANISM: Artificial sequence
<220> FEATURE:
<223> OTHER INFORMATION: HLA restricted peptide

<400> SEQUENCE: 692

Ser Gly His Val Leu Lys Ala Val Phe Ser
1               5                   10

<210> SEQ ID NO 693
<211> LENGTH: 9
<212> TYPE: PRT
<213> ORGANISM: Artificial sequence
<220> FEATURE:
<223> OTHER INFORMATION: HLA restricted peptide

<400> SEQUENCE: 693

Ser Gly Lys Leu Phe Met His Val Thr
1               5

<210> SEQ ID NO 694
<211> LENGTH: 10
<212> TYPE: PRT
<213> ORGANISM: Artificial sequence
<220> FEATURE:
<223> OTHER INFORMATION: HLA restricted peptide

<400> SEQUENCE: 694

Ser Gly Lys Leu Phe Met His Val Thr Leu
1               5                   10

<210> SEQ ID NO 695
<211> LENGTH: 9
<212> TYPE: PRT
<213> ORGANISM: Artificial sequence
<220> FEATURE:
<223> OTHER INFORMATION: HLA restricted peptide

<400> SEQUENCE: 695

Ser Gly Lys Gln Met Trp Gln Ala Arg
1               5

<210> SEQ ID NO 696
<211> LENGTH: 10
<212> TYPE: PRT
<213> ORGANISM: Artificial sequence
<220> FEATURE:
<223> OTHER INFORMATION: HLA restricted peptide

<400> SEQUENCE: 696

Ser Gly Lys Gln Met Trp Gln Ala Arg Leu
1               5                   10

<210> SEQ ID NO 697
<211> LENGTH: 10
<212> TYPE: PRT
<213> ORGANISM: Artificial sequence
<220> FEATURE:
<223> OTHER INFORMATION: HLA restricted peptide

<400> SEQUENCE: 697

Ser Gly Leu Ala Trp Thr Arg Gln Gln Asn
1               5                   10

<210> SEQ ID NO 698
<211> LENGTH: 9
<212> TYPE: PRT
```

<213> ORGANISM: Artificial sequence
<220> FEATURE:
<223> OTHER INFORMATION: HLA restricted peptide

<400> SEQUENCE: 698

Ser Gly Ser Asp Ser Asp Glu Glu Leu
1               5

<210> SEQ ID NO 699
<211> LENGTH: 10
<212> TYPE: PRT
<213> ORGANISM: Artificial sequence
<220> FEATURE:
<223> OTHER INFORMATION: HLA restricted peptide

<400> SEQUENCE: 699

Ser Gly Ser Asp Ser Asp Glu Glu Leu Val
1               5                   10

<210> SEQ ID NO 700
<211> LENGTH: 9
<212> TYPE: PRT
<213> ORGANISM: Artificial sequence
<220> FEATURE:
<223> OTHER INFORMATION: HLA restricted peptide

<400> SEQUENCE: 700

Ser Gly Val Met Thr Arg Gly Arg Leu
1               5

<210> SEQ ID NO 701
<211> LENGTH: 10
<212> TYPE: PRT
<213> ORGANISM: Artificial sequence
<220> FEATURE:
<223> OTHER INFORMATION: HLA restricted peptide

<400> SEQUENCE: 701

Ser Gly Val Met Thr Arg Gly Arg Leu Lys
1               5                   10

<210> SEQ ID NO 702
<211> LENGTH: 9
<212> TYPE: PRT
<213> ORGANISM: Artificial sequence
<220> FEATURE:
<223> OTHER INFORMATION: HLA restricted peptide

<400> SEQUENCE: 702

Ser His Glu His Phe Gly Leu Leu Cys
1               5

<210> SEQ ID NO 703
<211> LENGTH: 10
<212> TYPE: PRT
<213> ORGANISM: Artificial sequence
<220> FEATURE:
<223> OTHER INFORMATION: HLA restricted peptide

<400> SEQUENCE: 703

Ser His Glu His Phe Gly Leu Leu Cys Pro
1               5                   10

<210> SEQ ID NO 704
<211> LENGTH: 9
<212> TYPE: PRT
<213> ORGANISM: Artificial sequence
<220> FEATURE:

<223> OTHER INFORMATION: HLA restricted peptide

<400> SEQUENCE: 704

Ser His Ile Met Leu Asp Val Ala Phe
1               5

<210> SEQ ID NO 705
<211> LENGTH: 10
<212> TYPE: PRT
<213> ORGANISM: Artificial sequence
<220> FEATURE:
<223> OTHER INFORMATION: HLA restricted peptide

<400> SEQUENCE: 705

Ser His Ile Met Leu Asp Val Ala Phe Thr
1               5                   10

<210> SEQ ID NO 706
<211> LENGTH: 9
<212> TYPE: PRT
<213> ORGANISM: Artificial sequence
<220> FEATURE:
<223> OTHER INFORMATION: HLA restricted peptide

<400> SEQUENCE: 706

Ser Ile Cys Pro Ser Gln Glu Pro Met
1               5

<210> SEQ ID NO 707
<211> LENGTH: 10
<212> TYPE: PRT
<213> ORGANISM: Artificial sequence
<220> FEATURE:
<223> OTHER INFORMATION: HLA restricted peptide

<400> SEQUENCE: 707

Ser Ile Cys Pro Ser Gln Glu Pro Met Ser
1               5                   10

<210> SEQ ID NO 708
<211> LENGTH: 9
<212> TYPE: PRT
<213> ORGANISM: Artificial sequence
<220> FEATURE:
<223> OTHER INFORMATION: HLA restricted peptide

<400> SEQUENCE: 708

Ser Ile Asn Val His His Tyr Pro Ser
1               5

<210> SEQ ID NO 709
<211> LENGTH: 10
<212> TYPE: PRT
<213> ORGANISM: Artificial sequence
<220> FEATURE:
<223> OTHER INFORMATION: HLA restricted peptide

<400> SEQUENCE: 709

Ser Ile Asn Val His His Tyr Pro Ser Ala
1               5                   10

<210> SEQ ID NO 710
<211> LENGTH: 10
<212> TYPE: PRT
<213> ORGANISM: Artificial sequence
<220> FEATURE:
<223> OTHER INFORMATION: HLA restricted peptide -continued

```
<400> SEQUENCE: 710

Ser Ile Pro Gly Leu Ser Ile Ser Gly Asn
1               5                   10

<210> SEQ ID NO 711
<211> LENGTH: 9
<212> TYPE: PRT
<213> ORGANISM: Artificial sequence
<220> FEATURE:
<223> OTHER INFORMATION: HLA restricted peptide

<400> SEQUENCE: 711

Ser Ile Ser Gly Asn Leu Leu Met Asn
1               5

<210> SEQ ID NO 712
<211> LENGTH: 9
<212> TYPE: PRT
<213> ORGANISM: Artificial sequence
<220> FEATURE:
<223> OTHER INFORMATION: HLA restricted peptide

<400> SEQUENCE: 712

Ser Ile Tyr Val Tyr Ala Leu Pro Leu
1               5

<210> SEQ ID NO 713
<211> LENGTH: 10
<212> TYPE: PRT
<213> ORGANISM: Artificial sequence
<220> FEATURE:
<223> OTHER INFORMATION: HLA restricted peptide

<400> SEQUENCE: 713

Ser Ile Tyr Val Tyr Ala Leu Pro Leu Lys
1               5                   10

<210> SEQ ID NO 714
<211> LENGTH: 9
<212> TYPE: PRT
<213> ORGANISM: Artificial sequence
<220> FEATURE:
<223> OTHER INFORMATION: HLA restricted peptide

<400> SEQUENCE: 714

Ser Leu Ile Leu Val Ser Gln Tyr Thr
1               5

<210> SEQ ID NO 715
<211> LENGTH: 9
<212> TYPE: PRT
<213> ORGANISM: Artificial sequence
<220> FEATURE:
<223> OTHER INFORMATION: HLA restricted peptide

<400> SEQUENCE: 715

Ser Met Glu Asn Thr Arg Ala Thr Lys
1               5

<210> SEQ ID NO 716
<211> LENGTH: 10
<212> TYPE: PRT
<213> ORGANISM: Artificial sequence
<220> FEATURE:
<223> OTHER INFORMATION: HLA restricted peptide

<400> SEQUENCE: 716
```

Ser Met Glu Asn Thr Arg Ala Thr Lys Met
1               5                   10

<210> SEQ ID NO 717
<211> LENGTH: 9
<212> TYPE: PRT
<213> ORGANISM: Artificial sequence
<220> FEATURE:
<223> OTHER INFORMATION: HLA restricted peptide

<400> SEQUENCE: 717

Ser Gln Glu Pro Met Ser Ile Tyr Val
1               5

<210> SEQ ID NO 718
<211> LENGTH: 10
<212> TYPE: PRT
<213> ORGANISM: Artificial sequence
<220> FEATURE:
<223> OTHER INFORMATION: HLA restricted peptide

<400> SEQUENCE: 718

Ser Gln Glu Pro Met Ser Ile Tyr Val Tyr
1               5                   10

<210> SEQ ID NO 719
<211> LENGTH: 9
<212> TYPE: PRT
<213> ORGANISM: Artificial sequence
<220> FEATURE:
<223> OTHER INFORMATION: HLA restricted peptide

<400> SEQUENCE: 719

Ser Gln Pro Ser Leu Ile Leu Val Ser
1               5

<210> SEQ ID NO 720
<211> LENGTH: 10
<212> TYPE: PRT
<213> ORGANISM: Artificial sequence
<220> FEATURE:
<223> OTHER INFORMATION: HLA restricted peptide

<400> SEQUENCE: 720

Ser Gln Pro Ser Leu Ile Leu Val Ser Gln
1               5                   10

<210> SEQ ID NO 721
<211> LENGTH: 9
<212> TYPE: PRT
<213> ORGANISM: Artificial sequence
<220> FEATURE:
<223> OTHER INFORMATION: HLA restricted peptide

<400> SEQUENCE: 721

Ser Gln Tyr Arg Ile Gln Gly Lys Leu
1               5

<210> SEQ ID NO 722
<211> LENGTH: 10
<212> TYPE: PRT
<213> ORGANISM: Artificial sequence
<220> FEATURE:
<223> OTHER INFORMATION: HLA restricted peptide

<400> SEQUENCE: 722

Ser Gln Tyr Arg Ile Gln Gly Lys Leu Glu
1               5                   10

<210> SEQ ID NO 723
<211> LENGTH: 9
<212> TYPE: PRT
<213> ORGANISM: Artificial sequence
<220> FEATURE:
<223> OTHER INFORMATION: HLA restricted peptide

<400> SEQUENCE: 723

Ser Gln Tyr Thr Pro Asp Ser Thr Pro
1               5

<210> SEQ ID NO 724
<211> LENGTH: 10
<212> TYPE: PRT
<213> ORGANISM: Artificial sequence
<220> FEATURE:
<223> OTHER INFORMATION: HLA restricted peptide

<400> SEQUENCE: 724

Ser Gln Tyr Thr Pro Asp Ser Thr Pro Cys
1               5                   10

<210> SEQ ID NO 725
<211> LENGTH: 9
<212> TYPE: PRT
<213> ORGANISM: Artificial sequence
<220> FEATURE:
<223> OTHER INFORMATION: HLA restricted peptide

<400> SEQUENCE: 725

Ser Arg Gly Asp Thr Pro Val Leu Pro
1               5

<210> SEQ ID NO 726
<211> LENGTH: 10
<212> TYPE: PRT
<213> ORGANISM: Artificial sequence
<220> FEATURE:
<223> OTHER INFORMATION: HLA restricted peptide

<400> SEQUENCE: 726

Ser Arg Gly Asp Thr Pro Val Leu Pro His
1               5                   10

<210> SEQ ID NO 727
<211> LENGTH: 9
<212> TYPE: PRT
<213> ORGANISM: Artificial sequence
<220> FEATURE:
<223> OTHER INFORMATION: HLA restricted peptide

<400> SEQUENCE: 727

Ser Arg Gly Arg Arg Cys Pro Glu Met
1               5

<210> SEQ ID NO 728
<211> LENGTH: 10
<212> TYPE: PRT
<213> ORGANISM: Artificial sequence
<220> FEATURE:
<223> OTHER INFORMATION: HLA restricted peptide

<400> SEQUENCE: 728

Ser Arg Gly Arg Arg Cys Pro Glu Met Ile
1               5                   10

<210> SEQ ID NO 729
<211> LENGTH: 10
<212> TYPE: PRT
<213> ORGANISM: Artificial sequence
<220> FEATURE:
<223> OTHER INFORMATION: HLA restricted peptide

<400> SEQUENCE: 729

Ser Ser Ala Thr Ala Cys Thr Ala Gly Val
1               5                   10

<210> SEQ ID NO 730
<211> LENGTH: 10
<212> TYPE: PRT
<213> ORGANISM: Artificial sequence
<220> FEATURE:
<223> OTHER INFORMATION: HLA restricted peptide

<400> SEQUENCE: 730

Ser Ser Ala Thr Ala Cys Thr Ser Gly Val
1               5                   10

<210> SEQ ID NO 731
<211> LENGTH: 9
<212> TYPE: PRT
<213> ORGANISM: Artificial sequence
<220> FEATURE:
<223> OTHER INFORMATION: HLA restricted peptide

<400> SEQUENCE: 731

Ser Thr Pro Cys His Arg Gly Asp Asn
1               5

<210> SEQ ID NO 732
<211> LENGTH: 9
<212> TYPE: PRT
<213> ORGANISM: Artificial sequence
<220> FEATURE:
<223> OTHER INFORMATION: HLA restricted peptide

<400> SEQUENCE: 732

Ser Thr Ser Ala Gly Arg Lys Arg Lys
1               5

<210> SEQ ID NO 733
<211> LENGTH: 9
<212> TYPE: PRT
<213> ORGANISM: Artificial sequence
<220> FEATURE:
<223> OTHER INFORMATION: HLA restricted peptide

<400> SEQUENCE: 733

Ser Thr Val Ala Pro Glu Glu Asp Thr
1               5

<210> SEQ ID NO 734
<211> LENGTH: 9
<212> TYPE: PRT
<213> ORGANISM: Artificial sequence
<220> FEATURE:
<223> OTHER INFORMATION: HLA restricted peptide

<400> SEQUENCE: 734

Ser Val Leu Gly Pro Ile Ser Gly His
1               5

<210> SEQ ID NO 735
<211> LENGTH: 10

```
<212> TYPE: PRT
<213> ORGANISM: Artificial sequence
<220> FEATURE:
<223> OTHER INFORMATION: HLA restricted peptide

<400> SEQUENCE: 735

Ser Val Leu Gly Pro Ile Ser Gly His Val
1               5                   10

<210> SEQ ID NO 736
<211> LENGTH: 10
<212> TYPE: PRT
<213> ORGANISM: Artificial sequence
<220> FEATURE:
<223> OTHER INFORMATION: HLA restricted peptide

<400> SEQUENCE: 736

Ser Val Asn Val His Asn Pro Thr Gly Arg
1               5                   10

<210> SEQ ID NO 737
<211> LENGTH: 9
<212> TYPE: PRT
<213> ORGANISM: Artificial sequence
<220> FEATURE:
<223> OTHER INFORMATION: HLA restricted peptide

<400> SEQUENCE: 737

Thr Ala Cys Thr Ala Gly Val Met Thr
1               5

<210> SEQ ID NO 738
<211> LENGTH: 10
<212> TYPE: PRT
<213> ORGANISM: Artificial sequence
<220> FEATURE:
<223> OTHER INFORMATION: HLA restricted peptide

<400> SEQUENCE: 738

Thr Ala Cys Thr Ala Gly Val Met Thr Arg
1               5                   10

<210> SEQ ID NO 739
<211> LENGTH: 9
<212> TYPE: PRT
<213> ORGANISM: Artificial sequence
<220> FEATURE:
<223> OTHER INFORMATION: HLA restricted peptide

<400> SEQUENCE: 739

Thr Ala Cys Thr Ser Gly Val Met Thr
1               5

<210> SEQ ID NO 740
<211> LENGTH: 10
<212> TYPE: PRT
<213> ORGANISM: Artificial sequence
<220> FEATURE:
<223> OTHER INFORMATION: HLA restricted peptide

<400> SEQUENCE: 740

Thr Ala Cys Thr Ser Gly Val Met Thr Arg
1               5                   10

<210> SEQ ID NO 741
<211> LENGTH: 9
<212> TYPE: PRT
<213> ORGANISM: Artificial sequence
```

```
<220> FEATURE:
<223> OTHER INFORMATION: HLA restricted peptide

<400> SEQUENCE: 741

Thr Ala Gly Val Met Thr Arg Gly Arg
1               5

<210> SEQ ID NO 742
<211> LENGTH: 10
<212> TYPE: PRT
<213> ORGANISM: Artificial sequence
<220> FEATURE:
<223> OTHER INFORMATION: HLA restricted peptide

<400> SEQUENCE: 742

Thr Ala Gly Val Met Thr Arg Gly Arg Leu
1               5                   10

<210> SEQ ID NO 743
<211> LENGTH: 9
<212> TYPE: PRT
<213> ORGANISM: Artificial sequence
<220> FEATURE:
<223> OTHER INFORMATION: HLA restricted peptide

<400> SEQUENCE: 743

Thr Asp Glu Asp Ser Asp Asn Glu Ile
1               5

<210> SEQ ID NO 744
<211> LENGTH: 9
<212> TYPE: PRT
<213> ORGANISM: Artificial sequence
<220> FEATURE:
<223> OTHER INFORMATION: HLA restricted peptide

<400> SEQUENCE: 744

Thr Glu Arg Lys Thr Pro Arg Val Thr
1               5

<210> SEQ ID NO 745
<211> LENGTH: 9
<212> TYPE: PRT
<213> ORGANISM: Artificial sequence
<220> FEATURE:
<223> OTHER INFORMATION: HLA restricted peptide

<400> SEQUENCE: 745

Thr Gly Gly Gly Ala Met Ala Gly Ala
1               5

<210> SEQ ID NO 746
<211> LENGTH: 10
<212> TYPE: PRT
<213> ORGANISM: Artificial sequence
<220> FEATURE:
<223> OTHER INFORMATION: HLA restricted peptide

<400> SEQUENCE: 746

Thr Gly Gly Gly Ala Met Ala Gly Ala Ser
1               5                   10

<210> SEQ ID NO 747
<211> LENGTH: 9
<212> TYPE: PRT
<213> ORGANISM: Artificial sequence
<220> FEATURE:
<223> OTHER INFORMATION: HLA restricted peptide
```

```
<400> SEQUENCE: 747

Thr Gly Ser Glu Val Glu Asn Val Ser
1               5

<210> SEQ ID NO 748
<211> LENGTH: 10
<212> TYPE: PRT
<213> ORGANISM: Artificial sequence
<220> FEATURE:
<223> OTHER INFORMATION: HLA restricted peptide

<400> SEQUENCE: 748

Thr Gly Ser Glu Val Glu Asn Val Ser Val
1               5                   10

<210> SEQ ID NO 749
<211> LENGTH: 9
<212> TYPE: PRT
<213> ORGANISM: Artificial sequence
<220> FEATURE:
<223> OTHER INFORMATION: HLA restricted peptide

<400> SEQUENCE: 749

Thr Lys Asp Val Ala Leu Arg His Val
1               5

<210> SEQ ID NO 750
<211> LENGTH: 10
<212> TYPE: PRT
<213> ORGANISM: Artificial sequence
<220> FEATURE:
<223> OTHER INFORMATION: HLA restricted peptide

<400> SEQUENCE: 750

Thr Lys Asp Val Ala Leu Arg His Val Val
1               5                   10

<210> SEQ ID NO 751
<211> LENGTH: 10
<212> TYPE: PRT
<213> ORGANISM: Artificial sequence
<220> FEATURE:
<223> OTHER INFORMATION: HLA restricted peptide

<400> SEQUENCE: 751

Thr Lys Met Gln Val Ile Gly Asp Gln Tyr
1               5                   10

<210> SEQ ID NO 752
<211> LENGTH: 10
<212> TYPE: PRT
<213> ORGANISM: Artificial sequence
<220> FEATURE:
<223> OTHER INFORMATION: HLA restricted peptide

<400> SEQUENCE: 752

Thr Leu Gly Ser Asp Val Glu Glu Asp Leu
1               5                   10

<210> SEQ ID NO 753
<211> LENGTH: 9
<212> TYPE: PRT
<213> ORGANISM: Artificial sequence
<220> FEATURE:
<223> OTHER INFORMATION: HLA restricted peptide

<400> SEQUENCE: 753
```

Thr Met Thr Arg Asn Pro Gln Pro Phe
1               5

<210> SEQ ID NO 754
<211> LENGTH: 10
<212> TYPE: PRT
<213> ORGANISM: Artificial sequence
<220> FEATURE:
<223> OTHER INFORMATION: HLA restricted peptide

<400> SEQUENCE: 754

Thr Met Thr Arg Asn Pro Gln Pro Phe Met
1               5                   10

<210> SEQ ID NO 755
<211> LENGTH: 9
<212> TYPE: PRT
<213> ORGANISM: Artificial sequence
<220> FEATURE:
<223> OTHER INFORMATION: HLA restricted peptide

<400> SEQUENCE: 755

Thr Pro Cys His Arg Gly Asp Asn Gln
1               5

<210> SEQ ID NO 756
<211> LENGTH: 10
<212> TYPE: PRT
<213> ORGANISM: Artificial sequence
<220> FEATURE:
<223> OTHER INFORMATION: HLA restricted peptide

<400> SEQUENCE: 756

Thr Pro Cys His Arg Gly Asp Asn Gln Leu
1               5                   10

<210> SEQ ID NO 757
<211> LENGTH: 9
<212> TYPE: PRT
<213> ORGANISM: Artificial sequence
<220> FEATURE:
<223> OTHER INFORMATION: HLA restricted peptide

<400> SEQUENCE: 757

Thr Pro Asp Ser Thr Pro Cys His Arg
1               5

<210> SEQ ID NO 758
<211> LENGTH: 10
<212> TYPE: PRT
<213> ORGANISM: Artificial sequence
<220> FEATURE:
<223> OTHER INFORMATION: HLA restricted peptide

<400> SEQUENCE: 758

Thr Pro Asp Ser Thr Pro Cys His Arg Gly
1               5                   10

<210> SEQ ID NO 759
<211> LENGTH: 9
<212> TYPE: PRT
<213> ORGANISM: Artificial sequence
<220> FEATURE:
<223> OTHER INFORMATION: HLA restricted peptide

<400> SEQUENCE: 759

Thr Pro Arg Val Thr Gly Gly Gly Ala

<210> SEQ ID NO 760
<211> LENGTH: 10
<212> TYPE: PRT
<213> ORGANISM: Artificial sequence
<220> FEATURE:
<223> OTHER INFORMATION: HLA restricted peptide

<400> SEQUENCE: 760

Thr Pro Arg Val Thr Gly Gly Gly Ala Met
1               5                   10

<210> SEQ ID NO 761
<211> LENGTH: 9
<212> TYPE: PRT
<213> ORGANISM: Artificial sequence
<220> FEATURE:
<223> OTHER INFORMATION: HLA restricted peptide

<400> SEQUENCE: 761

Thr Pro Val Leu Pro His Glu Thr Arg
1               5

<210> SEQ ID NO 762
<211> LENGTH: 10
<212> TYPE: PRT
<213> ORGANISM: Artificial sequence
<220> FEATURE:
<223> OTHER INFORMATION: HLA restricted peptide

<400> SEQUENCE: 762

Thr Pro Val Leu Pro His Glu Thr Arg Leu
1               5                   10

<210> SEQ ID NO 763
<211> LENGTH: 9
<212> TYPE: PRT
<213> ORGANISM: Artificial sequence
<220> FEATURE:
<223> OTHER INFORMATION: HLA restricted peptide

<400> SEQUENCE: 763

Thr Arg Ala Thr Lys Met Gln Val Ile
1               5

<210> SEQ ID NO 764
<211> LENGTH: 10
<212> TYPE: PRT
<213> ORGANISM: Artificial sequence
<220> FEATURE:
<223> OTHER INFORMATION: HLA restricted peptide

<400> SEQUENCE: 764

Thr Arg Ala Thr Lys Met Gln Val Ile Gly
1               5                   10

<210> SEQ ID NO 765
<211> LENGTH: 9
<212> TYPE: PRT
<213> ORGANISM: Artificial sequence
<220> FEATURE:
<223> OTHER INFORMATION: HLA restricted peptide

<400> SEQUENCE: 765

Thr Arg Gly Arg Leu Lys Ala Glu Ser
1               5

<210> SEQ ID NO 766
<211> LENGTH: 10
<212> TYPE: PRT
<213> ORGANISM: Artificial sequence
<220> FEATURE:
<223> OTHER INFORMATION: HLA restricted peptide

<400> SEQUENCE: 766

Thr Arg Gly Arg Leu Lys Ala Glu Ser Thr
1               5                   10

<210> SEQ ID NO 767
<211> LENGTH: 9
<212> TYPE: PRT
<213> ORGANISM: Artificial sequence
<220> FEATURE:
<223> OTHER INFORMATION: HLA restricted peptide

<400> SEQUENCE: 767

Thr Arg Leu Leu Gln Thr Gly Ile His
1               5

<210> SEQ ID NO 768
<211> LENGTH: 10
<212> TYPE: PRT
<213> ORGANISM: Artificial sequence
<220> FEATURE:
<223> OTHER INFORMATION: HLA restricted peptide

<400> SEQUENCE: 768

Thr Arg Leu Leu Gln Thr Gly Ile His Val
1               5                   10

<210> SEQ ID NO 769
<211> LENGTH: 9
<212> TYPE: PRT
<213> ORGANISM: Artificial sequence
<220> FEATURE:
<223> OTHER INFORMATION: HLA restricted peptide

<400> SEQUENCE: 769

Thr Arg Asn Pro Gln Pro Phe Met Arg
1               5

<210> SEQ ID NO 770
<211> LENGTH: 10
<212> TYPE: PRT
<213> ORGANISM: Artificial sequence
<220> FEATURE:
<223> OTHER INFORMATION: HLA restricted peptide

<400> SEQUENCE: 770

Thr Arg Asn Pro Gln Pro Phe Met Arg Pro
1               5                   10

<210> SEQ ID NO 771
<211> LENGTH: 9
<212> TYPE: PRT
<213> ORGANISM: Artificial sequence
<220> FEATURE:
<223> OTHER INFORMATION: HLA restricted peptide

<400> SEQUENCE: 771

Thr Arg Gln Gln Asn Gln Trp Lys Glu
1               5

<210> SEQ ID NO 772

<211> LENGTH: 10
<212> TYPE: PRT
<213> ORGANISM: Artificial sequence
<220> FEATURE:
<223> OTHER INFORMATION: HLA restricted peptide

<400> SEQUENCE: 772

Thr Arg Gln Gln Asn Gln Trp Lys Glu Pro
1               5                   10

<210> SEQ ID NO 773
<211> LENGTH: 9
<212> TYPE: PRT
<213> ORGANISM: Artificial sequence
<220> FEATURE:
<223> OTHER INFORMATION: HLA restricted peptide

<400> SEQUENCE: 773

Thr Ser Ala Phe Val Phe Pro Thr Lys
1               5

<210> SEQ ID NO 774
<211> LENGTH: 10
<212> TYPE: PRT
<213> ORGANISM: Artificial sequence
<220> FEATURE:
<223> OTHER INFORMATION: HLA restricted peptide

<400> SEQUENCE: 774

Thr Ser Ala Gly Arg Lys Arg Lys Ser Ala
1               5                   10

<210> SEQ ID NO 775
<211> LENGTH: 10
<212> TYPE: PRT
<213> ORGANISM: Artificial sequence
<220> FEATURE:
<223> OTHER INFORMATION: HLA restricted peptide

<400> SEQUENCE: 775

Thr Ser Gly Ser Asp Ser Asp Glu Glu Leu
1               5                   10

<210> SEQ ID NO 776
<211> LENGTH: 9
<212> TYPE: PRT
<213> ORGANISM: Artificial sequence
<220> FEATURE:
<223> OTHER INFORMATION: HLA restricted peptide

<400> SEQUENCE: 776

Thr Ser Gly Val Met Thr Arg Gly Arg
1               5

<210> SEQ ID NO 777
<211> LENGTH: 10
<212> TYPE: PRT
<213> ORGANISM: Artificial sequence
<220> FEATURE:
<223> OTHER INFORMATION: HLA restricted peptide

<400> SEQUENCE: 777

Thr Ser Gly Val Met Thr Arg Gly Arg Leu
1               5                   10

<210> SEQ ID NO 778
<211> LENGTH: 9
<212> TYPE: PRT

<213> ORGANISM: Artificial sequence
<220> FEATURE:
<223> OTHER INFORMATION: HLA restricted peptide

<400> SEQUENCE: 778

Thr Ser His Glu His Phe Gly Leu Leu
1               5

<210> SEQ ID NO 779
<211> LENGTH: 10
<212> TYPE: PRT
<213> ORGANISM: Artificial sequence
<220> FEATURE:
<223> OTHER INFORMATION: HLA restricted peptide

<400> SEQUENCE: 779

Thr Ser His Glu His Phe Gly Leu Leu Cys
1               5                   10

<210> SEQ ID NO 780
<211> LENGTH: 9
<212> TYPE: PRT
<213> ORGANISM: Artificial sequence
<220> FEATURE:
<223> OTHER INFORMATION: HLA restricted peptide

<400> SEQUENCE: 780

Thr Ser Gln Tyr Arg Ile Gln Gly Lys
1               5

<210> SEQ ID NO 781
<211> LENGTH: 10
<212> TYPE: PRT
<213> ORGANISM: Artificial sequence
<220> FEATURE:
<223> OTHER INFORMATION: HLA restricted peptide

<400> SEQUENCE: 781

Thr Ser Gln Tyr Arg Ile Gln Gly Lys Leu
1               5                   10

<210> SEQ ID NO 782
<211> LENGTH: 9
<212> TYPE: PRT
<213> ORGANISM: Artificial sequence
<220> FEATURE:
<223> OTHER INFORMATION: HLA restricted peptide

<400> SEQUENCE: 782

Thr Thr Glu Arg Lys Thr Pro Arg Val
1               5

<210> SEQ ID NO 783
<211> LENGTH: 10
<212> TYPE: PRT
<213> ORGANISM: Artificial sequence
<220> FEATURE:
<223> OTHER INFORMATION: HLA restricted peptide

<400> SEQUENCE: 783

Thr Thr Glu Arg Lys Thr Pro Arg Val Thr
1               5                   10

<210> SEQ ID NO 784
<211> LENGTH: 9
<212> TYPE: PRT
<213> ORGANISM: Artificial sequence
<220> FEATURE:

<223> OTHER INFORMATION: HLA restricted peptide

<400> SEQUENCE: 784

Thr Val Ala Pro Glu Glu Asp Thr Asp
1               5

<210> SEQ ID NO 785
<211> LENGTH: 10
<212> TYPE: PRT
<213> ORGANISM: Artificial sequence
<220> FEATURE:
<223> OTHER INFORMATION: HLA restricted peptide

<400> SEQUENCE: 785

Thr Val Ala Pro Glu Glu Asp Thr Asp Glu
1               5                   10

<210> SEQ ID NO 786
<211> LENGTH: 10
<212> TYPE: PRT
<213> ORGANISM: Artificial sequence
<220> FEATURE:
<223> OTHER INFORMATION: HLA restricted peptide

<400> SEQUENCE: 786

Thr Val Glu Leu Arg Gln Tyr Asp Pro Val
1               5                   10

<210> SEQ ID NO 787
<211> LENGTH: 9
<212> TYPE: PRT
<213> ORGANISM: Artificial sequence
<220> FEATURE:
<223> OTHER INFORMATION: HLA restricted peptide

<400> SEQUENCE: 787

Thr Val Leu Cys Pro Lys Asn Met Ile
1               5

<210> SEQ ID NO 788
<211> LENGTH: 10
<212> TYPE: PRT
<213> ORGANISM: Artificial sequence
<220> FEATURE:
<223> OTHER INFORMATION: HLA restricted peptide

<400> SEQUENCE: 788

Thr Val Leu Cys Pro Lys Asn Met Ile Ile
1               5                   10

<210> SEQ ID NO 789
<211> LENGTH: 9
<212> TYPE: PRT
<213> ORGANISM: Artificial sequence
<220> FEATURE:
<223> OTHER INFORMATION: HLA restricted peptide

<400> SEQUENCE: 789

Thr Val Gln Gly Gln Asn Leu Lys Tyr
1               5

<210> SEQ ID NO 790
<211> LENGTH: 9
<212> TYPE: PRT
<213> ORGANISM: Artificial sequence
<220> FEATURE:
<223> OTHER INFORMATION: HLA restricted peptide

```
<400> SEQUENCE: 790

Thr Val Ser Gly Leu Ala Trp Thr Arg
1               5

<210> SEQ ID NO 791
<211> LENGTH: 9
<212> TYPE: PRT
<213> ORGANISM: Artificial sequence
<220> FEATURE:
<223> OTHER INFORMATION: HLA restricted peptide

<400> SEQUENCE: 791

Thr Trp Asp Arg His Asp Glu Gly Ala
1               5

<210> SEQ ID NO 792
<211> LENGTH: 10
<212> TYPE: PRT
<213> ORGANISM: Artificial sequence
<220> FEATURE:
<223> OTHER INFORMATION: HLA restricted peptide

<400> SEQUENCE: 792

Thr Trp Asp Arg His Asp Glu Gly Ala Ala
1               5                   10

<210> SEQ ID NO 793
<211> LENGTH: 9
<212> TYPE: PRT
<213> ORGANISM: Artificial sequence
<220> FEATURE:
<223> OTHER INFORMATION: HLA restricted peptide

<400> SEQUENCE: 793

Thr Trp Pro Pro Trp Gln Ala Gly Ile
1               5

<210> SEQ ID NO 794
<211> LENGTH: 10
<212> TYPE: PRT
<213> ORGANISM: Artificial sequence
<220> FEATURE:
<223> OTHER INFORMATION: HLA restricted peptide

<400> SEQUENCE: 794

Thr Trp Pro Pro Trp Gln Ala Gly Ile Leu
1               5                   10

<210> SEQ ID NO 795
<211> LENGTH: 10
<212> TYPE: PRT
<213> ORGANISM: Artificial sequence
<220> FEATURE:
<223> OTHER INFORMATION: HLA restricted peptide

<400> SEQUENCE: 795

Thr Tyr Phe Thr Gly Ser Glu Val Glu Asn
1               5                   10

<210> SEQ ID NO 796
<211> LENGTH: 9
<212> TYPE: PRT
<213> ORGANISM: Artificial sequence
<220> FEATURE:
<223> OTHER INFORMATION: HLA restricted peptide

<400> SEQUENCE: 796
```

```
Val Ala Ala Leu Phe Phe Phe Asp Ile
1               5

<210> SEQ ID NO 797
<211> LENGTH: 9
<212> TYPE: PRT
<213> ORGANISM: Artificial sequence
<220> FEATURE:
<223> OTHER INFORMATION: HLA restricted peptide

<400> SEQUENCE: 797

Val Ala Asp Ala Val Ile His Ala Ser
1               5

<210> SEQ ID NO 798
<211> LENGTH: 10
<212> TYPE: PRT
<213> ORGANISM: Artificial sequence
<220> FEATURE:
<223> OTHER INFORMATION: HLA restricted peptide

<400> SEQUENCE: 798

Val Ala Asp Ala Val Ile His Ala Ser Gly
1               5                   10

<210> SEQ ID NO 799
<211> LENGTH: 9
<212> TYPE: PRT
<213> ORGANISM: Artificial sequence
<220> FEATURE:
<223> OTHER INFORMATION: HLA restricted peptide

<400> SEQUENCE: 799

Val Ala Phe Thr Ser His Glu His Phe
1               5

<210> SEQ ID NO 800
<211> LENGTH: 10
<212> TYPE: PRT
<213> ORGANISM: Artificial sequence
<220> FEATURE:
<223> OTHER INFORMATION: HLA restricted peptide

<400> SEQUENCE: 800

Val Ala Phe Thr Ser His Glu His Phe Gly
1               5                   10

<210> SEQ ID NO 801
<211> LENGTH: 9
<212> TYPE: PRT
<213> ORGANISM: Artificial sequence
<220> FEATURE:
<223> OTHER INFORMATION: HLA restricted peptide

<400> SEQUENCE: 801

Val Ala Leu Arg His Val Val Cys Ala
1               5

<210> SEQ ID NO 802
<211> LENGTH: 10
<212> TYPE: PRT
<213> ORGANISM: Artificial sequence
<220> FEATURE:
<223> OTHER INFORMATION: HLA restricted peptide

<400> SEQUENCE: 802

Val Ala Leu Arg His Val Val Cys Ala His
1               5                   10
```

```
<210> SEQ ID NO 803
<211> LENGTH: 9
<212> TYPE: PRT
<213> ORGANISM: Artificial sequence
<220> FEATURE:
<223> OTHER INFORMATION: HLA restricted peptide

<400> SEQUENCE: 803

Val Ala Thr Val Gln Gly Gln Asn Leu
1               5

<210> SEQ ID NO 804
<211> LENGTH: 10
<212> TYPE: PRT
<213> ORGANISM: Artificial sequence
<220> FEATURE:
<223> OTHER INFORMATION: HLA restricted peptide

<400> SEQUENCE: 804

Val Ala Thr Val Gln Gly Gln Asn Leu Lys
1               5                   10

<210> SEQ ID NO 805
<211> LENGTH: 9
<212> TYPE: PRT
<213> ORGANISM: Artificial sequence
<220> FEATURE:
<223> OTHER INFORMATION: HLA restricted peptide

<400> SEQUENCE: 805

Val Cys Ala His Glu Leu Val Cys Ser
1               5

<210> SEQ ID NO 806
<211> LENGTH: 10
<212> TYPE: PRT
<213> ORGANISM: Artificial sequence
<220> FEATURE:
<223> OTHER INFORMATION: HLA restricted peptide

<400> SEQUENCE: 806

Val Cys Ala His Glu Leu Val Cys Ser Met
1               5                   10

<210> SEQ ID NO 807
<211> LENGTH: 9
<212> TYPE: PRT
<213> ORGANISM: Artificial sequence
<220> FEATURE:
<223> OTHER INFORMATION: HLA restricted peptide

<400> SEQUENCE: 807

Val Cys Ser Met Glu Asn Thr Arg Ala
1               5

<210> SEQ ID NO 808
<211> LENGTH: 9
<212> TYPE: PRT
<213> ORGANISM: Artificial sequence
<220> FEATURE:
<223> OTHER INFORMATION: HLA restricted peptide

<400> SEQUENCE: 808

Val Glu Glu Asp Leu Thr Met Thr Arg
1               5
```

```
<210> SEQ ID NO 809
<211> LENGTH: 10
<212> TYPE: PRT
<213> ORGANISM: Artificial sequence
<220> FEATURE:
<223> OTHER INFORMATION: HLA restricted peptide

<400> SEQUENCE: 809

Val Glu Glu Asp Leu Thr Met Thr Arg Asn
1               5                   10

<210> SEQ ID NO 810
<211> LENGTH: 9
<212> TYPE: PRT
<213> ORGANISM: Artificial sequence
<220> FEATURE:
<223> OTHER INFORMATION: HLA restricted peptide

<400> SEQUENCE: 810

Val Glu Leu Arg Gln Tyr Asp Pro Val
1               5

<210> SEQ ID NO 811
<211> LENGTH: 10
<212> TYPE: PRT
<213> ORGANISM: Artificial sequence
<220> FEATURE:
<223> OTHER INFORMATION: HLA restricted peptide

<400> SEQUENCE: 811

Val Glu Leu Arg Gln Tyr Asp Pro Val Ala
1               5                   10

<210> SEQ ID NO 812
<211> LENGTH: 9
<212> TYPE: PRT
<213> ORGANISM: Artificial sequence
<220> FEATURE:
<223> OTHER INFORMATION: HLA restricted peptide

<400> SEQUENCE: 812

Val Glu Asn Val Ser Val Asn Val His
1               5

<210> SEQ ID NO 813
<211> LENGTH: 10
<212> TYPE: PRT
<213> ORGANISM: Artificial sequence
<220> FEATURE:
<223> OTHER INFORMATION: HLA restricted peptide

<400> SEQUENCE: 813

Val Glu Asn Val Ser Val Asn Val His Asn
1               5                   10

<210> SEQ ID NO 814
<211> LENGTH: 9
<212> TYPE: PRT
<213> ORGANISM: Artificial sequence
<220> FEATURE:
<223> OTHER INFORMATION: HLA restricted peptide

<400> SEQUENCE: 814

Val Phe Pro Thr Lys Asp Val Ala Leu
1               5

<210> SEQ ID NO 815
<211> LENGTH: 10
```

```
<212> TYPE: PRT
<213> ORGANISM: Artificial sequence
<220> FEATURE:
<223> OTHER INFORMATION: HLA restricted peptide

<400> SEQUENCE: 815

Val Phe Pro Thr Lys Asp Val Ala Leu Arg
1               5                   10

<210> SEQ ID NO 816
<211> LENGTH: 9
<212> TYPE: PRT
<213> ORGANISM: Artificial sequence
<220> FEATURE:
<223> OTHER INFORMATION: HLA restricted peptide

<400> SEQUENCE: 816

Val Phe Ser Arg Gly Asp Thr Pro Val
1               5

<210> SEQ ID NO 817
<211> LENGTH: 10
<212> TYPE: PRT
<213> ORGANISM: Artificial sequence
<220> FEATURE:
<223> OTHER INFORMATION: HLA restricted peptide

<400> SEQUENCE: 817

Val Phe Ser Arg Gly Asp Thr Pro Val Leu
1               5                   10

<210> SEQ ID NO 818
<211> LENGTH: 9
<212> TYPE: PRT
<213> ORGANISM: Artificial sequence
<220> FEATURE:
<223> OTHER INFORMATION: HLA restricted peptide

<400> SEQUENCE: 818

Val Phe Thr Trp Pro Pro Trp Gln Ala
1               5

<210> SEQ ID NO 819
<211> LENGTH: 10
<212> TYPE: PRT
<213> ORGANISM: Artificial sequence
<220> FEATURE:
<223> OTHER INFORMATION: HLA restricted peptide

<400> SEQUENCE: 819

Val His His Tyr Pro Ser Ala Ala Glu Arg
1               5                   10

<210> SEQ ID NO 820
<211> LENGTH: 9
<212> TYPE: PRT
<213> ORGANISM: Artificial sequence
<220> FEATURE:
<223> OTHER INFORMATION: HLA restricted peptide

<400> SEQUENCE: 820

Val His Asn Pro Thr Gly Arg Ser Ile
1               5

<210> SEQ ID NO 821
<211> LENGTH: 10
<212> TYPE: PRT
<213> ORGANISM: Artificial sequence
```

```
<220> FEATURE:
<223> OTHER INFORMATION: HLA restricted peptide

<400> SEQUENCE: 821

Val His Asn Pro Thr Gly Arg Ser Ile Cys
1               5                   10

<210> SEQ ID NO 822
<211> LENGTH: 9
<212> TYPE: PRT
<213> ORGANISM: Artificial sequence
<220> FEATURE:
<223> OTHER INFORMATION: HLA restricted peptide

<400> SEQUENCE: 822

Val Ile Gly Asp Gln Tyr Val Lys Val
1               5

<210> SEQ ID NO 823
<211> LENGTH: 10
<212> TYPE: PRT
<213> ORGANISM: Artificial sequence
<220> FEATURE:
<223> OTHER INFORMATION: HLA restricted peptide

<400> SEQUENCE: 823

Val Ile Gly Asp Gln Tyr Val Lys Val Tyr
1               5                   10

<210> SEQ ID NO 824
<211> LENGTH: 9
<212> TYPE: PRT
<213> ORGANISM: Artificial sequence
<220> FEATURE:
<223> OTHER INFORMATION: HLA restricted peptide

<400> SEQUENCE: 824

Val Ile His Ala Ser Gly Lys Gln Met
1               5

<210> SEQ ID NO 825
<211> LENGTH: 10
<212> TYPE: PRT
<213> ORGANISM: Artificial sequence
<220> FEATURE:
<223> OTHER INFORMATION: HLA restricted peptide

<400> SEQUENCE: 825

Val Ile His Ala Ser Gly Lys Gln Met Trp
1               5                   10

<210> SEQ ID NO 826
<211> LENGTH: 9
<212> TYPE: PRT
<213> ORGANISM: Artificial sequence
<220> FEATURE:
<223> OTHER INFORMATION: HLA restricted peptide

<400> SEQUENCE: 826

Val Lys Val Tyr Leu Glu Ser Phe Cys
1               5

<210> SEQ ID NO 827
<211> LENGTH: 9
<212> TYPE: PRT
<213> ORGANISM: Artificial sequence
<220> FEATURE:
<223> OTHER INFORMATION: HLA restricted peptide
```

-continued

```
<400> SEQUENCE: 827

Val Leu Cys Pro Lys Asn Met Ile Ile
1               5

<210> SEQ ID NO 828
<211> LENGTH: 10
<212> TYPE: PRT
<213> ORGANISM: Artificial sequence
<220> FEATURE:
<223> OTHER INFORMATION: HLA restricted peptide

<400> SEQUENCE: 828

Val Leu Cys Pro Lys Asn Met Ile Ile Lys
1               5                   10

<210> SEQ ID NO 829
<211> LENGTH: 9
<212> TYPE: PRT
<213> ORGANISM: Artificial sequence
<220> FEATURE:
<223> OTHER INFORMATION: HLA restricted peptide

<400> SEQUENCE: 829

Val Leu Gly Pro Ile Ser Gly His Val
1               5

<210> SEQ ID NO 830
<211> LENGTH: 10
<212> TYPE: PRT
<213> ORGANISM: Artificial sequence
<220> FEATURE:
<223> OTHER INFORMATION: HLA restricted peptide

<400> SEQUENCE: 830

Val Leu Gly Pro Ile Ser Gly His Val Leu
1               5                   10

<210> SEQ ID NO 831
<211> LENGTH: 9
<212> TYPE: PRT
<213> ORGANISM: Artificial sequence
<220> FEATURE:
<223> OTHER INFORMATION: HLA restricted peptide

<400> SEQUENCE: 831

Val Leu Lys Ala Val Phe Ser Arg Gly
1               5

<210> SEQ ID NO 832
<211> LENGTH: 10
<212> TYPE: PRT
<213> ORGANISM: Artificial sequence
<220> FEATURE:
<223> OTHER INFORMATION: HLA restricted peptide

<400> SEQUENCE: 832

Val Leu Lys Ala Val Phe Ser Arg Gly Asp
1               5                   10

<210> SEQ ID NO 833
<211> LENGTH: 9
<212> TYPE: PRT
<213> ORGANISM: Artificial sequence
<220> FEATURE:
<223> OTHER INFORMATION: HLA restricted peptide

<400> SEQUENCE: 833
```

Val Leu Pro His Glu Thr Arg Leu Leu
1               5

<210> SEQ ID NO 834
<211> LENGTH: 9
<212> TYPE: PRT
<213> ORGANISM: Artificial sequence
<220> FEATURE:
<223> OTHER INFORMATION: HLA restricted peptide

<400> SEQUENCE: 834

Val Met Thr Arg Gly Arg Leu Lys Ala
1               5

<210> SEQ ID NO 835
<211> LENGTH: 9
<212> TYPE: PRT
<213> ORGANISM: Artificial sequence
<220> FEATURE:
<223> OTHER INFORMATION: HLA restricted peptide

<400> SEQUENCE: 835

Val Asn Val His Asn Pro Thr Gly Arg
1               5

<210> SEQ ID NO 836
<211> LENGTH: 10
<212> TYPE: PRT
<213> ORGANISM: Artificial sequence
<220> FEATURE:
<223> OTHER INFORMATION: HLA restricted peptide

<400> SEQUENCE: 836

Val Asn Val His Asn Pro Thr Gly Arg Ser
1               5                   10

<210> SEQ ID NO 837
<211> LENGTH: 9
<212> TYPE: PRT
<213> ORGANISM: Artificial sequence
<220> FEATURE:
<223> OTHER INFORMATION: HLA restricted peptide

<400> SEQUENCE: 837

Val Pro Met Val Ala Thr Val Gln Gly
1               5

<210> SEQ ID NO 838
<211> LENGTH: 10
<212> TYPE: PRT
<213> ORGANISM: Artificial sequence
<220> FEATURE:
<223> OTHER INFORMATION: HLA restricted peptide

<400> SEQUENCE: 838

Val Pro Met Val Ala Thr Val Gln Gly Gln
1               5                   10

<210> SEQ ID NO 839
<211> LENGTH: 9
<212> TYPE: PRT
<213> ORGANISM: Artificial sequence
<220> FEATURE:
<223> OTHER INFORMATION: HLA restricted peptide

<400> SEQUENCE: 839

Val Pro Ser Gly Lys Leu Phe Met His

-continued

<210> SEQ ID NO 840
<211> LENGTH: 10
<212> TYPE: PRT
<213> ORGANISM: Artificial sequence
<220> FEATURE:
<223> OTHER INFORMATION: HLA restricted peptide

<400> SEQUENCE: 840

Val Pro Ser Gly Lys Leu Phe Met His Val
1               5                   10

<210> SEQ ID NO 841
<211> LENGTH: 9
<212> TYPE: PRT
<213> ORGANISM: Artificial sequence
<220> FEATURE:
<223> OTHER INFORMATION: HLA restricted peptide

<400> SEQUENCE: 841

Val Gln Ala Ile Arg Glu Thr Val Glu
1               5

<210> SEQ ID NO 842
<211> LENGTH: 10
<212> TYPE: PRT
<213> ORGANISM: Artificial sequence
<220> FEATURE:
<223> OTHER INFORMATION: HLA restricted peptide

<400> SEQUENCE: 842

Val Gln Ala Ile Arg Glu Thr Val Glu Leu
1               5                   10

<210> SEQ ID NO 843
<211> LENGTH: 10
<212> TYPE: PRT
<213> ORGANISM: Artificial sequence
<220> FEATURE:
<223> OTHER INFORMATION: HLA restricted peptide

<400> SEQUENCE: 843

Val Gln Gly Gln Asn Leu Lys Tyr Gln Glu
1               5                   10

<210> SEQ ID NO 844
<211> LENGTH: 9
<212> TYPE: PRT
<213> ORGANISM: Artificial sequence
<220> FEATURE:
<223> OTHER INFORMATION: HLA restricted peptide

<400> SEQUENCE: 844

Val Gln His Thr Tyr Phe Thr Gly Ser
1               5

<210> SEQ ID NO 845
<211> LENGTH: 10
<212> TYPE: PRT
<213> ORGANISM: Artificial sequence
<220> FEATURE:
<223> OTHER INFORMATION: HLA restricted peptide

<400> SEQUENCE: 845

Val Gln His Thr Tyr Phe Thr Gly Ser Glu
1               5                   10

```
<210> SEQ ID NO 846
<211> LENGTH: 9
<212> TYPE: PRT
<213> ORGANISM: Artificial sequence
<220> FEATURE:
<223> OTHER INFORMATION: HLA restricted peptide

<400> SEQUENCE: 846

Val Arg Val Ser Gln Pro Ser Leu Ile
1               5

<210> SEQ ID NO 847
<211> LENGTH: 10
<212> TYPE: PRT
<213> ORGANISM: Artificial sequence
<220> FEATURE:
<223> OTHER INFORMATION: HLA restricted peptide

<400> SEQUENCE: 847

Val Arg Val Ser Gln Pro Ser Leu Ile Leu
1               5                   10

<210> SEQ ID NO 848
<211> LENGTH: 9
<212> TYPE: PRT
<213> ORGANISM: Artificial sequence
<220> FEATURE:
<223> OTHER INFORMATION: HLA restricted peptide

<400> SEQUENCE: 848

Val Ser Gln Pro Ser Leu Ile Leu Val
1               5

<210> SEQ ID NO 849
<211> LENGTH: 10
<212> TYPE: PRT
<213> ORGANISM: Artificial sequence
<220> FEATURE:
<223> OTHER INFORMATION: HLA restricted peptide

<400> SEQUENCE: 849

Val Ser Gln Pro Ser Leu Ile Leu Val Ser
1               5                   10

<210> SEQ ID NO 850
<211> LENGTH: 9
<212> TYPE: PRT
<213> ORGANISM: Artificial sequence
<220> FEATURE:
<223> OTHER INFORMATION: HLA restricted peptide

<400> SEQUENCE: 850

Val Ser Gln Tyr Thr Pro Asp Ser Thr
1               5

<210> SEQ ID NO 851
<211> LENGTH: 9
<212> TYPE: PRT
<213> ORGANISM: Artificial sequence
<220> FEATURE:
<223> OTHER INFORMATION: HLA restricted peptide

<400> SEQUENCE: 851

Val Ser Val Asn Val His Asn Pro Thr
1               5

<210> SEQ ID NO 852
```

```
<211> LENGTH: 10
<212> TYPE: PRT
<213> ORGANISM: Artificial sequence
<220> FEATURE:
<223> OTHER INFORMATION: HLA restricted peptide

<400> SEQUENCE: 852

Val Thr Gly Gly Gly Ala Met Ala Gly Ala
1               5                   10

<210> SEQ ID NO 853
<211> LENGTH: 9
<212> TYPE: PRT
<213> ORGANISM: Artificial sequence
<220> FEATURE:
<223> OTHER INFORMATION: HLA restricted peptide

<400> SEQUENCE: 853

Val Thr Thr Glu Arg Lys Thr Pro Arg
1               5

<210> SEQ ID NO 854
<211> LENGTH: 10
<212> TYPE: PRT
<213> ORGANISM: Artificial sequence
<220> FEATURE:
<223> OTHER INFORMATION: HLA restricted peptide

<400> SEQUENCE: 854

Val Thr Thr Glu Arg Lys Thr Pro Arg Val
1               5                   10

<210> SEQ ID NO 855
<211> LENGTH: 9
<212> TYPE: PRT
<213> ORGANISM: Artificial sequence
<220> FEATURE:
<223> OTHER INFORMATION: HLA restricted peptide

<400> SEQUENCE: 855

Val Val Cys Ala His Glu Leu Val Cys
1               5

<210> SEQ ID NO 856
<211> LENGTH: 10
<212> TYPE: PRT
<213> ORGANISM: Artificial sequence
<220> FEATURE:
<223> OTHER INFORMATION: HLA restricted peptide

<400> SEQUENCE: 856

Val Val Cys Ala His Glu Leu Val Cys Ser
1               5                   10

<210> SEQ ID NO 857
<211> LENGTH: 9
<212> TYPE: PRT
<213> ORGANISM: Artificial sequence
<220> FEATURE:
<223> OTHER INFORMATION: HLA restricted peptide

<400> SEQUENCE: 857

Val Trp Gln Pro Ala Ala Gln Pro Lys
1               5

<210> SEQ ID NO 858
<211> LENGTH: 10
<212> TYPE: PRT
```

```
<213> ORGANISM: Artificial sequence
<220> FEATURE:
<223> OTHER INFORMATION: HLA restricted peptide

<400> SEQUENCE: 858

Val Trp Gln Pro Ala Ala Gln Pro Lys Arg
1               5                   10

<210> SEQ ID NO 859
<211> LENGTH: 9
<212> TYPE: PRT
<213> ORGANISM: Artificial sequence
<220> FEATURE:
<223> OTHER INFORMATION: HLA restricted peptide

<400> SEQUENCE: 859

Val Tyr Ala Leu Pro Leu Lys Met Leu
1               5

<210> SEQ ID NO 860
<211> LENGTH: 10
<212> TYPE: PRT
<213> ORGANISM: Artificial sequence
<220> FEATURE:
<223> OTHER INFORMATION: HLA restricted peptide

<400> SEQUENCE: 860

Val Tyr Ala Leu Pro Leu Lys Met Leu Asn
1               5                   10

<210> SEQ ID NO 861
<211> LENGTH: 9
<212> TYPE: PRT
<213> ORGANISM: Artificial sequence
<220> FEATURE:
<223> OTHER INFORMATION: HLA restricted peptide

<400> SEQUENCE: 861

Val Tyr Leu Glu Ser Phe Cys Glu Asp
1               5

<210> SEQ ID NO 862
<211> LENGTH: 10
<212> TYPE: PRT
<213> ORGANISM: Artificial sequence
<220> FEATURE:
<223> OTHER INFORMATION: HLA restricted peptide

<400> SEQUENCE: 862

Val Tyr Leu Glu Ser Phe Cys Glu Asp Val
1               5                   10

<210> SEQ ID NO 863
<211> LENGTH: 9
<212> TYPE: PRT
<213> ORGANISM: Artificial sequence
<220> FEATURE:
<223> OTHER INFORMATION: HLA restricted peptide

<400> SEQUENCE: 863

Val Tyr Tyr Thr Ser Ala Phe Val Phe
1               5

<210> SEQ ID NO 864
<211> LENGTH: 9
<212> TYPE: PRT
<213> ORGANISM: Artificial sequence
<220> FEATURE:
```

<223> OTHER INFORMATION: HLA restricted peptide

<400> SEQUENCE: 864

Trp Asp Ala Asn Asp Ile Tyr Arg Ile
1               5

<210> SEQ ID NO 865
<211> LENGTH: 10
<212> TYPE: PRT
<213> ORGANISM: Artificial sequence
<220> FEATURE:
<223> OTHER INFORMATION: HLA restricted peptide

<400> SEQUENCE: 865

Trp Asp Ala Asn Asp Ile Tyr Arg Ile Phe
1               5                   10

<210> SEQ ID NO 866
<211> LENGTH: 9
<212> TYPE: PRT
<213> ORGANISM: Artificial sequence
<220> FEATURE:
<223> OTHER INFORMATION: HLA restricted peptide

<400> SEQUENCE: 866

Trp Asp Arg His Asp Glu Gly Ala Ala
1               5

<210> SEQ ID NO 867
<211> LENGTH: 9
<212> TYPE: PRT
<213> ORGANISM: Artificial sequence
<220> FEATURE:
<223> OTHER INFORMATION: HLA restricted peptide

<400> SEQUENCE: 867

Trp Lys Glu Pro Asp Val Tyr Tyr Thr
1               5

<210> SEQ ID NO 868
<211> LENGTH: 10
<212> TYPE: PRT
<213> ORGANISM: Artificial sequence
<220> FEATURE:
<223> OTHER INFORMATION: HLA restricted peptide

<400> SEQUENCE: 868

Trp Lys Glu Pro Asp Val Tyr Tyr Thr Ser
1               5                   10

<210> SEQ ID NO 869
<211> LENGTH: 9
<212> TYPE: PRT
<213> ORGANISM: Artificial sequence
<220> FEATURE:
<223> OTHER INFORMATION: HLA restricted peptide

<400> SEQUENCE: 869

Trp Pro Pro Trp Gln Ala Gly Ile Leu
1               5

<210> SEQ ID NO 870
<211> LENGTH: 10
<212> TYPE: PRT
<213> ORGANISM: Artificial sequence
<220> FEATURE:
<223> OTHER INFORMATION: HLA restricted peptide -continued

```
<400> SEQUENCE: 870

Trp Pro Pro Trp Gln Ala Gly Ile Leu Ala
1               5                   10

<210> SEQ ID NO 871
<211> LENGTH: 9
<212> TYPE: PRT
<213> ORGANISM: Artificial sequence
<220> FEATURE:
<223> OTHER INFORMATION: HLA restricted peptide

<400> SEQUENCE: 871

Trp Gln Ala Gly Ile Leu Ala Arg Asn
1               5

<210> SEQ ID NO 872
<211> LENGTH: 10
<212> TYPE: PRT
<213> ORGANISM: Artificial sequence
<220> FEATURE:
<223> OTHER INFORMATION: HLA restricted peptide

<400> SEQUENCE: 872

Trp Gln Ala Gly Ile Leu Ala Arg Asn Leu
1               5                   10

<210> SEQ ID NO 873
<211> LENGTH: 9
<212> TYPE: PRT
<213> ORGANISM: Artificial sequence
<220> FEATURE:
<223> OTHER INFORMATION: HLA restricted peptide

<400> SEQUENCE: 873

Trp Gln Ala Arg Leu Thr Val Ser Gly
1               5

<210> SEQ ID NO 874
<211> LENGTH: 10
<212> TYPE: PRT
<213> ORGANISM: Artificial sequence
<220> FEATURE:
<223> OTHER INFORMATION: HLA restricted peptide

<400> SEQUENCE: 874

Trp Gln Ala Arg Leu Thr Val Ser Gly Leu
1               5                   10

<210> SEQ ID NO 875
<211> LENGTH: 9
<212> TYPE: PRT
<213> ORGANISM: Artificial sequence
<220> FEATURE:
<223> OTHER INFORMATION: HLA restricted peptide

<400> SEQUENCE: 875

Trp Gln Pro Ala Ala Gln Pro Lys Arg
1               5

<210> SEQ ID NO 876
<211> LENGTH: 10
<212> TYPE: PRT
<213> ORGANISM: Artificial sequence
<220> FEATURE:
<223> OTHER INFORMATION: HLA restricted peptide

<400> SEQUENCE: 876
```

Trp Gln Pro Ala Ala Gln Pro Lys Arg Arg
1               5                   10

<210> SEQ ID NO 877
<211> LENGTH: 9
<212> TYPE: PRT
<213> ORGANISM: Artificial sequence
<220> FEATURE:
<223> OTHER INFORMATION: HLA restricted peptide

<400> SEQUENCE: 877

Trp Thr Arg Gln Gln Asn Gln Trp Lys
1               5

<210> SEQ ID NO 878
<211> LENGTH: 9
<212> TYPE: PRT
<213> ORGANISM: Artificial sequence
<220> FEATURE:
<223> OTHER INFORMATION: HLA restricted peptide

<400> SEQUENCE: 878

Tyr Ala Leu Pro Leu Lys Met Leu Asn
1               5

<210> SEQ ID NO 879
<211> LENGTH: 10
<212> TYPE: PRT
<213> ORGANISM: Artificial sequence
<220> FEATURE:
<223> OTHER INFORMATION: HLA restricted peptide

<400> SEQUENCE: 879

Tyr Ala Leu Pro Leu Lys Met Leu Asn Ile
1               5                   10

<210> SEQ ID NO 880
<211> LENGTH: 9
<212> TYPE: PRT
<213> ORGANISM: Artificial sequence
<220> FEATURE:
<223> OTHER INFORMATION: HLA restricted peptide

<400> SEQUENCE: 880

Tyr Asp Pro Val Ala Ala Leu Phe Phe
1               5

<210> SEQ ID NO 881
<211> LENGTH: 10
<212> TYPE: PRT
<213> ORGANISM: Artificial sequence
<220> FEATURE:
<223> OTHER INFORMATION: HLA restricted peptide

<400> SEQUENCE: 881

Tyr Asp Pro Val Ala Ala Leu Phe Phe Phe
1               5                   10

<210> SEQ ID NO 882
<211> LENGTH: 9
<212> TYPE: PRT
<213> ORGANISM: Artificial sequence
<220> FEATURE:
<223> OTHER INFORMATION: HLA restricted peptide

<400> SEQUENCE: 882

Tyr Phe Thr Gly Ser Glu Val Glu Asn
1               5

```
<210> SEQ ID NO 883
<211> LENGTH: 10
<212> TYPE: PRT
<213> ORGANISM: Artificial sequence
<220> FEATURE:
<223> OTHER INFORMATION: HLA restricted peptide

<400> SEQUENCE: 883

Tyr Phe Thr Gly Ser Glu Val Glu Asn Val
1               5                   10

<210> SEQ ID NO 884
<211> LENGTH: 9
<212> TYPE: PRT
<213> ORGANISM: Artificial sequence
<220> FEATURE:
<223> OTHER INFORMATION: HLA restricted peptide

<400> SEQUENCE: 884

Tyr Leu Glu Ser Phe Cys Glu Asp Val
1               5

<210> SEQ ID NO 885
<211> LENGTH: 9
<212> TYPE: PRT
<213> ORGANISM: Artificial sequence
<220> FEATURE:
<223> OTHER INFORMATION: HLA restricted peptide

<400> SEQUENCE: 885

Tyr Pro Ser Ala Ala Glu Arg Lys His
1               5

<210> SEQ ID NO 886
<211> LENGTH: 10
<212> TYPE: PRT
<213> ORGANISM: Artificial sequence
<220> FEATURE:
<223> OTHER INFORMATION: HLA restricted peptide

<400> SEQUENCE: 886

Tyr Pro Ser Ala Ala Glu Arg Lys His Arg
1               5                   10

<210> SEQ ID NO 887
<211> LENGTH: 9
<212> TYPE: PRT
<213> ORGANISM: Artificial sequence
<220> FEATURE:
<223> OTHER INFORMATION: HLA restricted peptide

<400> SEQUENCE: 887

Tyr Gln Glu Phe Phe Trp Asp Ala Asn
1               5

<210> SEQ ID NO 888
<211> LENGTH: 10
<212> TYPE: PRT
<213> ORGANISM: Artificial sequence
<220> FEATURE:
<223> OTHER INFORMATION: HLA restricted peptide

<400> SEQUENCE: 888

Tyr Gln Glu Phe Phe Trp Asp Ala Asn Asp
1               5                   10
```

```
<210> SEQ ID NO 889
<211> LENGTH: 9
<212> TYPE: PRT
<213> ORGANISM: Artificial sequence
<220> FEATURE:
<223> OTHER INFORMATION: HLA restricted peptide

<400> SEQUENCE: 889

Tyr Arg His Thr Trp Asp Arg His Asp
1               5

<210> SEQ ID NO 890
<211> LENGTH: 10
<212> TYPE: PRT
<213> ORGANISM: Artificial sequence
<220> FEATURE:
<223> OTHER INFORMATION: HLA restricted peptide

<400> SEQUENCE: 890

Tyr Arg His Thr Trp Asp Arg His Asp Glu
1               5                   10

<210> SEQ ID NO 891
<211> LENGTH: 9
<212> TYPE: PRT
<213> ORGANISM: Artificial sequence
<220> FEATURE:
<223> OTHER INFORMATION: HLA restricted peptide

<400> SEQUENCE: 891

Tyr Arg Ile Phe Ala Glu Leu Glu Gly
1               5

<210> SEQ ID NO 892
<211> LENGTH: 10
<212> TYPE: PRT
<213> ORGANISM: Artificial sequence
<220> FEATURE:
<223> OTHER INFORMATION: HLA restricted peptide

<400> SEQUENCE: 892

Tyr Arg Ile Phe Ala Glu Leu Glu Gly Val
1               5                   10

<210> SEQ ID NO 893
<211> LENGTH: 9
<212> TYPE: PRT
<213> ORGANISM: Artificial sequence
<220> FEATURE:
<223> OTHER INFORMATION: HLA restricted peptide

<400> SEQUENCE: 893

Tyr Arg Ile Gln Gly Lys Leu Glu Tyr
1               5

<210> SEQ ID NO 894
<211> LENGTH: 10
<212> TYPE: PRT
<213> ORGANISM: Artificial sequence
<220> FEATURE:
<223> OTHER INFORMATION: HLA restricted peptide

<400> SEQUENCE: 894

Tyr Arg Ile Gln Gly Lys Leu Glu Tyr Arg
1               5                   10

<210> SEQ ID NO 895
<211> LENGTH: 9
```

```
<212> TYPE: PRT
<213> ORGANISM: Artificial sequence
<220> FEATURE:
<223> OTHER INFORMATION: HLA restricted peptide

<400> SEQUENCE: 895

Tyr Ser Glu His Pro Thr Phe Thr Ser
1               5

<210> SEQ ID NO 896
<211> LENGTH: 10
<212> TYPE: PRT
<213> ORGANISM: Artificial sequence
<220> FEATURE:
<223> OTHER INFORMATION: HLA restricted peptide

<400> SEQUENCE: 896

Tyr Ser Glu His Pro Thr Phe Thr Ser Gln
1               5                   10

<210> SEQ ID NO 897
<211> LENGTH: 9
<212> TYPE: PRT
<213> ORGANISM: Artificial sequence
<220> FEATURE:
<223> OTHER INFORMATION: HLA restricted peptide

<400> SEQUENCE: 897

Tyr Thr Pro Asp Ser Thr Pro Cys His
1               5

<210> SEQ ID NO 898
<211> LENGTH: 10
<212> TYPE: PRT
<213> ORGANISM: Artificial sequence
<220> FEATURE:
<223> OTHER INFORMATION: HLA restricted peptide

<400> SEQUENCE: 898

Tyr Thr Pro Asp Ser Thr Pro Cys His Arg
1               5                   10

<210> SEQ ID NO 899
<211> LENGTH: 9
<212> TYPE: PRT
<213> ORGANISM: Artificial sequence
<220> FEATURE:
<223> OTHER INFORMATION: HLA restricted peptide

<400> SEQUENCE: 899

Tyr Thr Ser Ala Phe Val Phe Pro Thr
1               5

<210> SEQ ID NO 900
<211> LENGTH: 10
<212> TYPE: PRT
<213> ORGANISM: Artificial sequence
<220> FEATURE:
<223> OTHER INFORMATION: HLA restricted peptide

<400> SEQUENCE: 900

Tyr Thr Ser Ala Phe Val Phe Pro Thr Lys
1               5                   10

<210> SEQ ID NO 901
<211> LENGTH: 9
<212> TYPE: PRT
<213> ORGANISM: Artificial sequence
```

-continued

```
<220> FEATURE:
<223> OTHER INFORMATION: HLA restricted peptide

<400> SEQUENCE: 901

Tyr Val Lys Val Tyr Leu Glu Ser Phe
1               5

<210> SEQ ID NO 902
<211> LENGTH: 10
<212> TYPE: PRT
<213> ORGANISM: Artificial sequence
<220> FEATURE:
<223> OTHER INFORMATION: HLA restricted peptide

<400> SEQUENCE: 902

Tyr Val Lys Val Tyr Leu Glu Ser Phe Cys
1               5                   10

<210> SEQ ID NO 903
<211> LENGTH: 9
<212> TYPE: PRT
<213> ORGANISM: Artificial sequence
<220> FEATURE:
<223> OTHER INFORMATION: HLA restricted peptide

<400> SEQUENCE: 903

Tyr Val Tyr Ala Leu Pro Leu Lys Met
1               5

<210> SEQ ID NO 904
<211> LENGTH: 10
<212> TYPE: PRT
<213> ORGANISM: Artificial sequence
<220> FEATURE:
<223> OTHER INFORMATION: HLA restricted peptide

<400> SEQUENCE: 904

Tyr Val Tyr Ala Leu Pro Leu Lys Met Leu
1               5                   10
```

ANTIBODIES AND THEIR USES FOR DIAGNOSIS AND TREATMENT OF CYTOMEGALOVIRUS INFECTION AND ASSOCIATED DISEASES

RELATED APPLICATIONS

This Application is a National Phase of PCT Patent Application No. PCT/IL2008/000437 having International filing date of Mar. 27, 2008, which claims the benefit of U.S. Provisional Patent Application Nos. 60/929,207 filed on Jun. 18, 2007; and 60/907,343 filed on Mar. 29, 2007. The contents of the above Applications are all incorporated herein by reference.

FIELD AND BACKGROUND OF THE INVENTION

The present invention, in some embodiments thereof, relates to methods of diagnosing and treating cytomegalovirus diseases and, more particularly, but not exclusively, to antibodies capable of same.

Of all the human herpesviruses described to date, infection with cytomegalovirus (CMV) is considered to be the main cause of morbidity and mortality. Approximately 70% of the world population are carriers of the virus. Primary infection with the virus results in a life long persistence in a latent form and is therefore generally asymptomatic in healthy adults. However, some individuals, such as immuno-compromised organ transplant recipients, or individuals infected with human immunodeficiency virus (HIV), are at high risk of developing life threatening CMV disease due to CMV reactivation. In addition, CMV has emerged in recent years as the most important cause of congenital infection in the developed world, commonly leading to mental retardation and developmental disability.

Immunity to CMV is complex and involves humoral and cell-mediated responses. Studies showed that both natural killer (NK) cells and cytotoxic T-lymphocytes (CTLs) are of primary importance in prevention of recurrence. Many gene products participate in generating the CTL response to CMV infection, however, the high level expression frequencies of the viral protein pp65 (e.g., Genbank Accession No. M15120; SEQ ID NO:48) suggests pp65 as the main target of the CTL-mediated immune response. Among all pp65 peptides, CMV specific—CTL activity in HLA-A2 positive individuals was found to be mainly directed to the peptide pp65$_{495-503}$ (NLVPMVATV; SEQ ID NO:3) (Chee M S et al., 1990).

Cytosolic proteins, usually synthesized in the cells, such as CMV viral proteins, enter the class I MHC pathway of antigen presentation. In the first step, ubiquitinated cytoplasmic proteins are degraded by the proteasome, a cytoplasmic multiprotein complex which generates a large portion of peptides destined for display by class I MHC molecules. Peptides are then delivered from the cytoplasm to the endoplasmic reticulum (ER) by the transporter associated with antigen presentation (TAP) molecules. Newly formed class I MHC dimers in the ER associate with and bind peptides delivered by the TAP. Peptide binding stabilizes class I MHC molecules and permits their movement out of the ER, through the Golgi apparatus, to the cell surface. This pathway ensures that any cell synthesizing viral proteins can be marked for recognition and killing by CD8+ CTL.

Characterization of class I MHC-peptide presentation is essential for understanding the acquired arm of the immune response. The conventional strategy for detecting and studying rare populations of antigen (Ag)-specific CD8+ T cells is the application of tetrameric arrays of class I peptide-MHC complexes (Altman J D., et al., 1996; Lee P P et al., 1999).

The diagnosis of diseases associated with CMV infection such as retinitis, pneumonia, gastrointestinal disorders, and encephalitis is based on clinical, histological, virological and DNA tests.

Current methods of treating CMV in immuno-compromised (e.g., immuno-suppressed) subjects (e.g., HIV patients, bone marrow transplanted subjects), especially CMV retinitis, include anti viral drugs such as Foscarnet (FOSCAVIR®), Cidofovir (VISTIDE®) Valganciclovir (VALCYTE®) Ganciclovir implants (VITRASERT®) Fomivirsen (VITRAVENE®). However, the use of these drugs may be associated with serious side effects such as kidney damage, neutropenia and hypocalcemia. One strategy of directly targeting CMV associated pathologies includes the use of HLA-A2-restricted CD8(+) CTLs directed against pp65. However, attempts to use CMV-specific CD8+ T cell clones for killing CMV-infected retinal pigment epithelial cells have failed (Allart S, et al., 2003; Invest Ophthalmol Vis Sci. 44: 665-71).

Additional background art includes U.S. patent application Ser. Nos. 11/203,137; 11/074,803; 10/510,229; and 11/582,416 to Reiter Y, et al.

SUMMARY OF THE INVENTION

According to an aspect of some embodiments of the present invention there is provided an antibody comprising an antigen recognition domain capable of binding an MHC molecule being complexed with a cytomegalovirus (CMV) pp65 or pp64 peptide, wherein the antibody does not bind the MHC molecule in an absence of the complexed peptide, and wherein the antibody does not bind the peptide in an absence of the MHC molecule.

According to an aspect of some embodiments of the present invention there is provided an antibody comprising a multivalent form of the antibody of the present invention.

According to an aspect of some embodiments of the present invention there is provided a pharmaceutical composition comprising as an active ingredient the antibody of the antibody of the present invention.

According to an aspect of some embodiments of the present invention there is provided a method of detecting a cell expressing a cytomegalovirus (CMV) antigen, comprising contacting the cell with the antibody of the present invention under conditions which allow immunocomplex formation, wherein a presence or a level above a predetermined threshold of the immunocomplex is indicative of CMV expression in the cell.

According to an aspect of some embodiments of the present invention there is provided a method of diagnosing a cytomegalovirus (CMV) infection in a subject in need thereof, comprising contacting a cell of the subject with the antibody of the present invention under conditions which allow immunocomplex formation, wherein a presence or a level above a pre-determined threshold of the immunocomplex in the cell is indicative of the CMV infection in the subject.

According to an aspect of some embodiments of the present invention there is provided a method of treating a disease associated with cytomegalovirus (CMV) infection, comprising administering to a subject in need thereof a therapeutically effective amount of the antibody of the present invention, thereby treating the disease associated with CMV infection.

According to some embodiments of the invention, the cytomegalovirus (CMV) pp65 or pp64 peptide is set forth by SEQ ID NO:3.

According to some embodiments of the invention, the antigen recognition domain comprises complementarity determining region (CDR) amino acid sequences as set forth in SEQ ID NOs:24-26 and 30-32.

According to some embodiments of the invention, the antigen recognition domain comprises complementarity determining region (CDR) amino acid sequences as set forth in SEQ ID NOs: 36-38 and 42-44.

According to some embodiments of the invention, the antibody being conjugated to a therapeutic moiety.

According to some embodiments of the invention, the antibody is attached to a detectable moiety.

According to some embodiments of the invention, the antibody being an antibody fragment.

According to some embodiments of the invention, the multivalent form is an IgG antibody.

According to some embodiments of the invention, the subject has a suppressed or a compromised immune system.

According to some embodiments of the invention, the CMV infection is associated with a disease selected from the group consisting of mononucleosis, retinitis, pneumonia, gastrointestinal disorders, and encephalitis.

According to some embodiments of the invention, the cell is a retina cell, lung epithelial cell, a gastrointestinal epithelial cell or a brain cell.

According to some embodiments of the invention, the subject is an immuno-compromised organ transplant recipient.

According to some embodiments of the invention, the subject is infected with human immunodeficiency virus (HIV).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

As used herein, the terms "comprising" and "including" or grammatical variants thereof are to be taken as specifying the stated features, integers, steps or components but do not preclude the addition of one or more additional features, integers, steps, components or groups thereof. This term encompasses the terms "consisting of" and "consisting essentially of".

The phrase "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

The term "method" refers to manners, means, techniques and procedures for accomplishing a given task including, but not limited to, those manners, means, techniques and procedures either known to, or readily developed from known manners, means, techniques and procedures by practitioners of the biotechnology and medical art.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 5A:
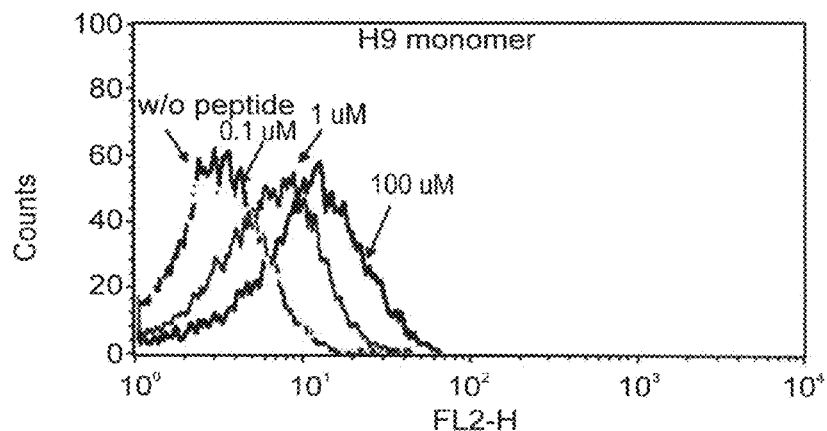

FIGS. 1a-d depict the specificity of recombinant Fab Abs to the MHC class I (HLA-A2)-CMV pp65-derived peptide (NLVPMVATV; SEQ ID NO:3) complex. FIG. 1a—A histogram depicting an ELISA assay in which phage Fab clones were reacted with HLA-A2/pp65 complexes. Fab clones were reacted against a specific MHC class I-peptide complex (HLA-A2/pp65$_{495-503}$, marked as "CMV") and control non-specific complexes containing gp100$_{280-288}$ peptide (SEQ ID NO:4; YLEPGPVTA; marked as "280"). FIG. 1b—An SDS-PAGE analysis depicting the expression and purification of HLA-A2/pp65 TCR-like Fabs. SDS-PAGE analysis of the purified Fab proteins was performed after metal affinity chromatography. Note the intense protein bands purified from phage clone F5 or H9 with a molecular weight of 45 kDa. FIGS. 1c and d—Bar graphs depicting an ELISA assay of the binding of soluble purified Fabs to the HLA-A2-peptide complexes. The soluble clones H9 (FIG. 1c) and F5 (FIG. 1d) were reacted against a specific complex (HLA-A2/pp65; "CMV") or control non specific complexes containing the following peptides: EBV (280-288; SEQ ID NO:5; GLCTLVAML), gp100 (280-288; SEQ ID NO:4), hTERT (540-548; SEQ ID NO:6; ILAKFLHWL), gp100 (209-217; SEQ ID NO:7; IMDQVPFSV), hTERT (865-873; SEQ ID NO:8; RLVDDFLLV), Gag (77-85; SEQ ID NO:9; SLYNTVATL), Pol (476-484; SEQ ID NO:10; ILEPVHGV), MART (26-35; SEQ ID NO:11; ELAGIGILTV), XAGE (SEQ ID NO:12; GVFPSAPSPV), TARP (29-37; SEQ ID NO:13; FLRNFSLML), TAX (11-19; SEQ ID NO:14; LLFGYPVYV). Specificity towards HLA-A2/pp65 complex can be observed in each of the two clones.

FIGS. 2a-d are flow cytometry analyses depicting the detection of MHC-peptide complexes on the surface of APCs using the H9 and F5 soluble Fabs. JY or RMAS-HHD cell lines were pulsed with various specific and nonspecific peptides. JY cells (FIGS. 2a and c) or RMAS-HHD cells (FIGS. 2b and d) loaded with the CMV pp65$_{495-503}$ peptide (SEQ ID NO:3) or control peptides ("280", "540"), incubated with the H9 (FIGS. 2a, b) or F5 (FIGS. 2c, d) Fab respectively. Specific staining of the pp65 loaded cells, but not the control cells, is shown. The same type of assay was performed with 10 different control HLA-A2-restricted peptides (data not shown).

FIGS. 3a-c are flow cytometry analyses depicting the detection of MHC-peptide complexes on the surface of JY cells using H9 Fab in its monomeric or tetrameric forms. The JY cell line was pulsed with different peptides. FIG. 3a—JY cells loaded with pp65$_{495-503}$ peptide (SEQ ID NO:3). Incubations were with H9 Fab monomer and PE-labeled anti human Fab, or with H9 Fab tetramer connected to PE labeled streptavidin. FIG. 3b—JY cells loaded with pp65$_{495-503}$ peptide (SEQ ID NO:3). Incubations were with H9 Fab monomer and FITC-labeled anti human Fab, or with H9 whole IgG Ab and FITC-labeled anti human Fab. FIG. 3c—JY cells loaded with gp100$_{280-288}$ 280-288 (SEQ ID NO:4) as a control. Incubations were with H9 Fab monomer and PE-labeled anti human Fab, H9 Fab tetramer connected to PE labeled streptavidin or with H9 IgG Ab and PE-labeled anti human Fab. Note the specific binding of the H9 Fab in its monomeric or tetrameric form, as well as the whole IgG H9 Ab to JY cells pulsed with the HLA-A2-CMV peptide (pp65 495-503) but not with JY cells when pulsed with the control peptide (gp100 280-288). Also note the increased avidity of the IgG Ab as compared to the monomeric Fab, or the increased avidity of the tetrameric Fab form as compared to the monomeric Fab form.

FIGS. 4a-c are graphs depicting the affinity determination of the H9 Ab in its monomeric (FIG. 4a) or IgG (FIG. 4b) forms, as detected by surface plasmon resonance (SPR) analysis. Each of the forms was flowed over the relevant wells at three different concentrations (0.05 µM, 0.1 µM, 0.2 µM) of biotinylated HLA-A2-pp65 495-503 complexes. As a control, H9 Ab were flowed over wells which were coated with control biotinylated HLA-A2/pEBV complexes (FIG. 4c). Note the absence of binding signal of the H9 Ab over the HLA-A2/pEBV complex (the concentration of HLA-A2/pEBV complex was 0.2 µM) as compared to the HLA-A2/pp65 complex (the concentration of HLA-A2/pp65 complex was 0.2 µM).

Figure 5B:
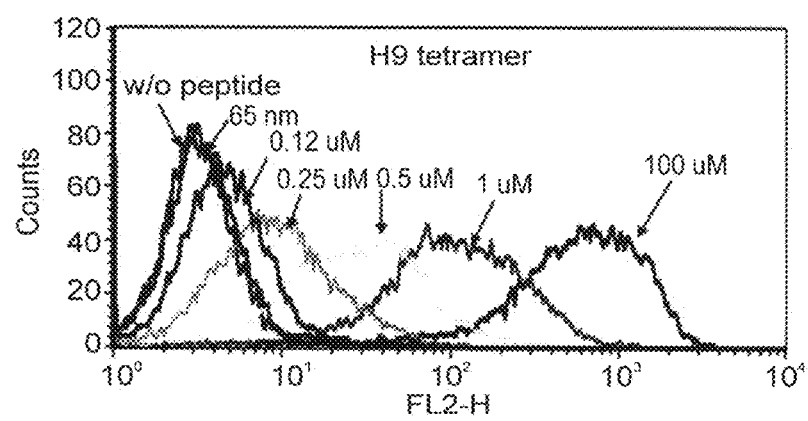
Figure 5C:
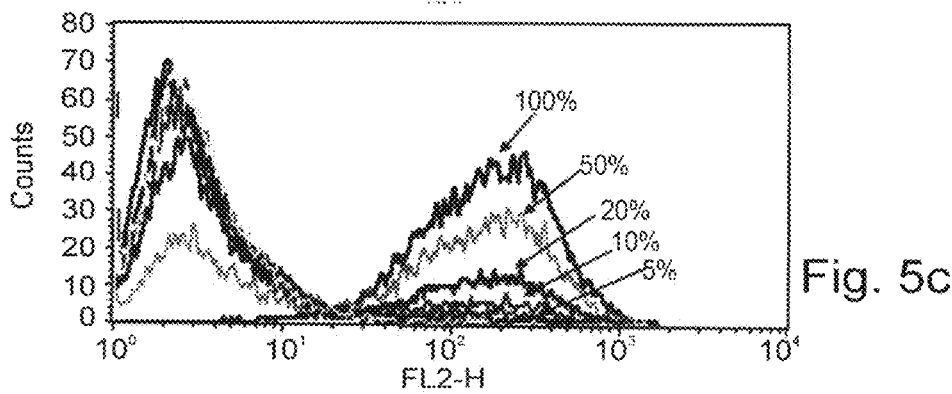

FIGS. 5a-c are flow cytometry analyses depicting the detection of Fab sensitivity threshold (FIGS. 5a-b) and of rare cells bearing the specific peptide-MHC complex in a heterogenous cell population (FIG. 5c). In order to detect Fab sensitivity threshold, JY cells were pulsed with various concentrations of $pp65_{495-503}$ peptide (0, 65 nM, 0.1 µM, 012 µM, 0.25 µM, 0.5 µM, 1 µM or 100 µM), and incubated with H9 Fab monomer (at a concentration of 10 µg/ml) and PE-labeled anti human Fab (FIG. 5a), or H9 Fab tetramer (at a concentration of 10 µg/ml connected to PE labeled streptavidin (FIG. 5b). Note the significantly low concentration of the $pp65_{495-503}$ peptide needed to pulse JY cells in order to obtain a significant binding with the H9 tetramer [e.g., a threshold of 65 nM) of the pp65 495-503 peptide] or the H9 monomer [e.g., a threshold of 0.1 µM of the pp65 495-503 peptide]. Detection of rare population of cells bearing the specific MHC-peptide complex was by pulsing JY APCs with the pp65 495-503 peptide and mixing them with APD cells (HLA-A2− B cell line) at different ratios (FIG. 5c) so as to obtain pre-determined concentrations of cells expressing the specific MHC-peptide complex. The mixed population was stained with H9 Fab (at a concentration of 10 µg/ml), and detection sensitivity was monitored by flow cytometry. Note the specific detection of as low as 5% cells bearing the specific MHC-pp65 495-503 complex.

FIGS. 6a-m are flow cytometry analyses (FIGS. 6a-l) and a bar graph (FIG. 6m) depicting the detection of the specific HLA-A2/pp65 complex by H9 tetramer (FIG. 6e-h) or H9 IgG Ab (Data not shown), after naturally occurring active intracellular processing. HLA-A2 positive fibroblasts were infected with the CMV laboratory strain AD169 (FIGS. 6a, e, i). HLA-A2 positive uninfected fibroblasts were used as a control (FIGS. 6c, g, k) as well as HLA-A2 negative infected fibroblasts (FIGS. 6b, f, j) or HLA-A2 negative uninfected fibroblasts (FIGS. 6d, h, l). Incubation were with PE labeled BB7.2 (FIGS. 6a-d), PE labeled H9 tetramer (FIGS. 6e-h) or anti pp65 FITC mAB (FIGS. 6i-l) followed by the secondary antibody FITC-labeled anti mouse IgG, 72 hours after infection. Note the specific binding of the H9 tetramer to HLA-A2 positive cells following infection with CMV (FIG. 6e) as compared to the absence of binding to HLA-A2 negative cells (FIG. 6f) or to uninfected cells (FIGS. 6g and h), demonstrating the specific HLA-A2-CMV (pp65 495-503) complex—dependent binding of the H9 antibody to cells ex vivo. In contrast, note the non-CMV-dependent binding of the BB7.2 Ab to HLA-A2 positive cells [same binding efficacy in the presence (FIG. 6a) or absence (FIG. 6c) of CMV peptide], and the non-HLA-A2-dependent binding of the Anti pp65 Ab in CMV-infected cells [same binding efficacy in HLA-A2 positive (FIG. 6i) or HLA-A2 negative (FIG. 6j) cells]. FIG. 6m—A cytotoxicity assay by which H9 IgG Ab is shown to block virus infected cells killing mediated by specific CTL line. Fibroblast cells were radioactively labeled with $S^{35}$ methionine before infection with the CMV virus and 72 hours later the cells were incubated with the H9 IgG Ab. CTLs were added at a target (fibroblast cells infected with CMV):effector (CTL) ratio of 1:10 and incubated for five hours. Cells incubated with W6 Ab (an antibody directed against HLA-A,B,C) were used as positive control, while cells without any Ab incubation served as a reference for the maximum killing rate. These results demonstrate the TCR-like specificity of the H9 IgG Ab to specific CMV-infected cells.

FIGS. 7a-t are flow cytometry analyses depicting kinetic assays which follow the dynamics between the HLA-A2 extracellular presentation, the HLA-A2/pp65 peptide extracellular and intracellular complex presentation and the pp65 expression, in HLA-A2+ (positive) cells infected with the CMV wild-type (WT) AD169 strain. 36 (FIGS. 7a-e), 72 (FIGS. 7f-j), 96 (FIGS. 7k-o), and 120 (FIGS. 7p-t) hours after infection the cells were harvested and incubated with the BB7.2 PE labeled Ab (FIGS. 7c, d, h, i, m, n, r, s), anti pp65 Ab (FIGS. 7e, j, o, t; intracellular) and H9 IgG Ab (FIGS. 7a, b, f, g, k, l, p, q) antibodies and analyzed by flow cytometry. FITC-labeled anti mouse antibody and Alexa fluor$^{488}$-labeled anti human antibody were used as secondary antibodies for the anti pp65 mAb and the H9 IgG Ab respectively. Intracellular staining was feasible by cells permeabilization.

FIGS. 8a-t are flow cytometry analyses depicting kinetic assays which follow the dynamics between the HLA-A2 extracellular presentation, the HLA-A2/pp65 peptide extracellular and intracellular complex presentation and the pp65 expression, in HLA-A2+ (positive) cells infected with the RV798 mutant strain. 36 (FIGS. 8a-e), 72 (FIGS. 8f-j), 96 (FIGS. 8k-o), and 120 (FIGS. 8p-t) hours after infection cells were harvested and incubated with BB7.2 PE labeled Ab (FIGS. 8c, d, h, i, m, n, r, s), anti pp65 Ab (FIGS. 8e, j, o, t; intracellular) and H9 IgG Ab (FIGS. 8a, b, f, g, k, l, p, q) antibodies and analyzed by flow cytometry. FITC-labeled anti mouse antibody and Alexa fluor$^{488}$-labeled anti human antibody were used as secondary antibodies for the anti pp65 mAb and the H9 IgG Ab respectively. Intracellular staining was feasible by cells permeabilization.

FIGS. 9a-y are flow cytometry analyses depicting kinetic assays which follow the dynamics between the HLA-A2 extracellular presentation, the HLA-A2/pp65 peptide extracellular and intracellular complex presentation and the pp65 expression, in HLA-A2+ (positive) uninfected cells (FIGS. 9a-t) or in HLA-A2− (negative) cells infected with the AD169 Wild Type strain of CMV. Staining with the H9 IgG antibody, BB7.2 antibody or the anti pp65 antibodies was effected in the uninfected cells harvested at parallel times [i.e., 36 (FIGS. 9a-e), 72 (FIGS. 9f-j), 96 (FIGS. 9k-o), and 120 (FIGS. 9p-t) hours] to the cells infected with the viruses as described in FIGS. 7a-t and 8a-t, hereinabove. Infected HLA-A2− (negative) cells were harvested and stained with the H9 IgG antibody, BB7.2 antibody or the anti pp65 antibody at 120 hours after infection with the AD169 CMV virus. Extracellular staining with the H9 IgG antibody is shown in FIGS. 9a, l, k, p and u. Intracellular staining with the H9 IgG antibody is shown in FIGS. 9b, g, l, q and v. Extracellular staining with the BB7.2 antibody is shown in FIGS. 9c, h, m, r and w. Intracellular staining with the BB7.2 antibody is shown in FIGS. 9d, i, n, s and x. Staining with the anti pp65 antibody is shown in FIGS. 9e, j, o, t, and y. FITC-labeled anti mouse antibody and Alexa fluor$^{488}$-labeled anti human antibody were used as secondary antibodies for the anti pp65 mAb and the H9 IgG Ab respectively. Intracellular staining was feasible by cells permeabilization.

FIGS. 10a-d are bar graphs depicting quantization of the number of HLA-A2/pp65 complexes inside and on the surface of virus infected cells. The level of fluorescence intensity on stained cells was compared with the fluorescence intensities of calibration beads with known numbers of PE molecules per bead, thus providing a mean of quantifying PE-stained cells using a flow cytometer. Incubations were with BB7.2 PE labeled Ab (FIGS. 10c and d), and H9 Ab (FIGS. 10a and b). PE-labeled anti kappa antibody was used as a secondary antibody for the H9 IgG Ab. The calculated number of HLA-A2/pp65 complexes inside cells (FIG. 10a) and on the surface (FIG. 10b) as well as the number of general HLA-A2 complexes inside the cells (FIG. 10c) and on the surface (FIG. 10d) in each time scale, is shown for cells infected with AD169 (WT), RV798 (mutant), and uninfected cells.

FIGS. 11a-o are confocal microscopy images of immunofluorescence analyses depicting direct visualization of HLA-A2/pp65 complexes in CMV infected fibroblasts. Infected cells were harvested at five time scales post infection [24 (FIGS. 11a-c), 48 (FIGS. 11d-f), 72 (FIGS. 11g-i), 96 (FIGS. 11j-l) and 120 (FIGS. 11m-o) hours]. Intracellular double staining were with the H9 Ab and Golgi marker. Secondary Ab for the H9 Ab was anti human alexa fluor$^{488}$. Secondary antibody for the Golgi marker was anti mouse alexa fluor$^{594}$. Shown are images of H9 Ab alone (FIGS. 11a, d, g, j, m), Golgi marker alone (FIGS. 11b, e, h, k, n) or merged images of H9 and Golgi marker (FIGS. 11c, f, I, l, o).

FIGS. 12a-o are confocal microscopy images of immunofluorescence analyses depicting direct visualization of HLA-A2/pp65 complexes in CMV infected fibroblasts. Infected cells were harvested at five time scales post infection [24 (FIGS. 12a-c), 48 (FIGS. 12d-f), 72 (FIGS. 12g-i), 96 (FIGS. 12j-l) and 120 (FIGS. 12m-o) hours]. Intracellular double staining were with the H9 Ab and the ER marker. Secondary Ab for the H9 Ab was anti human alexa fluor$^{488}$. Secondary antibody for the ER marker was anti mouse alexa fluor$^{594}$. Shown are images of H9 Ab alone (FIGS. 12a, d, g, j, m). ER marker alone (FIGS. 12b, e, h, k, n) or merged images of H9 and ER marker (FIGS. 12c, f, I, l, o).

FIGS. 13a-j are confocal microscopy images of immunofluorescence analyses depicting direct visualization of HLA-A2/pp65 complexes of the surface (extracellular) of CMV infected fibroblasts. The cells were extracellularly stained with the H9 Ab, and anti human alexa fluor$^{488}$ as a secondary Ab (FIGS. 13a-e). Noninfected fibroblast cells were used as a control (FIGS. 13f-h). Verification of the virus infection was with anti pp65 Ab and anti mouse alexa fluor$^{594}$ as a secondary Ab (FIGS. 13i-j).

FIGS. 14a-d depict the amino acid sequences (FIGS. 14a and c; SEQ ID NOs:16 and 18) and the nucleic acid sequences (FIGS. 14b and d; SEQ ID NOs:17 and 19) of the heavy chain (FIGS. 14a and b) and the light chain (FIGS. 14c and d) of Fab H9. The CDRs are shown in red; the constant regions are shown in green.

FIGS. 15a-d depict the amino acid sequences (FIGS. 15a and c; SEQ ID NOs:20 and 22) and the nucleic acid sequences (FIGS. 15b and d; SEQ ID NOs:21 and 23) of the heavy chain (FIGS. 15b and d) and the light chain (FIGS. 15c and d) of Fab F5. The CDRs are shown in red; the constant regions are shown in green.

FIGS. 16a-d are flow cytometry (FACS) analyses depicting the detection of HLA-A2/pp65 complexes on the surface of virus-infected cells taken from patients. PBMCs isolated from BMT recipients and healthy donors were stained extracellular and intracellular with the H9 Ab and the secondary anti human alexa fluor$^{488}$ Ab. FIG. 16a—Confirmation of the cells' typing by staining with anti HLA-A2 (BB7.2) Ab. FIG. 16b—Extracellular staining of the BMT recipient cells with the H9 Ab. No detection of HLA-A2/pp65 complexes is seen in the infected cells using the H9 Ab. FIGS. 16c-d—Intracellular staining of both BMT recipients (FIG. 16c) and health donor cells (FIG. 16d) with the H9 Ab. A significant specific staining with the H9 Ab of the permeabilized infected cells is seen in the BMT recipients (FIG. 16c). In contrast, no staining of the H9 Ab is seen in cells of the healthy control.

FIGS. 17a-i are flow cytometry (FACS) analyses depicting examination of the proteasome inhibitor effect on the complexes presentation. Infected (FIGS. 17a-f fibroblasts were harvested at three time scales post infection [48 (FIGS. 17a, d), 72 (FIGS. 17b, e), 96 (FIGS. 17c, f) hours], and treated overnight with 10 μg/ml ALLN (acetyl-leucyl-leucyl-norleucinal) (FIGS. 17a-c) or remained untreated (FIGS. 17d-f). The cells were stained with H9 Ab followed by anti human alexa fluor$^{488}$ as a secondary Ab. FACS analysis shows increased intensity of the signals after treatment with the proteasome inhibitor (FIGS. 17a-c), compared to untreated cells (FIGS. 17d-f). Control, uninfected cells (Figures g-i) showed no signal while stained with the H9 Ab.

DESCRIPTION OF SPECIFIC EMBODIMENTS OF THE INVENTION

The present invention, in some embodiments thereof, relates to antibodies capable of binding MHC molecules being complexed with cytomegalovirus (CMV) pp65 or pp64 peptides which can be used to detect CMV infection and presentation on the cell surface and, more particularly, but not exclusively, to methods of diagnosing and treating diseases associated with CMV infection.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

While reducing the invention to practice, the present inventors have generated human T cell receptor (TCR)-like antibodies directed against complexes of MHC and CMV pp65 or pp64 antigenic peptides which can recognize cells infected with CMV and thus can be used to diagnose and treat diseases associated with CMV infection.

As shown in the Examples section which follows, recombinant antibodies [e.g., clones H9 (the amino acid sequence of the heavy chain is set forth by SEQ ID NO:16; the amino acid sequence of the light chain is set forth by SEQ ID NO:18) and F5 (the amino acid sequence of the heavy chain is set forth by SEQ ID NO:20; the amino acid sequence of the light chain is set forth by SEQ ID NO:22] which can specifically recognize MHC molecules when complexed with CMV pp65-derived peptides such as the pp65$_{495-503}$ (SEQ ID NO:3) were isolated and were found to exhibit fine specificity to soluble or membrane-presented CMV pp65-MHC class I complex (Examples 1 and 2 of the Examples section which follows). In addition, multivalent forms of these antibodies (e.g., tetrameric Fabs or bivalent IgG) which exhibit increased avidity while preserving the specificity to the CMV pp65-MHC complex (Example 3 of the Examples section which follows) were capable of detecting as low as 5% of subpopulations of cells bearing CMV pp65 peptide-MHC complexes (Example 4 of the Examples section which follows). Cytotoxicity assays using pp65-specific CD8+ T lymphocytes further demonstrated the specificity of the TCR-like antibodies of the invention for CMV pp65-MHC complexes by their ability to block killing by the CTLs (Example 6 of the Examples section which follows). Moreover, the TCR-like antibodies of the invention enabled one, for the first time, to follow CMV pp65-MHC class I complexes both inside and on the surface of cells infected with CMV (Example 5 of the Examples section which follows). In addition, as shown in FIGS. 7-9 and described in Example 7 of the Examples section which follows, the TCR-like antibodies of the invention demonstrated that there is no correlation between class I MHC down regulation induced by wild-type virus and the generation/presentation of the virus-specific HLA-A2/pp65$_{495-503}$ complex. Further quantitative data revealed that specific HLA-A2/pp65 complexes are being generated in large amounts and accumulated inside the infected cell in a mechanism that is independent to the overall down regulation of HLA-A2 molecules in these cells (Example 8 of the Examples section which follows). In addition, confocal microscopy analysis demonstrated that immediately after CMV infection specific HLA-A2/pp65 complexes are being generated and accumulated in the Golgi compartment and only about 72 hours after infection are the HLA-A2/pp65 complexes displayed on the cell surface (Example 9 of the Examples section which follows). Moreover, as shown in FIGS. 16*a-d* and described in Example 12 of the Examples section which follows, the antibodies of the invention were shown to be capable of detecting HLA-A2/pp65 complexes in blood cells of subjects with CMV reactivation due to immune suppression (e.g., bone marrow transplanted subjects). In addition, as shown in FIGS. 17*a-j* and described in Example 13 of the Examples section which follows, incubation of cells with a proteasome inhibitor resulted in increased presentation of the MHC/pp65 complexes on the cell surface.

Thus, according to an aspect of some embodiments of the present invention there is provided an antibody comprising an antigen recognition domain capable of binding a Major histocompatibility complex (MHC) molecule being complexed with a cytomegalovirus (CMV) pp65 or pp64 peptide, wherein the antibody does not bind the MHC molecule in an absence of the complexed peptide, and wherein the antibody does not bind the peptide in an absence of the MHC molecule.

As used herein, the phrase "major histocompatibility complex (MHC)" refers to a complex of antigens encoded by a group of linked loci, which are collectively termed H-2 in the mouse and HLA in humans. The two principal classes of the MHC antigens, class I and class II, each comprise a set of cell surface glycoproteins which play a role in determining tissue type and transplant compatibility. In transplantation reactions, cytotoxic T-cells (CTLs) respond mainly against foreign class I glycoproteins, while helper T-cells respond mainly against foreign class II glycoproteins.

Major histocompatibility complex (MHC) class I molecules are expressed on the surface of nearly all cells. These molecules function in presenting peptides which are mainly derived from endogenously synthesized proteins to CD8+ T cells via an interaction with the αβ T-cell receptor. The class I MHC molecule is a heterodimer composed of a 46-kDa heavy chain which is non-covalently associated with the 12-kDa light chain β-2 microglobulin. In humans, there are several MHC haplotypes, such as, for example, HLA-A2, HLA-A1, HLA-A3, HLA-A24, HLA-A28, HLA-A31, HLA-A33, HLA-A34, HLA-B7, HLA-B45 and HLA-Cw8, their sequences can be found at the kabbat data base, at htexttransferprotocol://immuno.bme.nwu.edu. Further information concerning MHC haplotypes can be found in Paul, B. Fundamental Immunology Lippincott-Rven Press.

Cytomegalovirus (CMV) belongs to the human herpesviruses. There are several known strains of CMV, including strains 1042, 119, 2387. 4654, 5035, 5040, 5160, 5508, AD169, Eisenhardt, Merlin, P T, Toledo and Towne. During viral infection, the expressed viral proteins, e.g., pp65 of the CMV AD169 strain [GenBank Accession No. M15120 for nucleic acid coding sequence (SEQ ID NO:48) and GenBank Accession No. AAA45996.1 for amino acids (SEQ ID NO:50); or GenBank Accession No. P06725 (SEQ ID NO:53)] pp64 of the CMV Towne strain [GenBank Accession No. M67443 for nucleic acid coding sequence (SEQ ID NO:49) and GenBank Accession No. AAA45994.1 for amino acids (SEQ ID NO:51); or GenBank Accession No. P18139 (SEQ ID NO:52)] are subject to proteasomal degradation and the MHC-restricted peptides bind to the MHC molecules [e.g., MHC class I or MHC class II] and are further presented therewith on the cell surface. The pp65 (561 amino acids in length) and pp64 (551 amino acids in length) proteins of the CMV AD169 and Towne strains, respectively, are 99% identical proteins and share the same amino acid sequence from position 3-551 of pp64 and 13-561 of pp65.

As used herein the term "peptide" refers to native peptides (either proteolysis products or synthetically synthesized peptides) and further to peptidomimetics, such as peptoids and semipeptoids which are peptide analogs, which may have, for example, modifications rendering the peptides more stable while in a body, or more immunogenic. Such modifications include, but are not limited to, cyclization, N terminus modification, C terminus modification, peptide bond modification, including, but not limited to, $CH_2$—NH, $CH_2$—S, $CH_2$—S=O, O=C—NH, $CH_2$—O, $CH_2$—$CH_2$, S=C—NH, CH=CH or CF=CH, backbone modification and residue modification. Methods for preparing peptidomimetic compounds are well known in the art and are specified in Quantitative Drug Design, C. A. Ramsden Gd., Chapter 17.2, F. Choplin Pergamon Press (1992), which is incorporated by reference as if fully set forth herein. Further details in this respect are provided hereinunder.

As used herein in the specification and in the claims section below the term "amino acid" is understood to include the 20 naturally occurring amino acids; those amino acids often modified post-translationally in vivo, including for example hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids. Further elaboration of the possible amino acids usable according to the invention and examples of non-natural amino acids useful in MHC-I HLA-A2 recognizable peptide antigens are given herein under.

Based on accumulated experimental data, it is nowadays possible to predict which of the peptides of a protein will bind to MHC, class I. The HLA-A2 MHC class I has been so far characterized better than other HLA haplotypes, yet predictive and/or sporadic data is available for all other haplotypes.

With respect to HLA-A2 binding peptides, assume the following positions (P1-P9) in a 9-mer peptide:

P1-P2-P3-P4-P5-P6-P7-P8-P9

The P2 and P2 positions include the anchor residues which are the main residues participating in binding to MHC molecules. Amino acid resides engaging positions P2 and P9 are hydrophilic aliphatic non-charged natural amino (examples being Ala, Val, Leu, Ile, Gln, Thr, Ser, Cys, preferably Val and Leu) or of a non-natural hydrophilic aliphatic non-charged amino acid [examples being norleucine (Nle), norvaline (Nva), α-aminobutyric acid]. Positions P1 and P3 are also known to include amino acid residues which participate or assist in binding to MHC molecules, however, these positions can include any amino acids, natural or non-natural. The other positions are engaged by amino acid residues which typically do not participate in binding, rather these amino acids are presented to the immune cells. Further details relating to the binding of peptides to MHC molecules can be found in Parker, K. C., Bednarek, M. A., Coligan, J. E., Scheme for ranking potential HLA-A2 binding peptides based on independent binding of individual peptide side-chains. J Immunol. 152, 163-175, 1994, see Table V, in particular. Hence, scoring of HLA-A2.1 binding peptides can be performed using the HLA Peptide Binding Predictions software approachable through a worldwide web interface at hypertexttransferprotocol://worldwideweb (dot) bimas (dot) dcrt (dot) nih (dot) gov/molbio/hla_bind/index. This software is based on accumulated data and scores every possible peptide in an analyzed protein for possible binding to MHC HLA-A2.1 according to the contribution of every amino acid in the peptide. Theoretical binding scores represent calculated half-life of the HLA-A2.1-peptide complex.

Hydrophilic aliphatic natural amino acids at P2 and P9 can be substituted by synthetic amino acids, preferably Nleu, Nval and/or α-aminobutyric acid. P9 can be also substituted by aliphatic amino acids of the general formula —HN(CH$_2$)$_n$COOH, wherein n=3-5, as well as by branched derivatives thereof, such as, but not limited to,

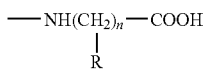

wherein R is, for example, methyl, ethyl or propyl, located at any one or more of the n carbons.

The amino terminal residue (position P1) can be substituted by positively charged aliphatic carboxylic acids, such as, but not limited to, H$_2$N(CH$_2$)$_n$COOH, wherein n=0.2-4 and H$_2$N—C(NH)—NH(CH$_2$)$_n$COOH, wherein n=2-3, as well as by hydroxy Lysine, methyl Lysine or ornithine (Orn). Additionally, the amino terminal residue can be substituted by enlarged aromatic residues, such as, but not limited to, H$_2$N—(C$_6$H$_6$)—CH$_2$—COOH, p-aminophenyl alanine, H$_2$N—F(NH)—NH—(C$_6$H$_6$)—CH$_2$—COOH, p-guanidinophenyl alanine or pyridinoalanine (Pal). These latter residues may form hydrogen bonding with the OH⁻ moieties of the CMV pp65 residues at the MHC-1 N-terminal binding pocket, as well as to create, at the same time aromatic-aromatic interactions.

Derivatization of amino acid residues at positions P4-P8, should these residues have a side-chain, such as, OH, SH or NH$_2$, like Ser, Tyr, Lys, Cys or Orn, can be by alkyl, aryl, alkanoyl or aroyl. In addition, OH groups at these positions may also be derivatized by phosphorylation and/or glycosylation. These derivatizations have been shown in some cases to enhance the binding to the T cell receptor.

Longer derivatives in which the second anchor amino acid is at position P10 may include at P9 most L amino acids. In some cases shorter derivatives are also applicable, in which the C terminal acid serves as the second anchor residue.

Cyclic amino acid derivatives can engage position P4-P8, preferably positions P6 and P7. Cyclization can be obtained through amide bond formation, e.g., by incorporating Glu, Asp, Lys, Orn, di-amino butyric (Dab) acid, di-aminopropionic (Dap) acid at various positions in the chain (—CO—NH or —NH—CO bonds). Backbone to backbone cyclization can also be obtained through incorporation of modified amino acids of the formulas H—N((CH$_2$)$_n$—COOH)—C(R)H—COOH or H—N((CH$_2$)$_n$—COOH)—C(R)H—NH$_2$, wherein n=1-4, and further wherein R is any natural or non-natural side chain of an amino acid.

Cyclization via formation of S—S bonds through incorporation of two Cys residues is also possible. Additional side-chain to side chain cyclization can be obtained via formation of an interaction bond of the formula —(—CH$_2$—)$_n$—S—CH$_2$—C—, wherein n=1 or 2, which is possible, for example, through incorporation of Cys or homoCys and reaction of its free SH group with, e.g., bromoacetylated Lys, Orn, Dab or Dap.

Peptide bonds (—CO—NH—) within the peptide may be substituted by N-methylated bonds (—N(CH$_3$)—CO—), ester bonds (—C(R)H—C—O—O—C(R)—N—), ketomethylen bonds (—CO—CH$_2$—), α-aza bonds (—NH—N(R)—CO—), wherein R is any alkyl, e.g., methyl, carba bonds (—CH$_2$—NH—), hydroxyethylene bonds (—CH(OH)—CH$_2$—), thioamide bonds (—CS—NH—), olefinic double bonds (—CH═CH—), retro amide bonds (—NH—CO—), peptide derivatives (—N(R)—CH$_2$—CO—), wherein R is the "normal" side chain, naturally presented on the carbon atom.

These modifications can occur at any of the bonds along the peptide chain and even at several (2-3) at the same time. According to some embodiments of the invention, but not in all cases necessary, these modifications should exclude anchor amino acids.

Natural aromatic amino acids, Trp, Tyr and Phe, may be substituted for synthetic non-natural acid such as TIC, naphthylelanine (Nol), ring-methylated derivatives of Phe, halogenated derivatives of Phe or o-methyl-Tyr.

Various pp65 or pp64 MHC restricted peptides can be used to form the MHC-CMV pp65 peptide complex. See for example, the peptides described in Examples 10 and 11 of the Examples section which follows (Tables 5-137).

According to some embodiments of the invention, the antibodies recognize a complex formed between the MHC class I molecule (HLA-A2) and the CMV pp65 peptide set forth by SEQ ID NO:3.

The term "antibody" as used herein includes intact molecules as well as functional fragments thereof, such as Fab, F(ab')$_2$, Fv and scFv that are capable of specific binding to a human major histocompatibility complex (MHC) class I-restricted CMV pp65 or pp64 epitope. These functional antibody fragments are defined as follows: (i) Fab, the fragment which contains a monovalent antigen-binding fragment of an antibody molecule, can be produced by digestion of whole antibody with the enzyme papain to yield an intact light chain and a portion of one heavy chain; (ii) Fab', the fragment of an antibody molecule that can be obtained by treating whole antibody with pepsin, followed by reduction, to yield an intact light chain and a portion of the heavy chain; two Fab' fragments are obtained per antibody molecule; (iii) F(ab')$_2$, the fragment of the antibody that can be obtained by treating whole antibody with the enzyme pepsin without subsequent reduction; F(ab')$_2$ is a dimer of two Fab' fragments held together by two disulfide bonds; (iv) Fv, defined as a genetically engineered fragment containing the variable region of the light chain and the variable region of the heavy chain expressed as two chains; and (v) scFv or "single chain antibody" ("SCA"), a genetically engineered molecule containing the variable region of the light chain and the variable region of the heavy chain, linked by a suitable polypeptide linker as a genetically fused single chain molecule.

Methods of making these fragments are known in the art (See for example, Harlow and Lane, Antibodies: A Laboratory Manual, Cold Spring Harbor Laboratory, New York, 1988, incorporated herein by reference) and are further described herein below.

An exemplary method for generating antibodies capable of specifically binding a CMV pp65 peptide restricted to an MHC-I complex is described in the Examples section herein below.

In addition, such antibodies may be generated by (i) immunizing a genetically engineered non-human mammal having cells expressing the human major histocompatibility complex (MHC) class I, with a soluble form of an MHC class I molecule being complexed with the HLA-restricted epitope; (ii) isolating mRNA molecules from antibody producing cells, such as splenocytes, of the non-human mammal; (iii) producing a phage display library displaying protein molecules encoded by the mRNA molecules; and (iv) isolating at least one phage clone from the phage display library, the at least one phage displaying the antibody specifically bindable (with an affinity below 200 nanomolar, e.g., below 100 nanomolar, e.g., below 50 nanomolar, e.g., below 30 nanomolar, e.g., below 20 nanomolar, e.g., below 10 nanomolar) to the human major histocompatibility complex (MHC) class I being complexed with the HLA-restricted epitope. The genetic material of the phage isolate is then used to prepare a single chain antibody or other forms of antibodies as is further described herein below. For example, the genetic material of the phage isolate can be used to prepare a single chain antibody which is conjugated to an identifiable or a therapeutic moiety. According to some embodiments of the invention, the non-human mammal is devoid of self MHC class I molecules. According to some embodiments of the invention, the soluble form of the MHC class I molecule is a single chain MHC class I polypeptide including a functional human β-2 microglobulin amino acid sequence directly or indirectly covalently linked to a functional human MHC class I heavy chain amino acid sequence.

Recombinant MHC class I and class II complexes which are soluble and which can be produced in large quantities are described in, for example, Denkberg, G. et al. 2002, and further in U.S. patent application Ser. No. 09/534,966 and PCT/IL01/00260 (published as WO 01/72768), all of which are incorporated herein by reference. Soluble MHC class I molecules are available or can be produced for any of the MHC haplotypes, such as, for example, HLA-A2, HLA-A1, HLA-A3, HLA-A24, HLA-A28, HLA-A31, HLA-A33, HLA-A34, HLA-B7, HLA-B45 and HLA-Cw8, following, for example the teachings of PCT/IL01/00260, as their sequences are known and can be found at the kabbat data base hypertexttransferprotocol://immuno (dot) bme (dot) nwu (dot) edu/, the contents of the site is incorporated herein by reference. Such soluble MHC class I molecules can be loaded with suitable HLA-restricted epitopes and used for vaccination of non-human mammal having cells expressing the human major histocompatibility complex (MHC) class I as is further detailed hereinbelow.

Non-human mammal having cells expressing a human major histocompatibility complex (MHC) class I and devoid of self major histocompatibility complex (MHC) class I can be produced using (i) the sequence information provided in the kabbat data base, at hypertexttransferprotocol://immuno (dot) bme (dot) nwu (dot) edu/, which is incorporated herein by reference and pertaining to human MHC haplotypes, such as, for example, HLA-A2, HLA-A1, HLA-A3, HLA-A24, HLA-A28, HLA-A31, HLA-A33, HLA-A34, HLA-B7, HLA-B45 and HLA-Cw8, (ii) conventional constructs preparation techniques, as described in, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); and (iii) conventional gene knock-in/knock-out techniques as set forth, for example, in U.S. Pat. Nos. 5,487,992, 5,464,764, 5,387,742, 5,360,735, 5,347,075, 5,298,422, 5,288,846, 5,221,778, 5,175,385, 5,175,384, 5,175,383, 4,736,866; in International Publications WO 94/23049, W093/14200, WO 94/06908 and WO 94/28123; as well as in Burke and Olson, Methods in Enzymology, 194:251-270, 1991; Capecchi, Science 244:1288-1292, 1989; Davies et al., Nucleic Acids Research, 20 (11) 2693-2698, 1992; Dickinson et al., Human Molecular Genetics, 2(8): 1299-1302, 1993; Duff and Lincoln, "Insertion of a pathogenic mutation into a yeast artificial chromosome containing the human APP gene and expression in ES cells", Research Advances in Alzheimer's Disease and Related Disorders, 1995; Huxley et al., Genomics, 9:742-750 1991; Jakobovits et al., Nature, 362: 255-261, 1993; Lamb et al., Nature Genetics, 5: 22-29, 1993; Pearson and Choi, Proc. Natl. Acad. Sci. USA, 1993. 90:10578-82; Rothstein, Methods in Enzymology, 194:281-301, 1991; Schedl et al., Nature, 362: 258-261, 1993; Strauss et al., Science, 259:1904-1907, 1993, all of which are incorporated herein by reference.

Of particular interest is the paper by Pascolo et al., published in J. Exp. Med. 185: 2043-2051, 1997, which describe the preparation of mice expressing the human HLA-A2.1, H-2Db and HHD MHC class I molecules and devoid of mice MHC class I altogether.

An exemplary antibody, referred to as the H9 antibody, capable of binding to an MHC class I complexed with a CMV pp65 epitope comprises complementarity determining region (CDR) amino acid sequences as set forth in SEQ ID NOs:24-26 (for the heavy chain) and 30-32 (for the light chain).

Another exemplary antibody, referred to as the F5 antibody, capable of binding to an MHC class I complexed with a CMV pp65 epitope comprises complementarity determining region (CDR) amino acid sequences as set forth in SEQ ID NOs:36-38 (for the heavy chain) and 42-44 (for the light chain).

The invention provides a nucleic acid construct comprising a nucleic acid sequence encoding the CDR sequences of the heavy chain and the light chain of the antibody of the invention. The nucleic acid construct may further comprise a promoter for directing expression of the nucleic acid sequence in a host cell.

According to some embodiments of the invention, the nucleic acid construct comprising the nucleic acid sequences set forth by SEQ ID NOs:27-29 (for the heavy chain CDRs) and SEQ ID NOs:33-35 (for the light chain CDRs).

According to some embodiments of the invention, the nucleic acid construct comprising the nucleic acid sequences set forth by SEQ ID NOs:39-41 (for the heavy chain CDRs) and SEQ ID NOs:45-47 (for the light chain CDRs).

According to some embodiments of the invention, the nucleic acid construct comprising the nucleic acid sequence set forth by SEQ ID NO:17 (for the heavy chain) and SEQ ID NO:19 (for the light chain).

According to some embodiments of the invention, the nucleic acid construct comprising the nucleic acid sequence set forth by SEQ ID NO:21 (for the heavy chain) and SEQ ID NO:23 (for the light chain).

As mentioned herein above, the antibodies of the invention may be antibody fragments. Antibody fragments according to the invention can be prepared by proteolytic hydrolysis of the antibody or by expression in E. coli or mammalian cells (e.g. Chinese hamster ovary cell culture or other protein expression systems) of a DNA sequence encoding the fragment.

Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R., Biochem. J., 73: 119-126, 1959. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of $V_H$ and $V_L$ chains. This association may be noncovalent, as described in Inbar et al., Proc. Nat'l Acad. Sci. USA 69:2659-62, 1972. Alternatively, the variable chains can be linked by an intermolecular disulfide bond or cross-linked by chemicals such as glutaraldehyde. According to some embodiments of the invention, the Fv fragments comprise $V_H$ and $V_L$ chains connected by a peptide linker. These single-chain antigen binding proteins (scFv) are prepared by constructing a structural gene comprising DNA sequences encoding the $V_H$ and $V_L$ domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing scFvs are described, for example, by Whitlow and Filpula, Methods, 2: 97-105, 1991; Bird et al., Science 242:423-426, 1988; Pack et al., Bio/Technology 11:1271-77, 1993; and Ladner et al., U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry, Methods, 2: 106-10, 1991.

According to some embodiments of the invention, the antibodies are multivalent forms such as tetrameric Fabs or IgG1 antibodies. The advantages of the multivalent forms of the antibody of the invention include increased avidity, yet without compromising the antibody specificity to its target (i.e., the MHC-CMV pp65 peptide complex). Exemplary methods for generating tetrameric Fabs or IgG1 antibodies are described in the general materials and experimental methods of the Examples section herein below.

Humanized forms of non-human (e.g., murine) antibodies are chimeric molecules of immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence.

The humanized antibody optimally also will comprise at least a portion of an immunoglobulin constant region (Fc), typically that of a human immunoglobulin [Jones et al., Nature, 321:522-525 (1986); Riechmann et al., Nature, 332: 323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boemer et al., J. Immunol., 147(1):86-95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545, 807; 5,545,806; 5,569,825; 5,625,126; 5,633,425; 5,661,016, and in the following scientific publications: Marks et al., Bio/Technology 10, 779-783 (1992); Lonberg et al., Nature 368 856-859 (1994); Morrison, Nature 368 812-13 (1994); Fishwild et al., Nature Biotechnology 14, 845-51 (1996); Neuberger, Nature Biotechnology 14, 826 (1996); Lonberg and Huszar, Intern. Rev. Immunol. 13 65-93 (1995).

It will be appreciated that once the CDRs of an antibody are identified, using conventional genetic engineering techniques, expressible polynucleotides encoding any of the forms or fragments of antibodies described herein can be devised and modified in one of many ways in order to produce a spectrum of related-products as further described herein below.

The antibody of the invention can be used in vitro, ex vivo and in vivo in various therapeutic or diagnostic applications.

In case the antibody of the invention is to be used for administration into an individual (e.g., human), the human or humanized antibody or antibody fragment will generally tend to be better tolerated immunologically than one of non human origin since non variable portions of non human antibodies will tend to trigger xenogeneic immune responses more potent than the allogeneic immune responses triggered by human antibodies which will typically be allogeneic with the individual. It will be preferable to minimize such immune responses since these will tend to shorten the half-life, and hence the effectiveness, of the antibody of the invention in the individual. Furthermore, such immune responses may be pathogenic to the individual, for example by triggering harmful inflammatory reactions.

Alternately, an antibody or antibody fragment of human origin, or a humanized antibody, will also be advantageous for applications in which a functional physiological effect, for example an immune response against a target cell, activated by a constant region of the antibody or antibody fragment in the individual is desired. For example, for applications including targeted cell killing a specific immune response is advantageous. Such applications particularly include those in which the functional interaction between a functional portion of the antibody or antibody fragment, such as an Fc region, with a molecule such as an Fc receptor or an Fc-binding complement component, is optimal when such a functional portion is, similarly to the Fc region, of human origin.

Depending on the application and purpose, the antibody of the invention which includes a constant region, or a portion thereof, of any of various isotypes may be employed. According to some embodiments of the invention, the isotype is selected so as to enable or inhibit a desired physiological effect, or to inhibit an undesired specific binding of the antibody of the invention via the constant region or portion thereof. For example, for inducing antibody-dependent cell mediated cytotoxicity (ADCC) by a natural killer (NK) cell, the isotype can be IgG; for inducing ADCC by a mast cell/basophil, the isotype can be IgE; and for inducing ADCC by an eosinophil, the isotype can be IgE or IgA. For inducing a complement cascade the composition-of-matter may comprise an antibody or antibody fragment comprising a constant region or portion thereof capable of initiating the cascade. For example, the antibody or antibody fragment may advantageously comprise a Cgamma2 domain of IgG or Cmu3 domain of IgM to trigger a C1q-mediated complement cascade.

Conversely, for avoiding an immune response, such as the aforementioned one, or for avoiding a specific binding via the constant region or portion thereof, the antibody of the invention may not comprise a constant region (be devoid of a constant region), or a portion thereof, of the relevant isotype.

Additionally or alternatively, depending on the application and purpose, the antibody or antibody fragment may be attached to any of various functional moieties. An antibody or antibody fragment, such as that of the invention, attached to a functional moiety may be referred to in the art as an "immunoconjugate".

According to some embodiments of the invention, the functional moiety is a detectable moiety or a toxin. An antibody or antibody fragment attached to a toxin may be referred to in the art as an "immunotoxin".

As is described and demonstrated in further detail hereinbelow, a detectable moiety or a toxin may be particularly advantageously employed in applications of the invention involving use of the antibody of the invention to detect the complex or cells expressing the complex of the MHC molecule and the cytomegalovirus (CMV) pp65 peptide and/or to kill cells expressing or presenting such a complex.

For applications involving using the antibody of the invention to detect the antigen-presenting portion of the complex, the detectable moiety attached to the antibody or antibody fragment can be a reporter moiety enabling specific detection of the MHC-CMV pp65 peptide complex bound by the antibody or antibody fragment of the invention.

While various types of reporter moieties may be utilized to detect the MHC-CMV pp65 peptide complex, depending on the application and purpose, the reporter moiety can be a fluorophore or an enzyme. Alternately, the reporter moiety may be a radioisotope, such as [125]iodine. Further examples of reporter moieties, including those detectable by Positron Emission Tomography (PET) and Magnetic Resonance Imaging (MRI), are well known to those of skill in the art.

A fluorophore may be advantageously employed as a detection moiety enabling detection of the MHC-CMV pp65 peptide complex via any of numerous fluorescence detection methods. Depending on the application and purpose, such fluorescence detection methods include, but are not limited to, fluorescence activated flow cytometry (FACS), immunofluorescence confocal microscopy, fluorescence in-situ hybridization (FISH), fluorescence resonance energy transfer (FRET), and the like.

Various types of fluorophores, depending on the application and purpose, may be employed to detect the MHC-CMV pp65 peptide complex.

Examples of suitable fluorophores include, but are not limited to, phycoerythrin (PE), fluorescein isothiocyanate (FITC), Cy-chrome, rhodamine, green fluorescent protein (GFP), blue fluorescent protein (BFP), Texas red, PE-Cy5, and the like.

Preferably, the fluorophore is phycoerythrin.

As is described and illustrated in the Examples section below, the antibody of the invention attached to a fluorophore, such as phycoerythrin, can be used to optimally detect the MHC-CMV pp65 peptide complex using various immunofluorescence-based detection methods.

Ample guidance regarding fluorophore selection, methods of linking fluorophores to various types of molecules, such as an antibody or antibody fragment of the invention, and methods of using such conjugates to detect molecules which are capable of being specifically bound by antibodies or antibody fragments comprised in such immunoconjugates is available in the literature of the art [for example, refer to: Richard P. Haugland, "Molecular Probes: Handbook of Fluorescent Probes and Research Chemicals 1992-1994", 5th ed., Molecular Probes, Inc. (1994); U.S. Pat. No. 6,037,137 to Oncoimmunin Inc.; Hermanson, "Bioconjugate Techniques", Academic Press New York, N.Y. (1995); Kay M. et al., 1995. Biochemistry 34:293; Stubbs et al., 1996. Biochemistry 35:937; Gakamsky D. et al., "Evaluating Receptor Stoichiometry by Fluorescence Resonance Energy Transfer," in "Receptors: A Practical Approach," 2nd ed., Stanford C. and Horton R. (eds.), Oxford University Press, UK. (2001); U.S. Pat. No. 6,350,466 to Targesome, Inc.]. While various methodologies may be employed to detect the MHC-CMV pp65 peptide complex using a fluorophore, such detection is preferably effected as described and demonstrated in the Examples section below.

Alternately, an enzyme may be advantageously utilized as the detectable moiety to enable detection of the antigen-presenting portion of the complex via any of various enzyme-based detection methods. Examples of such methods include, but are not limited to, enzyme linked immunosorbent assay (ELISA; for example, to detect the antigen-presenting portion of the complex in a solution), enzyme-linked chemiluminescence assay (for example, to detect the complex in an electrophoretically separated protein mixture), and enzyme-linked immunohistochemical assay (for example, to detect the complex in a fixed tissue).

Numerous types of enzymes may be employed to detect the antigen-presenting portion of the complex, depending on the application and purpose. For example, an antibody or antibody fragment attached to an enzyme such as horseradish peroxidase can be used to effectively detect the MHC-CMV pp65 peptide complex, such as via ELISA, or enzyme-linked immunohistochemical assay.

Examples of suitable enzymes include, but are not limited to, horseradish peroxidase (HPR), beta-galactosidase, and alkaline phosphatase (AP).

Ample guidance for practicing such enzyme-based detection methods is provided in the literature of the art (for example, refer to: Khatkhatay M I. and Desai M., 1999. J Immunoassay 20:151-83; Wisdom G B., 1994. Methods Mol Biol. 32:433-40; Ishikawa E. et al., 1983. J Immunoassay 4:209-327; Oellerich M., 1980. J Clin Chem Clin Biochem. 18:197-208; Schuurs A H. and van Weemen B K., 1980. J Immunoassay 1:229-49). While various methodologies may be employed to detect the antigen-presenting portion of the complex using an enzyme, such detection is preferably effected as described in the Examples section below.

The functional moiety may be attached to the antibody or antibody fragment in various ways, depending on the context, application and purpose.

A polypeptidic functional moiety, in particular a polypeptidic toxin, may be advantageously attached to the antibody or antibody fragment via standard recombinant techniques broadly practiced in the art (for Example, refer to Sambrook et al., infra, and associated references, listed in the Examples section which follows).

A functional moiety may also be attached to the antibody or antibody fragment using standard chemical synthesis techniques widely practiced in the art [for example, refer to the extensive guidelines provided by The American Chemical Society (for example at: hypertexttransferprotocol://worldwideweb (dot) chemistry (dot) org/portal/Chemistry)]. One of ordinary skill in the art, such as a chemist, will possess the required expertise for suitably practicing such chemical synthesis techniques.

Alternatively, a functional moiety may be attached to the antibody or antibody fragment by attaching an affinity tag-coupled antibody or antibody fragment of the invention to the functional moiety conjugated to a specific ligand of the affinity tag.

Various types of affinity tags may be employed to attach the antibody or antibody fragment to the functional moiety.

Examples of detectable moieties that can be used in the invention include but are not limited to radioactive isotopes, phosphorescent chemicals, chemiluminescent chemicals, fluorescent chemicals, enzymes, fluorescent polypeptides and epitope tags. The detectable moiety can be a member of a binding pair, which is identifiable via its interaction with an additional member of the binding pair, and a label which is directly visualized. In one example, the member of the binding pair is an antigen which is identified by a corresponding labeled antibody. In one example, the label is a fluorescent protein or an enzyme producing a colorimetric reaction.

When the detectable moiety is a polypeptide, the immuno-label (i.e. the antibody conjugated to the detectable moiety) may be produced by recombinant means or may be chemically synthesized by, for example, the stepwise addition of one or more amino acid residues in defined order using solid phase peptide synthetic techniques. Examples of polypeptide detectable moieties that can be linked to the antibodies of the invention using recombinant DNA technology include fluorescent polypeptides, phosphorescent polypeptides, enzymes and epitope tags.

Expression vectors can be designed to fuse proteins encoded by the heterologous nucleic acid insert to fluorescent polypeptides. For example, antibodies can be expressed from an expression vector fused with a green fluorescent protein (GFP)-like polypeptide. A wide variety of vectors are commercially available that fuse proteins encoded by heterologous nucleic acids to the green fluorescent protein from *Aequorea victoria* ("GFP"), the yellow fluorescent protein and the red fluorescent protein and their variants (e.g., Evrogen). In these systems, the fluorescent polypeptide is entirely encoded by its amino acid sequence and can fluoresce without requirement for cofactor or substrate. Expression vectors that can be employed to fuse proteins encoded by the heterologous nucleic acid insert to epitope tags are commercially available (e.g., BD Biosciences, Clontech).

Alternatively, chemical attachment of a detectable moiety to the antibodies of invention can be effected using any suitable chemical linkage, direct or indirect, as via a peptide bond (when the detectable moiety is a polypeptide), or via covalent bonding to an intervening linker element, such as a linker peptide or other chemical moiety, such as an organic polymer. Such chimeric peptides may be linked via bonding at the carboxy (C) or amino (N) termini of the peptides, or via bonding to internal chemical groups such as straight, branched or cyclic side chains, internal carbon or nitrogen atoms, and the like. Such modified peptides can be easily identified and prepared by one of ordinary skill in the art, using well known methods of peptide synthesis and/or covalent linkage of peptides. Description of fluorescent labeling of antibodies is provided in details in U.S. Pat. Nos. 3,940,475, 4,289,747, and 4,376,110.

Exemplary methods for conjugating two peptide moieties are described herein below:

SPDP Conjugation:

Any SPDP conjugation method known to those skilled in the art can be used. For example, in one illustrative embodiment, a modification of the method of Cumber et al. (1985, Methods of Enzymology 112: 207-224) as described below, is used.

A peptide, such as an identifiable or therapeutic moiety, (1.7 mg/ml) is mixed with a 10-fold excess of SPDP (50 mM in ethanol) and the antibody is mixed with a 25-fold excess of SPDP in 20 mM sodium phosphate, 0.10 M NaCl pH 7.2 and each of the reactions incubated, e.g., for 3 hours at room temperature. The reactions are then dialyzed against PBS.

The peptide is reduced, e.g., with 50 mM DTT for 1 hour at room temperature. The reduced peptide is desalted by equilibration on G-25 column (up to 5% sample/column volume) with 50 mM $KH_2PO_4$ pH 6.5. The reduced peptide is combined with the SPDP-antibody in a molar ratio of 1:10 antibody:peptide and incubated at 4° C. overnight to form a peptide-antibody conjugate.

Glutaraldehyde Conjugation:

Conjugation of a peptide (e.g., an identifiable or therapeutic moiety) with an antibody can be accomplished by methods known to those skilled in the art using glutaraldehyde. For example, in one illustrative embodiment, the method of conjugation by G. T. Hermanson (1996, "Antibody Modification and Conjugation, in Bioconjugate Techniques, Academic Press, San Diego) described below, is used.

The antibody and the peptide (1.1 mg/ml) are mixed at a 10-fold excess with 0.05% glutaraldehyde in 0.1 M phosphate, 0.15 M NaCl pH 6.8, and allowed to react for 2 hours at room temperature. 0.01 M lysine can be added to block excess sites. After-the reaction, the excess glutaraldehyde is removed using a G-25 column equilibrated with PBS (10% v/v sample/column volumes)

Carbodiimide Conjugation:

Conjugation of a peptide with an antibody can be accomplished by methods known to those skilled in the art using a dehydrating agent such as a carbodiimide. Most preferably the carbodiimide is used in the presence of 4-dimethyl aminopyridine. As is well known to those skilled in the art, carbodiimide conjugation can be used to form a covalent bond between a carboxyl group of peptide and an hydroxyl group of an antibody (resulting in the formation of an ester bond), or an amino group of an antibody (resulting in the formation of an amide bond) or a sulfhydryl group of an antibody (resulting in the formation of a thioester bond).

Likewise, carbodiimide coupling can be used to form analogous covalent bonds between a carbon group of an antibody and an hydroxyl, amino or sulfhydryl group of the peptide. See, generally, J. March, Advanced Organic Chemistry: Reaction's, Mechanism, and Structure, pp. 349-50 & 372-74 (3d ed.), 1985. By means of illustration, and not limitation, the peptide is conjugated to an antibody via a covalent bond using a carbodiimide, such as dicyclohexylcarbodiimide. See generally, the methods of conjugation by B. Neises et al. (1978, Angew Chem., Int. Ed. Engl. 17:522; A. Hassner et al. (1978, Tetrahedron Lett. 4475); E. P. Boden et al. (1986, J. Org. Chem. 50:2394) and L. J. Mathias (1979, Synthesis 561). The level of immunocomplex may be compared to a control sample from a non-diseased subject, wherein an up-regulation of immunocomplex formation is indicative of disease associated with CMV infection. Preferably, the subject is of the same species e.g. human, preferably matched with the same age, weight, sex etc. It will be appreciated that the control sample may also be of the same subject from a healthy tissue, prior to disease progression or following disease remission.

Preferably, the affinity tag is a biotin molecule, more preferably a streptavidin molecule.

A biotin or streptavidin affinity tag can be used to optimally enable attachment of a streptavidin-conjugated or a biotin-conjugated functional moiety, respectively, to the antibody or antibody fragment due to the capability of streptavidin and biotin to bind to each other with the highest non covalent binding affinity (i.e., with a Kd of about $10^{-14}$ to $10^{-15}$). A biotin affinity tag may be highly advantageous for applications benefiting from. Thus, the antibody of invention can be a multimeric form of the antibody or antibody fragment, which may be optimally formed by conjugating multiple biotin-attached antibodies or antibody fragments of the invention to a streptavidin molecule, as described in further detail below.

As used herein the term "about" refers to plus or minus 10 percent.

Various methods, widely practiced in the art, may be employed to attach a streptavidin or biotin molecule to a molecule such as the antibody or antibody fragment to a functional moiety.

For example, a biotin molecule may be advantageously attached to an antibody or antibody fragment of the invention attached to a recognition sequence of a biotin protein ligase. Such a recognition sequence is a specific polypeptide sequence serving as a specific biotinylation substrate for the biotin protein ligase enzyme. Ample guidance for biotinylating a target polypeptide such as an antibody fragment using a recognition sequence of a biotin protein ligase, such as the recognition sequence of the biotin protein ligase BirA, is provided in the literature of the art (for example, refer to: Denkberg, G. et al., 2000. Eur. J. Immunol. 30:3522-3532). Preferably, such biotinylation of the antibody or antibody fragment is effected as described and illustrated in the Examples section below.

Alternately, various widely practiced methods may be employed to attach a streptavidin molecule to an antibody fragment, such as a single chain Fv (for example refer to Cloutier S M. et al., 2000. Molecular Immunology 37:1067-1077; Dubel S. et al., 1995. J Immunol Methods 178:201; Huston J S. et al., 1991. Methods in Enzymology 203:46; Kipriyanov S M. et al., 1995. Hum Antibodies Hybridomas 6:93; Kipriyanov S M. et al., 1996. Protein Engineering 9:203; Pearce L A. et al., 1997. Biochem Molec Biol Intl 42:1179-1188).

Functional moieties, such as fluorophores, conjugated to streptavidin are commercially available from essentially all major suppliers of immunofluorescence flow cytometry reagents (for example, Pharmingen or Becton-Dickinson). Standard recombinant DNA chemical techniques are preferably employed to produce a fusion protein comprising streptavidin fused to a polypeptidic functional moiety. Standard chemical synthesis techniques may also be employed to form the streptavidin-functional moiety conjugate. Extensive literature is available providing guidance for the expression, purification and uses of streptavidin or streptavidin-derived molecules (Wu S C. et al., 2002. Protein Expression and Purification 24:348-356; Gallizia A. et al., 1998. Protein Expression and Purification 14:192-196), fusion proteins comprising streptavidin or streptavidin-derived molecules (Sano T. and Cantor C R., 2000. Methods Enzymol. 326:305-11), and modified streptavidin or streptavidin-derived molecules (see, for example: Sano T. et al., 1993. Journal of Biological Chemistry 270:28204-28209), including for streptavidin or streptavidin-derived molecules whose gene sequence has been optimized for expression in *E. coli* (Thompson L D. and Weber P C., 1993. Gene 136:243-6).

As mentioned, the antibody may be conjugated to a therapeutic moiety. The therapeutic moiety can be, for example, a cytotoxic moiety, a toxic moiety, a cytokine moiety and a second antibody moiety comprising a different specificity to the antibodies of the invention.

In a similar fashion to an immunolabel, an immunotoxin (i.e. a therapeutic moiety attached to an antibody of the invention) may be generated by recombinant or non-recombinant means. Thus, the invention envisages a first and second polynucleotide encoding the antibody of the invention and the therapeutic moiety, respectively, ligated in frame, so as to encode an immunotoxin. The following Table 1 provides examples of sequences of therapeutic moieties.

TABLE 1

| Therapeutic Moiety | Amino Acid sequence (Genbank Accession No.) | Nucleic Acid sequence (Genbank Accession No.) |
|---|---|---|
| *Pseudomonas* exotoxin | AAB25018 | S53109 |
| Diphtheria toxin | E00489 | E00489 |
| interleukin 2 | CAA00227 | A02159 |
| CD3 | P07766 | X03884 |
| CD16 | AAK54251 | AF372455 |
| interleukin 4 | P20096 | ICRT4 |
| HLA-A2 | P01892 | K02883 |
| interleukin 10 | P22301 | M57627 |
| Ricin A toxin | 225988 | A23903 |

According to some embodiments of the invention, the toxic moiety is PE38KDEL.

Exemplary methods of conjugating the antibodies of the invention to peptide therapeutic agents are described herein above.

As mentioned, the antibody of the invention, which is capable of specifically recognizing and binding an MHC-CMV pp65 peptide complex as described above, can be used to detecting cell expressing a cytomegalovirus (CMV) antigen.

Thus, according to an aspect of some embodiments of the invention there is provided a method of detecting a cell expressing a cytomegalovirus (CMV) antigen. The method is effected by contacting the cell with the antibody under conditions which allow immunocomplex formation, wherein a presence or a level above a predetermined threshold of the immunocomplex is indicative of CMV expression in the cell.

The contacting may be effected in vitro (e.g., in a cell line), ex vivo or in vivo.

As mentioned, the method of the invention is effected under conditions sufficient to form an immunocomplex (e.g. a complex between the antibodies of the invention and the MHC-CMV pp65 peptide); such conditions (e.g., appropriate concentrations, buffers, temperatures, reaction times) as well as methods to optimize such conditions are known to those skilled in the art, and examples are disclosed herein.

As described in the Examples section which follows, the immunocomplex can be formed and detected within the cell or on the cell surface. For detection in the cell, the conditions include a permeabilization agent (e.g., a solution including saponin), to enable penetration of the antibody inside the cell. According to some embodiments of the invention, the immunocomplex is formed on the surface of the cell.

Determining a presence or level of the immunocomplex of the invention is dependent on the detectable moiety to which the antibody is attached, essentially as described hereinabove.

A non-limiting example of the immunocomplex of the invention is the complex formed between the antibody of the invention (e.g., H9 or F5) and a protein complex comprising MHC class I heavy chain (HLA-A2) and pp65 peptide as set forth by SEQ ID NO:3.

As mentioned, the antibody of the invention, which is capable of specifically recognizing and binding an MHC-CMV pp65 peptide complex, can be used to diagnose CMV infection in a subject in need thereof.

Thus, according to another aspect of the invention, there is provided a method of diagnosing a cytomegalovirus (CMV) infection in a subject in need thereof. The method is effected by contacting a cell of the subject with the antibody under conditions which allow immunocomplex formation, wherein a presence or a level above a pre-determined threshold of the immunocomplex in the cell is indicative of the CMV infection in the subject.

As used herein the phrase "subject in need thereof" refers to a mammal, preferably, a human subject which is suspected of being infected with CMV.

According to some embodiments of the invention, the subject has a suppressed or a compromised immune system, such as an immuno-compromised organ transplant recipient or a subject infected with human immunodeficiency virus (HIV).

According to some embodiments of the invention, the CMV infection is associated with a disease selected from the group consisting of mononucleosis, retinitis, pneumonia, gastrointestinal disorders, and encephalitis.

According to some embodiments of the invention, the cell is a retina cell, lung epithelial cell, a gastrointestinal epithelial cell and/or a brain cell.

The antibody described herein can be used to treat a disease associated with CMV infection.

According to an additional aspect of the invention there is provided a method of treating a disease associated with cytomegalovirus (CMV) infection, the method is effected by administering to a subject in need thereof a therapeutically effective amount of the antibody thereby treating the disease associated with CMV infection.

The term "treating" refers to inhibiting or arresting the development of a disease, disorder or condition and/or causing the reduction, remission, or regression of a disease, disorder or condition. Those of skill in the art will understand that various methodologies and assays can be used to assess the development of a disease, disorder or condition, and similarly, various methodologies and assays may be used to assess the reduction, remission or regression of a disease, disorder or condition.

The antibodies of the invention may be provided per se or may be administered as a pharmaceutical composition.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the antibodies of the invention accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, intraperitoneal, intranasal, or intraocular injections.

Alternately, one may administer the pharmaceutical composition in a local rather than systemic manner, for example, via injection of the pharmaceutical composition directly into a tissue region of a patient.

Pharmaceutical compositions of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuos infusion. Formulations for injection may be presented in unit dosage form, e.g., in ampoules or in multi-dose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the invention may also be formulated in rectal compositions such as suppositories or retention enemas, using, e.g., conventional suppository bases such as cocoa butter or other glycerides.

Pharmaceutical compositions suitable for use in context of the invention include compositions wherein the active ingredients are contained in an amount effective to achieve the intended purpose. More specifically, a therapeutically effective amount means an amount of active ingredients (the antibody of the invention or the nucleic acid construct encoding same) effective to prevent, alleviate or ameliorate symptoms of a pathology, (e.g., a disease associated with cytomegalovirus infection) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide plasma or brain levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration and use. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as if further detailed above.

As used herein the term "about" refers to ±10%.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Bioloαgy" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Experimental Methods

Generation of biotinylated single-chain MHC/peptide complexes—Single-chain MHC (scMHC)/peptide complexes were produced by in vitro refolding of inclusion bodies produced in Escherichia coli, as described (Denkberg, G. et al., 2000). Briefly, a single-chain $\beta_2$-microglobulin ($\beta_2$m)-HLA/A2 (scMHC) construct, in which the $\beta_2$m and HLA-A2 genes are connected to each other by a flexible peptide linker (wherein the β2m gene is translationally fused upstream of the gene encoding the MHC heavy chain) (HLA-A2), was engineered to contain the BirA recognition sequence for site-specific biotinylation at the C terminus (scMHC-BirA). In vitro refolding was performed in the presence of a 5-10 molar excess of the antigenic peptides, as described (Denkberg, G. et al., 2000). Correctly folded MHC/peptide complexes were isolated and purified by anion exchange Q-Sepharose chromatography (Pharmacia, Peapack, N.J.), followed by site-specific biotinylation using the BirA enzyme (Avidity, Denver, Colo.), as previously described (Altman, J. D. et al., 1996). The homogeneity and purity of the scMHC-peptide complexes were analyzed by various biochemical means, including SDS-PAGE, size exclusion chromatography, and ELISA, as previously described (Denkberg, G. et al., 2000).

Selection of phage antibodies on biotinylated complexes—Selection of phage Abs on biotinylated complexes was preformed, as described (Denkberg, G., et al., 2002; Lev A., et al., 2002). Briefly, a large human Fab library containing $3.7 \times 10^{10}$ different Fab clones (De Haard, H J., et al., 1999) was used for the selection. Phages ($10^{13}$) were first preincubated with streptavidin-coated paramagnetic beads (200 μl; Dynal, Oslo, Norway) to deplete the streptavidin binders. The remaining phages were subsequently used for panning with decreasing amounts of biotinylated scMHC-peptide complexes. The streptavidin-depleted library was incubated in solution with soluble biotinylated scHLA-A2/pp65 complexes (500 nM for the first round, and 100 nM for the following rounds) for 30 minutes at room temperature (RT).

Streptavidin-coated magnetic beads (200 μl for the first round of selection, and 100 μl for the second and third rounds) were added to the mixture and incubated for 10-15 minutes at RT. The beads were washed extensively 12 times with PBS/Tween 0.1%, and additional two washes were with PBS. Bound phages were eluted with triethylamine (100 mM, 5 minutes at RT), followed by neutralization with Tris-HCl (1 M, pH 7.4), and used to infect E. coli TG1 cells (OD=0.5) for 30 minutes at 37° C.

The diversity of the selected Abs was determined by DNA fingerprinting using a restriction endonuclease (BstNI), which is a frequent cutter of Ab V gene sequences. The Fab DNA of different clones was PCR amplified using the primers pUC-reverse [5'-AGCGGATAACAATTTCACACAGG-3' (SEQ ID NO:1)] and fd-tet-seq24 [5'-TTTGTCGTCTTTC-CAGACGTTAGT-3' (SEQ ID NO:2)], followed by digestion with BstNI (NEB, Beverly, Mass.) (2 hours, 60° C.) and analysis on agarose gel electrophoresis.

Expression and purification of soluble recombinant Fab Abs—Fab Abs were expressed and purified, as described recently (Denkberg, G., et al., 2000). BL21 bacterial cells were grown to $OD_{600}$=0.8-1.0 and induced to express the recombinant Fab Ab by the addition of 1 mM isopropyl β-D-thiogalactoside (IPTG) for 3-4 hours at 30° C. Periplasmic content was released using the B-PER solution (Pierce, Rockford, Ill.), which was applied onto a prewashed TALON column (Clontech, Palo Alto, Calif.). Bound Fabs were eluted using 0.5 ml of 100 mM imidazole in PBS. The eluted Fabs were dialyzed twice against PBS (overnight, 4° C.) to remove residual imidazole.

ELISA with phage clones and purified Fab Abs—The binding specificities of individual phage clones and soluble Fab were determined by ELISA using biotinylated scMHC-peptide complexes. ELISA plates (Falcon) were coated overnight with BSA-biotin (1 μg/well). After having been washed, the plates were incubated (1 hour, RT) with streptavidin (1 μg/well), washed extensively, and further incubated (1 hour, RT) with 0.5 μg of MHC/peptide complexes. The plates were blocked for 30 minutes at RT with PBS/2% skim milk and subsequently were incubated for 1 hour at RT with phage clones (~$10^9$ phages/well) or various concentrations of soluble purified Fab. After having been washed, the plates were incubated with HRP-conjugated/anti-human Fab Ab (for soluble Fabs) or HRP-conjugated anti-M13 phage (for phage-displayed Fabs). Detection was performed using tetramethylbenzidine reagent (Sigma-Aldrich, St. Louis, Mo.). The HLA-A2-restricted peptides used for specificity studies of the Fab phage clones or purified Fab Abs are as described in Examples 1 and 2 below.

Generation of fluorescently-labeled tetrameric Fab—The genes encoding the L and H chain of Fab H9 were cloned separately into a T7-promotor pET-based expression vector. The L chain gene was engineered to contain the BirA recognition sequence for site-specific biotinylation at the C terminus. These constructs were expressed separately in E. coli BL21 cells and upon induction with IPTG, intracellular inclusion bodies that contain large amounts of the recombinant protein accumulated. Inclusion bodies of both chains were purified, solubilized, reduced with 10 mg/ml DTE (Dithioerithrol), and subsequently refolded at a 1:1 ratio in a redox-shuffling buffer system containing 0.1 M Tris, 0.5 M arginine, and 0.09 mM oxidized glutathione, pH 8.0. Correctly folded Fab was then isolated and purified by anion exchange MonoQ chromatography (Pharmacia). The Fab peak fractions were concentrated using Centricon-30 (Amicon, Beverly, Mass.) to 1 mg/ml, and the buffer was exchanged to Tris-HCl (10 mM, pH 8.0). Biotinylation was performed using the BirA enzyme (Avidity), as previously described. Excess biotin was removed from biotinylated Fabs using a G-25 desalting column. PE-labeled streptavidin (Jackson ImmunoResearch, West Grove, Pa.) was added at a molar ratio of 1:4 to produce fluorescent tetramers of the biotinylated Fab.

Generation of whole IgG from recombinant Fab—To transform the recombinant fragments into whole IgG molecules, the eukaryotic expression vector pCMV/myc/ER (Invitrogen) was used. The heavy and the light chains of the Fab were cloned separately. Each shuttle expression vector carries a different antibiotics resistance gene and thus expression was facilitated by co-transfection of the two constructs into human embryonic kidney HEK293 cells. Cotransfections of HEK293 cells were performed using the nonliposomal transfection reagent FuGene 6 (Roche, Brussels, Belgium) according to the manufacturer's instructions. The transfection was performed with serum free medium containing 0.8 mg/ml of G418, and 100 μg/ml of hygromycin. Forty-eight hours after transfection limiting dilutions were performed into medium containing 0.8 mg/ml of G418, and 100 μg/ml of hygromycin. Cells were plated in 96-well plates at 1000 cells per well. Medium was exchanged after 5 and 10 days. Wells in which a single colony grew up to 50% of the well were further trypsinized with 20 μl and 20 μl medium and splitted into two wells: 10 μl into a 24 well plate (backup) and 30 μl into a 24 well plate (experiment). When the plate reached 80% confluency, serum starvation was initiated by reducing each day serum percentile to 0.5%. After 48 hours of incubation with 0.5% fetal calf serum (FCS), screening of cell culture supernatants was performed by ELISA and FACS assays. The IgG secreting clones that exhibited the best binding reactivity as detected by ELISA, FACS and the highest amount of protein, were selected for antibody production and purification. Protein A-Sepharose™ 4 Fast Flow beads (Amersham) were prepared according to the manufacturer's instructions. Briefly, supernatant was loaded on the Protein A-Sepharose beads at 15-50 ml/h. Unbound immunoglobulins were washed with 0.001 M $NaH_2PO_4$ and 0.019 M $Na_2HPO_4$. Bound immunoglobulins were then eluted with 0.1 M citric acid at pH 3. Five fractions were collected with 250 μl of elusion buffer and immediately neutralized with 80 μl of Tris-HCL pH 9. IgG concentration was measured using the Pierce protein assay. The eluted protein was dialyzed against PBS pH 7.4 over night. 10 mgs of IgG were produced from 1 L of culture supernatant.

Flow cytometry—The B cell line RMAS-HHD, which is transfected with a single-chain $β_2$m-HLA-A2 gene, the EBV-transformed HLA-A2+ JY cells, and the HLA-A2− B cell line APD-70 were used to determine the reactivity of the recombinant Fab Abs with cell surface-expressed HLA-A2/peptide complexes. Peptide pulsing was performed as indicated: $10^6$ cells were washed twice with serum-free RPMI and incubated overnight at 26° C. or 37° C., respectively, in medium containing 1-50 µM of the peptide. The RMAS-HHD cells were subsequently incubated at 37° C. for 2-3 hours to stabilize cell surface expression of MHC-peptide complexes.

Cells were incubated for 60 minutes at 4° C. with recombinant Fab Abs (10 µg/ml) in 100 µl PBS. After one wash, the cells were incubated with 1 µg anti-human Fab (Jackson ImmunoResearch) for another 60 minutes at 4° C. After three washes, the cells were resuspended in ice-cold PBS. The cells were analyzed by a FACStar flow cytometer (BD Biosciences, San Jose, Calif.).

Surface Plasmon Resonance—0.0025 mg/ml of biotinylated HLA-A2/pp65 or control HLA-A2/EBV complexes were bound to a streptavidin (SA) sensor chip (Biacore, Uppsala, Sweden) per well. Measurements of 780-800 RU were detected for each well after complexes binding. Soluble isolated antibodies in their monomeric/IgG form were diluted in PBS at three concentration (0.05 µM, 0.1 µM, 0.2 µM) and were flowed over the relevant wells at a rate of 10 µl/min at room temperature. Responses were recorded using Biacore 2000 and analyzed using BIAevaluation software 3.2 (Biacore, Uppsala, Sweden).

Cell infection—Human fibroblasts which express the HLA-A2 allele were obtained from primary cultures of foreskins and grown in Dulbecco's modified Eagle's medium (DMEM), containing 2 mM Glutamine, 100 IU of penicillin/ml, 10% fetal calf serum (FCS), non essential amino acid (1:100), sodium Pyruvate (1:100) and 10 mM hepes. The cells were infected at an MOI of 0.5-1 with the laboratory strain AD169[41] and harvested at five time scales for FACS analysis. MHC expression on virus infected or uninfected cells was determined using PE conjugated anti HLA-A2 (BB7.2) monoclonal antibody. Detection of infection was with anti pp65 monoclonal antibody (clone IL11, Virusys, Sykesville, Md. USA) and anti mouse PE as secondary antibody. For intracellular staining cells were fixed with 0.3% formaldehyde and then permeabilized with PBS containing 0.05% Saponin and 1% goat serum used for blocking.

Cytotoxicity assay—Target cells were cultured in 48-well plates in DMEM medium plus 10% FCS and were grown up until confluent. Cells were washed and incubated overnight with 15 µCi/ml (1 Ci 37 GBq) [35$^S$] methionine (NEN). After 1 hour of incubation with the IgG H9 (10-20 µg/ml or the indicated concentration at 37° C.), effector CTL cells were added at a target:effector ratio of 1:3 respectively and incubated for 5 hours at 37° C. After incubation, [35$^S$] methionine release from target cells was measured in a 50-µl sample of the culture supernatant. All assays were performed in triplicate.

Confocal microscopy—Infected and noninfected fibroblast cells were fixed for 10 minutes with 0.5% paraformaldehyde, and washed twice with PBS containing 0.1% bovine serum albumin (BSA). The cells were permeabilized and incubated with anti pp65 mAb, H9 IgG, anti calnexin (Chemicon, cat. No. MAB3126), and/or cis-golgi matrix protein (GM130) (BD transduction laboratories, cat No. 610822) in the presence of a PBS medium containing 0.05% saponin, 1% fetal bovine serum, and 0.1% BSA, for 40 minutes at 4° C. Cells were subsequently washed and further incubated with goat anti mouse secondary Ab conjugated to Alexa-flour$^{594}$ (Molecular Probes, cat. No. A21216), and goat anti human secondary Ab conjugated to Alexa-flour$^{488}$ (Molecular Probes, cat. No. A11013), respectively. DRAQ5 (Alexis Biochemicals) was added to the stained cells before they were washed again. Images were collected on a LSM 510 META laser scanning microscope (Carl Zeiss Microimaging Inc) using a ×63 oil immersion objective numerical aperture 1.32, at different zoom factors. Alexa Fluor$^{488}$ was excited using an argon laser at 488 nm. Alexa Fluor$^{594}$ was excited using a krypton laser at 568 mm. Differential interference contrast images were collected simultaneous with the fluorescence images using the transmitted light detector. Z stacks of images were collected using a step increment of 0.3 µm between planes. All pictures were taken with identical settings.

Isolation of PBMCs—Samples of 20-30 ml blood obtained from healthy donors or BMT patients, containing 500 units (U) of heparin was added to 50 ml sterile tubes containing 15 ml Lymphoprep™ (Axis shield PoC AS, Oslo Norway). The blood was added gently without mixing between the Ficoll and the blood. The tubes were centrifuged for 30 minutes at 1000 g without brakes. The upper layer that contains the serum was removed and the Buffy coat that contains the peripheral blood mononuclear cells (PBMCs) was transferred to new tubes. The PBMCs were washed twice with 40 ml of phosphate buffer saline (PBS) and 2 mM EDTA (centrifuged at 700 g for 8 minutes). The PBMCs were resuspended in 20 ml PBS, counted, centrifuged at 500 g for 8 minutes and resuspended in PBMCs medium at $1-5\times10^6$ cells/ml. About $70\times10^6$ cells are isolated from a total of 50 ml blood sample.

Example 1

Selection and Cloning of Recombinant Antibodies Specific for HLA-A2-PP65 Complex Experimental Results Selection of recombinant antibodies specific for HLA-A2/pp65 complexes—Recombinant peptide-HLA-A2 complexes that present the $pp65_{495-503}$ (SEQ ID NO:3) CMV-derived peptide were generated using a single-chain MHC (scMHC) construct according to the method previously described previously (Denkberg G., et al., 2000). In this construct, the extracellular domains of HLA-A2 are connected into a single-chain molecule with $\beta_2$m using a 15-aa flexible linker (the $\beta_2$m is translationally fused upstream of the MHC heavy chain). The scMHC-peptide complexes were produced by in vitro refolding of inclusion bodies in the presence of the pp65 495-503 peptide (SEQ ID NO:3). The refolded scHLA-A2/pp65 complexes were found to be pure, homogenous, and monomeric by SDS-PAGE and size exclusion chromatography analyses (data not shown). Recombinant scMHC-peptide complexes generated by this strategy were previously characterized in detail for their biochemical, biophysical, and biological properties, and were found to be correctly folded and functional (Denkberg G., et al., 2000; Denkberg G., et al., 2001).

A large human Fab library containing $3.7\times10^{10}$ different Fab clones was used for the selection on biotinylatd HLA-A2/pp65 complexes (De Haard H J., et al., 1999). Phage displayed antibodies which were capable of binding to the specific biotinylated HLA-A2/peptide complex were selected as previously described (Denkberg G., et al., 2002; Lev A., et al., 2002). Enrichment in phage titer was observed after three rounds of panning (Table 2, hereinbelow). Specificity of the selected phage antibodies against the complex was analyzed by a differential ELISA assay in which binding was tested against specific (pp65 495-503 peptide; SEQ ID NO:3) and non specific (gp100 280-288 peptide; SEQ ID NO:4) biotinylated HLA-A2/peptide complexes. These were immobilized to wells through BSA-biotin-streptavidin. As shown in FIG. 1a, a high percentage of specific clones was observed; 54 clones of the 96 screened (56%), were peptide specific and bound the specific peptide/MHC used in the selection (i.e., the scHLA-A2/pp65 complex).

TABLE 2

Table 2: Results of the amounts of phages counted before and after each panning (inputs and outputs). Enrichment of the outputs can be seen in each panning round.

| Round of Panning | Phage input | Phage output | Enrichment |
|---|---|---|---|
| $1^{st}$ | $10^{12}$ | $4 \times 10^5$ | |
| $2^{nd}$ | $1.5 \times 10^{12}$ | $5 \times 10^6$ | 75 |
| $3^{rd}$ | $5 \times 10^{12}$ | $1.5 \times 10^9$ | 750 |

Cloning of two Fab clones with specificity to the HLA-A2-pp65$_{495-503}$ complex—The diversity within the selected TCR-like Fabs was assessed by DNA fingerprint analysis using the BstNI restriction enzyme. The analysis revealed two different clones, termed H9 and F5 with HLA-A2/pp65 specificity (data not shown). DNA sequencing analysis confirmed these observations. The nucleic acid and amino acid sequences of the heavy and light chains of H9 Fab clone are provided in FIGS. 14a-d (SEQ ID NOs:16-19). The nucleic acid and amino acid sequences of the heavy and light chains of F5 Fab clone are provided in FIGS. 15a-d (SEQ ID NOs: 20-23). The amino acid sequences of the CDRs of the H9 and F5 Fab Abs are provided in Table 3, hereinbelow. The nucleic acid sequences of the CDRs of the H9 and F5 Fab Abs are provided in Table 4, hereinbelow.

Production of the recombinant, soluble Fab clones—The isolated Fab clones with specificity toward the HLA-A2/pp65 complex (H9, F5) were produced in a soluble form in *E. coli* BL21 cells. These Fabs which are tagged at the CH1 domain with a hexahistidine sequence, were purified from the periplasmic fraction by metal affinity chromatography. SDS-PAGE analysis revealed the level of purification and the expected molecular size of the Fab antibodies (FIG. 1b).

These data demonstrate the isolation of recombinant antibodies with peptide-specific, MHC restricted binding to the CMV-derived T cell epitope pp65$_{495-503}$ (SEQ ID NO:3).

Example 2

Characterization of HLA-A2/PP65-Specific TCR-Like Recombinant Antibodies

Experimental Results

HLA-A2/pp65-specific TCR-like recombinant antibodies exhibit binding characteristics and fine specificity of a TCR-like molecule—The specificity of the two recombinant monoclonal Fab antibodies to the MHC-CMV peptide complex was tested by ELISA (FIGS. 1c and d). To determine the correct folding of the bound complexes and their stability during the binding assays, the ability of the complexes to react with the conformation-specific mAb, w6/32, that recognizes

TABLE 3

Amino acid sequences of the CDRs of the Fab antibodies

| Fab clone | CDRs heavy chain | CDRs light chain |
|---|---|---|
| H9 | SYAISW (SEQ ID NO: 24; CDR1)<br>GIIPIFGTANYAQKFQG (SEQ ID NO: 25; CDR2)<br>GDLYYYDSSGYPRYYFDY (SEQ ID NO: 26; CDR3) | RASQSVSSSYLA (SEQ ID NO: 30; CDR1)<br>GASSRAT (SEQ ID NO 31; CDR2)<br>QHYSTSPGFT (SEQ ID NO: 32; CDR3) |
| F5 | SSNYYWG (SEQ ID NO: 36; CDR1)<br>AIYYSGSTYYNPSLKS (SEQ ID NO: 37; CDR2)<br>RIGVAGQWYFDLWGRGTLVTVSS (SEQ ID NO: 38; CDR3) | TRSTGSITSNYVH (SEQ ID NO: 42; CDR1)<br>EDNERPS (SEQ ID NO: 43; CDR2)<br>QSYDDSNHISV (SEQ ID NO: 44; CDR3) |

Table 3: CDRs (amino acid sequences) of the heavy and light chains of Fabs H9 and F5.

TABLE 4

Nucleic acid sequences of the CDRs of the Fab antibodies

| Fab clone | CDRs heavy chain | CDRs light chain |
|---|---|---|
| H9 | GCTATGCTATCAGCTG (SEQ ID NO: 27; CDR1)<br>GGGATCATCCCTATCTTTGGTACAGCAAAC TACGCACAGAAGTTCCAGGG (SEQ ID NO: 28; CDR2)<br>GGGGATCTGTATTACTATGATAGTAGTGGT TATCCGCGATACTACTTTGACTA (SEQ ID NO: 29; CDR3) | AGGGCCAGTCAGAGTGTTAGCAGCA GCTACTTAGC (SEQ ID NO: 33; CDR1)<br>GGTGCATCCAGCAGGGCCACT (SEQ ID NO: 34; CDR2)<br>AGCACTATAGCACCTCACCTGGGTTC ACT (SEQ ID NO: 35; CDR3) |
| F5 | AGCAGTAATTACTACTGGGGC (SEQ ID NO: 39; CDR1)<br>GCTATCTATTATAGTGGGAGCACCTACTAC AACCCGTCCCTCAAGAGT (SEQ ID NO: 40; CDR2)<br>CGTATAGGAGTGGCTGGCCAATGGTATTTC GATCTCTGGGGCCGTGGCACCCTGGTCAC CGTCTCAAGC (SEQ ID NO: 41; CDR3) | ACCCGCAGCACTGGCAGCATTACCA GCAACTATGTGCAC (SEQ ID NO: 45; CDR1)<br>GAGGATAACGAAAGACCCTCT (SEQ ID NO: 46; CDR2)<br>CAGTCTTATGATGACAGCAATCATAT TTCTGTC (SEQ ID NO: 47; CDR3) |

Table 4: CDRs (nucleic acid sequences) of the heavy and light chains of Fabs H9 and F5.

HLA complexes only when folded correctly and when containing peptide was monitored. As shown in FIGS. 1c and d, the soluble Fab Abs reacted only with the specific HLA-A2/pp65 complex but not with other control HLA-A2/peptide complexes containing viral epitopes derived from the TAX protein (e.g., TAX 11-19; SEQ ID NO:14), Gag (e.g., Gag 77-85; SEQ ID NO:9) or Pol (e.g., Pol 476-484; SEQ ID NO:10), or a variety of tumor-associated epitopes such as telomerase epitopes [e.g., hTERT 540 (SEQ ID NO:6) or hTERT 865 (SEQ ID NO:8)], melanoma gp100 epitopes [e.g., 209 (SEQ ID NO:7) or 280 (SEQ ID NO:4)], XAGE (SEQ ID NO:12), TARP (SEQ ID NO:13) and MART-1-derived epitopes (e.g., MART 26-35; SEQ ID NO:11) (Pascolo S., et al., 1997). Thus, these peptide-specific and MHC-restricted Fab antibodies exhibit the binding characteristics and fine specificity of a TCR-like molecule.

HLA-A2/pp65-specific TCR-like recombinant antibodies specifically bind MHC-peptide complexes presented on cells—To demonstrate that the isolated Fab antibodies can bind the specific MHC-peptide complex not only in the recombinant soluble form, but also in the native form, as expressed on the cell surface, the present inventors used murine TAP2 (transporter associated with antigen presentation)-deficient RMA-S cells transfected with the human HLA-A2 gene in a single-chain format (Pascolo S., et al., 1997) (HLA-A2.1/Db-$\beta_2$m single chain, RMA-S-HHD cells). The $pp65_{495-503}$ peptide and control peptides were loaded on RMA-S-HHD cells and the ability of the selected Fab Abs to bind to peptide-loaded cells was monitored by flow cytometry. Peptide-induced MHC stabilization of the TAP2 mutant RMA-S-HHD cells was demonstrated by the reactivity of mAbs w6/32 (HLA conformation dependent) and BB7.2 (HLA-A2 specific) with peptide-loaded, but not unloaded cells (data not shown). As shown in FIGS. 2b and d, Fabs H9 and F5 reacted only with pp65-loaded RMA-S-HHD cells, but not with cells loaded with the EBV derived peptide. Similar results were observed in FACS analysis using 10 other HLA-A2-restricted peptides (data not shown).

In addition, the present inventors used the TAP$^+$ EBV-transformed B-lymphoblast HLA-A2$^+$ JY cells as APCs. These cells have normal TAP; consequently, peptide loading is facilitated by the exchange of endogenously derived peptides with HLA-A2-restricted peptides supplied externally by incubation of the cells with the desired peptides. As shown in FIGS. 2a and c, the Fab antibodies recognize only JY cells loaded with the specific pp65 peptide to which they were selected, but not with control HLA-A2-restricted peptides derived from melanoma gp100 [G9-154 (SEQ ID NO:15) and G9-280 (SEQ ID NO:4) epitopes] and MART1 peptides (SEQ ID NO:11), or a telomerase human telomerase reverse transcriptase (hTERT)-derived peptide (T540 epitope; SEQ ID NO:6). As a control, peptide-loaded HLA-A2$^-$/HLA-A1$^+$ APD B cells were used. No binding of the Fab Abs to these cells was observed (data not shown). These results demonstrate the ability of the selected Fabs to detect specifically complexes of HLA-A2 in association with the $pp65_{495-503}$ peptide (SEQ ID NO:3), on the surface of cells.

These results demonstrate the fine specificity of the recombinant Fab clones H9 and F5 to soluble or membrane-presented CMV-MHC class I complex.

Example 3

Generation of Multivalent Antibody Forms and their Binding to Peptide-Pulsed APCS Experimental Results Increased avidity of Fab tetramers to peptide-pulsed APCs—Fab fragments w/o peptide isolated from the phage library are monovalent. To increase the avidity of these fragments, Fab tetramers were generated. This approach was previously used to increase the binding avidity of peptide-MHC complexes to the TCR or to increase the sensitivity of recombinant Ab molecules (Cloutier S M., et al., 2000). To form a Fab tetramer with H9, a BirA tag sequence for site-specific biotinylation was introduced at the C-terminus of the light chain. The Fab domains were expressed separately in *E. coli* and were refolded in vitro followed by purification and in vitro biotinylation using the *E. coli*-derived BirA enzyme (Cohen C J., et al., 2002). H9 Fab tetramers were generated with a fluorescently labeled streptavidin and their reactivity was examined by flow cytometry with JY pulsed cells. As shown in FIG. 3a the fluorescence intensity measured on peptide-pulsed JY cells with the H9 Fab tetramer was significantly higher compared to the reactivity of the H9 Fab monomer. The specificity, however, was not altered (FIG. 3c).

Increased avidity of whole IgG antibodies to peptide-pulsed APCs—Another strategy for increasing the avidity was by creating a whole IgG antibody molecule which is bivalent. To transform the recombinant Fab fragment into a whole IgG molecule, eukaryotic shuttle expression vectors containing the constant regions of IgG1 for the heavy chain and a vector containing the constant domain of a kappa light chain were used. Recombinant H9 Fab-derived IgG was produced from these expression vectors by co-transfection of the two constructs into human embryonic kidney HEK293 cells. After proper selection and generation of stable secreting clones, purified TCR-like whole IgG molecules were produced and tested for binding specifically towards APCs pulsed with the pp65495-503 peptide. As shown in FIG. 3b, the binding specificity of the whole IgG molecule was maintained. As expected, the fluorescence intensity observed with the IgG was significantly higher compared to that of the Fab monomer. JY cells pulsed with control peptide (derived from gp100) were incubated with the three H9 constructs (monomer, tetramer, whole IgG Ab) to confirm specificity (FIG. 3c).

These results demonstrate the generation of bivalent (IgG) or tetrameric Fab antibodies and the increased avidity, yet without compromising specificity of the recombinant antibodies to the CMV-MHC class I complex.

Example 4

The TCR-Like Antibodies of the Invention are Highly Specific and Sensitive to MHC-CMV Peptide Complexes Experimental Results Determination of binding affinity of the recombinant TCR-like antibodies—Binding affinity determination of the H9 Ab was performed by surface plasmon resonance (SPR) analysis using streptavidin sensor chips coated with biotinylated HLA-A2/pp65 or control HLA-A2/EBV complexes. The apparent affinity of the monomeric/IgG forms of the H9 Ab indicated $K_D$ values of 8 nM and 5 nM, respectively. The time necessary for binding of the H9 Fab/IgG Ab to the specific complexes ($K_{on}$) was $1.05 \times 10^5$ 1/Ms and $5.99 \times 10^5$ 1/Ms, respectively. The dissociation rate (Kd or $K_{off}$) of the H9 Fab was $8.79 \times 10^{-4}$ 1/s compared to the H9 IgG Ab, which was $3.52 \times 10^{-3}$ 1/s (FIGS. 4a, b). No significant binding of the antibodies was detected when control HLA-A2/EBV complexes were immobilized to the sensor chip (FIG. 4c).

The recombinant TCR-like antibodies are highly specific to the MHC-pp65 complex—To study the sensitivity of ligand recognition by the Fab and its derivatives the reactivity threshold was examined by peptide titration on JY cells which were pulsed with different concentrations of the pp65 495-503 peptide. As shown in FIGS. 5a and b, peptide titration of pulsed JY demonstrated that the staining intensity was dependent on the concentration of the peptide used for pulsing, and that peptide concentrations at the low nM range were sufficient for Fab tetramer (FIG. 5b) but not for the monomer (FIG. 5a). Thus, the tetrameric form of H9 Fab was able to detect much lower numbers of peptide/HLA-A2 complexes on the surface of peptide-pulsed JY cells than the monomer. Similar results were observed with the whole IgG molecule (data not shown). Overall, these and additional studies revealed that the H9 tetramer and IgG molecules are capable of detecting HLA-A2/pp65 complexes on cells pulsed with as low as ~100 nM pp65$_{495-503}$ peptide.

The recombinant TCR-like antibodies can detect low amounts of MHC-pp65 complexes presented on cells in a mixed population of cells—The TCR-like Fab were further used to detect APCs bearing the specific peptide-MHC complexes in a heterogeneous cell population. This can verify the ability of the TCR-like Fab molecules to detect complexes on individual cell samples in a mixed cell population. To simulate the situation of a heterogeneous population of cells in which only a small fraction might express the specific peptide-MHC complex, pp65 peptide pulsed JY cells were mixed with HLA-A2$^-$/HLA-A1$^+$ APD B cells at various ratios and the reactivity of H9 Fab was analyzed by flow cytometry. As shown in FIG. 5c, staining with H9 Fab tetramer allows accurate identification of the admixed pp65 JY pulsed cells that express on their surface HLA-A2/pp65 complexes, using a simple one-color flow cytometry analysis. Using various ratios of mixtures between pulsed and nonpulsed cells, the H9 Fab was shown capable of detecting as low as 5% pp65 JY pulsed cells within a background population of 95% non-pulsed cells (FIG. 5c).

Altogether, these results demonstrate detection of cell sub-population bearing CMV peptide-MHC complexes.

Example 5

The TCR-Like Antibodies of the Invention can Detect HLA-A2/PP65 Complexes on Surface of Viral-Infected Cells Experimental Results Detection of HLA-A2/pp65 complexes on the surface of virus-infected cells—To test the ability of the isolated Fab to bind specifically HLA-A2/pp65 complexes produced under naturally occurring physiological Antigen (Ag) processing, HLA-A2 positive fibroblasts were infected with the CMV laboratory strain AD169 at multiplicity of infection (MOI) of 0.5 (FIGS. 6a-l). HLA-A2 negative fibroblasts infected with the virus, were used as control in addition to uninfected HLA-A2 negative and positive cells. 72 hours after infection, infected and control cells were incubated with the tetrameric form of H9. To verify the expression of HLA-A2 molecules on the surface of infected, versus uninfected cells, the human fibroblasts were also stained with PE-labeled BB7.2. Confirmation for efficiency of virus infection was monitored with anti pp65 mAb and the secondary antibody FITC-labeled anti mouse IgG. As shown in FIGS. 6a and c, there was a somewhat decrease in the expression of HLA-A2 complexes on the surface of the virus infected cells, due to the virus well known down regulation mechanism of the MHC expression. However, despite the relatively low amount of HLA-A2 expressed on the cell surface, there was still specific staining of infected cells with the H9 tetramer (FIGS. 6e and g), suggesting that the isolated antibody was able to detect not only complexes presented on peptide pulsed APCs but also specific MHC-peptide complexes expressed after active and naturally occurring endogenous intracellular processing. The H9 Ab showed no binding at all in the control uninfected cells (FIGS. 6g and h) as well as in the HLA-A2 negative cells (FIG. 6f), indicating its fine specificity towards HLA-A2/pp65 complexes presented on the cell surface. Staining with the anti pp65 mAb revealed the expression of the pp65 protein after successful infection of the fibroblasts (FIGS. 6i and j).

The specificity of the H9 Ab was verified using a control TCR-like Ab (2F1) which recognizes specifically class I MHC complexes in association with the gp100 280-288 peptide. No staining was visible in this assay, confirming again the H9 tetramer's specificity (data not shown).

These results demonstrate, for the first time, the ability to follow the CMV-MHC class I complexes on the cells surface of APC as well as inside infected cells.

Example 6

The TCR-Like Antibodies of the Invention can Compete with CTLS on Specific HLA-A2/PP65 Sites and Thereby CTL-Mediated Cytotoxicity Experimental Results The H9 Ab can prevent CTL-mediated cytotoxicity directed against the HLA-A2-pp65 complex—The specificity of the H9 Ab to the MHC-pp65 495-503 complex presented on cells was further demonstrated by the specific inhibition of CTL-mediated cell killing by the H9 antibody. Briefly, fibroblast cells were radioactively labeled with S$^{35}$-methionine before infection with the CMV virus and 72 hours later the cells were incubated with H9 Ab. CTLs from a line targeted to the pp65 (495-503) epitope were added at a target (i.e., fibroblast cells)—effector (i.e., CTL) ratio of 1:10 and incubated for five hours. Cells incubated with anti-HLA-A2 W6/32 MAb were used as positive control, while cells without any Ab incubation served as a reference for maximal killing. As shown in FIG. 6m, maximal percentage of killing was observed in the virus infected cells which were not incubated with Abs (CMV CTL alone). However, incubation with the H9 IgG Ab exhibited ~60% blockage of killing by the CTLs (CMV CTL+H9).

The cytotoxicity assay demonstrated the capability of the isolated antibody to recognize specifically complexes presented on virus infected cells and its potential to compete with the same sites recognized by CTLs, leading to the blockage of killing by these effector cells.

Example 7

The TCR-Like Antibodies of the Invention are Valuable Tools for Following the Dynamics of HLA-A2/PP65 Expression in Cells Infected with the CMV Virus Experimental Results The dynamics of HLA-A2/pp65 complex expression in cells infected with wild-type and mutant virus—The fact that the H9 Ab was able to detect specific complexes on virus infected cells enabled to follow the expression levels of the complexes throughout the virus infection cycle. Based on precedent results which showed down regulation of MHC class I expression after viral infection (Ahn, K. et al. 1996), the present inventors investigated whether the generation and presentation of HLA-A2/pp65 complexes throughout various time points after infection is influenced by the down regulation mechanism. To this end two strategies were employed; (i) the intracellular versus extracellular staining with H9 or anti-HLA-A2 BB7.2 Abs which enabled to determine if the level of the complexes generation/expression is correlated with their uptake to the cell surface; (ii) the usage of a mutant strain of CMV which does not induce down regulation of MHC class I. The level of expression of HLA-A2/pp65 complexes in cells infected with the wild type AD 169 strain was compared to that in cells infected with the mutant strain. For this purpose, the genetically modified CMV strain RV798 (Jones T R and Sun L., 1997), which lacks most of the genes responsible for the down regulation mechanism of MHC class I (US2 to US11 genes), was employed.

As shown in FIGS. 7*a-t*, 8*a-t* and 9*a-y*, the general expression of HLA-A2 class I MHC was followed throughout four time points (36, 72, 96 and 120 hours) after cell infection with AD169 WT CMV strain (FIGS. 7*a-t*) and RV798 mutant CMV strain (FIGS. 8*a-t*), as well as the expression of specific HLA-A2 complexes in association with the pp65 495-503 peptide using the H9 IgG Ab. The infection efficiency was monitored by following the expression of the pp65 protein in infected cells through the use of an anti-pp65 MAb. Detection with H9 or BB7.2 Abs was performed in each time point by intracellular and extracellular staining. To verify the specificity of the reagents used for detection, especially the reactivity of the anti-HLA-A2/pp65 495-503 TCR-like antibody, controls which were uninfected HLA-A2 positive fibroblasts (FIGS. 9*a-t*) or CMV infected human fibroblasts that are HLA-A2 negative (FIGS. 9*u-y*) were used. The results show progressive expression of pp65 in cells infected with wild-type (FIGS. 7*e, j, o, t*) and mutant (FIGS. 8*e, j, o, t*) CMV strains while in non-infected cells (FIGS. 9*e, j, o, t*) no expression was observed. The expression of pp65 in cells that were infected with the mutant stain RV798 was somewhat higher. Staining with the anti pp65 Ab also indicated that the cells begin to express the pp65 protein less than 36 hours after infection (data not shown). These data are in agreement with previous studies (Soderberg-Naucler C., et al., 1998). Expression of HLA-A2 on the surface of cells infected with wild-type virus clearly showed a phenotype involving significant down regulation of HLA-A2 expression (FIGS. 7*c, h, m* and *r*) compared to the uninfected fibroblasts (FIGS. 9*c, h, m, r*). This down regulation is increased over time through the progression of the time points. Also, the intracellular expression of HLA-A2 in infected cells seemed to be higher than the amount in the uninfected cells (Compare FIGS. 7*d, i, n* and *s* to FIGS. 9*d, i, n* and *s*, respectively). These data are in agreement with previous studies (Ahn K., et al., 1996).

When cells were infected with wild-type virus, a specific and gradual increase in staining with the H9 IgG TCR-like antibody was observed indicating the generation of HLA-A2/pp65 495-503 complexes inside infected cells (FIGS. 7*b, g, l* and *q*) as well as their presentation on the cell surface (FIGS. 7*a, f, k* and *p*). However, although the amount of complexes which bear the pp65 495-503 peptide seemed to be quite low at the cell surface (e.g., compare FIG. 7*f* with 7*g*), intracellular staining of these specific complexes revealed a very significant large pool of complexes inside the cell. This might indicate that although the pp65 is well processed inside the cell and its peptides are deposited on the class I MHC, it is avoided from being displayed on the cell surface as part of the virus evasion mechanisms. Interestingly, there was no correlation between HLA-A2 down regulation as clearly observed through the progression of time and the significant increase in the intracellular pools of HLA-A2/pp65 495-503 complexes or their expression on the cell surface. Most striking is that after 120 hours the expression of HLA-A2 is very low however both intracellular pools are very high and surface expression is significant.

The reactivity of the H9 IgG molecule to the MHC-CMV pp65 peptide complex both inside and on the surface of cells is highly specific—Non-infected HLA-A2 positive cells were stained with anti-HLA-A2 antibody BB7.2 both inside (FIGS. 9*d, i, n, s*) and on the surface (FIGS. 9*c, h, m, r*). As shown, there were no observed alterations in HLA-A2 expression inside the cells as well as its presentation on the cell surface throughout the time points tested after infection. In contrary to the infected fibroblasts, the amount of complexes as determined using the BB7.2 antibody on the cell surface of non-infected cells seemed to be higher than their amount inside the cells (compare FIGS. 9*c, h, m, r* with FIGS. 9*d, i, n, s*, respectively). No pools of complexes were observed inside the cells (FIGS. 9*d, i, n, s*) as seen in the infected fibroblasts (FIGS. 7*d, i, n, s*). This implies that the HLA-A2 complexes expressed inside the uninfected cells are freely presented on the cell surface, in contrast to the infected cells (see FIGS. 7*d, i, n, s*). In contrast, the H9 TCR-like antibody was not reactive with uninfected cells both inside (FIGS. 9*b, g, l, q*) and on the cell surface (FIGS. 9*a, f, k, p*), indicating its fine specificity towards its antigen.

When HLA-A2 negative human fibroblasts were infected with wild-type CMV, pp65 expression was clearly observed (FIG. 9*y*), however, no reactivity with the anti-HLA-A2 antibody (FIGS. 9*w, x*) or the H9 TCR-like antibody (FIGS. 9*u, v*) was observed inside or on the surface of the infected cells indicating the highly specific reactivity of the molecules.

The presentation of HLA-A2/pp65 complexes was further examined both inside the cells and on their surface less than 24 hours after infection. These studies demonstrated that although pp65 is expressed, there is no presentation of its peptides on HLA-A2 molecules (Data not shown).

FIGS. 8*a-t* follow the dynamics of antigen presentation in the mutant strain RV798. The infected cells were efficiently infected with the virus as observed from the staining with anti-pp65 (FIGS. 8*e, j, o, t*). It was clearly observed that the effect of the mutant virus on HLA-A2 expression inside and on the surface of infected cells was diminished, thus the mutant virus no longer significantly down regulates HLA-A2 expression, as expected. When using the H9 IgG TCR-like antibody, similar to the results observed with wild-type CMV, a gradual increase over time of intracellular pools of HLA-A2/pp65 495-503 complexes inside infected cells was observed (FIGS. 8*b, g, l, q*) as well as their gradual appearance on the cell surface (FIGS. 8*a, f, k, p*). Also, it was quite evident that the number of HLA-A2/pp65 495-503 complexes inside the infected cells was higher than those on the cell surface (Compare FIGS. 8*b, g, l, q* to FIGS. 8*a, f, k, p*, respectively). This may indicate that although the mutant virus does not activate the down regulation mechanism, there are still HLA-A2 pools as well as specific HLA-A2/pp65 pools inside the cells, which are avoided from being presented on the cell surface.

In general, these results present the usage of the H9 Ab to follow the dynamic expression and kinetics of HLA-A2/pp65 495-503 presentation intracellularly and on the surface of infected cells as a function of time after viral infection. Most striking is the observation that there is no correlation between class I MHC down regulation induced by wild-type virus and the generation/presentation of the viral specific HLA-A2/pp65 495-503 complex. On the contrary, the down regulation did not affect the generation of a significant and large intracellular pool of viral complexes and their appearance over time on the cell surface. Similar studies using the H9 antibody and a mutant virus that abolishes class I MHC down regulation showed a similar pattern of expression inside the cell and on its surface with somewhat increased number of complexes on both compared to wild-type virus especially between 24-72 hours after infection.

Example 8

The TCR-Like Antibodies of the Invention can be Used to Quantify the Number of HLA-A2/PP65 Complexes on Viral Infected Cells The knowledge of the number of complexes presented on the cell surface can be used to understand how the immune system identifies viral infection. Related to the studies presented herein, the present inventors attempted to quantify and compare the number of complexes generated inside the infected cells to those presented on the cell surface, as follows.

Experimental Results

Quantization of the number of HLA-A2/pp65 complexes on the surface of infected cells—The unique H9 IgG TCR-like antibody enables the present inventors to directly quantify the number and percentage of specific HLA-A2/pp65 complexes among HLA-A2-derived complexes which are displayed on the cell surface. Staining of virus infected cells with the H9 IgG TCR-like antibody enabled the present inventors to directly count the number of complexes on the surface of the infected cells using a PE-labeled anti kappa secondary monoclonal antibody that generates a 1:1 binding stoichiometry with the H9 IgG molecule. The level of fluorescence intensity resulting from specific reactivity of the H9 IgG antibody on infected cells can be directly correlated with the fluorescence intensities of calibration beads with known numbers PE molecules per bead (QuantiBRITE PE beads; BD Biosciences), using simple flow cytometry calibrations. This strategy enabled the present inventors to determine the number of PE molecules bound to the cells and thereby the number of sites which are bound by the H9 antibody.

In agreement to the results presented on FIGS. 7-9 (Example 7, hereinabove), there was an immediate and massive down regulation of HLA-A2 complexes (using the BB7 Ab) from the cell surface after infection with the CMV wild-type strain (FIG. 10*d*). In all time points there were about 5,000 complexes observed on the cell surface compared to ~25,000 complexes in the uninfected cells, implying that there was over 85% decrease in the amount of HLA-A2 complexes presented on the cell surface (FIG. 10*d*). The number of HLA-A2 complexes inside the cells in infected vs. uninfected cells remained almost the same (FIG. 10*c*). The number of HLA-A2/pp65 complexes presented on the cell surface was gradually increased over time (FIG. 10*b*). Specific complexes were observed using the H9 antibody starting at 36 hours after infection and the number reached to approximately 400 sites/cell 120 hours after infection (FIG. 10*c*). This implies that 120 hours after infection with the virus, about 10%-15% of the HLA-A2 complexes presented on the cell surfaces bear the pp65 495-503 peptide. Interestingly, the number of these specific complexes inside the cells reaches to ~2000/cell after 120 hours (FIG. 10A). This number is close to the total number of HLA-A2 complexes inside the cell, suggesting that most of the HLA-A2 complexes which accumulate inside infected cells are HLA-A2/pp65. This might also suggest that most of these specific complexes which are generated inside the cells are avoided from being presented on the surface.

Using the mutant virus, the same number of HLA-A2 molecules on the cell surface was observed as in the uninfected cells (FIG. 10*d*). The number of sites reached to approximately 20,000 (FIG. 10*d*). However, the number of complexes quantified inside the cells was significantly higher than the number observed in the uninfected cells, and approached to ~10,000 (FIG. 10*c*) compared to ~1,000 in the uninfected cells (FIG. 10*c*). As for HLA-A2/pp65 complexes, there were ~400 sites detected on the cell surface (FIG. 10*b*), implying that similar to cells infected with wild-type virus most of viral HLA-A2/pp65 complexes are avoided from being transported to the cell surface. The percentage of these complexes amongst HLA-A2 complexes on the cell surface is very low. However, the number of HLA-A2/pp65 complexes inside the infected cells reached to approximately 3,000 (FIG. 10*a*) in each time point after 72 hours thus until 120 hours after infection there is an accumulation of the specific complexes inside the cell. This accumulation might lead to the observation that after this time point, most of the complexes inside the cell are composed of HLA-A2/pp65.

These data provide a quantitative measure to the observation that specific HLA-A2/pp65 complexes are being generated in large amounts and accumulated inside the infected cell in a mechanism that is independent to the overall down regulation of HLA-A2 molecules in these cells. The accumulation was observed with wild-type and mutant virus strains and for both the accumulated HLA-A2/pp65 complexes were avoided from being presented in large amounts on the cell surface.

These results visualize large intracellular pools of the viral complexes after infection, follow and quantify their expression on the surface. These results demonstrate that despite significant down regulation of MHC expression by wild-type virus large pools of specific viral complexes are generated intracellularly, and their export to the cell surface occurs in a limited quantity. These studies describe the first attempt to directly visualize and analyze the dynamics of a naturally occurring viral-derived human MHC-peptide complex after viral infection.

The data also demonstrate the ability of the TCR-like antibody of the instant application to detect and accurately quantify the number of HLA-A2/peptide complexes on the surface of infected cells under naturally occurring intracellular processing. These results can be used to follow the effectiveness of viral strategies for immunization.

Example 9

Visualization Through Confocal Microscopy Imaging of HLA-A2/PP65 Expression in Virus-Infected Cells Experimental Results Visualization through confocal microscopy imaging of HLA-A2/pp65 expression in virus-infected cells—Confocal microscopy of CMV infected cells stained with the H9 IgG TCR-like antibody enabled the present inventors to visualize and image the specific HLA-A2/pp65 complexes generated inside the cells, as well as their display on the cell surface. Moreover, it enabled the present inventors to localize the complexes inside the cell during the virus infection cycle.

CMV infected cells were harvested every 24 hours for 5 days. At each time point cells were stained with the H9 Ab, and anti human alexa fluor$^{488}$ as a secondary Ab. The cells were also stained intracellularly with the H9 Ab, anti calnexin, cis Golgi matrix protein (GM130), and anti pp65 Ab, after fixation and permeabilization. Secondary antibody for the ER marker, Golgi marker and anti pp65 was anti mouse alexa fluor[594]. Noninfected fibroblast cells were used as a control.

The results of these assays further demonstrate and image the significant pool of specific HLA-A2/pp65 complexes generated inside infected cells (FIGS. 11*a-o*, 12*a-o*). The data also show that the specific complexes are densely colocalized with the cis-golgi apparatus (FIGS. 11*a-o*). This co-localization is observed clearly after 24 hours in comparison with the later time points, in which the complexes are more widely distributed and co-localized to the ER/cytosol as indicated by co-staining with the various localization markers (FIGS. 12*a-o*). Additionally, as time progresses, a significant enlargement of the Golgi apparatus is observed, as part of the morphological changes of the infected cells. Extracellular staining of the HLA-A2/pp65 complexes showed their display on the cell surface only after 72 hours post infection (FIGS. 13*a-e*). These results are with complete agreement with the flow cytometry analysis of the kinetic of HLA-A2/pp65 epitope presentation as shown in FIGS. 7*a-t*, 8*a-t* and 9*a-y*. Confocal microscopy analysis of control noninfected cells showed no staining with the H9 Ab (FIGS. 13*f-h*), indicating its fine specificity towards the HLA-A2/pp65 complexes. Staining with anti pp65 Ab confirmed the effectiveness of the viral infection in the experiments (FIGS. 13*i-j*).

These results visualize the present inventors' finding that specific HLA-A2/pp65 complexes are being generated and accumulate in infected cells and are localized in the Golgi compartment. They are prevented from being displayed on the cell surface at early time points and only 72 hours after infection they can be imaged on the cell surface. The fact that the specific complexes are prevented from being displayed on the cell surface is only temporary. Progressed time scales showed that the complexes are being significantly displayed on the cell surface. The intermediate time points clearly show that the complexes are less co-localized with the Golgi due to their movement to the cell membrane. The phenomena of Golgi enlargement is usually attributed to an extensive synthesis of proteins after viral infection. These results can imply that this enlargement is also due to the specific accumulation of complexes in the Golgi.

Example 10

CMV PP64 MHC Restricted Peptides

Tables 5-70 hereinbelow provide the user parameters and scoring information used to select CMV PP64 restricted peptides (each of 9 or 10 amino acids in length) of various HLA molecules. The analysis was performed using the Bimas software [hypertexttransferprotocol:///worldwideweb-bimas (dot) cit (dot) nih (dot) gov/molbio/hla_bind/]. The scoring results and the sequences of the selected peptides (according to each user parameters and scoring information) are provided in Table 137 in Example 11, hereinbelow. The CMV PP64 kDa protein used for analysis is provided by SEQ ID NO:52 [(GenBank Accession No. P18139; PP65_HCMVT 64 kDa lower matrix phosphoprotein—Human cytomegalovirus (strain Towne) (HHV-5) (Human herpesvirus 5)].

TABLE 5

| method selected to limit number of results | cutoff score |
|---|---|
| cutoff score selected | 1 |
| HLA molecule type selected | A1 |
| length selected for subsequences to be scored | 9 |

TABLE 5-continued

| method selected to limit number of results | cutoff score |
|---|---|
| echoing mode selected for input sequence | Y |
| echoing format | numbered lines |
| length of user's input peptide sequence | 551 |
| number of subsequence scores calculated | 543 |
| number of top-scoring subsequences reported back in scoring output table | 15 |

TABLE 6

| method selected to limit number of results | cutoff score |
|---|---|
| cutoff score selected | 1 |
| HLA molecule type selected | A1 |
| length selected for subsequences to be scored | 10 |
| echoing mode selected for input sequence | Y |
| echoing format | numbered lines |
| length of user's input peptide sequence | 551 |
| number of subsequence scores calculated | 542 |
| number of top-scoring subsequences reported back in scoring output table | 20 |

TABLE 7

| method selected to limit number of results | cutoff score |
|---|---|
| cutoff score selected | 1 |
| HLA molecule type selected | A_0201 |
| length selected for subsequences to be scored | 9 |
| echoing mode selected for input sequence | Y |
| echoing format | numbered lines |
| length of user's input peptide sequence | 551 |
| number of subsequence scores calculated | 543 |
| number of top-scoring subsequences reported back in scoring output table | 48 |

TABLE 8

| method selected to limit number of results | cutoff score |
|---|---|
| cutoff score selected | 1 |
| HLA molecule type selected | A_0201 |
| length selected for subsequences to be scored | 10 |
| echoing mode selected for input sequence | Y |
| echoing format | numbered lines |
| length of user's input peptide sequence | 551 |
| number of subsequence scores calculated | 542 |
| number of top-scoring subsequences reported back in scoring output table | 53 |

TABLE 9

| method selected to limit number of results | cutoff score |
|---|---|
| cutoff score selected | 1 |
| HLA molecule type selected | A_0205 |
| length selected for subsequences to be scored | 9 |
| echoing mode selected for input sequence | Y |
| echoing format | numbered lines |
| length of user's input peptide sequence | 551 |
| number of subsequence scores calculated | 543 |
| number of top-scoring subsequences reported back in scoring output table | 50 |

TABLE 10

| method selected to limit number of results | cutoff score |
|---|---|
| cutoff score selected | 1 |
| HLA molecule type selected | A_0205 |
| length selected for subsequences to be scored | 10 |
| echoing mode selected for input sequence | Y |
| echoing format | numbered lines |
| length of user's input peptide sequence | 551 |
| number of subsequence scores calculated | 542 |
| number of top-scoring subsequences reported back in scoring output table | 47 |

TABLE 11

| method selected to limit number of results | cutoff score |
|---|---|
| cutoff score selected | 1 |
| HLA molecule type selected | A24 |
| length selected for subsequences to be scored | 9 |
| echoing mode selected for input sequence | Y |
| echoing format | numbered lines |
| length of user's input peptide sequence | 551 |
| number of subsequence scores calculated | 543 |
| number of top-scoring subsequences reported back in scoring output table | 61 |

TABLE 12

| method selected to limit number of results | cutoff score |
|---|---|
| cutoff score selected | 1 |
| HLA molecule type selected | A24 |
| length selected for subsequences to be scored | 10 |
| echoing mode selected for input sequence | Y |
| echoing format | numbered lines |
| length of user's input peptide sequence | 551 |
| number of subsequence scores calculated | 542 |
| number of top-scoring subsequences reported back in scoring output table | 76 |

TABLE 13

| method selected to limit number of results | cutoff score |
|---|---|
| cutoff score selected | 1 |
| HLA molecule type selected | A3 |
| length selected for subsequences to be scored | 9 |
| echoing mode selected for input sequence | Y |
| echoing format | numbered lines |
| length of user's input peptide sequence | 551 |
| number of subsequence scores calculated | 543 |
| number of top-scoring subsequences reported back in scoring output table | 23 |

TABLE 14

| method selected to limit number of results | cutoff score |
|---|---|
| cutoff score selected | 1 |
| HLA molecule type selected | A3 |
| length selected for subsequences to be scored | 10 |
| echoing mode selected for input sequence | Y |
| echoing format | numbered lines |
| length of user's input peptide sequence | 551 |
| number of subsequence scores calculated | 542 |
| number of top-scoring subsequences reported back in scoring output table | 21 |

TABLE 15

| method selected to limit number of results | cutoff score |
|---|---|
| cutoff score selected | 1 |
| HLA molecule type selected | A68.1 |
| length selected for subsequences to be scored | 9 |
| echoing mode selected for input sequence | Y |
| echoing format | numbered lines |
| length of user's input peptide sequence | 551 |
| number of subsequence scores calculated | 543 |
| number of top-scoring subsequences reported back in scoring output table | 79 |

TABLE 16

| method selected to limit number of results | cutoff score |
|---|---|
| cutoff score selected | 1 |
| HLA molecule type selected | A68.1 |
| length selected for subsequences to be scored | 10 |
| echoing mode selected for input sequence | Y |
| echoing format | numbered lines |
| length of user's input peptide sequence | 551 |
| number of subsequence scores calculated | 542 |
| number of top-scoring subsequences reported back in scoring output table | 77 |

TABLE 17

| method selected to limit number of results | cutoff score |
|---|---|
| cutoff score selected | 1 |
| HLA molecule type selected | A_1101 |
| length selected for subsequences to be scored | 9 |
| echoing mode selected for input sequence | Y |
| echoing format | numbered lines |
| length of user's input peptide sequence | 551 |
| number of subsequence scores calculated | 543 |
| number of top-scoring subsequences reported back in scoring output table | 5 |

TABLE 18

| method selected to limit number of results | cutoff score |
|---|---|
| cutoff score selected | 1 |
| HLA molecule type selected | A_1101 |
| length selected for subsequences to be scored | 10 |
| echoing mode selected for input sequence | Y |
| echoing format | numbered lines |
| length of user's input peptide sequence | 551 |
| number of subsequence scores calculated | 542 |
| number of top-scoring subsequences reported back in scoring output table | 4 |

TABLE 19

| method selected to limit number of results | cutoff score |
|---|---|
| cutoff score selected | 1 |
| HLA molecule type selected | A_3101 |
| length selected for subsequences to be scored | 9 |
| echoing mode selected for input sequence | Y |
| echoing format | numbered lines |
| length of user's input peptide sequence | 551 |
| number of subsequence scores calculated | 543 |
| number of top-scoring subsequences reported back in scoring output table | 10 |

TABLE 20

| method selected to limit number of results | cutoff score |
|---|---|
| cutoff score selected | 1 |
| HLA molecule type selected | A_3101 |
| length selected for subsequences to be scored | 10 |
| echoing mode selected for input sequence | Y |
| echoing format | numbered lines |
| length of user's input peptide sequence | 551 |
| number of subsequence scores calculated | 542 |
| number of top-scoring subsequences reported back in scoring output table | 17 |

TABLE 21

| method selected to limit number of results | cutoff score |
|---|---|
| cutoff score selected | 1 |
| HLA molecule type selected | A_3302 |
| length selected for subsequences to be scored | 9 |
| echoing mode selected for input sequence | Y |
| echoing format | numbered lines |
| length of user's input peptide sequence | 551 |
| number of subsequence scores calculated | 543 |
| number of top-scoring subsequences reported back in scoring output table | 39 |

TABLE 22

| method selected to limit number of results | cutoff score |
|---|---|
| cutoff score selected | 1 |
| HLA molecule type selected | A_3302 |
| length selected for subsequences to be scored | 10 |
| echoing mode selected for input sequence | Y |
| echoing format | numbered lines |
| length of user's input peptide sequence | 551 |
| number of subsequence scores calculated | 542 |
| number of top-scoring subsequences reported back in scoring output table | 34 |

TABLE 23

| method selected to limit number of results | cutoff score |
|---|---|
| cutoff score selected | 1 |
| HLA molecule type selected | B14 |
| length selected for subsequences to be scored | 9 |
| echoing mode selected for input sequence | Y |
| echoing format | numbered lines |
| length of user's input peptide sequence | 551 |
| number of subsequence scores calculated | 543 |
| number of top-scoring subsequences reported back in scoring output table | 61 |

TABLE 24

| method selected to limit number of results | cutoff score |
|---|---|
| cutoff score selected | 1 |
| HLA molecule type selected | B14 |
| length selected for subsequences to be scored | 10 |
| echoing mode selected for input sequence | Y |
| echoing format | numbered lines |
| length of user's input peptide sequence | 551 |
| number of subsequence scores calculated | 542 |
| number of top-scoring subsequences reported back in scoring output table | 60 |

TABLE 25

| method selected to limit number of results | cutoff score |
|---|---|
| cutoff score selected | 1 |
| HLA molecule type selected | B40 |
| length selected for subsequences to be scored | 9 |
| echoing mode selected for input sequence | Y |
| echoing format | numbered lines |
| length of user's input peptide sequence | 551 |
| number of subsequence scores calculated | 543 |
| number of top-scoring subsequences reported back in scoring output table | 36 |

TABLE 26

| method selected to limit number of results | cutoff score |
|---|---|
| cutoff score selected | 1 |
| HLA molecule type selected | B40 |
| length selected for subsequences to be scored | 10 |
| echoing mode selected for input sequence | Y |
| echoing format | numbered lines |
| length of user's input peptide sequence | 551 |
| number of subsequence scores calculated | 542 |
| number of top-scoring subsequences reported back in scoring output table | 42 |

TABLE 27

| method selected to limit number of results | cutoff score |
|---|---|
| cutoff score selected | 1 |
| HLA molecule type selected | B60 |
| length selected for subsequences to be scored | 9 |
| echoing mode selected for input sequence | Y |
| echoing format | numbered lines |
| length of user's input peptide sequence | 551 |
| number of subsequence scores calculated | 543 |
| number of top-scoring subsequences reported back in scoring output table | 41 |

TABLE 28

| method selected to limit number of results | cutoff score |
|---|---|
| cutoff score selected | 1 |
| HLA molecule type selected | B60 |
| length selected for subsequences to be scored | 10 |
| echoing mode selected for input sequence | Y |
| echoing format | numbered lines |
| length of user's input peptide sequence | 551 |
| number of subsequence scores calculated | 542 |
| number of top-scoring subsequences reported back in scoring output table | 49 |

TABLE 29

| method selected to limit number of results | cutoff score |
|---|---|
| cutoff score selected | 1 |
| HLA molecule type selected | B61 |
| length selected for subsequences to be scored | 9 |
| echoing mode selected for input sequence | Y |
| echoing format | numbered lines |
| length of user's input peptide sequence | 551 |
| number of subsequence scores calculated | 543 |
| number of top-scoring subsequences reported back in scoring output table | 44 |

TABLE 30

| method selected to limit number of results | cutoff score |
|---|---|
| cutoff score selected | 1 |
| HLA molecule type selected | B61 |
| length selected for subsequences to be scored | 10 |
| echoing mode selected for input sequence | Y |
| echoing format | numbered lines |
| length of user's input peptide sequence | 551 |
| number of subsequence scores calculated | 542 |
| number of top-scoring subsequences reported back in scoring output table | 45 |

TABLE 31

| method selected to limit number of results | cutoff score |
|---|---|
| cutoff score selected | 1 |
| HLA molecule type selected | B62 |
| length selected for subsequences to be scored | 9 |
| echoing mode selected for input sequence | Y |
| echoing format | numbered lines |
| length of user's input peptide sequence | 551 |
| number of subsequence scores calculated | 543 |
| number of top-scoring subsequences reported back in scoring output table | 57 |

TABLE 32

| method selected to limit number of results | cutoff score |
|---|---|
| cutoff score selected | 1 |
| HLA molecule type selected | B62 |
| length selected for subsequences to be scored | 10 |
| echoing mode selected for input sequence | Y |
| echoing format | numbered lines |
| length of user's input peptide sequence | 551 |
| number of subsequence scores calculated | 542 |
| number of top-scoring subsequences reported back in scoring output table | 54 |

TABLE 33

| method selected to limit number of results | cutoff score |
|---|---|
| cutoff score selected | 1 |
| HLA molecule type selected | B7 |
| length selected for subsequences to be scored | 9 |
| echoing mode selected for input sequence | Y |
| echoing format | numbered lines |
| length of user's input peptide sequence | 551 |
| number of subsequence scores calculated | 543 |
| number of top-scoring subsequences reported back in scoring output table | 55 |

TABLE 34

| method selected to limit number of results | cutoff score |
|---|---|
| cutoff score selected | 1 |
| HLA molecule type selected | B7 |
| length selected for subsequences to be scored | 10 |
| echoing mode selected for input sequence | Y |
| echoing format | numbered lines |
| length of user's input peptide sequence | 551 |
| number of subsequence scores calculated | 542 |
| number of top-scoring subsequences reported back in scoring output table | 62 |

TABLE 35

| method selected to limit number of results | cutoff score |
|---|---|
| cutoff score selected | 1 |
| HLA molecule type selected | B8 |
| length selected for subsequences to be scored | 9 |
| echoing mode selected for input sequence | Y |
| echoing format | numbered lines |
| length of user's input peptide sequence | 551 |
| number of subsequence scores calculated | 543 |
| number of top-scoring subsequences reported back in scoring output table | 12 |

TABLE 36

| method selected to limit number of results | cutoff score |
|---|---|
| cutoff score selected | 1 |
| HLA molecule type selected | B8 |
| length selected for subsequences to be scored | 10 |
| echoing mode selected for input sequence | Y |
| echoing format | numbered lines |
| length of user's input peptide sequence | 551 |
| number of subsequence scores calculated | 542 |
| number of top-scoring subsequences reported back in scoring output table | 14 |

TABLE 37

| method selected to limit number of results | cutoff score |
|---|---|
| cutoff score selected | 1 |
| HLA molecule type selected | B_2702 |
| length selected for subsequences to be scored | 9 |
| echoing mode selected for input sequence | Y |
| echoing format | numbered lines |
| length of user's input peptide sequence | 551 |
| number of subsequence scores calculated | 543 |
| number of top-scoring subsequences reported back in scoring output table | 71 |

TABLE 38

| method selected to limit number of results | cutoff score |
|---|---|
| cutoff score selected | 1 |
| HLA molecule type selected | B_2702 |
| length selected for subsequences to be scored | 10 |
| echoing mode selected for input sequence | Y |
| echoing format | numbered lines |
| length of user's input peptide sequence | 551 |
| number of subsequence scores calculated | 542 |
| number of top-scoring subsequences reported back in scoring output table | 72 |

TABLE 39

| method selected to limit number of results | cutoff score |
|---|---|
| cutoff score selected | 1 |
| HLA molecule type selected | B_2705 |
| length selected for subsequences to be scored | 9 |
| echoing mode selected for input sequence | Y |
| echoing format | numbered lines |
| length of user's input peptide sequence | 551 |
| number of subsequence scores calculated | 543 |
| number of top-scoring subsequences reported back in scoring output table | 276 |

TABLE 40

| method selected to limit number of results | cutoff score |
|---|---|
| cutoff score selected | 1 |
| HLA molecule type selected | B_2705 |
| length selected for subsequences to be scored | 10 |
| echoing mode selected for input sequence | Y |
| echoing format | numbered lines |
| length of user's input peptide sequence | 551 |
| number of subsequence scores calculated | 542 |
| number of top-scoring subsequences reported back in scoring output table | 283 |

TABLE 41

| method selected to limit number of results | cutoff score |
|---|---|
| cutoff score selected | 1 |
| HLA molecule type selected | B_3501 |
| length selected for subsequences to be scored | 9 |
| echoing mode selected for input sequence | Y |
| echoing format | numbered lines |
| length of user's input peptide sequence | 551 |
| number of subsequence scores calculated | 543 |
| number of top-scoring subsequences reported back in scoring output table | 72 |

TABLE 42

| method selected to limit number of results | cutoff score |
|---|---|
| cutoff score selected | 1 |
| HLA molecule type selected | B_3501 |
| length selected for subsequences to be scored | 10 |
| echoing mode selected for input sequence | Y |
| echoing format | numbered lines |
| length of user's input peptide sequence | 551 |
| number of subsequence scores calculated | 542 |
| number of top-scoring subsequences reported back in scoring output table | 81 |

TABLE 43

| method selected to limit number of results | cutoff score |
|---|---|
| cutoff score selected | 1 |
| HLA molecule type selected | B_3701 |
| length selected for subsequences to be scored | 9 |
| echoing mode selected for input sequence | Y |
| echoing format | numbered lines |
| length of user's input peptide sequence | 551 |
| number of subsequence scores calculated | 543 |
| number of top-scoring subsequences reported back in scoring output table | 90 |

TABLE 44

| method selected to limit number of results | cutoff score |
|---|---|
| cutoff score selected | 1 |
| HLA molecule type selected | B_3701 |
| length selected for subsequences to be scored | 10 |
| echoing mode selected for input sequence | Y |
| echoing format | numbered lines |
| length of user's input peptide sequence | 551 |
| number of subsequence scores calculated | 542 |
| number of top-scoring subsequences reported back in scoring output table | 100 |

TABLE 45

| method selected to limit number of results | cutoff score |
|---|---|
| cutoff score selected | 1 |
| HLA molecule type selected | B_3801 |
| length selected for subsequences to be scored | 9 |
| echoing mode selected for input sequence | Y |
| echoing format | numbered lines |
| length of user's input peptide sequence | 551 |
| number of subsequence scores calculated | 543 |
| number of top-scoring subsequences reported back in scoring output table | 50 |

TABLE 46

| method selected to limit number of results | cutoff score |
|---|---|
| cutoff score selected | 1 |
| HLA molecule type selected | B_3801 |
| length selected for subsequences to be scored | 10 |
| echoing mode selected for input sequence | Y |
| echoing format | numbered lines |
| length of user's input peptide sequence | 551 |
| number of subsequence scores calculated | 542 |
| number of top-scoring subsequences reported back in scoring output table | 59 |

TABLE 47

| method selected to limit number of results | cutoff score |
|---|---|
| cutoff score selected | 1 |
| HLA molecule type selected | B_3901 |
| length selected for subsequences to be scored | 9 |
| echoing mode selected for input sequence | Y |
| echoing format | numbered lines |
| length of user's input peptide sequence | 551 |
| number of subsequence scores calculated | 543 |
| number of top-scoring subsequences reported back in scoring output table | 100 |

TABLE 48

| method selected to limit number of results | cutoff score |
|---|---|
| cutoff score selected | 1 |
| HLA molecule type selected | B_3901 |
| length selected for subsequences to be scored | 10 |
| echoing mode selected for input sequence | Y |
| echoing format | numbered lines |
| length of user's input peptide sequence | 551 |
| number of subsequence scores calculated | 542 |
| number of top-scoring subsequences reported back in scoring output table | 102 |

TABLE 49

| method selected to limit number of results | cutoff score |
|---|---|
| cutoff score selected | 1 |
| HLA molecule type selected | B_3902 |
| length selected for subsequences to be scored | 9 |
| echoing mode selected for input sequence | Y |
| echoing format | numbered lines |
| length of user's input peptide sequence | 551 |
| number of subsequence scores calculated | 543 |
| number of top-scoring subsequences reported back in scoring output table | 61 |

TABLE 50

| method selected to limit number of results | cutoff score |
|---|---|
| cutoff score selected | 1 |
| HLA molecule type selected | B_3902 |
| length selected for subsequences to be scored | 10 |
| echoing mode selected for input sequence | Y |
| echoing format | numbered lines |
| length of user's input peptide sequence | 551 |
| number of subsequence scores calculated | 542 |
| number of top-scoring subsequences reported back in scoring output table | 69 |

TABLE 51

| method selected to limit number of results | cutoff score |
|---|---|
| cutoff score selected | 1 |
| HLA molecule type selected | B_4403 |
| length selected for subsequences to be scored | 9 |
| echoing mode selected for input sequence | Y |
| echoing format | numbered lines |
| length of user's input peptide sequence | 551 |
| number of subsequence scores calculated | 543 |
| number of top-scoring subsequences reported back in scoring output table | 47 |

TABLE 52

| method selected to limit number of results | cutoff score |
|---|---|
| cutoff score selected | 1 |
| HLA molecule type selected | B_4403 |
| length selected for subsequences to be scored | 10 |
| echoing mode selected for input sequence | Y |
| echoing format | numbered lines |
| length of user's input peptide sequence | 551 |
| number of subsequence scores calculated | 542 |
| number of top-scoring subsequences reported back in scoring output table | 56 |

TABLE 53

| method selected to limit number of results | cutoff score |
|---|---|
| cutoff score selected | 1 |
| HLA molecule type selected | B_5101 |
| length selected for subsequences to be scored | 9 |
| echoing mode selected for input sequence | Y |
| echoing format | numbered lines |
| length of user's input peptide sequence | 551 |
| number of subsequence scores calculated | 543 |
| number of top-scoring subsequences reported back in scoring output table | 139 |

TABLE 54

| method selected to limit number of results | cutoff score |
|---|---|
| cutoff score selected | 1 |
| HLA molecule type selected | B_5101 |
| length selected for subsequences to be scored | 10 |
| echoing mode selected for input sequence | Y |
| echoing format | numbered lines |
| length of user's input peptide sequence | 551 |
| number of subsequence scores calculated | 542 |
| number of top-scoring subsequences reported back in scoring output table | 127 |

TABLE 55

| method selected to limit number of results | cutoff score |
|---|---|
| cutoff score selected | 1 |
| HLA molecule type selected | B_5102 |
| length selected for subsequences to be scored | 9 |
| echoing mode selected for input sequence | Y |
| echoing format | numbered lines |
| length of user's input peptide sequence | 551 |
| number of subsequence scores calculated | 543 |
| number of top-scoring subsequences reported back in scoring output table | 149 |

TABLE 56

| method selected to limit number of results | cutoff score |
|---|---|
| cutoff score selected | 1 |
| HLA molecule type selected | B_5102 |
| length selected for subsequences to be scored | 10 |
| echoing mode selected for input sequence | Y |
| echoing format | numbered lines |
| length of user's input peptide sequence | 551 |
| number of subsequence scores calculated | 542 |
| number of top-scoring subsequences reported back in scoring output table | 140 |

TABLE 57

| method selected to limit number of results | cutoff score |
|---|---|
| cutoff score selected | 1 |
| HLA molecule type selected | B_5103 |
| length selected for subsequences to be scored | 9 |
| echoing mode selected for input sequence | Y |
| echoing format | numbered lines |
| length of user's input peptide sequence | 551 |
| number of subsequence scores calculated | 543 |
| number of top-scoring subsequences reported back in scoring output table | 89 |

TABLE 58

| method selected to limit number of results | cutoff score |
|---|---|
| cutoff score selected | 1 |
| HLA molecule type selected | B_5103 |
| length selected for subsequences to be scored | 10 |
| echoing mode selected for input sequence | Y |
| echoing format | numbered lines |
| length of user's input peptide sequence | 551 |
| number of subsequence scores calculated | 542 |
| number of top-scoring subsequences reported back in scoring output table | 86 |

TABLE 59

| method selected to limit number of results | cutoff score |
|---|---|
| cutoff score selected | 1 |
| HLA molecule type selected | B_5201 |
| length selected for subsequences to be scored | 9 |
| echoing mode selected for input sequence | Y |
| echoing format | numbered lines |
| length of user's input peptide sequence | 551 |
| number of subsequence scores calculated | 543 |
| number of top-scoring subsequences reported back in scoring output table | 111 |

TABLE 60

| method selected to limit number of results | cutoff score |
|---|---|
| cutoff score selected | 1 |
| HLA molecule type selected | B__5201 |
| length selected for subsequences to be scored | 10 |
| echoing mode selected for input sequence | Y |
| echoing format | numbered lines |
| length of user's input peptide sequence | 551 |
| number of subsequence scores calculated | 542 |
| number of top-scoring subsequences reported back in scoring output table | 120 |

TABLE 61

| method selected to limit number of results | cutoff score |
|---|---|
| cutoff score selected | 1 |
| HLA molecule type selected | B__5801 |
| length selected for subsequences to be scored | 9 |
| echoing mode selected for input sequence | Y |
| echoing format | numbered lines |
| length of user's input peptide sequence | 551 |
| number of subsequence scores calculated | 543 |
| number of top-scoring subsequences reported back in scoring output table | 55 |

TABLE 62

| method selected to limit number of results | cutoff score |
|---|---|
| cutoff score selected | 1 |
| HLA molecule type selected | B__5801 |
| length selected for subsequences to be scored | 10 |
| echoing mode selected for input sequence | Y |
| echoing format | numbered lines |
| length of user's input peptide sequence | 551 |
| number of subsequence scores calculated | 542 |
| number of top-scoring subsequences reported back in scoring output table | 50 |

TABLE 63

| method selected to limit number of results | cutoff score |
|---|---|
| cutoff score selected | 1 |
| HLA molecule type selected | Cw__0301 |
| length selected for subsequences to be scored | 9 |
| echoing mode selected for input sequence | Y |
| echoing format | numbered lines |
| length of user's input peptide sequence | 551 |
| number of subsequence scores calculated | 543 |
| number of top-scoring subsequences reported back in scoring output table | 99 |

TABLE 64

| method selected to limit number of results | cutoff score |
|---|---|
| cutoff score selected | 1 |
| HLA molecule type selected | Cw__0301 |
| length selected for subsequences to be scored | 10 |
| echoing mode selected for input sequence | Y |
| echoing format | numbered lines |
| length of user's input peptide sequence | 551 |
| number of subsequence scores calculated | 542 |
| number of top-scoring subsequences reported back in scoring output table | 91 |

TABLE 65

| method selected to limit number of results | cutoff score |
|---|---|
| cutoff score selected | 1 |
| HLA molecule type selected | Cw__0401 |
| length selected for subsequences to be scored | 9 |
| echoing mode selected for input sequence | Y |
| echoing format | numbered lines |
| length of user's input peptide sequence | 551 |
| number of subsequence scores calculated | 543 |
| number of top-scoring subsequences reported back in scoring output table | 88 |

TABLE 66

| method selected to limit number of results | cutoff score |
|---|---|
| cutoff score selected | 1 |
| HLA molecule type selected | Cw__0401 |
| length selected for subsequences to be scored | 10 |
| echoing mode selected for input sequence | Y |
| echoing format | numbered lines |
| length of user's input peptide sequence | 551 |
| number of subsequence scores calculated | 542 |
| number of top-scoring subsequences reported back in scoring output table | 96 |

TABLE 67

| method selected to limit number of results | cutoff score |
|---|---|
| cutoff score selected | 1 |
| HLA molecule type selected | Cw__0602 |
| length selected for subsequences to be scored | 9 |
| echoing mode selected for input sequence | Y |
| echoing format | numbered lines |
| length of user's input peptide sequence | 551 |
| number of subsequence scores calculated | 543 |
| number of top-scoring subsequences reported back in scoring output table | 115 |

TABLE 68

| method selected to limit number of results | cutoff score |
|---|---|
| cutoff score selected | 1 |
| HLA molecule type selected | Cw__0602 |
| length selected for subsequences to be scored | 10 |
| echoing mode selected for input sequence | Y |
| echoing format | numbered lines |
| length of user's input peptide sequence | 551 |
| number of subsequence scores calculated | 542 |
| number of top-scoring subsequences reported back in scoring output table | 117 |

TABLE 69

| method selected to limit number of results | cutoff score |
|---|---|
| cutoff score selected | 1 |
| HLA molecule type selected | Cw__0702 |
| length selected for subsequences to be scored | 9 |
| echoing mode selected for input sequence | Y |
| echoing format | numbered lines |
| length of user's input peptide sequence | 551 |
| number of subsequence scores calculated | 543 |
| number of top-scoring subsequences reported back in scoring output table | 61 |

TABLE 70

| method selected to limit number of results | cutoff score |
|---|---|
| cutoff score selected | 1 |
| HLA molecule type selected | Cw_0702 |
| length selected for subsequences to be scored | 10 |
| echoing mode selected for input sequence | Y |
| echoing format | numbered lines |
| length of user's input peptide sequence | 551 |
| number of subsequence scores calculated | 542 |
| number of top-scoring subsequences reported back in scoring output table | 73 |

Example 11

CMV PP65 MHC Restricted Peptides

Tables 71-136 hereinbelow provide the user parameters and scoring information used to select CMV PP65 restricted peptides (each of 9 or 10 amino acids in length) of various HLA molecules. The analysis was performed using the Bimas software [hypertexttransferprotocol://worldwideweb-bimas (dot) cit (dot) nih (dot) gov/molbio/hla_bind/]. The scoring results and the sequences of the selected peptides (according to each user parameters and scoring information) are provided in Table 137, hereinbelow. The CMV PP65 kDa protein used for analysis is provided by SEQ ID NO:53 [GenBank Accession No. P06725; PP65_HCMVA 65 kDa lower matrix phosphoprotein—Human cytomegalovirus (strain AD169) (HHV-5) (Human herpesvirus 5)].

TABLE 71

| method selected to limit number of results | cutoff score |
|---|---|
| cutoff score selected | 1 |
| HLA molecule type selected | A1 |
| length selected for subsequences to be scored | 9 |
| echoing mode selected for input sequence | Y |
| echoing format | numbered lines |
| length of user's input peptide sequence | 561 |
| number of subsequence scores calculated | 553 |
| number of top-scoring subsequences reported back in scoring output table | 15 |

TABLE 72

| method selected to limit number of results | cutoff score |
|---|---|
| cutoff score selected | 1 |
| HLA molecule type selected | A1 |
| length selected for subsequences to be scored | 10 |
| echoing mode selected for input sequence | Y |
| echoing format | numbered lines |
| length of user's input peptide sequence | 561 |
| number of subsequence scores calculated | 552 |
| number of top-scoring subsequences reported back in scoring output table | 20 |

TABLE 73

| method selected to limit number of results | cutoff score |
|---|---|
| cutoff score selected | 1 |
| HLA molecule type selected | A_0201 |
| length selected for subsequences to be scored | 9 |
| echoing mode selected for input sequence | Y |
| echoing format | numbered lines |
| length of user's input peptide sequence | 561 |
| number of subsequence scores calculated | 553 |

TABLE 73-continued

| method selected to limit number of results | cutoff score |
|---|---|
| number of top-scoring subsequences reported back in scoring output table | 48 |

TABLE 74

| method selected to limit number of results | cutoff score |
|---|---|
| cutoff score selected | 1 |
| HLA molecule type selected | A_0201 |
| length selected for subsequences to be scored | 10 |
| echoing mode selected for input sequence | Y |
| echoing format | numbered lines |
| length of user's input peptide sequence | 561 |
| number of subsequence scores calculated | 552 |
| number of top-scoring subsequences reported back in scoring output table | 53 |

TABLE 75

| method selected to limit number of results | cutoff score |
|---|---|
| cutoff score selected | 1 |
| HLA molecule type selected | A_0205 |
| length selected for subsequences to be scored | 9 |
| echoing mode selected for input sequence | Y |
| echoing format | numbered lines |
| length of user's input peptide sequence | 561 |
| number of subsequence scores calculated | 553 |
| number of top-scoring subsequences reported back in scoring output table | 51 |

TABLE 76

| method selected to limit number of results | cutoff score |
|---|---|
| cutoff score selected | 1 |
| HLA molecule type selected | A_0205 |
| length selected for subsequences to be scored | 10 |
| echoing mode selected for input sequence | Y |
| echoing format | numbered lines |
| length of user's input peptide sequence | 561 |
| number of subsequence scores calculated | 552 |
| number of top-scoring subsequences reported back in scoring output table | 47 |

TABLE 77

| method selected to limit number of results | cutoff score |
|---|---|
| cutoff score selected | 1 |
| HLA molecule type selected | A24 |
| length selected for subsequences to be scored | 9 |
| echoing mode selected for input sequence | Y |
| echoing format | numbered lines |
| length of user's input peptide sequence | 561 |
| number of subsequence scores calculated | 553 |
| number of top-scoring subsequences reported back in scoring output table | 64 |

TABLE 78

| method selected to limit number of results | cutoff score |
|---|---|
| cutoff score selected | 1 |
| HLA molecule type selected | A24 |
| length selected for subsequences to be scored | 10 |

TABLE 78-continued

| method selected to limit number of results | cutoff score |
|---|---|
| echoing mode selected for input sequence | Y |
| echoing format | numbered lines |
| length of user's input peptide sequence | 561 |
| number of subsequence scores calculated | 552 |
| number of top-scoring subsequences reported back in scoring output table | 76 |

TABLE 79

| method selected to limit number of results | cutoff score |
|---|---|
| cutoff score selected | 1 |
| HLA molecule type selected | A3 |
| length selected for subsequences to be scored | 9 |
| echoing mode selected for input sequence | Y |
| echoing format | numbered lines |
| length of user's input peptide sequence | 561 |
| number of subsequence scores calculated | 553 |
| number of top-scoring subsequences reported back in scoring output table | 23 |

TABLE 80

| method selected to limit number of results | cutoff score |
|---|---|
| cutoff score selected | 1 |
| HLA molecule type selected | A3 |
| length selected for subsequences to be scored | 10 |
| echoing mode selected for input sequence | Y |
| echoing format | numbered lines |
| length of user's input peptide sequence | 561 |
| number of subsequence scores calculated | 552 |
| number of top-scoring subsequences reported back in scoring output table | 21 |

TABLE 81

| method selected to limit number of results | cutoff score |
|---|---|
| cutoff score selected | 1 |
| HLA molecule type selected | A68.1 |
| length selected for subsequences to be scored | 9 |
| echoing mode selected for input sequence | Y |
| echoing format | numbered lines |
| length of user's input peptide sequence | 561 |
| number of subsequence scores calculated | 553 |
| number of top-scoring subsequences reported back in scoring output table | 79 |

TABLE 82

| method selected to limit number of results | cutoff score |
|---|---|
| cutoff score selected | 1 |
| HLA molecule type selected | A68.1 |
| length selected for subsequences to be scored | 10 |
| echoing mode selected for input sequence | Y |
| echoing format | numbered lines |
| length of user's input peptide sequence | 561 |
| number of subsequence scores calculated | 552 |
| number of top-scoring subsequences reported back in scoring output table | 77 |

TABLE 83

| method selected to limit number of results | cutoff score |
|---|---|
| cutoff score selected | 1 |
| HLA molecule type selected | A_1101 |
| length selected for subsequences to be scored | 9 |
| echoing mode selected for input sequence | Y |
| echoing format | numbered lines |
| length of user's input peptide sequence | 561 |
| number of subsequence scores calculated | 553 |
| number of top-scoring subsequences reported back in scoring output table | 5 |

TABLE 84

| method selected to limit number of results | cutoff score |
|---|---|
| cutoff score selected | 1 |
| HLA molecule type selected | A_1101 |
| length selected for subsequences to be scored | 10 |
| echoing mode selected for input sequence | Y |
| echoing format | numbered lines |
| length of user's input peptide sequence | 561 |
| number of subsequence scores calculated | 552 |
| number of top-scoring subsequences reported back in scoring output table | 4 |

TABLE 85

| method selected to limit number of results | cutoff score |
|---|---|
| cutoff score selected | 1 |
| HLA molecule type selected | A_3101 |
| length selected for subsequences to be scored | 9 |
| echoing mode selected for input sequence | Y |
| echoing format | numbered lines |
| length of user's input peptide sequence | 561 |
| number of subsequence scores calculated | 553 |
| number of top-scoring subsequences reported back in scoring output table | 10 |

TABLE 86

| method selected to limit number of results | cutoff score |
|---|---|
| cutoff score selected | 1 |
| HLA molecule type selected | A_3101 |
| length selected for subsequences to be scored | 10 |
| echoing mode selected for input sequence | Y |
| echoing format | numbered lines |
| length of user's input peptide sequence | 561 |
| number of subsequence scores calculated | 552 |
| number of top-scoring subsequences reported back in scoring output table | 17 |

TABLE 87

| method selected to limit number of results | cutoff score |
|---|---|
| cutoff score selected | 1 |
| HLA molecule type selected | A_3302 |
| length selected for subsequences to be scored | 9 |
| echoing mode selected for input sequence | Y |
| echoing format | numbered lines |
| length of user's input peptide sequence | 561 |
| number of subsequence scores calculated | 553 |
| number of top-scoring subsequences reported back in scoring output table | 40 |

TABLE 88

| method selected to limit number of results | cutoff score |
|---|---|
| cutoff score selected | 1 |
| HLA molecule type selected | A_3302 |
| length selected for subsequences to be scored | 10 |
| echoing mode selected for input sequence | Y |
| echoing format | numbered lines |
| length of user's input peptide sequence | 561 |
| number of subsequence scores calculated | 552 |
| number of top-scoring subsequences reported back in scoring output table | 36 |

TABLE 89

| method selected to limit number of results | cutoff score |
|---|---|
| cutoff score selected | 1 |
| HLA molecule type selected | B14 |
| length selected for subsequences to be scored | 9 |
| echoing mode selected for input sequence | Y |
| echoing format | numbered lines |
| length of user's input peptide sequence | 561 |
| number of subsequence scores calculated | 553 |
| number of top-scoring subsequences reported back in scoring output table | 65 |

TABLE 90

| method selected to limit number of results | cutoff score |
|---|---|
| cutoff score selected | 1 |
| HLA molecule type selected | B14 |
| length selected for subsequences to be scored | 10 |
| echoing mode selected for input sequence | Y |
| echoing format | numbered lines |
| length of user's input peptide sequence | 561 |
| number of subsequence scores calculated | 552 |
| number of top-scoring subsequences reported back in scoring output table | 63 |

TABLE 91

| method selected to limit number of results | cutoff score |
|---|---|
| cutoff score selected | 1 |
| HLA molecule type selected | B40 |
| length selected for subsequences to be scored | 9 |
| echoing mode selected for input sequence | Y |
| echoing format | numbered lines |
| length of user's input peptide sequence | 561 |
| number of subsequence scores calculated | 553 |
| number of top-scoring subsequences reported back in scoring output table | 35 |

TABLE 92

| method selected to limit number of results | cutoff score |
|---|---|
| cutoff score selected | 1 |
| HLA molecule type selected | B40 |
| length selected for subsequences to be scored | 10 |
| echoing mode selected for input sequence | Y |
| echoing format | numbered lines |
| length of user's input peptide sequence | 561 |
| number of subsequence scores calculated | 552 |
| number of top-scoring subsequences reported back in scoring output table | 42 |

TABLE 93

| method selected to limit number of results | cutoff score |
|---|---|
| cutoff score selected | 1 |
| HLA molecule type selected | B60 |
| length selected for subsequences to be scored | 9 |
| echoing mode selected for input sequence | Y |
| echoing format | numbered lines |
| length of user's input peptide sequence | 561 |
| number of subsequence scores calculated | 553 |
| number of top-scoring subsequences reported back in scoring output table | 42 |

TABLE 94

| method selected to limit number of results | cutoff score |
|---|---|
| cutoff score selected | 1 |
| HLA molecule type selected | B60 |
| length selected for subsequences to be scored | 10 |
| echoing mode selected for input sequence | Y |
| echoing format | numbered lines |
| length of user's input peptide sequence | 561 |
| number of subsequence scores calculated | 552 |
| number of top-scoring subsequences reported back in scoring output table | 50 |

TABLE 95

User Parameters and Scoring Information
User Parameters and Scoring Information

| method selected to limit number of results | cutoff score |
|---|---|
| cutoff score selected | 1 |
| HLA molecule type selected | B61 |
| length selected for subsequences to be scored | 9 |
| echoing mode selected for input sequence | Y |
| echoing format | numbered lines |
| length of user's input peptide sequence | 561 |
| number of subsequence scores calculated | 553 |
| number of top-scoring subsequences reported back in scoring output table | 44 |

TABLE 96

| method selected to limit number of results | cutoff score |
|---|---|
| cutoff score selected | 1 |
| HLA molecule type selected | B61 |
| length selected for subsequences to be scored | 10 |
| echoing mode selected for input sequence | Y |
| echoing format | numbered lines |
| length of user's input peptide sequence | 561 |
| number of subsequence scores calculated | 552 |
| number of top-scoring subsequences reported back in scoring output table | 46 |

TABLE 97

| method selected to limit number of results | cutoff score |
|---|---|
| cutoff score selected | 1 |
| HLA molecule type selected | B62 |
| length selected for subsequences to be scored | 9 |
| echoing mode selected for input sequence | Y |
| echoing format | numbered lines |
| length of user's input peptide sequence | 561 |
| number of subsequence scores calculated | 553 |
| number of top-scoring subsequences reported back in scoring output table | 57 |

TABLE 98

| method selected to limit number of results | cutoff score |
|---|---|
| cutoff score selected | 1 |
| HLA molecule type selected | B62 |
| length selected for subsequences to be scored | 10 |
| echoing mode selected for input sequence | Y |
| echoing format | numbered lines |
| length of user's input peptide sequence | 561 |
| number of subsequence scores calculated | 552 |
| number of top-scoring subsequences reported back in scoring output table | 54 |

TABLE 99

| method selected to limit number of results | cutoff score |
|---|---|
| cutoff score selected | 1 |
| HLA molecule type selected | B7 |
| length selected for subsequences to be scored | 9 |
| echoing mode selected for input sequence | Y |
| echoing format | numbered lines |
| length of user's input peptide sequence | 561 |
| number of subsequence scores calculated | 553 |
| number of top-scoring subsequences reported back in scoring output table | 57 |

TABLE 100

| method selected to limit number of results | cutoff score |
|---|---|
| cutoff score selected | 1 |
| HLA molecule type selected | B7 |
| length selected for subsequences to be scored | 10 |
| echoing mode selected for input sequence | Y |
| echoing format | numbered lines |
| length of user's input peptide sequence | 561 |
| number of subsequence scores calculated | 552 |
| number of top-scoring subsequences reported back in scoring output table | 63 |

TABLE 101

| method selected to limit number of results | cutoff score |
|---|---|
| cutoff score selected | 1 |
| HLA molecule type selected | B8 |
| length selected for subsequences to be scored | 9 |
| echoing mode selected for input sequence | Y |
| echoing format | numbered lines |
| length of user's input peptide sequence | 561 |
| number of subsequence scores calculated | 553 |
| number of top-scoring subsequences reported back in scoring output table | 12 |

TABLE 102

| method selected to limit number of results | cutoff score |
|---|---|
| cutoff score selected | 1 |
| HLA molecule type selected | B8 |
| length selected for subsequences to be scored | 10 |
| echoing mode selected for input sequence | Y |
| echoing format | numbered lines |
| length of user's input peptide sequence | 561 |
| number of subsequence scores calculated | 552 |
| number of top-scoring subsequences reported back in scoring output table | 15 |

TABLE 103

| method selected to limit number of results | cutoff score |
|---|---|
| cutoff score selected | 1 |
| HLA molecule type selected | B_2702 |
| length selected for subsequences to be scored | 9 |
| echoing mode selected for input sequence | Y |
| echoing format | numbered lines |
| length of user's input peptide sequence | 561 |
| number of subsequence scores calculated | 553 |
| number of top-scoring subsequences reported back in scoring output table | 74 |

TABLE 104

| method selected to limit number of results | cutoff score |
|---|---|
| cutoff score selected | 1 |
| HLA molecule type selected | B_2702 |
| length selected for subsequences to be scored | 9 |
| echoing mode selected for input sequence | Y |
| echoing format | numbered lines |
| length of user's input peptide sequence | 561 |
| number of subsequence scores calculated | 553 |
| number of top-scoring subsequences reported back in scoring output table | 74 |

TABLE 105

| method selected to limit number of results | cutoff score |
|---|---|
| cutoff score selected | 1 |
| HLA molecule type selected | B_2705 |
| length selected for subsequences to be scored | 9 |
| echoing mode selected for input sequence | Y |
| echoing format | numbered lines |
| length of user's input peptide sequence | 561 |
| number of subsequence scores calculated | 553 |
| number of top-scoring subsequences reported back in scoring output table | 282 |

TABLE 106

| method selected to limit number of results | cutoff score |
|---|---|
| cutoff score selected | 1 |
| HLA molecule type selected | B_2705 |
| length selected for subsequences to be scored | 10 |
| echoing mode selected for input sequence | Y |
| echoing format | numbered lines |
| length of user's input peptide sequence | 561 |
| number of subsequence scores calculated | 552 |
| number of top-scoring subsequences reported back in scoring output table | 287 |

TABLE 107

| method selected to limit number of results | cutoff score |
|---|---|
| cutoff score selected | 1 |
| HLA molecule type selected | B_3501 |
| length selected for subsequences to be scored | 9 |
| echoing mode selected for input sequence | Y |
| echoing format | numbered lines |
| length of user's input peptide sequence | 561 |
| number of subsequence scores calculated | 553 |
| number of top-scoring subsequences reported back in scoring output table | 74 |

TABLE 108

| method selected to limit number of results | cutoff score |
|---|---|
| cutoff score selected | 1 |
| HLA molecule type selected | B_3501 |
| length selected for subsequences to be scored | 10 |
| echoing mode selected for input sequence | Y |
| echoing format | numbered lines |
| length of user's input peptide sequence | 561 |
| number of subsequence scores calculated | 552 |
| number of top-scoring subsequences reported back in scoring output table | 82 |

TABLE 109

| method selected to limit number of results | cutoff score |
|---|---|
| cutoff score selected | 1 |
| HLA molecule type selected | B_3701 |
| length selected for subsequences to be scored | 9 |
| echoing mode selected for input sequence | Y |
| echoing format | numbered lines |
| length of user's input peptide sequence | 561 |
| number of subsequence scores calculated | 553 |
| number of top-scoring subsequences reported back in scoring output table | 93 |

TABLE 110

| method selected to limit number of results | cutoff score |
|---|---|
| cutoff score selected | 1 |
| HLA molecule type selected | B_3701 |
| length selected for subsequences to be scored | 10 |
| echoing mode selected for input sequence | Y |
| echoing format | numbered lines |
| length of user's input peptide sequence | 561 |
| number of subsequence scores calculated | 552 |
| number of top-scoring subsequences reported back in scoring output table | 103 |

TABLE 111

| method selected to limit number of results | cutoff score |
|---|---|
| cutoff score selected | 1 |
| HLA molecule type selected | B_3801 |
| length selected for subsequences to be scored | 9 |
| echoing mode selected for input sequence | Y |
| echoing format | numbered lines |
| length of user's input peptide sequence | 561 |
| number of subsequence scores calculated | 553 |
| number of top-scoring subsequences reported back in scoring output table | 51 |

TABLE 112

| method selected to limit number of results | cutoff score |
|---|---|
| cutoff score selected | 1 |
| HLA molecule type selected | B_3801 |
| length selected for subsequences to be scored | 10 |
| echoing mode selected for input sequence | Y |
| echoing format | numbered lines |
| length of user's input peptide sequence | 561 |
| number of subsequence scores calculated | 552 |
| number of top-scoring subsequences reported back in scoring output table | 59 |

TABLE 113

| method selected to limit number of results | cutoff score |
|---|---|
| cutoff score selected | 1 |
| HLA molecule type selected | B_3901 |
| length selected for subsequences to be scored | 9 |
| echoing mode selected for input sequence | Y |
| echoing format | numbered lines |
| length of user's input peptide sequence | 561 |
| number of subsequence scores calculated | 553 |
| number of top-scoring subsequences reported back in scoring output table | 104 |

TABLE 114

| method selected to limit number of results | cutoff score |
|---|---|
| cutoff score selected | 1 |
| HLA molecule type selected | B_3901 |
| length selected for subsequences to be scored | 10 |
| echoing mode selected for input sequence | Y |
| echoing format | numbered lines |
| length of user's input peptide sequence | 561 |
| number of subsequence scores calculated | 552 |
| number of top-scoring subsequences reported back in scoring output table | 105 |

TABLE 115

| method selected to limit number of results | cutoff score |
|---|---|
| cutoff score selected | 1 |
| HLA molecule type selected | B_3902 |
| length selected for subsequences to be scored | 9 |
| echoing mode selected for input sequence | Y |
| echoing format | numbered lines |
| length of user's input peptide sequence | 561 |
| number of subsequence scores calculated | 553 |
| number of top-scoring subsequences reported back in scoring output table | 63 |

TABLE 116

| method selected to limit number of results | cutoff score |
|---|---|
| cutoff score selected | 1 |
| HLA molecule type selected | B_3902 |
| length selected for subsequences to be scored | 10 |
| echoing mode selected for input sequence | Y |
| echoing format | numbered lines |
| length of user's input peptide sequence | 561 |
| number of subsequence scores calculated | 552 |
| number of top-scoring subsequences reported back in scoring output table | 70 |

TABLE 117

| method selected to limit number of results | cutoff score |
|---|---|
| cutoff score selected | 1 |
| HLA molecule type selected | B_4403 |
| length selected for subsequences to be scored | 9 |
| echoing mode selected for input sequence | Y |
| echoing format | numbered lines |
| length of user's input peptide sequence | 561 |
| number of subsequence scores calculated | 553 |
| number of top-scoring subsequences reported back in scoring output table | 47 |

TABLE 118

| method selected to limit number of results | cutoff score |
|---|---|
| cutoff score selected | 1 |
| HLA molecule type selected | B__4403 |
| length selected for subsequences to be scored | 10 |
| echoing mode selected for input sequence | Y |
| echoing format | numbered lines |
| length of user's input peptide sequence | 561 |
| number of subsequence scores calculated | 552 |
| number of top-scoring subsequences reported back in scoring output table | 57 |

TABLE 119

| method selected to limit number of results | cutoff score |
|---|---|
| cutoff score selected | 1 |
| HLA molecule type selected | B__5101 |
| length selected for subsequences to be scored | 9 |
| echoing mode selected for input sequence | Y |
| echoing format | numbered lines |
| length of user's input peptide sequence | 561 |
| number of subsequence scores calculated | 553 |
| number of top-scoring subsequences reported back in scoring output table | 141 |

TABLE 120

| method selected to limit number of results | cutoff score |
|---|---|
|  | 1 |
| HLA molecule type selected | B__5101 |
| length selected for subsequences to be scored | 10 |
| echoing mode selected for input sequence | Y |
| echoing format | numbered lines |
| length of user's input peptide sequence | 561 |
| number of subsequence scores calculated | 552 |
| number of top-scoring subsequences reported back in scoring output table | 128 |

TABLE 121

| method selected to limit number of results | cutoff score |
|---|---|
| cutoff score selected | 1 |
| HLA molecule type selected | B__5102 |
| length selected for subsequences to be scored | 9 |
| echoing mode selected for input sequence | Y |
| echoing format | numbered lines |
| length of user's input peptide sequence | 561 |
| number of subsequence scores calculated | 553 |
| number of top-scoring subsequences reported back in scoring output table | 151 |

TABLE 122

| method selected to limit number of results | cutoff score |
|---|---|
| cutoff score selected | 1 |
| HLA molecule type selected | B__5102 |
| length selected for subsequences to be scored | 10 |
| echoing mode selected for input sequence | Y |
| echoing format | numbered lines |
| length of user's input peptide sequence | 561 |
| number of subsequence scores calculated | 552 |
| number of top-scoring subsequences reported back in scoring output table | 140 |

TABLE 123

| method selected to limit number of results | cutoff score |
|---|---|
| cutoff score selected | 1 |
| HLA molecule type selected | B__5103 |
| length selected for subsequences to be scored | 9 |
| echoing mode selected for input sequence | Y |
| echoing format | numbered lines |
| length of user's input peptide sequence | 561 |
| number of subsequence scores calculated | 553 |
| number of top-scoring subsequences reported back in scoring output table | 90 |

TABLE 124

| method selected to limit number of results | cutoff score |
|---|---|
| cutoff score selected | 1 |
| HLA molecule type selected | B__5103 |
| length selected for subsequences to be scored | 10 |
| echoing mode selected for input sequence | Y |
| echoing format | numbered lines |
| length of user's input peptide sequence | 561 |
| number of subsequence scores calculated | 552 |
| number of top-scoring subsequences reported back in scoring output table | 86 |

TABLE 125

| method selected to limit number of results | cutoff score |
|---|---|
| cutoff score selected | 1 |
| HLA molecule type selected | B__5201 |
| length selected for subsequences to be scored | 9 |
| echoing mode selected for input sequence | Y |
| echoing format | numbered lines |
| length of user's input peptide sequence | 561 |
| number of subsequence scores calculated | 553 |
| number of top-scoring subsequences reported back in scoring output table | 114 |

TABLE 126

| method selected to limit number of results | cutoff score |
|---|---|
| cutoff score selected | 1 |
| HLA molecule type selected | B__5201 |
| length selected for subsequences to be scored | 10 |
| echoing mode selected for input sequence | Y |
| echoing format | numbered lines |
| length of user's input peptide sequence | 561 |
| number of subsequence scores calculated | 552 |
| number of top-scoring subsequences reported back in scoring output table | 120 |

TABLE 127

| method selected to limit number of results | cutoff score |
|---|---|
| cutoff score selected | 1 |
| HLA molecule type selected | B__5801 |
| length selected for subsequences to be scored | 9 |
| echoing mode selected for input sequence | Y |
| echoing format | numbered lines |
| length of user's input peptide sequence | 561 |
| number of subsequence scores calculated | 553 |
| number of top-scoring subsequences reported back in scoring output table | 55 |

TABLE 128

| method selected to limit number of results | cutoff score |
|---|---|
| cutoff score selected | 1 |
| HLA molecule type selected | B__5801 |
| length selected for subsequences to be scored | 10 |
| echoing mode selected for input sequence | Y |
| echoing format | numbered lines |
| length of user's input peptide sequence | 561 |
| number of subsequence scores calculated | 552 |
| number of top-scoring subsequences reported back in scoring output table | 49 |

TABLE 129

| method selected to limit number of results | cutoff score |
|---|---|
| cutoff score selected | 1 |
| HLA molecule type selected | Cw__0301 |
| length selected for subsequences to be scored | 9 |
| echoing mode selected for input sequence | Y |
| echoing format | numbered lines |
| length of user's input peptide sequence | 561 |
| number of subsequence scores calculated | 553 |
| number of top-scoring subsequences reported back in scoring output table | 103 |

TABLE 130

| method selected to limit number of results | cutoff score |
|---|---|
| cutoff score selected | 1 |
| HLA molecule type selected | Cw__0301 |
| length selected for subsequences to be scored | 10 |
| echoing mode selected for input sequence | Y |
| echoing format | numbered lines |
| length of user's input peptide sequence | 561 |
| number of subsequence scores calculated | 552 |
| number of top-scoring subsequences reported back in scoring output table | 93 |

TABLE 131

| method selected to limit number of results | cutoff score |
|---|---|
| cutoff score selected | 1 |
| HLA molecule type selected | Cw__0401 |
| length selected for subsequence to be scored | 9 |
| echoing mode selected for input sequence | Y |
| echoing format | numbered lines |
| length of user's input peptide sequence | 561 |
| number of subsequence scores calculated | 553 |
| number of top-scoring subsequences reported back in scoring output table | 90 |

TABLE 132

| method selected to limit number of results | cutoff score |
|---|---|
| cutoff score selected | 1 |
| HLA molecule type selected | Cw__0401 |
| length selected for subsequences to be scored | 10 |
| echoing mode selected for input sequence | Y |
| echoing format | numbered lines |
| length of user's input peptide sequence | 561 |
| number of subsequence scores calculated | 552 |
| number of top-scoring subsequences reported back in scoring output table | 98 |

TABLE 133

| method selected to limit number of results | cutoff score |
|---|---|
| cutoff score selected | 1 |
| HLA molecule type selected | Cw__0602 |
| length selected for subsequences to be scored | 9 |
| echoing mode selected for input sequence | Y |
| echoing format | numbered lines |
| length of user's input peptide sequence | 561 |
| number of subsequence scores calculated | 553 |
| number of top-scoring subsequences reported back in scoring output table | 119 |

TABLE 134

| method selected to limit number of results | cutoff score |
|---|---|
| cutoff score selected | 1 |
| HLA molecule type selected | Cw__0602 |
| length selected for subsequences to be scored | 10 |
| echoing mode selected for input sequence | Y |
| echoing format | numbered lines |
| length of user's input peptide sequence | 561 |
| number of subsequence scores calculated | 552 |
| number of top-scoring subsequences reported back in scoring output table | 120 |

TABLE 135

| method selected to limit number of results | cutoff score |
|---|---|
| cutoff score selected | 1 |
| HLA molecule type selected | Cw__0702 |
| length selected for subsequences to be scored | 9 |
| echoing mode selected for input sequence | Y |
| echoing format | numbered lines |
| length of user's input peptide sequence | 561 |
| number of subsequence scores calculated | 553 |
| number of top-scoring subsequences reported back in scoring output table | 62 |

TABLE 136

| method selected to limit number of results | cutoff score |
|---|---|
| cutoff score selected | 1 |
| HLA molecule type selected | Cw__0702 |
| length selected for subsequences to be scored | 10 |
| echoing mode selected for input sequence | Y |
| echoing format | numbered lines |
| length of user's input peptide sequence | 561 |
| number of subsequence scores calculated | 552 |
| number of top-scoring subsequences reported back in scoring output table | 74 |

Table 137 hereinbelow, depicts subsequence residue listing (Sequence), SEQ ID NO: and scoring results [Rank and Score (the estimate of half time of disassociation of a molecule containing this subsequence)] obtained according to the user parameters and scoring information summarized in Tables 5-136, hereinabove, for HLA restricted peptides derived from the CMV pp65 (SEQ ID NO:53) or pp64 (SEQ ID NO:52) polypeptides. For each row, a reference to the relevant "user parameters and scoring information Table" is made by indicating the "Table No." on the last column.

Lengthy table referenced here

US08361473-20130129-T00001

Please refer to the end of the specification for access instructions.

Example 12

Detection of HLA-A2/PP65 Complexes on the Surface of Virus-Infected Cells of Patients The ability of the H9 Ab to detect HLA-A2/pp65 complexes was further evaluated in heterogeneous population of cells taken from CMV infected individuals. Briefly, samples were taken from bone marrow transplanted (BMT) patients whom are under reactivation of CMV infection due to immuno-suppression. Healthy donors were used as a control to verify the H9 Fab specificity.

Experimental Results

Peripheral blood mononuclear cells (PBMCs) were isolated from samples taken from BMT patients and healthy donors. The isolated cells were stained with the H9 Ab and the secondary anti human alexa fluor$^{488}$ Ab. For intracellular staining with the H9 Ab, the cells were permeabilized as described under "General Materials and Experimental Methods".

Both healthy donors and BMT patients were HLA-A2+ (i.e., express the HLA-A2 allele) as detected by the anti HLA-A2 Ab (BB7.2) and anti mouse alexa fluor$^{488}$ Abs (FIG. 16a and data not shown). Extracellular staining with the H9 Ab did not detect complexes of the HLA-A2/pp65 on the surface of infected cells taken from BMT patients or healthy controls (FIG. 16b and data not shown). However, as shown in FIGS. 16c and d, intracellular staining with the H9 Ab demonstrated a significant binding of the antibody to the infected cells from BMT patients (FIG. 16c) as compared to the control cells taken from healthy donors (FIG. 16d). These results confirm the ability of the isolated H9 Ab to detect specific HLA-A2/pp65 complexes not only after directed infection with laboratory strain of the CMV, but also complexes derived from cells undergoing reactivation of the virus e.g., due to immuno-suppression.

Example 13

Proteasome Inhibitor Effect on HLA-A2/PP65 Complexes in Virus Infected Cells Experimental Results The release of complexes accumulation from their intracellular location to the cell surface by proteasome inhibitor—The proteasome inhibitor acetyl-leucyl-leucyl-norleucinal (ALLN; available from CALBIOCHEM Cat. No. 208750) was used in order to understand the mechanism by which complexes are prevented from reaching the cell membrane. The effect of the proteasome inhibitor was examined by FACS analysis, while treating the infected cells with ALLN at three time scales after infection. At each time scale, the cells were extracellularly stained with the H9 Ab and anti human alexa-flour$^{488}$ as a secondary Ab. As shown in FIGS. 17a-i there was a significant effect of the inhibitor on the presentation of the complexes on the cell surface. Presence of the inhibitor at each time scale caused an increased presentation of the complexes on the cell surface compared to untreated cells. The effect of the increased presentation was more significant at the lower time scales, and seamed to reach a steady state at 96 hours post infection. Control uninfected cells showed no staining with the H9 Ab. Thus, incubation with the proteasome inhibitor ALLN increased presentation of the MHC/pp65 complexes on the cell surface.

Summary

In this study, the present inventors have demonstrated the selection of recombinant Fab Abs directed against a human viral T cell epitope derived from CMV, from a large nonimmune human Ab phage library. These Abs exhibit an exquisite, very specific, and special binding pattern: they can bind in a peptide-specific manner only to HLA-A2/pp65 complexes; hence, these are recombinant Abs with T cell Ag receptor-like specificity. In contrast to the inherent low affinity of TCRs, these molecules display the high affinity binding characteristics of Abs, in the nM range, while retaining TCR specificity. The present inventors have demonstrated here the ability of these Abs to bind specifically to recombinant class I peptide-MHC complexes, as well as to complexes presented on the surface of peptide pulsed APCs.

An important feature of the TCR-like Fab Abs isolated in this study is their capability to detect TCR ligands at cell surface densities close to the threshold limit for T cell recognition. The H9 HLA-A2/pp65-specific TCR-like Fab Ab was able to detect in a reproducible manner as low as 100 sites/cell. Using flow cytometry, it was possible to use the H9 Fab Ab to detect the specific ligand on cells pulsed with peptide concentrations similar to those required to activate T cell hybridoma or CTL lines to cytokine secretion and within a few fold of the minimal concentration able to sensitize target cells for lysis in a short-term assay (Porgador A., et al., 1997).

These data indicate that when applied to dissociated cell populations using flow cytometry, the detection of ligand with H9 and other TCR-like Fabs with similar affinity approaches the sensitivity of T cells, and hence that these molecules are suitable reagents for evaluating antigenic complex expression at low, but physiologically relevant levels. In this study, the detection sensitivity of specific ligand was observed with as low as 100 complexes per cell. Thus, this principle has been applied in this study to mixtures of peptide pulsed HLA-A2+ JY cells, and the HLA-A2− B cell line APD. By using the H9 tetramer in a single-step staining for flow cytometry, it was possible to readily identify pp65 495-503 peptide pulsed JY cells admixed with APD cells in as low proportion as 5%.

The avidity of the TCR-like Ab molecules was improved by making the recombinant monovalent molecules into multivalent molecules. This was feasible by altering the basic Fab form to a tetrameric molecule or to a whole bivalent IgG Ab.

Detection of class I MHC complexes in association with the pp65 495-503 peptide on virus infected cells, showed the ability of the H9 Ab to recognize complexes not only on the surface of peptide pulsed APCs, but also complexes which were produced by naturally occurring active antigen processing. Cytotoxicity assays directed to virus infected cells confirmed these findings. The blockage of killing by the CTLs after incubation with the H9 Ab showed a competition between the cytotoxic T-cell receptor and the H9 TCR-like Ab on the same site presented on the virus infected cell.

Using the H9 Ab at various time points following infection the present inventors could track the presentation level of HLA-A2/pp65 complexes during the course of virus infection cycle. Specific staining with the H9 Ab lead to the observation that the expression level of the specific HLA-A2/pp65 complexes on the cell surface does not represent the overall quantity of these specific complexes, because as shown most of them are located inside the cell. The results presented herein demonstrate the existence of a significant large pool of specific HLA-A2/pp65 complexes inside virus infected cells, which increased as a function of time after viral infection. The use of a CMV mutant strain which lacks the genes responsible for MHC class I down regulation revealed similar findings. Large pools of specific complexes, bearing the pp65 495-503 peptide, were found inside the cells. In contrast to the uninfected cells, there is a large amount of MHC class I complexes inside the cells which are infected with the wild-type/mutant strain.

The results of the kinetic assays also clearly show that there is a great correlation between the pp65 expression level and its presentation level. Both increase as time goes by. Moreover, the timing of the pp65 expression might precede the processing and presentation of this protein, as presented in the results.

This work provides also quantitative data about the number of specific HLA-A2/pp65 complexes generated inside infected cells as well as presented on the cell surface after active intracellular processing by virus infected cells. The results revealed for the first time the number of sites which are presented on the cell surface and recognized by the immune system. Moreover, quantization of general HLA-A2 complexes enabled the present inventors to determine the percentage of complexes down regulated after viral infection. It also enabled the present inventors to compare between the number of general complexes and the number of specific HLA-A2/pp65 complexes inside the cells and on their surface. This analysis enables the determination of the percentage of the specific complexes among the general complexes. The results indicated quantitatively that most of the complexes inside the virus infected cells are bearing the pp65 495-503 peptide. Large numbers of specific complexes were also found in the cells infected with the mutant strain, strengthening the previous data, regarding the pools which are prevented from being translocated to the membrane.

Confocal immunofluorescence microscopy enabled for the first time direct visualization of the intracellular and extracellular sites of peptide-MHC molecules throughout virus infection cycle, as well as determination of their localization inside the cell. This visualization revealed the colocalization of the HLA-A2/pp65 complexes with the cis-golgi apparatus. It also showed the exact movement of the complexes from this location to the cell surface, in correlation to the virus infection kinetics. At the progressed time scales there was a significant display of the complexes on the cell surface.

The study presented here shows the usage of an isolated human recombinant Ab towards a specific viral peptide-MHC class I in the following: (i) tracking the level of specific complexes throughout time scale which represents a viral infection cycle; (ii) tracking the number of complexes throughout time scale inside the cell and on its surface and analysis of this data; (iii) visualization of complexes in a viral infection system which demonstrate the intracellular localization of the complexes throughout time scale, and; (iv) detection of the correlation between protein expression and its derived peptide presentation on HLA-A2 complexes after processing.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

REFERENCES

Additional References are Cited in Text

1. Ahn, K. et al. Human cytomegalovirus inhibits antigen presentation by a sequential multistep process Proc. Natl. Acad. Sci. U.S.A 93, 10990-10995 (1996).
2. Allart S, et al., 2003; Invest Ophthalmol Vis Sci. 44: 665-71
3. Altman, J. D. et al. Phenotypic analysis of antigen-specific T lymphocytes. Science 274, 94-96 (1996).
4. Chee, M. S. et al. Analysis of the protein-coding content of the sequence of human cytomegalovirus strain AD169. Curr. Top. Microbiol. Immunol. 154, 125-169 (1990).
5. Cohen, C. J. et al. Direct detection and quantitation of a distinct T-cell epitope derived from tumor-specific epithelial cell-associated mucin using human recombinant antibodies endowed with the antigen-specific, major histocompatibility complex-restricted specificity of T cells Cancer Res. 62, 5835-5844 (2002).
6. Cloutier, S. M. et al. Streptabody, a high avidity molecule made by tetramerization of in vivo biotinylated, phage display-selected scFv fragments on streptavidin. Mol. Immunol. 37, 1067-1077 (2000).
7. De Haard, H. J. et al. A large non-immunized human Fab fragment phage library that permits rapid isolation and kinetic analysis of high affinity antibodies. J. Biol. Chem. 274, 18218-18230 (1999).
8. Denkberg, G., Cohen, C. J., Segal, D., Kirkin, A. F. & Reiter, Y. Recombinant human single-chain MHC-peptide complexes made from E. coli By in vitro refolding: functional single-chain MHC-peptide complexes and tetramers with tumor associated antigens. Eur. J. Immunol. 30, 3522-3532 (2000).
9. Denkberg, G., Cohen, C. J. & Reiter, Y. Critical role for CD8 in binding of MHC tetramers to TCR: CD8 antibodies block specific binding of human tumor-specific MHC-peptide tetramers to TCR. J. Immunol. 167, 270-276 (2001).
10. Denkberg, G. et al. Direct visualization of distinct T cell epitopes derived from a melanoma tumor-associated antigen by using human recombinant antibodies with MHC-restricted T cell receptor-like specificity. Proc. Natl. Acad. Sci. U.S.A 99, 9421-9426 (2002).
11. Jones, T. R. & Sun, L. Human cytomegalovirus US2 destabilizes major histocompatibility complex class I heavy chains J. Virol. 71, 2970-2979 (1997).
12. Lee, P. P. et al. Characterization of circulating T cells specific for tumor-associated antigens in melanoma patients. Nat Med 5, 677-685 (1999).
13. Lev, A. et al. Isolation and characterization of human recombinant antibodies endowed with the antigen-specific, major histocompatibility complex-restricted specificity of T cells directed toward the widely expressed tumor T-cell epitopes of the telomerase catalytic subunit. Cancer Res. 62, 3184-3194 (2002).
14. Pascolo, S. et al. HLA-A2.1-restricted education and cytolytic activity of CD8(+) T lymphocytes from beta2 microglobulin (beta2m) HLA-A2.1 monochain transgenic H-2Db beta2m double knockout mice. J. Exp. Med. 185, 2043-2051 (1997).
15. Porgador, A., Yewdell, J. W., Deng, Y. P., Bennink, J. R. & Germain, R. N. Localization, quantitation, and in situ detection of specific peptide MHC class I complexes using a monoclonal antibody. Immunity 6, 715-726 (1997).
16. Soderberg-Naucler, C., Fish, K. N. & Nelson, J. A. Growth of human cytomegalovirus in primary macrophages. Methods 16, 126-+ (1998).

LENGTHY TABLES

The patent contains a lengthy table section. A copy of the table is available in electronic form from the USPTO web site (http://seqdata.uspto.gov/?pageRequest=docDetail&DocID=US08361473B2). An electronic copy of the table will also be available from the USPTO upon request and payment of the fee set forth in 37 CFR 1.19(b)(3).

What is claimed is:

1. An isolated antibody comprising an antigen recognition domain capable of binding with a binding affinity below 50 nanomolar to a human MHC molecule being complexed with a cytomegalovirus (CMV) pp65 or pp64 peptide, wherein the antibody does not bind said human MHC molecule in an absence of said complexed peptide, and wherein the antibody does not bind said peptide in an absence of said MHC molecule, wherein said antigen recognition domain comprises complementarity determining region (CDR) amino acid sequences as set forth in SEQ ID NOs:24-26 and 30-32.

2. An isolated antibody comprising an antigen recognition domain capable of binding with a binding affinity below 50 nanomolar to a human MHC molecule being complexed with a cytomegalovirus (CMV) pp65 or pp64 peptide, wherein the antibody does not bind said human MHC molecule in an absence of said complexed peptide, and wherein the antibody does not bind said peptide in an absence of said MHC molecule, wherein said antigen recognition domain comprises complementarity determining region (CDR) amino acid sequences as set forth in SEQ ID NOs: 36-38 and 42-44.

3. The antibody of claim 1, being conjugated to a therapeutic moiety.

4. The antibody of claim 1, attached to a detectable moiety.

5. The antibody of claim 1, being an antibody fragment.

6. An antibody comprising a multivalent form of the antibody of claim 1.

7. The antibody of claim 6, wherein said multivalent form is an IgG antibody.

8. A composition comprising as an active ingredient the antibody of claim 1.

9. A method of detecting a cell expressing a cytomegalovirus (CMV) antigen, comprising contacting the cell with the antibody of claim 1, under conditions which allow immunocomplex formation, wherein a presence or a level above a predetermined threshold of said immunocomplex is indicative of CMV expression in the cell.

10. A method of diagnosing a cytomegalovirus (CMV) infection in a subject in need thereof, comprising contacting a cell of the subject with the antibody of claim 1, under conditions which allow immunocomplex formation, wherein a presence or a level above a pre-determined threshold of said immunocomplex in the cell is indicative of the CMV infection in the subject.

11. The method of claim 10, wherein said CMV infection is associated with a disease selected from the group consisting of mononucleosis, retinitis, pneumonia, gastrointestinal disorders, and encephalitis.

12. The method of claim 9, wherein said cell is a retina cell, lung epithelial cell, a gastrointestinal epithelial cell or a brain cell.

13. The method of claim 10, wherein said cell is a retina cell, lung epithelial cell, a gastrointestinal epithelial cell or a brain cell.

14. A composition comprising as an active ingredient the antibody of claim 2.

15. A method of detecting a cell expressing a cytomegalovirus (CMV) antigen, comprising contacting the cell with the antibody of claim 2 under conditions which allow immunocomplex formation, wherein a presence or a level above a predetermined threshold of said immunocomplex is indicative of CMV expression in the cell.

16. A method of diagnosing a cytomegalovirus (CMV) infection in a subject in need thereof, comprising contacting a cell of the subject with the antibody of claim 2 under conditions which allow immunocomplex formation, wherein a presence or a level above a pre-determined threshold of said immunocomplex in the cell is indicative of the CMV infection in the subject.

17. The antibody of claim 2, being conjugated to a therapeutic moiety.

18. The antibody of claim 2, attached to a detectable moiety.

19. The antibody of claim 2, being an antibody fragment.

20. An antibody comprising a multivalent form of the antibody of claim 2.

21. The antibody of claim 20, wherein said multivalent form is an IgG antibody.

* * * * *